US00RE50996E

(19) United States
(12) Reissued Patent
Akinc et al.

(10) Patent Number: US RE50,996 E
(45) **Date of Reissued Patent: *Aug. 18, 2026**

(54) Serpinc1 iRNA COMPOSITIONS AND METHODS OF USE THEREOF

(71) Applicant: Genzyme Corporation, Cambridge, MA (US)

(72) Inventors: Akin Akinc, Needham Heights, MA (US); Alfica Sehgal, Belmont, MA (US); Ivanka Toudjarska, Medford, MA (US); Donald Foster, Attleboro, MA (US); Stuart Milstein, Arlington, MA (US); Brian Bettencourt, Groton, MA (US); Martin A. Maier, Belmont, MA (US); Klaus Charisse, Acton, MA (US); Satyanarayana Kuchimanchi, Acton, MA (US); Kallanthottathil G. Rajeev, Wayland, MA (US); Muthiah Manoharan, Weston, MA (US)

(73) Assignee: Genzyme Corporation, Cambridge, MA (US)

( * ) Notice: This patent is subject to a terminal disclaimer.

(21) Appl. No.: 17/396,331

(22) Filed: Aug. 6, 2021

Related U.S. Patent Documents

Reissue of:
(64) Patent No.: 9,127,274
Issued: Sep. 8, 2015
Appl. No.: 13/837,129
Filed: Mar. 15, 2013

U.S. Applications:
(60) Provisional application No. 61/734,573, filed on Dec. 7, 2012, provisional application No. 61/669,249, filed on Jul. 9, 2012, provisional application No. 61/638,952, filed on Apr. 26, 2012.

(51) Int. Cl.
*C12N 15/113* (2010.01)
*A61K 31/713* (2006.01)

(52) U.S. Cl.
CPC ..... *C12N 15/113* (2013.01); *A61K 31/713* (2013.01); *C12N 2310/14* (2013.01); *C12N 2310/315* (2013.01); *C12N 2310/321* (2013.01); *C12N 2310/322* (2013.01)

(58) Field of Classification Search
CPC ..... C12N 15/113; C12N 2310/14; C12N 2310/315; C12N 2310/321; C12N 2310/322; C12N 2310/335; C12N 2310/351; C12N 2310/3515; C12N 2310/3521; C12N 2310/3533; C12N 2320/30; C12N 2310/3523; C12N 2310/3525; A61K 31/713; A61K 31/7088; A61P 7/04; A61P 43/00; C07H 21/04
See application file for complete search history.

(56) References Cited

U.S. PATENT DOCUMENTS

| | | | |
|---|---|---|---|
| 4,517,294 | A | 5/1985 | Bock et al. |
| 6,794,493 | B2 | 9/2004 | Walston et al. |
| 8,071,291 | B2 | 12/2011 | Bare et al. |
| 8,090,542 | B2 | 1/2012 | Khvorova et al. |
| 8,106,022 | B2 | 1/2012 | Manoharan et al. |
| 8,222,222 | B2 | 7/2012 | Tan |
| 8,232,383 | B2 | 7/2012 | McSwiggen |
| 8,376,680 | B2 | 2/2013 | Haasz |
| 8,507,661 | B2 | 8/2013 | Manoharan |
| 8,546,143 | B2 | 10/2013 | Kreutzer |
| 8,741,844 | B2 | 6/2014 | Borgel Born Botbol et al. |
| 8,809,292 | B2 | 8/2014 | Tan |
| 8,828,956 | B2 | 9/2014 | Manoharan |
| 8,830,801 | B2 | 9/2014 | Yoshizawa et al. |
| 9,074,213 | B2 | 7/2015 | Kreutzer |
| 9,127,274 | B2 | 9/2015 | Akinc |
| 9,133,461 | B2 | 9/2015 | Bettencourt |
| 9,150,605 | B2 | 10/2015 | Allerson |
| 9,260,471 | B2 | 2/2016 | Cancilla |
| 9,290,760 | B2 | 3/2016 | Rajeev |
| 9,370,581 | B2 | 6/2016 | Manoharan |
| 9,370,582 | B2 | 6/2016 | Manoharan |
| 9,376,680 | B2 | 6/2016 | Akinc |
| 9,399,775 | B2 | 7/2016 | Rajeev |
| 9,631,193 | B2 | 4/2017 | Bettencourt |
| 9,708,607 | B2 | 7/2017 | Rajeev |
| 9,708,610 | B2 | 7/2017 | Allerson |
| 9,708,615 | B2 | 7/2017 | Manoharan |

(Continued)

FOREIGN PATENT DOCUMENTS

| | | | |
|---|---|---|---|
| CN | 1890262 | A | 1/2007 |
| CN | 102006890 | A | 4/2011 |

(Continued)

OTHER PUBLICATIONS

Akinc et al., "An RNAi Therapeutic Targeting Antithrombin Increases Thrombin Generation in Nonhuman Primates," 54th Annual Meeting and Exposition of the American Society of Hematology (ASH); Dec. 7, 2012.

(Continued)

*Primary Examiner* — Lora E Barnhart Driscoll
(74) *Attorney, Agent, or Firm* — MORRISON & FOERSTER LLP

(57) ABSTRACT

The invention relates to iRNA, e.g., double-stranded ribonucleic acid (dsRNA), compositions targeting the Serpinc1 gene, and methods of using such iRNA, e.g., dsRNA, compositions to inhibit expression of Serpinc1 and methods of treating subjects having a bleeding disorder, such as a hemophilia.

63 Claims, 47 Drawing Sheets

Specification includes a Sequence Listing.

(56) References Cited

U.S. PATENT DOCUMENTS

| | | | |
|---|---|---|---|
| 9,828,606 | B2 | 11/2017 | Brown |
| 9,970,005 | B2 | 5/2018 | Cancilla |
| 10,119,143 | B2 | 11/2018 | Bettencourt |
| 10,125,364 | B2 | 11/2018 | Bettencourt |
| 10,125,369 | B2 | 11/2018 | Borodovsky |
| 10,131,907 | B2 | 11/2018 | Forst |
| 10,208,307 | B2 | 2/2019 | Zimmermann |
| 10,266,825 | B2 | 4/2019 | Allerson |
| 10,273,477 | B2 | 4/2019 | Manoharan |
| 10,344,278 | B2 | 7/2019 | Hinkle |
| 10,407,488 | B2 | 9/2019 | Griffin et al. |
| 10,435,692 | B2 | 10/2019 | Brown |
| 10,465,195 | B2 | 11/2019 | Brown |
| 10,478,500 | B2 | 11/2019 | Querbes |
| 10,487,330 | B2 | 11/2019 | Brown |
| 10,570,391 | B2 | 2/2020 | Rajeev |
| 10,590,418 | B2 | 3/2020 | Kay |
| 10,612,024 | B2 | 4/2020 | Maier |
| 10,612,027 | B2 | 4/2020 | Maier |
| 10,669,544 | B2 | 6/2020 | Manoharan |
| 10,683,501 | B2 | 6/2020 | Zimmermann |
| 10,689,648 | B2 | 6/2020 | Carr |
| 10,806,791 | B2 | 10/2020 | Manoharan |
| 10,808,246 | B2 | 10/2020 | Manoharan |
| 10,851,377 | B2 | 12/2020 | Fitzgerald |
| 11,028,392 | B2 | 6/2021 | Bettencourt |
| 11,060,093 | B2 | 7/2021 | Brown |
| 11,078,485 | B2 | 8/2021 | Allerson |
| 11,091,759 | B2 | 8/2021 | Akinc et al. |
| 11,193,126 | B2 | 12/2021 | Cancilla |
| 11,261,447 | B2 | 3/2022 | Erbe |
| 11,286,486 | B2 | 3/2022 | Zimmermann |
| 11,401,517 | B2 | 8/2022 | Maier |
| 11,446,380 | B2 | 9/2022 | Querbes |
| 11,530,408 | B2 | 12/2022 | Manoharan |
| 2005/0020525 | A1 | 1/2005 | Mcswiggen et al. |
| 2005/0080032 | A1 | 4/2005 | Gross et al. |
| 2006/0024793 | A1 | 2/2006 | Yamada et al. |
| 2007/0031844 | A1* | 2/2007 | Khvorova et al. ..... 435/6 |
| 2008/0113351 | A1 | 5/2008 | Naito et al. |
| 2008/0152661 | A1 | 6/2008 | Rozema et al. |
| 2008/0221062 | A1 | 9/2008 | Miyamoto et al. |
| 2009/0239814 | A1* | 9/2009 | Manoharan et al. ..... 514/26 |
| 2010/0010066 | A1 | 1/2010 | Fitzgerald et al. |
| 2010/0112687 | A1 | 5/2010 | Quay et al. |
| 2010/0266680 | A1 | 10/2010 | Andre et al. |
| 2010/0267090 | A1 | 10/2010 | Sato |
| 2010/0298224 | A1 | 11/2010 | Bianchini et al. |
| 2011/0110861 | A1 | 5/2011 | Lahoud et al. |
| 2011/0196020 | A1 | 8/2011 | Carter et al. |
| 2011/0269823 | A1 | 11/2011 | Nakayama et al. |
| 2013/0317081 | A1 | 11/2013 | Akinc |
| 2014/0350071 | A1 | 11/2014 | Sehgal |
| 2014/0356377 | A1 | 12/2014 | Hack et al. |
| 2015/0118495 | A1 | 4/2015 | Day et al. |
| 2016/0017330 | A1 | 1/2016 | Akinc |
| 2016/0257954 | A1 | 9/2016 | Akinc et al. |
| 2017/0159053 | A1 | 6/2017 | Akinc |
| 2020/0163987 | A1 | 5/2020 | Akinc |
| 2020/0216844 | A1 | 7/2020 | Akinc et al. |
| 2021/0254063 | A1 | 8/2021 | Akinc et al. |
| 2021/0393669 | A1 | 12/2021 | Mei et al. |
| 2022/0017902 | A1 | 1/2022 | Akinc et al. |
| 2022/0079971 | A1 | 3/2022 | Akinc |
| 2023/0158058 | A1 | 5/2023 | Akinc |
| 2023/0365965 | A1 | 11/2023 | Akinc |
| 2024/0000744 | A1 | 1/2024 | Andersson |
| 2024/0027478 | A1 | 1/2024 | Poloskey |
| 2025/0064842 | A1 | 2/2025 | Andersson et al. |

FOREIGN PATENT DOCUMENTS

| | | | |
|---|---|---|---|
| CN | 108601795 | A | 9/2018 |
| CN | 104520310 | B | 7/2019 |
| EP | 2704742 | B1 | 7/2017 |
| GB | 2237570 | A | 5/1991 |
| JP | S54117486 | A | 9/1979 |
| JP | S62132862 | A | 6/1987 |
| JP | S6399056 | A | 4/1988 |
| JP | 2010144740 | A | 7/2010 |
| JP | 2011511004 | A | 4/2011 |
| JP | 2012500780 | A | 1/2012 |
| KR | 20150003344 | A | 1/2015 |
| KR | 20180095843 | A | 8/2018 |
| WO | 2004/045543 | A2 | 6/2004 |
| WO | 2006/006948 | A2 | 1/2006 |
| WO | 2007053696 | A2 | 5/2007 |
| WO | 2008101354 | A1 | 8/2008 |
| WO | 2009/073809 | A2 | 6/2009 |
| WO | 2009082607 | A2 | 7/2009 |
| WO | 2009/134487 | A2 | 11/2009 |
| WO | 2010020423 | A2 | 2/2010 |
| WO | 2010081878 | A1 | 7/2010 |
| WO | 2010120525 | A1 | 10/2010 |
| WO | 2010120526 | A2 | 10/2010 |
| WO | 2010/130825 | A2 | 11/2010 |
| WO | 2010/144740 | A1 | 12/2010 |
| WO | 2010148013 | A2 | 12/2010 |
| WO | 2011104159 | A1 | 9/2011 |
| WO | 2011104169 | A1 | 9/2011 |
| WO | 2012111184 | A1 | 8/2012 |
| WO | 2012177784 | A2 | 12/2012 |
| WO | 2012177949 | A2 | 12/2012 |
| WO | 2013/159108 | A2 | 10/2013 |
| WO | 2013163430 | A2 | 10/2013 |
| WO | 2015175510 | A1 | 11/2015 |
| WO | 2016183009 | A2 | 11/2016 |
| WO | 2017100236 | A1 | 6/2017 |
| WO | 2018185241 | A1 | 10/2018 |
| WO | 2019014187 | A1 | 1/2019 |
| WO | 2020150431 | A1 | 7/2020 |
| WO | 2021262695 | A1 | 12/2021 |
| WO | 2022120291 | A1 | 6/2022 |
| WO | 2022120292 | A1 | 6/2022 |
| WO | 2023122713 | A1 | 6/2023 |
| WO | 2023240193 | A1 | 12/2023 |
| WO | 2023240199 | A1 | 12/2023 |
| WO | 2025059635 | A1 | 3/2025 |

OTHER PUBLICATIONS

"Blood coagulation and its regulation pathway," J of Mie Pref Coll of Nurs. (2008) 12:1-6.

Bolliger et al., "Heterozygous antithrombin deficiency improves in vivo haemostasis in factor VIII-deficient mice," Thromb Haemost. (2010) 103(6):1233-8.

Di Micco et al., "Inhibition of antithrombin by protein SV-IV normalizes the coagulation of hemophilic blood," Eur J of Pharm. (2000) 391:1-9.

GenBank JA674123.1 "Sequence 513 from Patent WO2011144718," of Dec. 11, 2011.

Hong et al., "A phase 1 dose escalation, pharmacokinetic, and pharmacodynamic evaluation of eIF-4E antisense oligonucleotide LY2275796 in patients with advanced cancer," Clin Cancer Res. (2011) 17(20):6582-91.

J of Jap Surg Soc. (2003) 104(12):840-46.

Majlessi et al., "Advantages of 2'-O-methyl oligoribonucleotide probes for detecting RNA targets," Nuc Acids Res. (1998) 26(9):2224-9.

Parunov et al., "Improvement of spatial fibrin formation by the anti-TFPI aptamer BAX499: changing clot size by targeting extrinsic pathway initiation," J of Throm and Haem. (2011) 9:1825-34.

Pon et al., "Tandem oligonucleotide synthesis using linker phosphoramidites," Nucleic Acids Res. (2005) 33(6):1940-48.

Prochownik et al., "Isolation of a cDNA clone for human antithrombin III," J of Biolog Chem. (1983) 258(13):8389-94.

Roberts et al., "Rebase—enzymes and genes for DNA restriction and modification," Nucleic Acids Res. (2007) 35(Database issue); D269-270.

Schmidt, "Dose-finding studies in clinical drug development," Eur J Clin Pharmacol. (1988) 34:15.

(56) References Cited

OTHER PUBLICATIONS

Shetty et al., "Contribution of natural anticoagulant and fibrinolytic factors in modulating the clinical severity of haemophilia patients," Br J of Haem. (2007) 138:541-4.
Waters et al., "Aptamer ARC19499 mediates a procoagulant hemostatic effect by inhibiting tissue factor pathway inhibitor," Blood (2011) 117(20): 5514-22.
"Diagnosis and Management of Hemophilia," J. Thromb. Haemost. (2007) 18(6):568-71. [Including partial English translation].
Yazaki M. et al., "Experiences of Regular Long—Term Continuous Replacement Therapy for Hemophilia," J. Pediatr. Hematol. (2006) 20(1):22-5. [Including partial English translation].
Rusin, "RNA-Interference: Micro-RNAs as a New Regulators of Genes and Perspective Therapeutic Targets," (2006). [English translation of abstract on last page].
Advisory Action Before the Filing of an Appeal Brief mailed on Feb. 20, 2020, for U.S. Appl. No. 15/371,300, filed Dec. 7, 2016, 2 pages.
Akin, A. (May 15, 2014). "ALN-AT3: An Investigational Rnai Therapeutic Targeting Antithrombin For The Treatment Of Hemophilia," Poster presented at World Federation of Hemophilia (WHF) 2014 World Congress, 16 pages.
Akin, A. (Jul. 2, 2013). "An RNAi Therapeutic Targeting Antithrombin Increases Thrombin Generation and Improves Hemostasis," Poster presented atXXIV Congress of the International Society on Thrombosis and Haemostasis (ISTH), 14 pages.
Barros, S. et al. (2016). "Safety Evaluation Of Chronic Antithrombin Silencing In Non-Human Primate And Expanded Therapeutic Index In A Hemophilia A Mouse Model," Int J of Toxic. 35:79, 1 page.
Barros, S.A. et al. (Nov. 15, 2013). "Expanded Therapeutic Index Of Antithrombin Silencing and Correction Of Aptt In a Hemophilia A Mouse Model," Blood 122(21):3585, 2 pages.
Final Office Action mailed on Jun. 7, 2019, for U.S. Appl. No. 15/371,300, filed Dec. 7, 2016, 11 pages.
Final Office Action mailed on Nov. 16, 2023, for U.S. Appl. No. 15/371,300, filed Dec. 7, 2016, 11 pages.
Final Office Action mailed on Nov. 27, 2019, for U.S. Appl. No. 15/371,300, filed Dec. 7, 2016, 10 pages.
Fryar, C.D. et al. (Aug. 2016). "Anthropometric Reference Data For Children And Adults: United States, 2011-2014," Natl Ctr for Hlth Stat. Vital Health Stat 3(39), 46 pages.
International Preliminary Report on Patentability issued on Oct. 28, 2014 for PCT Application No. PCT/US13/38218, filed on Apr. 25, 2013, 13 pages.
International Search Report and Written Opinion of the International Searching Authority mailed on Dec. 2, 2013 for PCT Application No. PCT/US13/38218 filed on Apr. 25, 2013, 20 pages.
Invitation to Pay Additional Fees mailed on Sep. 5, 2013 for PCT Application No. PCT/US13/38218, filed on Apr. 25, 2013, 3 pages.
Kenet, G. et al. (Dec. 3, 2015). "Antithrombin Reduction Corrected Thrombin Generation in Samples from Hemophilia A and B Patients with Inhibitors," Blood (2015) 126(23):552, 57th Annual Meeting of the American Society of Hematology, Orlando, FL, USA, Dec. 5-8, 2015, Abstract Only, 5 pages.
Non-Final Office Action mailed on Apr. 11, 2023, for U.S. Appl. No. 15/371,300, filed Dec. 7, 2016, 9 pages.
Non-Final Office Action mailed on Aug. 31, 2018, for U.S. Appl. No. 15/371,300, filed Dec. 7, 2016, 10 pages.
Non-Final Office Action mailed on Jul. 11, 2024, for U.S. Appl. No. 15/371,300, filed Dec. 7, 2016, 10 pages.
Non-Final Office Action mailed on May 13, 2020, for U.S. Appl. No. 15/371,300, filed Dec. 7, 2016, 15 pages.
Pasi, J.K. et al. (Dec. 7, 2015). "A Subcutaneously Administered Investigational RNAi Therapeutic (ALN-AT3) Targeting Antithrombin for Treatment of Hemophilia: Interim Weekly and Monthly Dosing Results in Patients with Hemophilia A or B," Blood (2015) 126(23):551, Poster presented at 57th Annual Meeting of the American Society of Hematology, Orlando, FL, USA, Dec. 5-8, 2015, 16 pages.
Pasi, J.K. et al. (Dec. 2, 2016). "Fitusiran, an Investigational RNAi Therapeutic Targeting Antithrombin for the Treatment of Hemophilia: Updated Results from a Phase 1 and Phase ½ Extension Study in Patients with Inhibitors," Blood 128(22):1397, 6 pages.
Pasi, J.K. et al. (Dec. 3, 2016). "Fitusiran, an Investigational RNAi Therapeutic Targeting Antithrombin for the Treatment of Hemophilia: Updated Results from Phase 1 and Phase 2 Extension Studies in Patients with Inhibitors," Poster presented in 60th American Society of Hemophilia Meeting and Exposition, San Diego, CA, USA, 12 pages.
Pasi, J.K. et al. (Jul. 10, 2017). "Fitusiran, an Investigational RNAi Therapeutic Targeting Antithrombin for the Treatment of Hemophilia: Interim Results from a Phase 2 Extension Study in Patients with Hemophilia A or B with and Without Inhibitors," Poster presented in International Society on Thrombosis and Haemostasis (ISTH) 2017 Congress, Berlin, Germany, 14 pages.
Pasi, J.K. et al. (Jul. 25, 2016). "A Subcutaneously Administered Investigational RNAi Therapeutic (Fitusiran) Targeting Antithrombin for Treatment of Hemophilia: Interim Weekly and Monthly Dosing Results in Patients with Hemophilia A or B," Poster presented at World Federation of Hemophilia (WFH) 2016 World Congress, Orlando, FL, USA, 20 pages.
Pasi, K.J. et al. (Aug. 31, 2017, e-pub. Jul. 10, 2017). "Targeting of Antithrombin in Hemophilia A or B with RNAi Therapy," The New England Journal of Medicine 377(9):819-828.
Ragni, M.V. et al. (Dec. 2, 2016). "Fitusiran, an Investigational RNAi Therapeutic Targeting Antithrombin for the Treatment of Hemophilia: Updated Results from a Phase 1 and Phase 1 and 2 Extension Study in Patients without Inhibitors," Blood 128(22):2572, 5 pages.
Response to Final Office Action dated Jan. 29, 2020, for U.S. Appl. No. 15/371,300, filed Dec. 7, 2016, 24 pages.
Response to Final Office Action dated Mar. 18, 2024, for U.S. Appl. No. 15/371,300, filed Dec. 7, 2016, 10 pages.
Response to Final Office Action dated Mar. 27, 2020, for U.S. Appl. No. 15/371,300, filed Dec. 7, 2016, 24 pages.
Response to Final Office Action dated Nov. 7, 2019, for U.S. Appl. No. 15/371,300, filed Dec. 7, 2016, 23 pages.
Response to Non-Final Office Action dated Aug. 11, 2023, for U.S. Appl. No. 15/371,300, filed Dec. 7, 2016, 13 pages.
Response to Non-Final Office Action dated Feb. 28, 2019, for U.S. Appl. No. 15/371,300, filed Dec. 7, 2016, 20 pages.
Response to Non-Final Office Action dated Jan. 13, 2025, for U.S. Appl. No. 15/371,300, filed Dec. 7, 2016, 11 pages.
Response to Non-Final Office Action dated Sep. 9, 2020, for U.S. Appl. No. 15/371,300, filed Dec. 7, 2016, 22 pages.
Safdar, H. et al. (May 23, 2013, e-pub. Apr. 2, 2013). "Acute And Severe Coagulopathy In Adult Mice Following Silencing Of Hepatic Antithrombin And Protein C Production," Blood 121(21):4413-4416, 6 pages.
Sehgal, A. et al. (May 2015). "An Rnai Therapeutic Targeting Antithrombin To Rebalance The Coagulation System And Promote Hemostasis In Hemophilia," Nat Med. 21(5):492-497.
Sorensen, B. et al. (Dec. 6, 2014). "A Subcutaneously Administered RNAi Therapeutic (ALN-AT3) Targeting Antithrombin for Treatment of Hemophilia: Interim Phase 1 Study Results in Healthy Volunteers and Patients with Hemophilia a or B," Blood 124(21):693, 3 pages.
U.S. Appl. No. 15/955,873, filed Apr. 18, 2018, for Akinc et al. (Copy not submitted herewith pursuant to the waiver of 37 C.F.R. 1.98(a)(2)(iii) issued by the Office on Sep. 21, 2004).
U.S. Appl. No. 18/723,352, filed Jun. 21, 2024, for Shauna et al. (Copy not submitted herewith pursuant to the waiver of 37 C.F.R. 1.98(a)(2)(iii) issued by the Office on Sep. 21, 2004).
U.S. Appl. No. 18/872,107, filed Dec. 5, 2024, for Shauna et al. (Copy not submitted herewith pursuant to the waiver of 37 C.F.R. 1.98(a)(2)(iii) issued by the Office on Sep. 21, 2004).
Akinc A. (Jun. 29, 2013). "An RNAi Therapeutic Targeting Antithrombin Increases Thrombin Generation and Improves Hemostasis in Hemophilia Mice," Journal of Thrombosis and Haemostasis 11(Supp. 2): 169-70, 24th Congress of the International Society on Thrombosis and Haemostasis. Amsterdam, Netherlands, Abstract No. OC 37.4, 2 pages.
Akinc, A. (Jul. 2, 2013). "An RNAi Therapeutic Targeting Antithrombin Increases Thrombin Generation and Improves Hemostasis," Poster

(56) References Cited

OTHER PUBLICATIONS presented at XXIV Congress of the International Society on Thrombosis and Haemostasis (ISTH), 14 pages.
Akinc, A. (May 15, 2014). "ALN-AT3: An Investigational RNAi Therapeutic Targeting Antithrombin for the treatment of Hemophilia," Poster presented at World Federation of Hemophilia (WFH) 2014 World Congress, May 15, 2014, 16 pages.
Akinc, A. et al. (Jun. 20, 2015). "Thrombin Generation In Human Hemophilia Plasma At Reduced Antithrombin Levels And Concomitant Factor Or Bypass Agent Addition," Journal of Thrombosis and Haemostasis 13( SUPPL. 2):564, 25th Congress of the International Society on Thrombosis and Haemostasis, ISTH 2015, Toronto, ON, Canada, Abstract No. PO154-TUE, 1 page.
Aledort, L.M. (2019). "The Ongoing Imperative For Immune Tolerance Induction In Inhibitor Management," Haemophilia 25(2):183-186.
Anonymous (2013). "Guideline for Hemostasis Treatment for Hemophilia Patients Without Inhibitors," Japanese Society of Thrombosis and Hemostasis, p. 1-21, 29 pages (Partial English Translation).
Anonymous (2022). "NCT03417102: A Study of Fitusiran (ALN-AT3SC) in Severe Hemophilia A and B Patients with Inhibitors (Atlas-INH)," 1-19 (available via clinicaltrials.qov).
Anonymous (Dec. 1, 2021). "Medication Guide Hemlibra (Emicizumab)," 139 pages, retrieved on Aug. 2, 2022, from https://www.accessdata.fda.gov/drugsatfda_docs/label/2021/761083s0131bl.pdf#page=22.
Anonymous, "Clark's Rule—Wikipedia" (2022) 1-2.
Anonymous, "Correction: Drugs that made headlines in 2017," Nature Medicine, (2018) 24(1): 5.
Anonymous, "Drugs that made headlines in 2017," Nature Medicine (2017) 23(12):1393.
Anonymous, "Record History: NCT03417102" (2021) (available via clinicaltrials.qov).
Anonymous, Record History: NCT03549871 (ver. 27) (2022) (available via clinicaltrials.gov).
Anonymous, "What the Neighbors Say," Journal of Thrombosis and Haemostasis (2017) 15( 9):1716.
Anonymous, Record History for NCT03974113 Version 23 (2022) 1-8 (available via clinicaltrials.gov). Apr. 7, 2022, 1-8.
Applicant-Initiated Interview Summary mailed on Aug. 4, 2020, for U.S. Appl. No. 15/371,300, filed Dec. 7, 2016, 3 pages.
Arruda, V.R. et al. (Nov. 23, 2017, e-pub. Oct. 10, 2017). "Novel Approaches To Hemophilia Therapy: Successes And Challenges," Blood 130(21):2251-2256.
Astermark, J. et al. (2007). "Current Use Of By-Passing Agents In Europe In The Management Of Acute Bleeds In Patients With Haemophilia And Inhibitors," Haemophilia 13(1):38-45.
Atkinson, M. J. et al. (Feb. 26, 2004). "Validation Of A General Measure Of Treatment Satisfaction, The Treatment Satisfaction Questionnaire For Medication (TSQM), Using A National Panel Study Of Chronic Disease," Health And Quality Of Life Outcomes 2:1-13.
Attarwala, H. et al. (Jul. 10, 2017). "Development Of A Pharmacokinetic-Pharmacodynamic (PK-PD) Model Of Fitusiran, An Investigational Rnai Therapeutic Targeting Antithrombin For The Treatment Of Hemophilia In Patients With And Without Inhibitors," Poster in Research and Practice in Thrombosis and Haemostasis 1(Supp. 1): 750, 26th International Society on Thrombosis and Haemostasis Congress, ISTH 2017, Berlin, Germany, 18 pages.
Attarwala, H. et al. (Jul. 10, 2017). "Development Of A Pharmacokinetic-Pharmacodynamic (PK-PD) Model Of Fitusiran, An Investigational Rnai Therapeutic Targeting Antithrombin For The Treatment Of Hemophilia In Patients With And Without Inhibitors," Research and Practice in Thrombosis and Haemostasis 1(Supp. 1):750, 26th International Society on Thrombosis and Haemostasis Congress, ISTH 2017, Berlin, Germany, Abstract No. PB 1066, 1 page.
Auerswald, G. et al. (2016). "Pain And Pain Management In Haemophilia," Blood Coagul Fibrinolysis 27(8):845-854.
Ayyar, V.S. et al. (Nov. 2021). "Minimal Physiologically Based Pharmacokinetic-Pharmacodynamic (PBPK-PD) Model of N-Acetylgalactosamine-Conjugated Small Interfering RNA Disposition and Gene Silencing in Preclinical Species and Humans," J , Pharmacology and Experimental Therapeutics 379(2): 134-146, S1-S13.
Bajwa, N. et al. (Jun. 14, 2020) "Overview Of The Clinical Development Of Fitusiran," Haemophilia (2020) 26(Supp. 4):6-8, World Federation of Hemophilia, Virtual Summit—Connecting the Global Bleeding Disorders Community, Kuala Lumpur, Malaysia, Abstract No. MED-FP-002 (598), 159 pages.
Balkaransingh, P. et al. (2018). "Novel Therapies And Current Clinical Progress In Hemophilia A," Therapeutic Advances in Hematology 9(2): 49-61.
Barros, S. et al. (Jun. 20, 2015) "Safety Evaluation Of Chronic Antithrombin Silencing In Non-Human Primate And Expanded Therapeutic Index In A Hemophilia A Mouse Model," Journal of Thrombosis and Haemostasis (2015) 13 (Suppl. 2):771, 25th Congress of the International Society on Thrombosis and Haemostasis, ISTH 2015. Toronto, ON, Canada, Abstract No. PO049-WED, 1 page.
Barros, S.A. et al. (Nov. 15, 2013). "Expanded Therapeutic Index Of Antithrombin Silencing and Correction Of APTT In a Hemophilia A Mouse Model," Blood 122(21):3585, located at https://ashpublications.org/blood/article/122/21 /3585/11420/Expanded-Therapeutic-Index-Of-Antithrombin, last visited on Sep. 2, 2020, 4 pages.
Barros, S.A. et al. (Nov. 2015). "Safety Evaluation Of Chronic Antithrombin Silencing In Non-Human Primate And Expanded Therapeutic Index In A Hemophilia A Mouse Model," Int J of Toxic. (2016) 35(1):79, Poster, presented at 36th Annual Meeting of the American College ofToxicology (ACT), Summerlin, NV, USA, Nov. 8-11, 2015, 1 page.
Batra, K. et al. (2021). "An Insight on RNA Based Therapeutics and Vaccines: Challenges and Op-portunities," Current Topics in Medicinal Chemistry 21(32):2851-2855.
Bauer, K. A. (Mar. 30, 2015). "Current Challenges In The Management Of Hemophilia," Am J Manag Care 21(6):S112-S122.
Bejar, N. et al. (2022, e-pub. Apr. 2, 2022). "RNA Therapeutics: The Next Generation of Drugs for Cardiovascular Diseases," Current Atherosclerosis Reports (2022) 24(5):307-321.
Benson, G. et al. (2012). "Immune Tolerance Induction In Patients With Severe Hemophilia With Inhibitors: Expert Panel Views And Recommendations For Clinical Practice," European Journal Of Haematology 88(5):371-379.
Bergmeier, W. et al. (2018, e-pub. Apr. 12, 2018). "Advances in Clinical and Basic Science of Coagulation: Illustrated abstracts of the 9th Chapel Hill Symposium on Hemostasis," Research and Practice in Thrombosis and Haemostasis 2(3):407-428.
Berk, C. et al. (2021). "Pharmacodynamic and Pharmacokinetic Properties of Full Phosphorothioate Small Interfering RNAs for Gene Silencing In Vivo," Nucleic Acid Therapeutics 31(3):237-244.
Berntorp, E. et al. (2021, e-pub. Jun. 24, 2021) "Haemophilia," Nature Reviews Disease Primers 7(1):45.
Bhagunde, P. et al. (2018). "PB0526: Fitusiran Population Pharmacokinetic And Pharmacodynamic (Poppk/PD) Modeling To Support Revised Dose, Dosing Regimens, And Dose Mitigation Scheme," Research and Practice in Thrombosis and Haemostasis—Abstracts of the 64th Annual Meeting of the Scientific Standardization Committee of the International Society on Thrombosis and Haemostasis 5(S2):399-401.
Bhagunde, P. et al. (Jul. 17, 2021). "Fitusiran Population Pharmacokinetic And Pharmacodynamic (POPPK/PD) Modeling To Support Revised Dose, Dosing Regimens & Dose Mitigation Scheme," Research and Practice in Thrombosis and Haemostasis 5(Suppl 2), 2021 Congress of the International Society of Thrombosis and Haemostasis, ISTH 2021, Virtual, Abstract No. PB0526, 3 pages.
Bharmal, M. et al. (Apr. 27, 2009). "Validation Of An Abbreviated Treatment Satisfaction Questionnaire For Medication (TSQM-9) Among Patients On Antihypertensive Medications," Health And Quality Of Life Outcomes 7(36):1-10.
Bolliger, D. et al. (2022). "Management of Patients With Hemophilia Undergoing Cardiac Surgery," Journal of Cardiothoracic and Vascular Anesthesia 36(2):539-541.
Brackmann, H.H. et al. (2020)."Origins, Development, Current Challenges and Future Directions with Activated Prothrombin Com-

(56) References Cited

OTHER PUBLICATIONS plex Concentrate for the Treatment of Patients with Congenital Haemophilia with Inhibitors," Hamostaseologie 40(5):606-620.
Bullinger, M. et al. (2009). "Challenges Of Patient-Reported Outcome Assessment In Hemophilia Care—A State Of The Art Review," Value in Health 12(5): 808-820.
Butterfield, J.S.S. et al. (Apr. 2020). "A Molecular Revolution in the Treatment of Hemophilia," Molecular Therapy 28(4):997-1015.
Callaghan, M.U. et al. (Jul. 5, 2018, e-pub. May 16, 2018). "Novel Therapeutics For Hemophilia And Other Bleeding Disorders," Blood 132(1):23-30.
Cano, V. et al. (2021). "Sustained Improvement In Health-Related Quality Of Life In Patients With Hemophilia A With Or Without Inhibitors Treated With Fitusiran Prophylaxis," Blood (2021) 138(Suppl 1):3197, Abstract, presented at 63rd American Society of Hematology Annual Meeting and Exposition, ASH 2021, Atlanta, GA, United States, Dec. 11, 2021, 3 pages.
Cano, V. et al. (2022) "Patients with Hemophilia and Their Caregivers Prefer Treatment Attributes That Enable a More Active Lifestyle with Lower Risk of Inhibitor Development," Blood (2022) 140(S1):7991-2, Abstract, presented at American Society of Hematology—64th Annual Meeting, New Orleans, LA, USA, as posted on https://ash.confex.com/ash/2022/cop/papers/index.cgi?username=168405&password=*cookie, last visited on Aug. 2, 2022, 8 pages.
Cano, V. et al., "Patients with Hemophilia and Their Caregivers Prefer Treatment Attributes That Enable a More Active Lifestyle with Lower Risk of Inhibitor Development," Blood (2022) 140(S1):7991-2, Poster presented at American Society of Hematology—64th Annual Meeting, New Orleans, LA, USA, Dec. 10-13, 2022, 1 page.
Carr, M.E. et al. (2015). "Emerging And Future Therapies For Hemophilia," Journal of Blood Medicine 6:245-255.
Castaman, G. et al. (2019, e-pub. May 9, 2019). "Current and Emerging Biologics for the Treatment of Hemophilia," Expert Opinion on Biological Theraov 19(8):801-810.
Chowdary, P. et al. (2017). "Phase 1 And Phase ½ Extension Study Of Fitusiran, An Investigation AI Rnai Therapeutic Targeting Antithrombin For The Treatment Of Hemophilia: Updated Results In Patients Without Inhibitors," Haemophilia, 23(Supp. 2):118-119, 10th Annual Congress of the European Association for Haemophilia and Allied Disorders, Paris, France, Feb. 1, 2017, Abstract No. P149.
Chowdary, P. et al. (2021, e-pub. Jun. 29, 2021). "Nonfactor Therapies: New Approaches to Prophylactic Treatment of Haemophilia," Hämostaseologie 41(4):247-256.
Chowdary, P. et al. (Sep. 15, 2017). "Fitusiran, An Investigational Rnai Therapeutic Targeting Antithrombin For The Treatment Of Hemophilia A Orb With And Without Inhibitors: Interim Results From A Phase 2 Extension Study," Blood Transfusion (2017) 1S(Supp. 3):s480, 9th BIC International Conference, Rome, Italy, Abstract No. OC-05, 1 page.
clinicaltrials.gov (Feb. 6, 2023). "A Study of Fitusiran in Severe Hemophilia A and B Patients Previously Receiving Factor or Bypassing Agent Prophylaxis (ATLAS-PPX)," webpage https://classic.clinicaltrials.gov/ct2/show/results/NCT03549871?term=EFC15110&draw=2&rank=1&view=results retrieved on Sep. 20, 2023, 41 pages.
clinicaltrials.gov (Jul. 19, 2016). "An Open-Label Extension Study Of An Investigational Drug, ALN-AT3SC, In Patients With Moderate Or Severe Hemophilia A Or B," ClinicalTrials.gov No. NCT02554773, 11 pages.
Collins et al. (2021). "Clinical Phenotype Of Severe And Moderate Haemophilia: Who Should Receive Prophylaxis And What Is The Target Trough Level?," Haemophilia 27(2): 192-198.
Collins, P. (Feb. 2022). "Current and Future Products," Haemophilia 28(SUPPL 1):8, presented at 15th Annual Congress of European Association for Haemophilia and Allied Disorders, Virtual, Feb. 2, 2022, Abstract No. SP009, 1 page.
Collins, P. W. et al. (2013). "Diagnosis And Treatment Of Factor VIII And IX Inhibitors In Congenital Haemophilia," British Journal Of Haematology 160(2):153-170.
Couch, D. et al. (Mar. 6, 2014). "At 150 Kg, You Can't Run Men's Weight Loss Stories In A Popular Health Magazine Provide Appropriate Examples Of Good Health Practice", Health Psychology and Behavioral Medicine: An Open Access Journal 2(1):252-267.
Crooke, S.T. et al. (Apr. 3, 2018). "RNA-Targeted Therapeutics," Cell Metabolism 27(4):714-739.
Croteau, S. (2018). "Evolving Complexity in Hemophilia Management," Pediatric Clinics of North America 65(3):407-425.
Czajkowska, S. et al. (Oct. 3, 2020). "Practical Recommendations For Treatment Of Dental Patients With Congenital Bleeding Disorders During The Covid-19 Pandemic: A Narrative Review," International Journal of Environmental Research and Public Health 17(19):1-16.
Dargaud. Y. et al. (Dec. 7, 2021). "Clinical Utility Of Subcutaneous Factor VIII Replacement Therapies In Hemophilia A: A Review Of The Evidence," Journal of Blood Medicine, 1031-1036.
Dasmahapatra, P. et al. (2019). "Treatment Patterns, Determinants and Outcomes of Hemophilia: Results from a Multinational Survey," (2019) 25(S1):P249, Abstract presented at European Association for Haemophilia and Allied Disorders—12th Annual Congress (2019).
De Brito E Cunha, D. et al. (May 5, 2022). "Biotechnological Evolution of siRNA Molecules: From Bench Tool to the Refined Drug," Pharmaceuticals 15(5): 575, 21 pages.
Delgado, D.D. (Mar. 1, 2021). "Fitusiran Dosing in Trials Reduced to Lower Risk of Blood Clots," Hemophilia News Today 1-7.
Di Minno, A. et al. (2019). "Attempting to Remedy Sub-Optimal Medication Adherence in Haemophilia: The Rationale for Repeated Ultrasound Visualisations of the Patient's Joint Status," Blood Reviews 33:106-116.
Di Minno, A. et al. (2021, e-pub. May 7, 2021). "Perspective—The case for zero bleeds and drug bioequivalence in the treatment of congenital hemophilia A in 2021," Blood Reviews 50:100849.
Dobrowolski, C. et al. (2021). "Therapeutic RNA Delivery for COVID and Other Diseases," Advanced Healthcare Materials 10(15): 2002022, 16 pages.
Dolan, G. et al. (2018). "Haemophilia B: Where Are We Now And What Does The Future Hold?," Blood Reviews 32(1):52-60.
Dong, Y. et al. (2019). "Strategies, Design, and Chemistry in siRNA Delivery Systems," Advanced Drug Delivery Reviews 144:133-147, 32 pages.
Duda, H. et al. (Oct. 24, 2020). "The German Hemophilia Registry: Growing With Its Tasks," Journal of Clinical Medicine 9(3408):1-11.
Eichinger, S. et al. (2009). "Thrombin Generation In Haemophilia A Patients With Factor VIII Inhibitors After Infusion Of Recombinant Factor Vlla," European Journal Of Clinical Investigation 39(8):707-713.
Escuriola-Ettingshausen, C. et al. (2021). "Optimizing The Management Of Patient With Haemophilia A And Inhibitors In The Era Of Emicizumab: Recommendations From A German Expert Panel," Haemophilia 27(3):e305-e313.
EU Clinical Trials Register (Oct. 11, 2022). "Clinical Trial Results: Atlas-PPX Trial: An open-label, Multinational, Switching Study to Describe the Efficacy and Safety of Fitusiran Prophylaxis in Hemophilia A and B Patients Previously Receiving Factor or Bypassing Agent Prophylaxis," webpage https://www.clinicaltrialsregister.eu/ctrsearch/trial/2016-004087-19/results, retrieved on Sep. 20, 2023, 43 pages.
Examiner Interview Slide Deck dated Jul. 29, 2020 mailed on Aug. 4, 2020 for U.S. Appl. No. 15/371,300, filed Dec. 7, 2016.
Final Office Action mailed on Feb. 20, 2024, for U.S. Appl. No. 17/396,331, filed Aug. 6, 2021, 16 pages.
Final Office Action mailed on Mar. 28, 2025, for U.S. Appl. No. 17/375,785, filed Jul. 14, 2021, 10 pages.
Final Office Action mailed on May 5, 2025, for U.S. Appl. No. 17/396,331, filed Aug. 6, 2021, 13 pages.
Final Office Action mailed on Nov. 16, 2023, for U.S. Appl. No. 17/375,785, filed Jul. 14, 2021, 11 pages.

(56) References Cited

OTHER PUBLICATIONS

Franchini, M. et al. (2018).“Non-Factor Replacement Therapy for Haemophilia: a Current Update,” Trasfusione def Sanaue 16(5):457-461.
Fransson, J. et al. (Oct. 1, 1996). “Local Tolerance of Subcutaneous Injections,” Journal of Pharmacy and Pharmacology 48(10):1012-1015.
George, L.A. et al. (2016, e-pub. Apr. 24, 2015). “Profile of Efraloctocog Alfa and Its Potential In The Treatment of hemophilia A,” Journal of Blood Medicine 6:131-141.
Giesen, P. et al. (2017). “Measurement Of Thrombin Generation In Conditions Of Low Antithrombin,” Research and Practice in Thrombosis and Haemostasis 1(Supp. 1): 570-571, Abstract No. PB 1420, presented in 26th International Society on Thrombosis and Haemostasis Congress, ISTH 2017, Berlin, Germany, Jul. 8, 2017.
Gokirmak, T. et al. (Jul. 2021). “Overcoming The Challenges Of Tissue Delivery For Oligonucleotide Therapeutics,” Trends In Pharmacological Sciences 42(7):588-604.
Gonzalez-Aseguinolaza, G. (Jun. 11, 2020). “Givosiran—Running RNA Interference To Fight Porphyria Attacks,” New England Journal of Medicine 382(24):2366-2367.
Graf, M. et al. (Aug. 2021). “Understanding the Evolution of Coverage Policies for Prophylaxis Treatments of Hemophilia A Without Inhibitors: a Payer Delphi Panel,” Journal of Managed Care & Specialty Pharmacy 27(8):996-1008.
Gualtierotti, R. et al. (Sep. 23, 2022). “Updates on Novel Non-Replacement Drugs for Hemophilia” Pharmaceuticals 1183, 18 pages.
Guy-Young (Oct. 1, 2024). “Safety And Efficacy Of The Fitusiran Revised Antithrombin-Based Dose Regimen In People With Haemophilia A Or B, With Or Without Inhibitors (Atlas-Ole)”, Hematology, Transfusion And Cell Therapy 46(S4):S564-S565.
Hart, D.P. et al. (2022). “International Consensus Recommendations On The Management Of People With Haemophilia B,” Therapeutic Advances In Hematology 13(1S):1-22.
Haya, S. (2019). “Prophylactic Treatment In Hemophilic Patients With Inhibitors,” Blood Coagulation And Fibrinolysis 30(1S):S14-S18.
Herdman, M. et al. (Dec. 2011, e-pub. Apr. 9, 2011). “Development and Preliminary Testing Of The New Five-Level Version Of EQ-5D (EQ-5D-5L),” Qual. Life Res. 20(10):1727-1736.
Hermans, C. et al. (2021). “Invasive Procedures in Patients with Haemophilia: Review of Low-Dose Protocols and Experience with Extended Half-Life FVIII and FIX Concentrates and Non-Replacement Therapies,” Haemophilia 27 (S3):46-52.
Hermans, C. et al. (Nov. 5, 2020). “Potential Usefulness of D-Dimers Assay in Treated Patients with FVIII Deficiency to Detect a Prothrombotic State,” Blood 136(Suppl 1):24, Abstract presented in 62nd American Society of Hematology Annual Meeting and Exposition, ASH 2020, San Diego, CA, United States, Dec. 5, 2020, 2 pages.
Hoffman, M. (Feb. 2, 2022). “Thrombosis and the Novel Haemophilia Therapies,” Haemophilia (2022) 28 (Suppl 1):8-9, 15th Annual Congress of European Association for Haemophilia and Allied Disorders, Virtual, Abstract No. SP011, 2 pages.
Hoffman, M. (Sep. 28, 2021). “Thrombosis and Novel Hemophilia Therapies: The Fine Line Between Clottinq and Bleedino,” Blood Advances 5(18):3736.
Holm, A. et al. (2021). “Development Of Sirna Therapeutics For The Treatment Of Liver Diseases,” Chapter 5 in Methods in Molecular Bioloav 2282:57-75.
Hu, B. et al. (2020, e-pub. Jun. 19, 2020). “Therapeutic siRNA: State of the Art,” Signal Transduction and Targeted Therapy 5(1):101, 1-25.
Hu, B. et al. (May 9, 2019). “Clinical advances of siRNA therapeutics,” Journal of Gene Medicine 21(7):e3097, 31 pages.
International Preliminary Report on Patentability issued Dec. 10, 2024 mailed on Jan. 10, 2024, for International Application No. PCT/US2023/068137, filed on Jun. 8, 2023, 41 pages.
International Preliminary Report on Patentability issued Dec. 10, 2024 mailed on Jan. 10, 2024, for International Application No. PCT/US2023/068143, filed on Jun. 8, 2023, 30 pages.
International Preliminary Report on Patentability issued Dec. 13, 2022, mailed on Sep. 29, 2021, for International Application No. PCT Application No. PCT/US2021/038445, filed on Jun. 22, 2021, 7 pages.
International Preliminary Report on Patentability issued Jan. 14, 2020, mailed on Sep. 28, 2018, for International Application No. PCT Application No. PCT/US2018/041400, filed on Jul. 10, 2018, 7 pages.
International Preliminary Report on Patentability issued Jun. 12, 2018, mailed on Mar. 2, 2017, for International Application No. PCT Application No. PCT/US2016/065245, filed on Dec. 7, 2016, 11 pages.
International Preliminary Report on Patentability issued Jun. 16, 2021, mailed on May 11, 2020, for International Application No. PCT Application No. PCT/US2020/013811, filed on Jan. 16, 2020, 6 pages.
International Preliminary Report on Patentability issued Jun. 20, 2024, mailed on May 25, 2023, for International Application No. PCT Application No. PCT/US2022/082213 filed on Dec. 22, 2022, 7 pages.
International Preliminary Report on Patentability issued May 2, 2017, mailed on Apr. 25, 2016, for International Application No. PCT/US2015/057717, filed on Oct. 28, 2015, 10 pages.
International Preliminary Report on Patentability issued May 30, 2023, mailed on Mar. 3, 2022, for International Application No. PCT Application No. PCT/US2021/062076, filed on Dec. 6, 2021, 9 pages.
International Preliminary Report on Patentability issued May 30, 2023, mailed on May 20, 2022, for International Application No. PCT Application No. PCT/US2021/062078, filed on Mar. 7, 2022, 8 pages.
International Preliminary Report on Patentability issued Nov. 15, 2016, mailed on Aug. 12, 2015, for International Application No. PCT/US2015/030337, filed on May 12, 2015, 7 pages.
International Search Report and Written Opinion mailed on Mar. 2, 2017 for PCT Application No. PCT/US2016/065245, filed on Dec. 7, 2016, 17 pages.
International Search Report and Written Opinion mailed on Mar. 3, 2022, for International Application No. PCT Application No. PCT/US2021/062076, filed on Dec. 6, 2021, 15 pages.
International Search Report and Written Opinion mailed on May 11, 2020, for International Application No. PCT Application No. PCT/US2020/013811, filed on Jan. 16, 2020, 9 pages.
International Search Report and Written Opinion mailed on May 20, 2022, for International Application No. PCT Application No. PCT/US2021/062078, filed on Mar. 7, 2022, 14 pages.
International Search Report and Written Opinion mailed on Sep. 28, 2018, for International Application No. PCT Application No. PCT/US2018/041400, filed on Jul. 10, 2018, 15 pages.
International Search Report and Written Opinion mailed on Sep. 29, 2021, for International Application No. PCT Application No. PCT/US2021/038445, filed on Jun. 22, 2021, 11 pages.
International Search Report and Written Opinion of the International Searching Authority mailed on Apr. 28, 2025 for PCT Application No. PCT/US2025/015037 filed on Feb. 7, 2025, 18 pages.
International Search Report and Written Opinion of the International Searching Authority mailed on Dec. 11, 2024 for PCT Application No. PCT/US2024/046873, filed on Sep. 16, 2024, 17 pages.
International Search Report and Written Opinion of the International Searching Authority mailed on Jan. 10, 2024 for PCT Application No. PCT/US2023/068137 filed on Jun. 8, 2023, 52 pages.
International Search Report and Written Opinion of the International Searching Authority mailed on Jan. 10, 2024 for PCT Application No. PCT/US2023/068143, filed on Jun. 8, 2023, 40 pages.

(56) References Cited

OTHER PUBLICATIONS

International Search Report and Written Opinion of the International Searching Authority mailed on May 25, 2023 for PCT Application No. PCT/US2022/082213 filed on Dec. 22, 2022, 13 pages.
Isfordink, C.J. et al. (2021 e-pub. May 6, 2021). "Viral Hepatitis In Haemophilia: Historical Perspective And Current Management," British Journal of Haematology 195(2):174-185.
Janas, M.M. et al. (2018). "The Nonclinical Safety Profile of GalNAc-Conjugated RNAi Therapeutics in Subacute Studies," Toxicologic Pathology 46(7):735-745.
Jimenez-Yuste, V. et al. (2021). "Practical Considerations For Nonfactor-Replacement Therapies In The Treatment Of Haemophilia With Inhibitors," Haemophilia 27(3):340-350.
Kaczmarek, J.C. et al. (2017, e-pub. Jun. 27, 2017). "Advances In The Delivery Of RNA Therapeutics: From Concept To Clinical Reality," Genome Medicine 9(1):60, 16 pages.
Kaczmarek, R. (2018). "Gene Therapy of Haemophilia—Has the Cure Come Within Reach?" Postepy biochemii 64(4): 318-322, English Abstract Only.
Kaddi, C. et al. (Nov. 15, 2022). "Development of a Quantitative Systems Pharmacology Model to Explore Hemostatic Equivalency of Antithrombin Lowering," Blood (2022) 240(81):5606-5607, Abstract No. 322, 6 pages.
Kattula et al. (2020). "Mechanistic studies ofthrombin generation assay to evaluate procoagulant potential of fitusiran," Blood (2020) 136(SUPPL 1):6, Abstract presented at 62nd American Society of Hematology Annual Meeting and Exposition, ASH 2020, San Diego, CA, United States, Dec. 5, 2020.
Kavakli, K. et al. (2022). "Fitusiran Prophylaxis Improves Health-Related Quality of Life in People with Hemophilia A or B without Inhibitors: Results of Phase 3 Atlas-A/B Randomized Control Trial," Abstract presented at National Hemophilia Foundation—74th Annual Meeting, 2 pages.
Kavakli, K. et al. (2022). "Fitusiran Prophylaxis Improves Health-Related Quality of Life in People with Hemophilia A or B without Inhibitors: Results of Phase 3 Atlas-A/B Randomized Control Trial," Poster presented at National Hemophilia Foundation—74th Annual Meeting, Aug. 25-27, 2022, Houston, Texas, USA, 1 page.
Kavakli, K. et al. (2022). "Fitusiran Prophylaxis Improves Health-Related Quality of Life in People with Hemophilia A or B without Inhibitors: Results of the Phase 3 Atlas-A/B Randomized Control Trial," Abstract presented at World Federation of Hemophilia—XXXV Congress, 2 pages.
Kavakli, K. et al. (2022). "Fitusiran Prophylaxis Improves Health-Related Quality of Life in People with Hemophilia A or B without Inhibitors: Results of the Phase 3 Atlas-A/B Randomized Control Trial," Poster presented at World Federation of Hemoohilia—XXXV Congress, May 8-11, 2022, Montreal Canada, 1 page.
Kempton, C. L. et al. (Nov. 27, 2014, e-pub. Nov. 26, 2014). "Toward Optimal Therapy For Inhibitors In Hemophilia," Blood 124(23):3365-3372.
Kenet, G. et al. (2023). "PO 119 Subgroup Analysis of Fitusiran Efficacy and Safety in Adolescents with Haemophilia A or B, with or Without Inhibitors, from Three Phase 3 Trials" [EAHAD Abstract] Haemophilia 29(suppl 1):85-86.
Kenet, G. et al. (2023). "S301 Consumption of Factor Concentrates and Bypassing Agents for Management of Breakthrough Bleeds with Fitusiran Prophylaxis in People with Haemophilia A or B: Analysis of Atlas-PPX,"HemaSphere 7(S3):2 pages.
Kenet, G. et al. (2023). "S303 A Phase 3 Study to Evaluate Efficacy and Safety of Fitusiran in People with Hemophilia A or B who Switched from Factor or Bypassing Agent Prophylaxis" HemaSphere 7(S3):3 pages.
Kenet, G. et al. (May 30, 2024). "Fitusiran Prophylaxis In People With Hemophilia A Or B Who Switched From Prior BPA/CFC Prophylaxis: The Atlas-PPX Trial," Blood 143(22):2256-2269.
Kenet, G. et al. (Nov. 15, 2022). "Fitusiran Prophylaxis Improves Health-Related Quality of Life in People with Hemophilia A or B, with or without Inhibitors: Results of Atlas-PPX Study," Blood 140(S1):7977-7978, 7 pages.
Kessler, C.M. (Feb. 2017, e-pub. Dec. 3-6, 2016). "Highlights In Gene Therapy And Alternative Therapies In Nonmalignant Hematology From The 2016 American Society Of Hematology Meeting," Clinical Advances In Hematology And Oncology 15(2):113-116.
Kizilocak, H. et al. (Jun. 2019). "Diagnosis And Treatment Of Hemophilia," Clinical Advances In Hematology And Oncology 17(6):344-351.
Knobe, K. et al. (2011). "Haemophilia And Joint Disease: Pathophysiology, Evaluation, And Management," J Comorbidity 1:51-59.
Knobl, P. (2018, e-pub. Dec. 12, 2018). "Prevention and Management of Bleeding Episodes in Patients with Acquired Hemophilia A," Drugs 78(18):1861-1872.
Korte, W. et al. (2018, e-pub. Mar. 28, 2018). "The Potential Close Future of Hemophilia Treatment—Gene Therapy, TFPI Inhibition, Antithrombin Silencing, and Mimicking Factor VIII with an Engineered Antibody," Transfusion Medicine and Hemotherapy 45(2):92-96.
Lassila, R. (2019). "Management Of Coagulation Factor VIII (FVIII) Inhibitors," Thrombosis Research (2019) 181 (Supp.1)S60-S61.
Leissinger, C.A. et al. (Jul. 9, 2015, e-pub. Mar. 31, 2015). "How I Use Bypassing Therapy For Prophylaxis In Patients With Hemophilia A And Inhibitors," Blood 126:153-159.
Lenting, P.J. (2020, e-pub. May 12, 2020) "Laboratory Monitoring of Hemophilia A Treatments: New Challenges," Blood Advances 4(9):2111-2118.
Lewandowska, M. et al. (2022). "Therapeutic And Technological Advancements In Haemophilia Care: Quantum Leaps Forward," Haemophilia 28(S4):77-92.
Lillicrap, D. (2018). "Immunogenicity Of New Treatments: Current Status Of Knowledge," Haemophilia 24(Supp. 1): 21, Abstract No. SP17, presented at 11th Annual Congress of the European Association for Haemophilia and Allied Disorders 2018, Madrid, Spain, Feb. 7, 2018.
Ling, G. et al. (2020, e-pub. Jan. 3, 2020). "Factor VIII: The Protein, Cloning Its Gene, Synthetic Factor And Now—35 Years Later—Gene Therapy; What Happened In Between?," British Journal of Haematology 189(3):400-407.
Ling, G. et al. (Jan. 23, 2018). Recent Advances In Developing Specific Therapies For Haemophilia, British Journal Of Haematology 181(2):161-172.
Livnat, G. et al. (2017, e-pub. Feb. 14, 2017). "Rare Bleeding Disorders—Old Diseases In The Era Of Novel Options For Therapy," Blood Cells, Molecules, And Diseases 67:63-68.
Livnat, G. et al. (2020). "Thrombin Generation In Plasma Of Patients With Haemophilia A And B With Inhibitors: Effects Of Bypassing Agents And Antithrombin Reduction," Blood Cells, Molecules, and Diseases 82(102416):6 pages.
Livnat, T. et al. (2017). "The Combined Use Of Bypassing Agents With Antithrombin Reduction In Plasma Of Hemophilia A And B Patients With Inhibitors," Research and Practice in Thrombosis and Haemostasis 1(Supp. 1):839-840, Abstract No. PB 1982, presented at 26th International Society on Thrombosis and Haemostasis Congress, ISTH 2017, Berlin, Germany, Jul. 8, 2017, 2 pages.
Ljung, R. et al. (2015, e-pub. Mar. 29, 2015). "The Current Status Of Prophylactic Replacement Therapy In Children And Adults With Haemophilia," British Journal Of Haematology 169(6):777-786.
Machin, N. et al. (2018). "An Investigational RNAi Therapeutic Targeting Antithrombin for the Treatment of Hemophilia A and B," Journal of Blood Medicine 9:135-140.
Mahlangu, J. et al. (2018). "Emerging Therapies For Haemophilia—Global Perspective," Haemophilia 24(Supp. 6):15-21.
Makris, M. et al. (2018). "A Golden Age For Haemophilia Treatment?," Haemophilia 24(2):175-176.
Manco-Johnson, M.J. et al. (Nov. 30, 2017). "Effect Of Late Prophylaxis In Hemophilia On Joint Status: A Randomized Trial," Journal of Thrombosis and Haemostasis 15(11):2115-2124.

(56) References Cited

OTHER PUBLICATIONS

Mancuso, M.E. et al. (2021, e-pub. Jan. 15, 2021). "The Changing Treatment Landscape In Haemophilia: From Standard Half-Life Clotting Factor Concentrates To Gene Editing," The Lancet 397(10274):630-640.
Mancuso, M.E. et al. (2022). "Managing Invasive Procedures in Haemophilia Patients wit Limited Resources, Extended Half-Life Concentrates or Non-Replacement Therapies in 2022," Haemophilia 28(S4):93-102.
Mannucci, P. M. et al. (2013). "Present And Future Challanges In The Treatment Of Haemophilia: A Clinician's Perspective," Blood Transfusion 11(Suppl 4):s77-s81.
Mannucci, P.M. et al. (2016). "Tailoring Hemostatic Therapies To Lower Inhibitor Development In Previously Untreated Patients With Severe Hemophilia A," Journal of Thrombosis and Haemostasis 14(7):1330-1336.
Manoharan, M. (2013). "Delivery Strategies for RNA Interference (RNAi) Based Therapeutics," Abstracts of Papers presented at 246th ACS National Meeting & Exposition, Indianapolis, IN, United States, Sep. 8-12, 2013, 2 pages.
Marchesini, E. et al. (2021). "Recent Advances In The Treatment Of Hemophilia: A Review," Biologics: Targets And Therapy 15:221-235.
Marietta, M. et al. (2018). "Non-Replacement Therapy For Haemophilia Treatment: Fetching The East By The West," Blood Transfusion 16(5):408-409.
Massy, Z. A. et al. (2022). "Running Interference: Lumasiran and Other RNA Interference Therapeutics for Kidney Diseases," Kidney International 101(2):208-211.
McKinney, E. et al. (2017). "Evaluation Of Room Temperature And Accelerated Stability Data For Fitusiran, An Investigational Rnai Therapeutic Targeting Antithrombin For Treatment Of Hemophilia And Rare Bleeding Disorders," Haemophilia 23(Supp. 2):59, Abstract No. P051, presented at 10th Annual Congress of the European Association for Haemophilia and Allied Disorders, Paris, France, Feb. 1, 2017, 1 page.
Meeks, S. L. et al. (2016). "Hemophilia And Inhibitors: Current Treatment Options And Potential New Therapeutic Approaches," Hematology, the American Society of Hematology Education Program Book 2016(1):657-662.
Miesbach, et al., "Current and Future Options of Haemophilia A Treatments," Expert Opinion on Biological Therapy (2021) 1-8.
Miguelino, M.G. et al. (Aug. 8, 2014). "Clinical Utility And Patient Perspectives On The Use Of Extended Half-Life Rfixfc In The Management Of Hemophilia B," Patient Preference and Adherence 8:1073-1083.
Monahan, P.E. (2015). "Emerging Genetic and Pharmacologic Therapies for Controlling Hemostasis: Beyond Recombinant Clotting Factors," Hematology: American Society of Hematology Education Program 33-40.
Morfini, M. et al. (2007). "European Study On Orthopaedic Status Of Haemophilia Patients With Inhibitors," Haemophilia 13(5):606-612.
Morfini, M. et al. (2016). "Emerging Drugs For The Treatment Of Hemophilia A And B," Expert Opinion on Emerging Drugs 21(3):301-313.
Morrison, C. (Mar. 2018, e-pub. Feb. 28, 2018). "Alnylam Prepares To Land First RNai Drug Approval," Nature Reviews Drug Discovery 17(3):156-157.
Muczynski, M. et al. (2017, e-pub. Jul. 27, 2017). "Emerging Therapeutic Strategies in the Treatment of Hemophilia A," Seminars in Thrombosis and Hemostasis 43(6):581-590.
NCBI (Jul. 22, 2009). "Homo Sapiens Serpin Peptidase Inhibitor, Clade C (antithrombin), Member 1 (SERPINC1), mRNA," NCBI Reference Sequence: NM_000488.2, accessed and retrieved from ncbi.nlm.nih.gov on Jul. 17, 2025, 5 pages.
Negrier, C. et al. (2017). "Perioperative Management In Patients With Hemophilia Receiving Fitusiran, An Investigational Rnai Therapeutic Targeting Antithrombin For The Treatment Of Hemophilia," Blood 130(Supp. 1), Abstract No. 2366, presented at 59th Annual Meeting of the American Society of Hematology, ASH 2017, Atlanta, GA, United States, Dec. 7, 2017, 3 pages.
Negrier, C. et al. (2018). "Perioperative Management In Patients With Hemophilia Receiving Fitusiran, An Investigational Rnai Therapeutic Targeting Antithrombin For The Treatment Of Hemophilia," Haemophilia 24(Supp. 1):27, Abstract No. OR08, presented at 11th Annual Congress of the European Association for Haemophilia and Allied Disorders 2018. Madrid, Spain, Feb. 7, 2018.
Negrier, C. et al. (2019). "The Central Role Ofthrombin In Bleeding Disorders," Blood 38(100582), 8 pages.
Negrier, C. et al. (2020). "Longitudinal Assessment Of Thrombin Generation In Patients With Hemophilia Receiving Fitusiran Prophylaxis: Phase II Study Results," Blood 136(Suppl 1):36-37, Abstract presented at 62nd American Society of Hematology Annual Meeting and Exposition, ASH 2020, San Diego, CA, United States, Dec. 5, 2020.
Negrier, C. et al. (2021). "Long-term Efficacy and Safety of Fitusiran in Participants with Hemophilia A and B: An Interim Analysis of the Phase ½ Open-Label Extension Study," Abstract presented at the GTH 2021 (Gesellschaft für Thrombose- und Hämostaseforschung 2021) Conference, 3 pages.
Negrier, C. et al. (2021, e-pub. Jun. 18, 2021). "Long-term Efficacy and Safety of Fitusiran in Participants with Hemophilia A and B: An Interim Analysis of the Phase ½ Open-Label Extension Study," Hamostaseologie 41(Suppl 1):S7, Abstract No. OC03-04, presented at 65th Annual Meeting of the Society of Thrombosis and Haemostasis Research, Online, Feb. 22, 2021, 1 page.
Negrier, C. et al. (2022). "Health-Related Qualify of Life (HRQoL) Improves in People with Hemophilia A or B (PwHA/B) with Inhibitors Receiving Fitusiran Prophylaxis: Results of Phase 3 Atlas-INH," Haemophilia 28(Suppl 1):57-58, Abstract No. P0067, presented at 15th Annual Congress of European Association for Haemophilia and Allied Disorders, Virtual, Feb. 2, 2022.
Negrier, C. et al. (2022). "Health-Related Qualify of Life (HRQOL) Improves in People with Hemophilia A or B (PwHA/B) with Inhibitors Receiving Fitusiran Prophylaxis: Results of Phase 3 Atlas-INH," Haemophilia 28(Suppl 1):57-58, Abstract No. PO067 presented at 15th Annual Congress of European Association for Haemophilia and Allied Disorder, Virtual, Feb. 2-4, 2022, 1 page.
Negrier, C. et al. (2022). "Health-Related Quality of Life (HRQoL) Improves in People with Hemophilia A or B (PwHA/B) with Inhibitors Receiving Fitusiran Prophylaxis: Results of Phase 3 Atlas-INH," Abstract presented at National Hemophilia Foundation—74th Annual Meeting (2022), 2 pages.
Negrier, C. et al. (2022). "Health-Related Quality of Life (HRQoL) Improves in People with Hemophilia A or B (PwHA/B) with Inhibitors Receiving Fitusiran Prophylaxis: Results of Phase 3 Atlas-INH," Poster presented at National Hemophilia Foundation—74th Annual Meeting (2022), 1 page.
Negrier, C. et al. (Feb. 5, 2021). "Fitusiran, an siRNA Therapeutic Targeting Antithrombin for the Treatment of Haemophilia: Proposed Revisions to Dose and Regimen as a Risk Mitigation for Vascular Thrombosis," Sanofi, 11 pages.
Ning, B. et al. (Jul. 2021). "RNA therapeutics: From Biochemical Pharmacology To Technology Development And Clinical Applications," Biochemical Pharmacology 189:114567, 6 pages.
Nogami, K. et al. (Jan. 31, 2019). "New Therapies Using Nonfactor Products for Patients with Hemophilia and Inhibitors," Blood 133(5):399-406.
Nogrady, B. (Oct. 17, 2019). "Strand And Deliver: The Difficulties Of Delivering RNA Interference Therapeutics To Their Target Cells Brought The Nascent Research Field To Its Knees, But A Landmark Drug Approval Offers Hope," Nature 574(7778):S8-S9.
Non-Final Office Action mailed on Apr. 11, 2023, for U.S. Appl. No. 17/375,785, filed Jul. 14, 2021, 9 pages.
Non-Final Office Action mailed on Jan. 8, 2025, for U.S. Appl. No. 17/422,982, filed Jul. 14, 2021, 46 pages.
Non-Final Office Action mailed on Jul. 3, 2023, for U.S. Appl. No. 17/396,331, filed Aug. 6, 2021, 13 pages.
Non-Final Office Action mailed on Jul. 11, 2024, for U.S. Appl. No. 17/375,785, filed Jul. 14, 2021, 10 pages.
Non-Final Office Action mailed on Jul. 22, 2025, for U.S. Appl. No. 18/155,655, filed Jan. 17, 2023, 12 pages.

(56) References Cited

OTHER PUBLICATIONS

Non-Final Office Action mailed on Oct. 18, 2017, for U.S. Appl. No. 15/070,358, filed Mar. 15, 2016, 16 pages.
O'Mahony, B. (2020). "Haemophilia care in Europe: Past progress and future promise," Haemophilia 26(5):752-758.
Okaygoun, D. et al. (2021, e-pub. Sep. 14, 2021) "Advances in the Management of Haemophilia: Emerging Treatments and their Mechanisms," Journal of Biomedical Science 28(1):64, 13 pages.
Oladapo, A. O. et al. (2018, e-pub. Nov. 9, 2018). "Inhibitor Clinical Burden Of Disease: A Comparative Analysis Of The Chess Data," Orphanet Journal Of Rare Diseases 13(198):1-11.
Olasupo, O.O. et al. (2021). "Non-Clotting Factor Therapies For Preventing Bleeds In People With Hemophilia," Cochrane Database of Systematic Reviews 8:CD014544, 13 pages.
Ozcan, G. et al. (Jun. 29, 2015). "Preclinical And Clinical Development Of siRNA-Based Therapeutics," Advanced Drue, Delivery Reviews 87:108-119.
Ozelo,M.C. et al. (2022). "Impact of Novel Hemophilia Therapies Around the World," Research and Practice in Thrombosis and Haemostasis 6(3):e12695, 14 pages.
Pasca, S. (Apr. 16, 2022). "Concizumab as a Subcutaneous Prophylactic Treatment Option for Patients with Hemophilia A or B: A Review of the Evidence and Patient's Perspectives," Journal of Blood Medicine, (2022) 13:191-199.
Pasca, S. et al. (2020)."Light and Shadows of the New Therapies for Haemophilia Treatment in the COVID-19 Era," Blood Transfus 19(1):73-76.
Pasi et al., "Targeting of Antithrombin in Hemophilia A or B within Investigational siRNA Therapeutic Fitusiran—Results of the Phase 1 Inhibitor Cohort," J of Thrombosis and Haemostasis (2021) 19(6):1436-46.
Pasi et al. (2019). "Fitusiran, An Rnai Therapeutic Targeting Antithrombin To Restore Hemostatic Balance In Hemophilia: Interim Analysis From The Open-Label Extension Study," Research And Practice In Thrombosis And Haemostasis 3(Supplement 1):86, Abstract No. OC 11.3, Presented at 27th Congress of the International Society on Thrombosis and Haemostasis, Melbourne, SA, Australia, Jul. 6, 2019.
Pasi, J. et al. (2019). "The Role Of Antithrombin Lowering In Patients With Hemophilia: Hemostatic Control Pre-And Post-Fitusiran Dosing Interruption," Haemophilia 25(Supp. 1):33-34, Abstract No. OR16, Presented at 12th Annual Congress of the European Association for Haemophilia and Allied Disorders. Prague, Czech Republic, Feb. 6, 2019.
Pasi, J.K. et al. (Jul. 11, 2016). "A Subcutaneously Administered Investigational RNAi Therapeutic, Fitusiran (ALN-AT3), Targeting Antithrombin for Treatment of Hemophilia: Interim Results in Patients with Hemophilia A or B," Haemophilia 22(Suppl. 4):3-138, 1 page (Abstract Only).
Pasi, J.K. et al. (2020). "Interim Analysis of Measures of Safety, Efficacy, and Spontaneous Bleeding Events in the Phase 2 Open-Label Extension Study of Fitusiran in Subjects With Hemophilia A or B, With or Without Inhibitors" Haemophilia 26(S4):154, Abstract No. F-FP-LBA-4.1, [WFH Virtual Summit Abstract].
Pasi, J.K. et al. (Jun. 2021). "Supplementary Material: Targeting Of Antithrombin In Hemophilia A Or B With Investigational Sirna Therapeutic Fitusiran-Results Of The Phase 1 Inhibitor Cohort", Journal of Thrombosis and Haemostasis 19(6):S1-S9, as retrieved from https://ars.els-cdn.com/content/image/1-s2.0-S1538783622007760-jth15270-sup-0001-Supinfo.docx.
Pasi, K.J. et al. (2017). "Phase 1 And Phase ½ Extension Study Offitusiran, An Investigational Rnai Therapeutic Targeting Antithrombin For The Treatment Of Hemophilia: Updated Results In Patients With Inhibitors," Haemophilia 23(Supp. 2):88-89, Abstract No. P099, Presented At 10th Annual Congress Of The European Association For Haemophilia And Allied Disorders. Paris, France, Feb. 1, 2017.
Pasi, K.J. et al. (2020). "Perioperative management of patients with hemophilia receiving fitusiran, an investigational rnai therapeutic targeting antithrombin for the treatment of hemophilia," Research and Practice in Thrombosis and Haemostasis 4(Suppl 1):578, Abstract No. PB1142, Presented at International Society on Thrombosis and Haemostasis Congress, ISTH 2020. Virtual, United States, Jul. 12, 2020.
Pelland-Marcotte, M-C. et al. (2019). Hemophilia in a Changing Treatment Landscape, Hematology/Oncology Clinics of North America 33(3):409-423.
Peters, R. et al. (Jul. 2018, e-pub. Jun. 8, 2018). "Advances And Innovations In Haemophilia Treatment," Nature Reviews Drug Discovery 17(7):493-508.
Peyvandi, F. (2015). "Emerging Therapies for Rare Bleeding Disorders-FV, FX," Haemophilia 21(Suppl. 2):8-9, Abstract No. SP013, presented at Meeting Info: 8th Annual Congress of the European Association for Haemophilia and Allied Disorders, Helsinki, Finland, Feb. 11, 2015.
Peyvandi, F. (2016). "Advances in the Treatment of Bleeding Disorders," Journal of Thrombosis and Haemostasis 14(11):2095-2106.
Peyvandi, F. (Nov. 7, 2014). "Novel Treatments in Hemophilia," Thrombosis Research 134(Suppl. 2):S40-S41, Abstract No. SY-43, presented at 23rd National Congress of the Italian Society on Haemostasis and Thrombosis, Milano, Italy, Nov. 6, 2014.
Peyvandi, F. et al. (2016, e-pub. Feb. 17, 2016). "The Past And Future Of Haemophilia: Diagnosis, Treatments, And Its Complications," The Lancet 388(10040):187-197.
Peyvandi, F. et al. (2021). "Post-Authorization Pharmacovigilance For Hemophilia In Europe And The USA: Independence And Transparency Are Keys," Blood Reviews 49:100828, 8 pages.
Pipe et al., "Presentation of the Long-Term Durability, Safety and Efficacy of Fitusiran Prophylaxis in People with Hemophilia a or B, with or without Inhibitors—Results from the Phase II Study," 62nd ASH Annual Meeting and Exhibition, Dec. 7, 2020.
Pipe, S. at al. (Nov. 13, 2019). "Fitusiran, An Rnai Therapeutic Targeting Antithrombin To Restore Hemostatic Balance In Patients With Hemophilia A Or B With Or Without Inhibitors: Management Of Acute Bleeding Events," Blood, American Society of Hematology 134(S1):1138, Abstract presented at 61st ASH Annual Meetina. Orlando, FL, United States, Dec. 7, 2019, 4 pages.
Pipe, S. et al. (2022). "Fitusiran, an Investigational siRNA Therapeutic Targeting Antithrombin: Analysis of Antithrombin Levels and Thrombin Generation from a Phase 3 Study in People with Hemophilia A or B Without Inhibitors," [ISTH Abstract] Res Pract Thromb Haemost 6(Suppl 1):e12787, 2 pages.
Pipe, S. et al. (2023). "Fitusiran Prophylaxis Demonstrates Sustained Bleed Protection in People with Hemophilia A or B: An Exploratory Analysis of Antithrombin Levels and Peak Thrombin Generation from Three Phase 3 Trials," Research and Practice in Thrombosis and Haemostasis 7(81):100233, 2 pages.
Pipe, S. et al. (Nov. 13, 2019). "Fitusiran, an RNAi Therapeutic Targeting Antithrombin to Restore Hemostatic Balance in Patients with Hemophilia a or B with or without Inhibitors: Management of Acute Bleeding Events," Blood 134(1138), 7 pages, Abstract No. 322, as retrieved onhttps://doi.org/10.1182/blood-2019-124108.
Pipe, S.W. et al. (2007). "Optimizing Outcomes For Patients With Severe Haemophilia A," Haemophilia 13(Suppl 4):1-16.
Pipe, S.W. et al. (2019). "Fitusiran, An Rnai Therapeutic Targeting Antithrombin To Restore Hemostatic Balance In Hemophilia: Management Of Acute Bleeding Events," Research and Practice in Thrombosis and Haemostasis 3(Supp. 1):314-315, Abstract No. PB0324, presented at 27th Congress of the International Society on Thrombosis and Haemostasis. Melbourne, SA, Australia, Jul. 6, 2019.
Pipe, S.W. et al. (2020). "Long-Term Durability, Safety And Efficacy Of Fitusiran Prophylaxis In People With Hemophilia A Or B, With Or Without Inhibitors—Results From The Phase II Study," Blood 136(Suppl 1):3-4, 62nd American Society of Hematology Annual Meeting and Exposition, ASH 2020, San Diego, CA, United States, Dec. 7, 2020, 9 pages.
Pipe, S.W. et al. (2020). "The Management Of Breakthrough Bleeding Events In Patients Treated With Fitusiran, An Rnai Therapeutic For The Treatment Of Hemophilia," Haemophilia 26 (Supp. 2):24, Abstract No. OR08, Presented at 13th Annual Congress of

(56) References Cited

OTHER PUBLICATIONS

European Association for Haemophilia and Allied Disorders, The Hague, Netherlands, Feb. 5, 2020.
Pipe, S.W. et al. (2024). "Long-Term Safety And Efficacy Of Fitusiran Prophylaxis, And Perioperative Management In People With Hemophilia A or B," Blood Advances, American Society of Hematology, with supplemental figures/tables, 51 pages.
Prezotti, A.N.L. et al. (2020). "Perioperative Management of Patients with Hemophilia Receiving Fitusiran, an Investigational RNAi Therapeutic Targeting Antithrombin for the Treatment of Hemophilia," Hematology Transfusion and Cell Therapy 42(Supp. 2):S74-S75, Abstract No. 123, as presented at Hemo Play 2020, Virtual, Online, Nov. 30, 2020.
Qian, K. et al. (2018). "Effect Of Antithrombin Lowering On Thrombin Generation In Rare Bleeding Disorder Patient Plasma," Haemophilia 24(Supp. 5):105, Abstract No. T-P-121, presented at World Congress of the World Federation of Hemophilia, WFH 2018. Glasgow, United Kinadom, May 20, 2018.
Qian, K. et al. (2018). "Thrombin Generation Response With The Addition Of Bypassing Agents In Plasma Of Patients Treated With Fitusiran, An Investigational Rnai Therapeutic Targeting Antithrombin For The Treatment Of Hemophilia," Haemophilia 24(Supplement 5):55, Abstract No. M-P-219 (141), presented at World Congress of the World Federation of Hemophilia, WFH 2018, Glasgow, United Kingdom, May 20, 2018.
Quinsey, N. S. et al. (2004). "Antithrombin: In Control Of Coagulation," The International Journal Of Biochemistry & Cell Biology 36(3):386-389.
Ragni, M.V. (2017). "Novel Alternate Hemostatic Agents For Patients With Inhibitors: Beyond Bypass Therapy," Hematology 1:605-609.
Ragni, M.V. (Oct. 1, 2021). "Hemophilia As A Blueprint For Gene Therapy," Science 374(6563):40-41.
Ragni, M.V. et al. (2021). "Perioperative Management Of Patients With Hemophilia (Pwh) Receiving Fitusiran Prophylaxis With Reduced Doses Of Bpa Or Factor Replacement," Haemophilia, (2021) 27(Suppl 2):105, Abstract No. ABS156, presented at Congress of the European Association for Haemophilia and Allied Disorders, Virtual, Feb. 3, 2021.
Ragni, M.V. et al. (Dec. 4, 2016). "Fitusiran, an investigational RNAi Therapeutic Targeting Antithrombin for the Treatment of Hemophilia: Results from Phase 1 and Phase 2 Extension Studies in Patients without Inhibitors," Poster presented in American Society of Hematology (ASH) 2016 Annual Meeting, San Diego, CA, Dec. 4, 2016, 13 pages.
Ragni, M.V. et al. (Nov. 29, 2018). "The Role Of Antithrombin Lowering In Patients With Hemophilia: Hemostatic Control Pre-And Post-Fitusiran Dosing Interruption," Blood 132(Supp. 1), Abstract No. 2477, presented at 60th Annual Meeting of the American Society of Hematology, ASH 2018, San Diego, CA, United States, Dec. 1, 2018, 3 pages.
Rangarajan, S. et al. (2017) "Management Of Bleed Events In The Phase 1 Study Of Fitusiran, An Investigational Rnai Therapeutic Targeting Antithrombin For The Treatment Of Hemophilia In Patients With And Without Inhibitors," Haemophilia 23(Supp. 2):20-21, Abstract No. OR23, presented at 10th Annual Congress of the European Association for Haemophilia and Allied Disorders, Paris, France, Feb. 1, 2017.
Regling, K. et al. (Feb. 15, 2022). "Managing Severe Hemophilia A in Children: Pharmacotherapeutic Options," Pediatric Health, Medicine and Therapeutics 13:27-35.
Remor, E. (2013, e-pub. Sep. 5, 2012). "Development And Psychometric Testing Of The Hemophilia Well-Being Index," International Journal Of Behavioral Medicine 20(4):609-617.
Response to Final Office Action dated Jan. 3, 2024, for U.S. Appl. No. 17/396,331, filed Aug. 6, 2021, 23 pages.
Response to Final Office Action dated Jan. 21, 2025, for U.S. Appl. No. 17/396,331, filed Aug. 6, 2021, 22 pages.
Response to Final Office Action dated Mar. 18, 2024, for U.S. Appl. No. 17/375,785, filed Jul. 14, 2021, 10 pages.
Response to Non-Final Office Action dated Aug. 11, 2023, for U.S. Appl. No. 17/375,785, filed Jul. 14, 2021, 13 pages.
Response to Non-Final Office Action dated Jan. 13, 2025, for U.S. Appl. No. 17/375,785, filed Jul. 14, 2021, 11 pages.
Roberts, T.C. et al. (Oct. 2020). "Advances In Oligonucleotide Drug Delivery," Nat. Rev. Drug Discov. 19:673-694.
Rodriguez-Santana, I. et al. (Dec. 2020). "The Economic Burden of Congenital Haemophilia Without Inhibitors by Disease Severity: a Regression Analysis of Paediatric and Adult Patients in the 'Cost of Haemophilia in Europe: a Socioeconomic Survey'" [ISPOR-EU Abstract], Value in Health 23(Supplement 2):S698-S699.
Rodriguez-Santana, I. et al. (Dec. 2022). "Exploring the Relationship Between Prophylactic Infusion Frequency and Patient Utility for People with Haemophilia in Europe" Value in Health, Abstract No. RWD 119, S472.
Ruhl, H. (2020). "Innovations In Hemophilia Treatment: Indications For Novel Procoagulant Drugs, Such As Emicizumab," Transfusion Medicine and Hemotherapy 47(Suppl 1):5, Abstract No. ZF-1-1\, presented at Meeting: 53, Jahrestagung der Deutschen Gesellschaft fur Transfusionsmedizin und Immunhamatologie, DGTI, Virtual, Sep. 16, 2020.
Rusin, I.V. (2006). "[RNA-Interference: Micro-RNAs as a New Regulators of Genes and Perspective Therapeutic Targets]," Electronic Collection of Scientific Papers "Health and Education in the 21st Century," 11(6):268-269, (English Abstract).
Sacha, G. et al. (2015). "Pre-Filled Syringes: A Review Of The History, Manufacturing And Challenges," Pharmaceutical Development And Technology 20(1):1-11.
Sanofi (Jun. 19, 2020). "Sanofi Announces Positive Long-Term Efficacy And Safety Data For Fitusiran From Interim Analysis Of Phase 2 Extension Study In People With Hemophilia A and B, With Or With Inhibitors," 5 pages, retrieved on Aug. 4, 2025 from https://www.sanofi.com/en/media-room/press-releases/2020/2020-06-19-13-00-00-2050713.
Sanofi (Jun. 27, 2018). "Clinical Study Protocol ALN-AT3SC-003 (Sanofi Genzyme EFC14768)," Sanofi Group, 81 pages, as retrieved onhttps://cdn.clinicaltrials.gov/large-docs/02/NCT03417102/Prot_000.pdf.
Santagostino, F. (2017). "Non-replacement Therapy in Hemophilia," Blood Transfusion 15(Supp. 4):S525, Abstract No. RE01, presented at Meeting: 16th Convegno Triennale sui Problemi Clinici e Sociali dell'Emofilia e delle Malattie Emorraqiche Conqenite, Napoli, Italy, Nov. 9-12, 2017.
Seaman, C.D. et al. (2021). "Hemophilia A (Factor VIII Deficiency)," Hematology/Oncology Clinics of North America 35(6):1117-1129.
Sehgal, A. et al. (2014). "ALN-AT3: An sRNAi Therapeutic Targeting Antithrombin For The Treatment Of Hemophilia," Haemophilia 20(Suppl. 3):82, Abstract presented at World Federation of Hemophilia, WFH 2014 World Congress, Melbourne, VIC, Australia, May 11, 2014.
Sehgal, A. et al. (2015). "Antithrombin Reduction Improves Coagulation In Rare Bleeding Disorder Plasma," Journal of Thrombosis and Haemostasis13(Suppl. 2):162, Abstract No. OR177, presented at 25th Congress of the International Society on Thrombosis and Haemostasis, ISTH 2015, Toronto, ON, Canada, Jun. 20, 2015.
Seth Chhabra, E. et al. (2022). "Impact of Antithrombin Reduction in Plasma on Coagulation Assays," Haemophilia 28(Suppl 1):28, Abstract No. PO007, presented at Meeting Info: 15th Annual Congress of European Association for Haemophilia and Allied Disorders, Virtual, Feb. 2, 2022.
Setten, R.L. et al. (Jun. 2019). "The Current State and Future Directions of RNAi-based Therapeutics," Nature Reviews Drug Discovery 18(6):421-446.
Shapiro, A.D. et al. (2018). "The Future of Bypassing Agents for Hemophilia with Inhibitors in the Era of Novel Agents," Journal of Thrombosis and Haemostasis 16(12): 2362-2374.
Shen, X. et al. (2018, e-pub. Dec. 12, 2017). "Chemistry, Mechanism And Clinical Status Of Antisense Oligonucleotides And Duplex Rnas," Nucleic Acids Research 46(4):1584-1600.
Sherman, A. et al. (2017, e-pub. Nov. 24, 2017). "Innovative Approaches For Immune Tolerance To Factor Viii In The Treatment Of Hemophilia A," Frontiers in Immunology 8(1604):25-36.

(56) References Cited

OTHER PUBLICATIONS

Shetty, S. et al. (2015). "Novel Therapeutic Approaches for Haemophilia," Haemophilia 21(2):152-161.
Shima, M. et al. (2016). "Alternative Therapies for the Management of Inhibitors," Haemophilia 22(S5):36-41.
Shima, M. et al. (2021). "Substitution Therapy," Haemophilia 27(S3):53-59.
Sidonio, R.F. et al. (2023). "Thrombin Generation and Implications for Hemophilia Therapies: A Narrative Review," Res Pract Throm Haemost 7(1):100018, 11 pages.
Smith, L. (Sep. 2017). "XXVI Congress of the International Society on Thrombosis and Haemostasis," The Lancet Haematoloav 4(9):e411-4112.
Soni, P. et al. (Nov. 2020). "A Novel In-House Clot Based Assay For Measuring Endogenous Thrombin Potential (ETP)," Indian Journal of Hematology and Blood Transfusion 36(1 Suppl):S10-S11, presented at 61st Annual Conference of Indian Society of Hematology and Blood Transfusion, ISHBT, Virtual, Nov. 21, 2020.
Sorensen, B. et al. (2015). "A Subcutaneously Administered Investigational Rnai Therapeutic (Aln-At3) Targeting Antithrombin For Treatment Of Hemophilia: Interim Phase 1 Study Results In Patients With Hemophilia A Or B," Journal of Thrombosis and Haemostasis 13(Suppl. 2):176-177, Abstract No. OR213, presented at 25th Congress of the International Society on Thrombosis and Haemostasis, ISTH 2015, Toronto, ON, Canada, Jun. 20, 2015.
Sorensen, B. et al. (Dec. 6, 2014). "A Subcutaneously Administered RNAi Therapeutic (ALN-AT3) Targeting Antithrombin for Treatment of Hemophilia: Interim Phase 1 Study Results in Healthy Volunteers and Patients with Hemophilia a or B," Blood (2014) 124(21):693, Abstract, presented at 56th Annual Meeting of the American Society of Hematology, ASH 2014, San Francisco, CA, United States, Dec. 6, 2014, as posted on https://ashpublications.org/blood/article/124/21/693/102161/A-Subcutaneously-Administered-RNAi-Therapeutic-ALN, last visited on.
Spadarella, G. et al. (2020). "Paradigm Shift for the Treatment of Hereditary Haemophilia: Towards Precision Medicine," Blood Reviews 39:100618.
Sridharan, G. et al. (2018). "P093 Modeling The Impact Of Factor Administration And Antithrombin Level On Thrombin Generation," Haemophilia 24:75-76, Abstract presented Meeting Info: 11th Annual Congress of the European Association for Haemophilia and Allied Disorders 2018, Madrid, Spain, Feb. 7, 2018.
Sridharan, G. et al. (2018). "Quantitative Systems Pharmacology (Qsp) To Predict Thrombin Generation With Concomitant At Lowering And Factor Replacement Or Bypassing Agents," Research and Practice in Thrombosis and Haemostasis 2(Supp. 1):64-65, Abstract No. PB138, presented at 64th Annual Meeting of the Scientific Standardization Committee of the International Society on Thrombosis and Haemostasis, Dublin, Ireland, Jul. 18, 2018.
Sridharan, G. et al. (Dec. 7, 2017). "In Silico Modeling Of The Impact Of Antithrombin Lowering On Thrombin Generation In Rare Bleeding Disorders," Blood 130(Supp. 1), Abstract No. 3659, presented at 59th Annual Meeting of the American Society of Hematology, ASH 2017, Atlanta, GA, United States, Dec. 9, 2017.
Srivastava, A. et al. (2013). "Guidelines For The Management Of Hemophilia," Haemophilia 19(1):e1-e47.
Srivastava, A. et al. (2021). "Fitusiran, an Investigational siRNA Therapeutic Targeting Antithrombin for the Treatment of Hemophilia: First Results from a Phase 3 Study to Evaluate Efficacy and Safety in People with Hemophilia a or B without Inhibitors (Atlas-A/B)," Blood 138(Suppl 2), Abstract No. LBA-3, presented at 63rd American Society of Hematology Annual Meeting and Exposition, ASH 2021, Atlanta, GA, United States, Dec. 11, 2021.
Srivastava, A. et al. (2022). "Fitusiran Reaches People's With Hemophilia And Their Caregivers' Treatment Expectations: Qualitative Semi-Structured Interviews Of Participants Of Atlas-OLE Trial," American Society Of Hematology, Poster presented at 64th Annual Meeting and Exposition 2022, Dec. 10-13, 2022, Hybrid Event (Virtual and In-Person) New Orleans, Lousiana, USA.
Srivastava, A. et al. (2023)."Consumption of On-demand Factor Concentrates and Bypassing Agents for Management of Breakthrough Bleeds with Fitusiran Prophylaxis in People with Haemophilia A or B: An Analysis of Two Phase 3 Studies," Abstract presented at ISTH 2022 Congress, 2 pages.
Srivastava, A. et al. (May 2023, e-pub. Mar. 29, 2023). "Fitusiran Prophylaxis In People With Severe Haemophilia A Or Haemophilia B Without Inhibitors (Atlas-A/B): A Multicentre, Open-Label, Randomised, Phase 3 Trial," Lancet Haemotol 10(5):e322-e332, 15 pages.
Sussebach, C. et al. (Jun. 26, 2023). "Atlas-Neo: A Phase 3, Single-Arm, Multicenter, Multinational, Open-Label, One-Way Crossover Study To Evaluate The Efficacy And Safety Of Fitusiran Prophylaxis In Males Aged 2:12 Years With Severe Hemophilia A Or B, With Or Without Inhibitors," Abstract presented at ISTH 2023 Congress, Montreal, Canada, Jun. 24-28, 2023.
Sutphin, J. et al. (2021). "Treatment Preferences in Hemophilia: Results From a Targeted Literature Review," Haemophilia 27(S2):134, presented at European Association for Haemophilia and Allied Disorders—14th Annual Congress (2021), Feb. 3-5, 2021.
Teichman, J. et al. (2018). "Novel Assays In The Coagulation Laboratory: A Clinical And Laboratory Perspective," Transfusion and Apheresis Science 57(4):480-484.
Terminal disclaimer filed on Feb. 26, 2016, for U.S. Appl. No. 14/806,084, filed Jul. 22, 2015, 2 pages.
The EuroQol Group (1990). "EuroQol—a New Facility For The Measurement Of Health-Related Quality Of Life," Health Policy 16(3):199-208.
The Lancet Haematology (2017). "A Promising New Treatment Horizon For Haemophilia A," The Lancet Haematology 4(9):e399.
Tiede, A. (2016). "Congenital and Acquired Hemophilia: Update 2016," Oncology Research and Treatment 39(Supp. 3):191-192, Abstract No. V627, presented at Meeting: Jahrestagung der Deutschen, Osterreichischen und Schweizerischen Gesellschaften fur Hamatologie und Medizinische Onkologie 2016, Leipzig, Germany, Oct. 14, 2016.
Tiede, A. (2017). "Thromboembolic Risks of Non-Factor Replacement Therapies in Hemophilia," Hamostaseologie 37(4):307-310.
Trinchero, A. et al. (2020). "The Evolution of Hemophilia Care: Clinical and Laboratory Advances, Opportunities, and Challenoes," Hamostaseologie 40(3):311-321.
Trindade, G. et al. (2019). "Evaluation Of Quality Of Life In Hemophilia Patients Using The WHOQOL—Bref And Haemo—A-Qol Questionnaires," Hematology, Transfusion, and Cell Therapy 41(4):335-341.
Tripodi, A. et al. (2019). "Advances in the Treatment of Hemophilia: Implications for Laboratory Testing," Clinical Chemistry 65(2):254-262.
Tripodi, A. et al. (2019). "Position Paper On Laboratory Testing For Patients With Haemophilia, A Consensus Document from Siset, Aice, SIBioC and SIPMeL," Blood Transfusion 17(3):229-236.
U.S. Appl. No. 19/231,316, filed Jun. 6, 2025, for Akinc et al. (Copy not submitted herewith pursuant to the waiver of 37 C.F.R. 1.98(a)(2)(iii) issued by the Office on Sep. 21, 2004).
Unanonymous (Sep. 15, 2022). "Annex 1—Summary of Product Characteristics—Hemlibra", 21 pages, retrieved from https://www.ema.europa.eu/en/documents/product-information/hemlibra-epar-product-information_en.pdf.
Valentino, L. A. et al. (2011). "Venous Access In The Management Of Hemophilia," Blood Reviews 25(1):11-15.
Van Balen, E.C. et al. (2020). "Patient Perspectives on Novel Treatments in Haemophilia: A Qualitative Study," Patient 13(2):201-210.
Van Genderen, F. R. et al. (Feb. 2006). "Measuring Patients' Perceptions On Their Functional Abilities: Validation Of The Haemophilia Activities List," Haemophilia 12(1):36-46.
Verhenne, S. et al.(2024). "Fitusiran Reduces Bleeding In Factor X-Deficient Mice," Blood 144(2):227-236.
Von Mackensen, S. et al. (2005). "PHM5 Assessment Of Health-Related Quality Of Life In Patients With Haemophilia With The Newly Developed Haemophilia-Specific Instrument HAEM-A-QOL," Value In Health 6(8):A127.

(56) References Cited

OTHER PUBLICATIONS

Von Mackensen, S. et al. (2010). "Quality of Life in Hemophilia," Chapter 112 from the Handbook of Disease Burdens and Quality of Life Measures, Springer Science, pp. 1895-1920.
Von Mackensen, S. et al. (2017). "Measurement Properties Of The Haem-A-Qol In Haemophilia Clinical Trials," Haemophilia 23(3):383-391.
Von Mackensen, S. et al. (Nov. 5, 2020). "Fitusiran Treatment Impacts on Health-Related Quality of Life in Subjects with Hemophilia A and B with Inhibitors Assessed with the Haemophilia Quality of Life Questionnaire for Adults (Haem-A-QoL)," Blood 136(Suppl 1):23-34, presented at 62nd American Society of Hematology Annual Meeting and Exposition, ASH 2020, San Diego, CA, United States, Dec. 5, 2020.
Wang, S. et al. (2020). "Reducing Antithrombin in Plasma to Levels Observed in Fitusiran—Treated Patients Does Not Interfere with Coagulation Assays," Blood 136(Suppl 1):10, presented at 62nd American Society of Hematology Annual Meeting and Exposition, ASH 2020. San Dieao, CA, United States, Dec. 5, 2020.
Weyand, A.C. et al. (Jan. 31, 2019). "New Therapies for Hemophilia," Blood 133(5):389-398.
Windyga, J. et al. (2022). "Changing Paradigms Of Hemophilia Care Across Larger Specialized Treatment Centers In The European Region," Therapeutic Advances in Hematology 13:1-15.
Wu, I. Y. et al. (2017, e-pub. May 26, 2017). "Influence Of The Environmental Tonicity Perturbations On The Release Of Model Compounds From Large Unilamellar Vesicles (Luvs): A Mechanistic Investigation," Colloids And Surfaces B: Biointerfaces 157:65-71.
Wu, S.Y. et al. (Jun. 11, 2014). "RNAi therapies: Drugging the Undruggable," Science Translational Medicine 6(240):1-7.
Wyrwich, K. W. et al. (2015). "Interpreting Important Health-Related Quality Of Life Change Using The Haem-A-Qol," Haemophilia 21(5):578-584.
Yamada, Y. (Oct. 5, 2021). "Nucleic Acid Drugs-Current Status, Issues, And Expectations For Exosomes," Cancers 13(19):5002, 19 pages.
Young et al. (Nov. 5, 2021)."Efficacy and Safety of Fitusiran Prophylaxis, an siRNA Therapeutic, in a Multicenter Phase 3 Study (Atlas-INH) in People With Hemophilia A or B, With Inhibitors (PWHI)," Blood 138(Suppl 1):4, 3 pages.
Young, G. (2019). "How I Treat Children With Haemophilia And Inhibitors," British Journal Of Haematology 186(3):400-408.
Young, G. et al. (2023). "Antithrombin-Lowering in Hemophilia: A Closer Look at Fitusiran" Res Pract Throm Haemost 7(4):100179, 13 pages.
Young, G. et al. (Apr. 29, 2023, e-pub. Mar. 29, 2023). "Efficacy And Safety Of Fitusiran Prophylaxis In People With Haemophilia A Or B With Inhibitors (Atlas-INH): A Multicentre, Open-Label, Randomised Phase 3 Trial," Lancet 401:1427-1436.
Zhang, M.M. et al. (2021). "The Growth of siRNA-Based Therapeutics: Updated Clinical Studies," Biochemical Pharmacology 189:114432, 45 pages.
Zhang, S. et al. (2021). "The Risks Of Mirna Therapeutics: In A Drug Target Perspective," Drug Design, Development and Therapy 15:721-733.
Zhao, W. et al. (Oct. 2019). "RNA Delivery Biomaterials For The Treatment Of Genetic And Rare Diseases," Biomaterials 217:119291, 42 pages.
Zhao, Y. et al. (Apr. 5, 2022). "Registered Clinical Trials Comprising Pregnant Women in China: A Cross-Sectional Study," Frontiers in Pharmacology 13(850080):1-8.
Zhao, Y. et al. (Dec. 2021). "The Development And Improvement Of Ribonucleic Acid Therapy Strategies," Molecular Therapy—Nucleic Acids 26:997-1013.
Zhu, S. et al. (Apr. 23, 2020). "RNA-Targeted Therapies And High-Throughput Screening Methods," International Journal of Molecular Sciences 21(8), 29 pages.
Alnylam Pharmaceuticals (Apr. 13, 2015). "Alnylam and Collaborators Publish Pre-clinical Study Results in Nature Medicine on ALN-AT3, an Investigational RNAi Therapeutic Targeting Antithrombin (AT) for the Treatment of Hemophilia and Rare Bleeding Disorders (RBD)," Press Release: Alnylam Pharmaceuticals, Inc., 7 pages, retrieved on Jul. 3, 2023, from https://investors.alnylam.com/press-release?id=15356.
Alnylam Pharmaceuticals (Aug. 14, 2013). "Alnylam Receives Orphan Drug Designation from US Food & Drug Administration for ALN-AT3, an RNAi Therapeutic for the Treatment of Hemophilia," Press Release: Alnylam Pharmaceuticals, Inc., 7 pages, retrieved on Jul. 3, 2023, from https://investors.alnylam.com/press-release?id=14636.
Alnylam Pharmaceuticals (Aug. 2, 2018). "Alnylam Pharmaceuticals Reports Second Quarter 2018 Financial Results and Highlights Recent Period Activity," Press Release: Alnylam Pharmaceuticals, Inc., 14 pages, retrieved on Jul. 3, 2023, from https://investors.alnylam.com/press-release?id=22886.
Alnylam Pharmaceuticals (Aug. 20, 2013). "Alnylam Receives Additional Orphan Drug Designation from US Food & Drug Administration for ALN-AT3, an RNAi Therapeutic for the Treatment of Hemophilia," Press Release: Alnylam Pharmaceuticals, Inc., 7 pages, retrieved on Jul. 3, 2023, from https://investors.alnylam.com/press-release?id=14631.
Alnylam Pharmaceuticals (Aug. 4, 2016). "Alnylam Pharmaceuticals Reports Second Quarter 2016 Financial Results and Highlights Recent Period Progress," Press Release: Alnylam Pharmaceuticals, Inc., 14 pages, retrieved on Jul. 3, 2023, from https://investors.alnylam.com/press-release?id=15731.
Alnylam Pharmaceuticals (Aug. 6, 2012). "Alnylam Pharmaceuticals Reports Second Quarter 2012 Financial Results," Press Release: Alnylam Pharmaceuticals, Inc., 13 pages, as retrieved on Jul. 3, 2023, from https://investors.alnylam.com/press-release?id=13386.
Alnylam Pharmaceuticals (Aug. 6, 2012). "Alnylam Presents New Data from its Conjugate Delivery Platform, Enabling Subcutaneous Administration of RNAi Therapeutics with Wide Therapeutic Index," Press Release: Alnylam Pharmaceuticals, Inc., 6 pages, as retrieved on Jul. 3, 2023, from https://investors.alnylam.com/press-release?id=13421.
Alnylam Pharmaceuticals (Aug. 6, 2015). "Alnylam Pharmaceuticals Reports Second Quarter 2015 Financial Results and Highlights Recent Period Activities," Press Release: Alnylam Pharmaceuticals, Inc., 16 pages, retrieved on Jul. 3, 2023, from https://investors.alnylam.com/press-release?id=15456.
Alnylam Pharmaceuticals (Aug. 7, 2014). "Alnylam Received Orphan Drug Designations in the European Union for ALN-AT3, an RNAi Therapeutic in Development for the Treatment of Hemophilia," Press Release: Alnylam Pharmaceuticals, Inc.,7 pages, retrieved on Jul. 3, 2023, from https://investors.alnylam.com/press-release?id=15081.
Alnylam Pharmaceuticals (Aug. 8, 2013). "Alnylam Pharmaceuticals Reports Second Quarter 2013 Financial Results," Press Release: Alnylam Pharmaceuticals, Inc., 12 pages, retrieved on Jul. 3, 2023, from https://investors.alnylam.com/press-release?id=14641.
Alnylam Pharmaceuticals (Aug. 9, 2017). "Alnylam Pharmaceuticals Reports Second Quarter 2017 Financial Results and Highlights Recent Period Activity," Press Release: Alnylam Pharmaceuticals, Inc., 11 pages, retrieved on Jul. 3, 2023, from https://investors.alnylam.com/press-release?id=21831.
Alnylam Pharmaceuticals (Dec. 1, 2014). "New Paper in Journal of the American Chemical Society Documents Pioneering Discovery of GalNAc-Conjugated siRNA by Alnylam Scientists," Press Release: Alnylam Pharmaceuticals, Inc., 8 pages, retrieved on Jul. 3, 2023, from https://investors.alnylam.com/press-release?id=15221.
Alnylam Pharmaceuticals (Dec. 10, 2012) "Alnylam Presents New Pre-clinical Data on RNAi Therapeutics for the Treatment of Hemophilia and Other Bleeding Disorders at 54th American Society of Hematology (ASH) Annual Meeting," Press Release: Alnylam Pharmaceuticals, Inc., 7 pages, as retrieved on Jul. 3, 2023, from https://investors.alnylam.com/press-release?id=13931.
Alnylam Pharmaceuticals (Dec. 15, 2017). "FDA Lifts Clinical Hold on Fitusiran," Press Release: Alnylam Pharmaceuticals, Inc., 7 pages, retrieved on Jul. 3, 2023, from https://investors.alnylam.com/press-release?id=22161.

(56) References Cited

OTHER PUBLICATIONS

Alnylam Pharmaceuticals (Dec. 16, 2016). "Alnylam Presents Initial 2017 Pipeline Goals at R&D Day with Focus on Alnylam 2020 Strategy," Press Release: Alnylam Pharmaceuticals, Inc., 7 pages, retrieved on Jul. 3, 2023, from https://investors.alnylam.com/press-release?id=15851.
Alnylam Pharmaceuticals (Dec. 19, 2013). "Alnylam Presents New Pre-Clinical Data on Pharmacology of GalNAc-siRNA Conjugates," Press Release: Alnylam Pharmaceuticals, Inc., 6 pages, retrieved on Jul. 3, 2023, from https://investors.alnylam.com/press-release?id=14691.
Alnylam Pharmaceuticals (Dec. 3, 2016). "Alnylam Reports Positive Interim Phase 1 Results for Fitusiran in Hemophilia A and B Patients with Inhibitors," Press Release: Alnylam Pharmaceuticals, Inc., 7 pages, retrieved on Jul. 3, 2023, from https://investors.alnylam.com/press-release?id=15831.
Alnylam Pharmaceuticals (Dec. 4, 2016). "Alnylam Reports Positive Interim Clinical Results for Fitusiran from Ongoing Phase 2 Open Label Extension Study in Patients with Hemophilia A or B without Inhibitors," Press Release: Alnylam Pharmaceuticals, Inc., 7 pages, retrieved on Jul. 3, 2023, from https://investors.alnylam.com/press-release?id=15836.
Alnylam Pharmaceuticals (Dec. 6, 2018). "Alnylam Provides R&D Updates and Announces 2019 Product and Pipeline Goals at R&D Day," Press Release: Alnylam Pharmaceuticals, Inc., 7 pages, retrieved on Jul. 3, 2023, from https://investors.alnylam.com/press-release?id=23336.
Alnylam Pharmaceuticals (Dec. 7, 2015). "Alnylam Reports Positive Phase 1 Study Results for Once-Monthly Subcutaneous Fitusiran (ALN-AT3) in Patients with Hemophilia A and B," Press Release: Alnylam Pharmaceuticals, Inc., 10 pages, retrieved on Jul. 3, 2023, from https://investors.alnylam.com/press-release?id=15561.
Alnylam Pharmaceuticals (Dec. 8, 2014). "Alnylam Reports Positive Initial Results for ALN-AT3, an Investigational RNAi Therapeutic Targeting Antithrombin (AT) for the Treatment of Hemophilia and Rare Bleeding Disorders, from Ongoing Phase 1 Trial," Press Release: Alnylam Pharmaceuticals, Inc., 10 pages, retrieved on Jul. 3, 2023, from https://investors.alnylam.com/press-release?id=15241.
Alnylam Pharmaceuticals (Dec. 9, 2013). "Alnylam Presents New Pre-clinical Data on ALN-AT3, an RNAi Therapeutic Targeting Antithrombin (AT) for the Treatment of Hemophilia and Rare Bleeding Disorders (RBD)," Press Release: Alnylam Pharmaceuticals, Inc., 8 pages, retrieved on Jul. 3, 2023, from https://investors.alnylam.com/press-release?id=14701.
Alnylam Pharmaceuticals (Feb. 10, 2022). "Alnylam Pharmaceuticals Reports Fourth Quarter and Full Year 2021 Financial Results and Highlights Recent Period Activity," Press Release: Alnylam Pharmaceuticals, Inc., 20 pages, retrieved on Jul. 3, 2023, from https://investors.alnylam.com/press-release?id=26471.
Alnylam Pharmaceuticals (Feb. 11, 2016). "Alnylam Pharmaceuticals Reports Fourth Quarter and Full Year 2015 Financial Results and Highlights Recent Period Progress," Press Release: Alnylam Pharmaceuticals, Inc., 15 pages, retrieved on Jul. 3, 2023, from https://investors.alnylam.com/press-release?id=15616.
Alnylam Pharmaceuticals (Feb. 11, 2021). "Alnylam Pharmaceuticals Reports Fourth Quarter and Full Year 2020 Financial Results and Highlights Recent Period Activity," Press Release: Alnylam Pharmaceuticals, Inc., 21 pages, retrieved on Jul. 3, 2023, from https://investors.alnylam.com/press-release?id=25471.
Alnylam Pharmaceuticals (Feb. 12, 2015). "Alnylam Pharmaceuticals Reports Fourth Quarter and Full Year 2014 Financial Results and Highlights Recent Period Progress," Press Release: Alnylam Pharmaceuticals, Inc., 15 pages, retrieved on Jul. 3, 2023, from https://investors.alnylam.com/press-release?id=15321.
Alnylam Pharmaceuticals (Feb. 13, 2014). "Alnylam Pharmaceuticals Reports Fourth Quarter and Full Year 2013 Financial Results and Highlights Recent Period Activities," Press Release: Alnylam Pharmaceuticals, Inc., 17 pages, retrieved on Jul. 3, 2023, from https://investors.alnylam.com/press-release?id=14766.
Alnylam Pharmaceuticals (Feb. 2, 2017). "Alnylam Presents New Data on Fitusiran at EAHAD," Press Release: Alnylam Pharmaceuticals, Inc., 7 pages, retrieved on Jul. 3, 2023, from https://investors.alnylam.com/press-release?id=15871.
Alnylam Pharmaceuticals (Feb. 6, 2020). "Alnylam Pharmaceuticals Reports Fourth Quarter and Full Year 2019 Financial Results and Highlights Recent Period Activity," Press Release: Alnylam Pharmaceuticals, Inc., 19 pages, retrieved on Jul. 3, 2023, from https://investors.alnylam.com/press-release?id=24491.
Alnylam Pharmaceuticals (Feb. 7, 2019). "Alnylam Pharmaceuticals Reports Fourth Quarter and Full Year 2018 Financial Results and Highlights Recent Period Activity," Press Release: Alnylam Pharmaceuticals, Inc., 17 pages, retrieved on Jul. 3, 2023, from https://investors.alnylam.com/press-release?id=23496.
Alnylam Pharmaceuticals (Feb. 8, 2018). "Alnylam Pharmaceuticals Reports Fourth Quarter and Full Year 2017 Financial Results and Highlights Recent Period Activity," Press Release: Alnylam Pharmaceuticals, Inc., 14 pages, retrieved on Jul. 3, 2023, from https://investors.alnylam.com/press-release?id=22326.
Alnylam Pharmaceuticals (Jan. 11, 2015). "Alnylam Reports Initial Evidence for Potential Correction of the Hemophilia Phenotype in Phase 1 Study of ALN-AT3, a Subcutaneously Administered Investigational RNAi Therapeutic Targeting Antithrombin for the Treatment of Hemophilia," Press Release: Alnylam Pharmaceuticals, Inc., 9 pages, retrieved on Jul. 3, 2023, from https://investors.alnylam.com/press-release?id=15291.
Alnylam Pharmaceuticals (Jan. 22, 2014). "Alnylam Initiates Phase 1 Clinical Trial with ALN-AT3, a Subcutaneously Administered RNAi Therapeutic Targeting Antithrombin (AT) in Development for the Treatment of Hemophilia and Rare Bleeding Disorders (RBD)," Press Release: Alnylam Pharmaceuticals, Inc., 8 pages, retrieved on Jul. 3, 2023, from https://investors.alnylam.com/press-release?id=14751.
Alnylam Pharmaceuticals (Jan. 7, 2018). "Alnylam and Sanofi Enter into Strategic Restructuring of RNAi Therapeutics Rare Disease Alliance," Press Release: Alnylam Pharmaceuticals, Inc., 8 pages, retrieved on Jul. 3, 2023, from https://investors.alnylam.com/press-release?id=22251.
Alnylam Pharmaceuticals (Jan. 7, 2018). "Alnylam Announces 2018 Corporate Goals," Press Release: Alnylam Pharmaceuticals, Inc., 7 pages, retrieved on Jul. 3, 2023, from https://investors.alnylam.com/press-release?id=22261.
Alnylam Pharmaceuticals (Jul. 10, 2017). "Alnylam and Sanofi Genzyme Report Positive Results from Ongoing Phase 2 Open-Label Extension Study with Investigational RNAi Therapeutic Fitusiran in Patients with Hemophilia A and B with or without Inhibitors," Press Release: Alnylam Pharmaceuticals, Inc., 10 pages, retrieved on Jul. 3, 2023, from https://investors.alnylam.com/press-release?id=21816.
Alnylam Pharmaceuticals (Jul. 11, 2012). "Alnylam Presents New Pre-clinical Data with its RNAi Therapeutic Program in Hemophilia," Press Release: Alnylam Pharmaceuticals, Inc., 7 pages, as retrieved on Jul. 3, 2023, from https://investors.alnylam.com/press-release?id=13396.
Alnylam Pharmaceuticals (Jul. 2, 2013). "Alnylam Presents New Pre-clinical Data on ALN-AT3, an RNAi Therapeutic Targeting Antithrombin (AT) for the Treatment of Hemophilia and Rare Bleeding Disorders," Press Release: Alnylam Pharmaceuticals, Inc., 9 pages, as retrieved on Jul. 3, 2023, from https://investors.alnylam.com/press-release?id=14651.
Alnylam Pharmaceuticals (Jul. 25, 2016). "Alnylam Announces New Positive Interim Phase 1 Study Results for Fitusiran, a Once-Monthly, Subcutaneous, Investigational RNAi Therapeutic Targeting Antithrombin for the Treatment of Hemophilia and Rare Bleeding Disorders," Press Release: Alnylam Pharmaceuticals, Inc., 11 pages, retrieved on Jul. 3, 2023, from https://investors.alnylam.com/press-release?id=15716.
Alnylam Pharmaceuticals (Jul. 25, 2016). "Alnylam to Report New Clinical Results with Fitusiran at the World Federation of Hemophilia (WFH) 2016 World Congress," Press Release: Alnylam Pharmaceuticals, Inc., 4 pages, retrieved on Jul. 3, 2023, from https://investors.alnylam.com/press-release?id=15711.

(56) References Cited

OTHER PUBLICATIONS

Alnylam Pharmaceuticals (Jul. 7, 2017). "Alnylam and Sanofi Genzyme Initiate Atlas Phase 3 Program with Investigational RNAi Therapeutic Fitusiran in Patients with Hemophilia A and B with or without Inhibitors," Press Release: Alnylam Pharmaceuticals, Inc., 8 pages, retrieved on Jul. 3, 2023, from https://investors.alnylam.com/press-release?id=21811.
Alnylam Pharmaceuticals (Jun. 23, 2015). "Alnylam Reports New Positive Clinical Data for ALN-AT3, a Subcutaneously Administered, Investigational RNAi Therapeutic Targeting Antithrombin (AT) for the Treatment of Hemophilia and Rare Bleeding Disorders," Press Release: Alnylam Pharmaceuticals, Inc., 10 pages, retrieved on Jul. 3, 2023, from https://investors.alnylam.com/press-release?id=15421.
Alnylam Pharmaceuticals (Jun. 26, 2017). "Alnylam and Sanofi Genzyme to Present New Clinical Trial Results at the International Society of Thrombosis and Haemostasis (ISTH) Congress," Press Release: Alnylam Pharmaceuticals, Inc., 8 pages, retrieved on Jul. 3, 2023, from https://investors.alnylam.com/press-release?id=21806.
Alnylam Pharmaceuticals (Jun. 5, 2015). "Alnylam to Present New Data at International Society on Thrombosis and Haemostasis (ISTH) 2015 Congress with ALN-AT3, an Investigational RNAi Therapeutic for the Treatment of Hemophilia and Rare Bleeding Disorders (RBD)," Press Release: Alnylam Pharmaceuticals, Inc., 6 pages, retrieved on Jul. 3, 2023, from https://investors.alnylam.com/press-release?id=15401.
Alnylam Pharmaceuticals (Mar. 14, 2016). "Alnylam Initiates Fitusiran (ALN-AT3) Dosing in Hemophilia A and B Patients with Inhibitors in Ongoing Phase 1 Study," Press Release: Alnylam Pharmaceuticals, Inc., 7 pages, retrieved on Jul. 3, 2023, from https://investors.alnylam.com/press-release?id=15631.
Alnylam Pharmaceuticals (May 1, 2019). "Alnylam Pharmaceuticals Reports First Quarter 2019 Financial Results and Highlights Recent Period Activity," Press Release: Alnylam Pharmaceuticals, Inc., 15 pages, retrieved on Jul. 3, 2023, from https://investors.alnylam.com/press-release?id=23756.
Alnylam Pharmaceuticals (May 13, 2014). "Alnylam Reports Initial Positive Top-Line Data from Phase 1 Clinical Trial with ALN-AT3, an RNAi Therapeutic Targeting Antithrombin (AT) in Development for the Treatment of Hemophilia and Rare Bleeding Disorders (RBD)," Press Release: Alnylam Pharmaceuticals, Inc., 10 pages, retrieved on Jul. 3, 2023, from https://investors.alnylam.com/press-release?id=15011.
Alnylam Pharmaceuticals (May 2, 2016). "Alnylam Pharmaceuticals Reports First Quarter 2016 Financial Results and Highlights Recent Period Progress," Press Release: Alnylam Pharmaceuticals, Inc., 13 pages, retrieved on Jul. 3, 2023, from https://investors.alnylam.com/press-release?id=15661.
Alnylam Pharmaceuticals (May 3, 2018). "Alnylam Pharmaceuticals Reports First Quarter 2018 Financial Results and Highlights Recent Period Activity," Press Release: Alnylam Pharmaceuticals, Inc., 13 pages, retrieved on Jul. 3, 2023, from https://investors.alnylam.com/press-release?id=22641.
Alnylam Pharmaceuticals (May 4, 2023). "Alnylam Pharmaceuticals Reports First Quarter 2023 Financial Results and Highlights Recent Period Activity," Press Release: Alnylam Pharmaceuticals, Inc., 19 pages, retrieved on Jul. 3, 2023, from https://investors.alnylam.com/press-release?id=27491.
Alnylam Pharmaceuticals (May 5, 2017). "Alnylam Pharmaceuticals Reports First Quarter 2017 Financial Results and Highlights Recent Period Activity," Press Release: Alnylam Pharmaceuticals, Inc., 9 pages, retrieved on Jul. 3, 2023, from https://investors.alnylam.com/press-release?id=21361.
Alnylam Pharmaceuticals (May 7, 2015). "Alnylam Pharmaceuticals Reports First Quarter 2015 Financial Results and Highlights Recent Period Progress," Press Release: Alnylam Pharmaceuticals, Inc., 14 pages, retrieved on Jul. 3, 2023, from https://investors.alnylam.com/press-release?id=15376.
Alnylam Pharmaceuticals (May 8, 2014). "Alnylam Pharmaceuticals Reports First Quarter 2014 Financial Results and Highlights Recent Period Activities," Press Release: Alnylam Pharmaceuticals, Inc., 19 pages, retrieved on Jul. 3, 2023, from https://investors.alnylam.com/press-release?id=15001.
Alnylam Pharmaceuticals (Nov. 14, 2016). "Alnylam Pharmaceuticals Announces Sanofi Genzyme Opt-in Decision for Co-Development and Co-Commercialization of Fitusiran in Hemophilia and Rare Bleeding Disorders," Press Release: Alnylam Pharmaceuticals, Inc., 7 pages, retrieved on Jul. 3, 2023, from https://investors.alnylam.com/press-release?id=15816.
Alnylam Pharmaceuticals (Nov. 2, 2016). "Alnylam Pharmaceuticals Reports Third Quarter 2016 Financial Results and Highlights Recent Period Activity," Press Release: Alnylam Pharmaceuticals, Inc., 13 pages, retrieved on Jul. 3, 2023, from https://investors.alnylam.com/press-release?id=15801.
Alnylam Pharmaceuticals (Nov. 22, 2019). "Alnylam Announces 2020 Product and Pipeline Goals and Provides Updates at R&D Day," Press Release: Alnylam Pharmaceuticals, Inc., 9 pages, retrieved on Jul. 3, 2023, from https://investors.alnylam.com/press-release?id=24306.
Alnylam Pharmaceuticals (Nov. 3, 2016). "Alnylam to Present New Clinical Results at 58th Annual Meeting of the American Society of Hematology (ASH)," Press Release: Alnylam Pharmaceuticals, Inc., 7 pages, retrieved on Jul. 3, 2023, from https://investors.alnylam.com/press-release?id=15806.
Alnylam Pharmaceuticals (Nov. 5, 2012). "Alnylam Pharmaceuticals Reports Third Quarter 2012 Financial Results," Press Release: Alnylam Pharmaceuticals, Inc., 14 pages, as retrieved on Jul. 3, 2023, from https://investors.alnylam.com/press-release?id=13341.
Alnylam Pharmaceuticals (Nov. 5, 2014). "Alnylam Pharmaceuticals Reports Third Quarter 2014 Financial Results and Highlights Recent Period Progress," Press Release: Alnylam Pharmaceuticals, Inc., 17 pages, retrieved on Jul. 3, 2023, from https://investors.alnylam.com/press-release?id=15191.
Alnylam Pharmaceuticals (Nov. 6, 2013). "Alnylam Pharmaceuticals Reports Third Quarter 2013 Financial Results," Press Release: Alnylam Pharmaceuticals, Inc., 15 pages, retrieved on Jul. 3, 2023, from https://investors.alnylam.com/press-release?id=14726.
Alnylam Pharmaceuticals (Nov. 7, 2017). "Alnylam Pharmaceuticals Reports Third Quarter 2017 Financial Results and Highlights Recent Period Activity," Press Release: Alnylam Pharmaceuticals, Inc., 14 pages, retrieved on Jul. 3, 2023, from https://investors.alnylam.com/press-release?id=21986.
Alnylam Pharmaceuticals (Nov. 7, 2018). "Alnylam Pharmaceuticals Reports Third Quarter 2018 Financial Results and Highlights Recent Period Activity," Press Release: Alnylam Pharmaceuticals, Inc., 16 pages, retrieved on Jul. 3, 2023, from https://investors.alnylam.com/press-release?id=23256.
Alnylam Pharmaceuticals (Nov. 9, 2015). "Alnylam Pharmaceuticals Reports Third Quarter 2015 Financial Results and Highlights from Recent Period," Press Release: Alnylam Pharmaceuticals, Inc., 13 pages, retrieved on Jul. 3, 2023, from https://investors.alnylam.com/press-release?id=15536.
Alnylam Pharmaceuticals (Nov. 9, 2017). "Alnylam Announces Successful Outcome Following FDA Type A Meeting to Discuss Fitusiran Program in Hemophilia," Press Release: Alnylam Pharmaceuticals, Inc., 6 pages, retrieved on Jul. 3, 2023, from https://investors.alnylam.com/press-release?id=22026.
Alnylam Pharmaceuticals (Oct. 1, 2015). "Alnylam and Genzyme Announce that Genzyme Opts into ALN-AT3 Hemophilia Program for Development and Commercialization Outside of North America and Western Europe," Press Release: Alnylam Pharmaceuticals, Inc., 8 pages, retrieved on Jul. 3, 2023, from https://investors.alnylam.com/press-release?id=15491.
Alnylam Pharmaceuticals (Oct. 28, 2021). "Alnylam Pharmaceuticals Reports Third Quarter 2021 Financial Results and Highlights Recent Period Activity," Press Release: Alnylam Pharmaceuticals, Inc., 20 pages, retrieved on Jul. 3, 2023, from https://investors.alnylam.com/press-release?id=26171.
Alnylam Pharmaceuticals (Oct. 29, 2013). "Alnylam Files Clinical Trial Application to Initiate a Phase I Study for ALN-AT3, a Subcutaneously Administered RNAi Therapeutic Targeting Antithrombin

(56) References Cited

OTHER PUBLICATIONS (AT) for the Treatment of Hemophilia A and B," Press Release: Alnylam Pharmaceuticals, Inc., 8 pages, retrieved on Jul. 3, 2023, from https://investors.alnylam.com/press-release?id=14731.
Alnylam Pharmaceuticals (Oct. 8, 2015). "Alnylam Initiates Phase 1 Open Label Extension (OLE) Study with ALN-AT3, an Investigational RNAi Therapeutic for the Treatment of Hemophilia and Rare Bleeding Disorders," Press Release: Alnylam Pharmaceuticals, Inc., 6 pages, retrieved on Jul. 3, 2023, from https://investors.alnylam.com/press-release?id=15496.
Alnylam Pharmaceuticals (Sep. 7, 2017). "Alnylam Provides Pipeline Update on Fitusiran and Givosiran Investigational RNAi Therapeutic Programs," 10 pages, retrieved on Jul. 30, 2020 from https://investors.alnylam.com/press-release?id=21846.
Anonymous (Jul. 22, 2012). "Drugs & Biologics Search Results: Fitusiran", Integrity, 1 page, retrieved on Sep. 19, 2018, fromhttps://integrity.thomson-pharma.com/integrity/xmlxsl/pkqcksrch.showrecords?sessionID=I&history=&query=fitusiran&abbreviation=PRO&language=en.
European Haemophilia Consortium (EHC) (Jun. 2021). "Novel Treatments in Haemophilia and Other Bleeding Disorders: A Periodic EHC Review," pp. 1-56, as retrieved on https://www.hemophilia.ca/wp-content/uploads/2021/06/EHC-NPR-2021_Vol1_FINAL_web.pdf.
International Search Report and Written Opinion of the International Searching Authority mailed on Jun. 24, 2025 for PCT Application No. PCT/US2025/022329 filed on Mar. 31, 2025, 20 pages.
Sanofi (Apr. 26, 2019). "Sanofi Delivers Strong Q1 2019 Business EPS Growth Of 9.4% At CER," Press Release: Sanofi, 4 pages, as retrieved from https://www.news.sanofi.us/2019-04-26-Sanofi-delivers-strong-Q1-2019-business-EPS-growth-of-9-4-at-CER.
Sanofi (Apr. 27, 2018). "Sanofi: First-quarter 2018 Business EPS(1) up 1.4% at CER," Press Release: Sanofi, 15 pages, retrieved on Jul. 7, 2025, from https://streetinsider.com/press+releases/sanofi%3A+First-quarter+2018+Business+EPS%281%29+up+1.4%25+at+CERR/1405443.html.
Sanofi (Apr. 28, 2021). "Sanofi Continued Its Growth Trajectory: Strong Increase In Q1 2021 Business EPS(1) At CER," Press Release: Sanofi, 19 pages, as retrieved from https://www.sanofi.com/en/media-room/press-releases/2021/2021-04-28-05-30-00-2218251.
Sanofi (Apr. 4, 2023). "Two Fitusiran Phase 3 Studies Published In The Lancet And The Lancet Haematology Highlight Potential To Address Unmet Needs Across All Types Of Hemophilia," Press Release: Sanofi, 3 pages, as retrieved from https://www.sanofi.com/en/media-room/press-releases/2023/2023-04-04-05-00-00-2640246.
Sanofi (Apr. 8, 2019). "Sanofi: Sanofi And Alnylam Conclude Research And Option Phase Of 2014 Rare Disease Alliance," Press Release: Sanofi, 2 pages, as retrieved on https://www.globenewswire.com/news-release/2019/04/08/1851083/0/en/Sanofi-Sanofi-and-Alnylam-conclude-research-and-option-phase-of-2014-rare-disease-alliance.html.
Sanofi (Dec. 10, 2020)."Sanofi To Resume Dosing In Fitusiran Clinical Studies In The U.S.," Press Release: Sanofi, 2 pages, as retrieved from https://www.sanofi.com/en/media-room/press-releases/2020/2020-12-10-22-00-00-2143446.
Sanofi (Dec. 14, 2021). "Data From Two Phase 3 Studies Demonstrating Fitusiran Significantly Reduced Bleeds In People With Hemophilia A Or B, With Or Without Inhibitors, Were Featured At ASH's Plenary And Late-Breaking Sessions," Press Release: Sanofi, 4 pages, as retrieved fromhttps://www.sanofi.com/en/media-room/press-releases/2021/2021-12-14-14-00-00-2351761.
Sanofi (Dec. 15, 2017). "Sanofi: FDA Lifts Clinical Hold on Fitusiran," Press Release: Sanofi, 3 pages, as retrieved from https://www.globenewswire.com/news-release/2017/12/15/1262714/0/en/Sanofi-FDA-lifts-clinical-hold-on-fitusiran.html.
Sanofi (Feb. 4, 2022). "Strong 2021 Sales And Business EPS Growth Enabling Increased Investment In R&D," Press Release: Sanofi, 30 pages, as retrieved from https://www.sanofi.com/en/media-room/press-releases/2022/2022-02-04-06-30-00-2379020.
Sanofi (Feb. 5, 2021). "Sanofi Delivered Close To Double-Digit Q4 2020 Business EPS(1) Growth At CER," Press Release: Sanofi, 25 pages, as retrieved from https://www.sanofi.com/en/media-room/press-releases/2021/2021-02-05-06-30-00-2170436.
Sanofi (Feb. 5, 2021). "Sanofi Presents Amended Protocols In Fitusiran Clinical Studies At EAHAD 2021," Press Release: Sanofi, 3 pages, as retrieved from https://www.sanofi.com/en/media-room/press-releases/2021/2021-02-05-16-30-00-2170841.
Sanofi (Jan. 7, 2018). "Sanofi And Alnylam Enter Into Strategic Restructuring Of RNAi Therapeutics Rare Disease Alliance," Press Release: Sanofi, 5 pages, as retrieved from https://www.globenewswire.com/news-release/2018/01/07/1284695/0/en/Sanofi-and-Alnylam-enter-into-strategic-restructuring-of-RNAi-therapeutics-rare-disease-alliance.html.
Sanofi (Jul. 10, 2022). "Fitusiran Prophylaxis Reduced Bleeds By 61% In People With Hemophilia A Or B, With Or Without Inhibitors, Compared To Prior Factor Or Bypassing Agent Prophylaxis," Press Release: Sanofi, 3 pages, as retrieved from https://www.sanofi.com/en/media-room/press-releases/2022/2022-07-10-13-45-00-2476896.
Sanofi (Jul. 2, 2021). "Sanofi Highlights Scientific Innovations In The Field Of Rare Blood Disorders At ISTH 2021," Press Release: Sanofi, 5 pages, as retrieved from https://www.sanofi.com/en/media-room/press-releases/2021/2021-07-02-13-00-00-2257163.
Sanofi (Jul. 29, 2019). "Sanofi Delivered Solid Growth In Q2 2019," Press Release: Sanofi, 29 pages, as retrieved from https://www.news.sanofi.us/2019-07-29-Sanofi-delivered-solid-growth-in-Q2-2019.
Sanofi (Jul. 29, 2020). "Sanofi H1 2020 Business EPS(1) Growth Of 9.2% Driven By Transformation," Press Release: Sanofi, 31 pages, as retrieved from https://www.news.sanofi.us/2020-07-29-Sanofi-H1-2020-business-EPS-1-growth-of-9-2-2-driven-by-transformation.
Sanofi (Jul. 31, 2017). "Sanofi Raises FY 2017 Business EPS(1) Guidance to Broadly Stable at CER(2)," Press Release: Sanofi, 26 pages, as retrieved from https://www.globenewswire.com/news-release/2017/07/31/1685042/0/en/Sanofi-Raises-FY-2017-Business-EPS-1-Guidance-to-Broadly-Stable-at-CER-2.html.
Sanofi (Jun. 23, 2020). "Sanofi's Virtual R&D Day Event To Highlight Capabilities, Platforms, And Expertise In Disease Pathways To Deliver Potentially Transformative Treatments To Patients," Press Release: Sanofi, 6 pages, as retrieved from https://www.sanofi.com/en/media-room/press-releases/2020/2020-06-23-05-00-00-2051688.
Sanofi (Nov. 30, 2022). "Media Update: Sanofi To Present New Clinical Data Reinforcing Novel Therapies Across Rare Blood Disorders At ASH 2022," Press Release: Sanofi, 4 pages, as retrieved from https://www.sanofi.com/en/media-room/press-releases/2022/2022-11-30-12-00-00-2564784.
Sanofi (Nov. 4, 2021). "New Data In Blood Cancers, Hemophilia, And Other Hematological Disorders To Be Presented At ASH 2021," Press Release: Sanofi, 6 pages, as retrieved from https://www.sanofi.com/en/media-room/press-releases/2021/2021-11-04-15-30-00-2327804.
Sanofi (Oct. 28, 2021). "Sanofi: Strong Q3 Performance Drives Guidance Upgrade To Around 14% Business EPS Growth At CER(1)," Press Release: Sanofi, 24 pages, as retrieved from https://www.sanofi.com/en/media-room/press-releases/2021/2021-10-28-05-30-00-2322319.
U.S. Appl. No. 19/331,354, filed Sep. 17, 2025, for Baisong et al. (Copy not submitted herewith pursuant to the waiver of 37 C.F.R. 1.98(a)(2)(iii) issued by the Office on Sep. 21, 2004).
Von Mackensen, S. et al. (2005). "Healthrelated Quality Of Life In Adult Patients With Haemophilia—Assessment With A New Disease-Specific Questionnaire," J Thromb Haemost 3:P0813, 1 page.
Von Mackensen, S. et al. (2005). "Validation Of The Haemophilia-Specific Quality Of Life Questionnaire For Adult Patients With Haemophilia (Haem-A-Qol)," Haematologica 90(Suppl 2):115-116.
Von Mackensen, S. et al. (2014). "Quality of Life in Hemophilia," Chapter 64 in Textbook of Hemophilia, John Wiley & Sons, pp. 478-488.

(56) References Cited

OTHER PUBLICATIONS

Zozulya, N.I. et al. (Nov. 2014). "Clinical Guidelines for the Diagnosis and Treatment of Hemophilia," National Hematological Society, 43 pages (Partial English Translation).
International Search Report & Written Opinion issued in PCT/US13/38218, date of mailing Dec. 2, 2013.
Invitation to Pay Additional Fees, issued in PCT/US13/38218, date of mailing Sep. 5, 2013.

* cited by examiner

A.

B.

SEQ ID NO:1
>gi|254588059|ref|NM_000488.3| Homo sapiens serpin peptidase inhibitor, clade C (antithrombin), member 1 (SERPINC1), mRNA
TCTGCCCCACCCTGTCCTCTGGAACCTCTGCGAGATTTAGAGGAAAGAACCAGTTTTCAGGCGGATTGCC
TCAGATCACACTATCTCCACTTGCCCAGCCCTGTGGAAGATTAGCGGCCATGTATTCCAATGTGATAGGA
ACTGTAACCTCTGGAAAAAGGAAGGTTTATCTTTTGTCCTTGCTGCTCATTGGCTTCTGGGACTGCGTGA
CCTGTCACGGGAGCCCTGTGGACATCTGCACAGCCAAGCCGCGGGACATTCCCATGAATCCCATGTGCAT
TTACCGCTCCCCGGAGAAGAAGGCAACTGAGGATGAGGGCTCAGAACAGAAGATCCCGGAGGCCACCAAC
CGGCGTGTCTGGGAACTGTCCAAGGCCAATTCCCGCTTTGCTACCACTTTCTATCAGCACCTGGCAGATT
CCAAGAATGACAATGATAACATTTTCCTGTCACCCCTGAGTATCTCCACGGCTTTTGCTATGACCAAGCT
GGGTGCCTGTAATGACACCCTCCAGCAACTGATGGAGGTATTTAAGTTTGACACCATATCTGAGAAAACA
TCTGATCAGATCCACTTCTTCTTTGCCAAACTGAACTGCCGACTCTATCGAAAAGCCAACAAATCCTCCA
AGTTAGTATCAGCCAATCGCCTTTTTGGAGACAAATCCCTTACCTTCAATGAGACCTACCAGGACATCAG
TGAGTTGGTATATGGAGCCAAGCTCCAGCCCCTGGACTTCAAGGAAAATGCAGAGCAATCCAGAGCGGCC
ATCAACAAATGGGTGTCCAATAAGACCGAAGGCCGAATCACCGATGTCATTCCCTCGGAAGCCATCAATG
AGCTCACTGTTCTGGTGCTGGTTAACACCATTTACTTCAAGGGCCTGTGGAAGTCAAAGTTCAGCCCTGA
GAACACAAGGAAGGAACTGTTCTACAAGGCTGATGGAGAGTCGTGTTCAGCATCTATGATGTACCAGGAA
GGCAAGTTCCGTTATCGGCGCGTGGCTGAAGGCACCCAGGTGCTTGAGTTGCCCTTCAAAGGTGATGACA
TCACCATGGTCCTCATCTTGCCCAAGCCTGAGAAGAGCCTGGCCAAGGTAGAGAAGGAACTCACCCCAGA
GGTGCTGCAAGAGTGGCTGGATGAATTGGAGGAGATGATGCTGGTGGTCCACATGCCCCGCTTCCGCATT
GAGGACGGCTTCAGTTTGAAGGAGCAGCTGCAAGACATGGGCCTTGTCGATCTGTTCAGCCCTGAAAAGT
CCAAACTCCCAGGTATTGTTGCAGAAGGCCGAGATGACCTCTATGTCTCAGATGCATTCCATAAGGCATT
TCTTGAGGTAAATGAAGAAGGCAGTGAAGCAGCTGCAAGTACCGCTGTTGTGATTGCTGGCCGTTCGCTA
AACCCCAACAGGGTGACTTTCAAGGCCAACAGGCCTTTCCTGGTTTTTATAAGAGAAGTTCCTCTGAACA
CTATTATCTTCATGGGCAGAGTAGCCAACCCTTGTGTTAAGTAAAATGTTCTTATTCTTTGCACCTCTTC
CTATTTTTGGTTTGTGAACAGAAGTAAAAATAAATACAAACTACTTCCATCTCACATTA

Figure 30A

SEQ ID NO:2
>gi|157167169|ref|NM_001104583.1| Macaca mulatta serpin peptidase inhibitor, clade C (antithrombin), member 1 (SERPINC1), mRNA GGCACGAGGACCATCTCCACTTGCCCAGCCCTGTGGAAGATTAGCGACCATGTATTCCAATGTGATAGGA
ACCGTAGCCTCTGGAAAAAGGAAGGTTTATCTTCTGTCCTTGCTGCTCATTGGCCTCTGGGACTGTATGA
CCTGTCACGGGAGCCCTGTGGACATCTGCACAGCCAAGCCGCGGGACATTCCCATGAATCCCATGTGCAT
TTACCGCTCCCCGGAGAAGAAGGCAACTGAGGATGAGGGCTCAGAACAGAAGATCCCCGAGGCCACCAAC
CGGCGCGTCTGGGAACTGTCCAAGGCCAATTCCCGCTTTGCTACCACTTTCTATCAGCACCTGGCAGATT
CCAAGAACGACAAGGATAACATTTTCCTGTCACCCCTGAGTGTCTCCACGGCTTTTGCTATGACCAAGCT
GGGTGCCTGTAATGACACCCTCAAGCAACTGATGGAGGTATTTAAGTTTGACACCATATCTGAGAAAACA
TCTGATCAGATCCACTTCTTCTTTGCCAAACTGAACTGCCGACTCTATCGAAAAGCCAACAAATCCTCCA
AGTTAGTATCAGCCAATCGCCTTTTTGGAGACAAATCCCTTACCTTCAATGAGACCTACCAGGACATCAG
TGAGTTGGTATACGGAGCCAAGCTCCAGCCCCTGGACTTCAAGGAAAATGCAGAGCAATCCAGAGCGGCC
ATCAACAAATGGGTGTCCAATAAGACCGAAGGCCGAATCACCGATGTCATTCCCCCGGAAGCCATCAACG
AGCTCACTGTTCTGGTGCTGGTTAACACCATTTACTTCAAGGGCCTGTGGAAGTCAAAGTTTAGCCCTGA
GAACACAAGGATGGAACCGTTCTACAAGGCTGATGGAGAGTCGTGTTCAGCGTCTATGATGTACCAGGAA
GGCAAGTTCTGTTATCGGCGCGTGGCTGAAGGCACCCAGGTGCTTGAGTTGCCCTTCAAGGGTGATGACA
TCACCATGGTGCTCATCCTGCCCAAGCCTGAGAAGAGCCTGACCAAGGTGGAGCAGGAACTCACCCCAGA
GGTGCTGCAGGAGTGGCTGGATGAGTTGGAGGAGATGATGCTGGTGGTTCACATGCCCCGCTTCCGCATT
GAGGACGGCTTCAGTTTGAAGGAGCAGCTGCAAGACATGGGCCTTGTCGATCTGTTCAGCCCTGAAAAGT
CCAAACTCCCAGGTATTGTTGCAGAAGGCCGGGATGACCTCTATGTCTCCGATGCATTCCATAAGGCATT
TCTTGAGGTAAATGAAGAAGGCAGTGAAGCAGCTGCAAGTACCGCCATTGGGATTGCTGGCCGTTCGCTA
AACCCCAACAGGGTGACCTTCAAGGCCAACAGGCCTTTCCTGGTTTTTATAAGAGAAGTTCCTCTGAACA
CTATTATCTTCATGGGCAGAGTAGCCAACCCTTGTGTGAGCTAAACTGTTCTTATTCTTTGTACCTCTTC
CTATTTTGGTTTGTGAATAGAAGTAAAAATAAATACAACTACTCCCATCTTACATTAAAAAAAAAAAAAA
AAAAA

Figure 30B

SEQ ID NO:3
>gi|237874216|ref|NM_080844.4| Mus musculus serine (or cysteine) peptidase inhibitor, clade C (antithrombin), member 1 (Serpinc1), mRNA
ATAGGTAATTTTAGAAATAGATCTGATTTGTATCTGAGACATTTTAGTGAAGTGGTGAGATATAAGACAT
AATCAGAAGACATATCTACCTGAAGACTTTAAGGGGAGAGCTCCCTCCCCCACCTGGCCTCTGGACCTCT
CAGATTTAGGGGAAAGAACCAGTTTTCGGAGTGATCGTCTCAGTCAGCACCATCTCTGTAGGAGCATCGG
CCATGTATTCCCCTGGGGCAGGAAGTGGGGCTGCTGGTGAGAGGAAGCTTTGTCTCCTCTCTCTGCTCCT
CATCGGTGCCTTGGGCTGTGCTATCTGTCACGGAAACCCTGTGGACGACATCTGCATAGCGAAGCCCCGA
GACATCCCCGTGAATCCCTTGTGCATTTACCGCTCCCCTGGGAAGAAGGCCACCGAGGAGGATGGCTCAG
AGCAGAAGGTTCCAGAAGCCACCAACCGGCGGGTCTGGGAACTGTCCAAGGCCAATTCGCGATTTGCCAC
TAACTTCTACCAGCACCTGGCAGACTCCAAGAATGACAACGACAACATTTTCCTGTCACCCTTGAGCATC
TCCACTGCTTTTGCTATGACCAAGCTGGGTGCCTGTAACGACACTCTCAAGCAGCTGATGGAGGTTTTTA
AATTTGATACCATCTCCGAGAAGACATCCGACCAGATCCACTTCTTCTTTGCCAAACTGAACTGCCGACT
CTATCGAAAAGCCAACAAGTCCTCTGACTTGGTATCAGCCAACCGCCTTTTTGGAGACAAATCCCTCACC
TTCAACGAGAGCTATCAAGATGTTAGTGAGGTTGTCTATGGAGCCAAGCTCCAGCCCCTGGACTTCAAGG
AGAATCCGGAGCAATCCAGAGTGACCATCAACAACTGGGTAGCTAATAAGACTGAAGGCCGCATCAAAGA
TGTCATCCCACAGGGCGCCATTAACGAGCTCACTGCCCTGGTTCTGGTTAACACCATTTACTTCAAGGGC
CTGTGGAAGTCAAAGTTCAGCCCTGAGAACACAAGGAAGGAACCGTTCTATAAGGTCGATGGGCAGTCAT
GCCCAGTGCCTATGATGTACCAGGAAGGCAAATTCAAATACCGGCGCGTGGCAGAGGGCACCCAGGTGCT
AGAGCTGCCCTTCAAGGGGGATGACATCACCATGGTGCTCATCCTGCCCAAGCCTGAGAAGAGCCTGGCC
AAGGTGGAGCAGGAGCTCACCCCAGAGCTGCTGCAGGAGTGGCTGGATGAGCTGTCAGAGACTATGCTTG
TGGTCCACATGCCCCGCTTCCGCACCGAGGATGGCTTCAGTCTGAAGGAGCAGCTGCAAGACATGGGCCT
CATTGATCTCTTCAGCCCTGAAAAGTCCCAACTCCCAGGGATCGTTGCTGGAGGCAGGGACGACCTCTAT
GTCTCCGACGCATTCCACAAAGCATTTCTTGAGGTAAATGAGGAAGGCAGTGAAGCAGCAGCGAGTACTT
CTGTCGTGATTACTGGCCGGTCACTGAACCCCAATAGGGTGACCTTCAAGGCCAACAGGCCCTTCCTGGT
TCTTATAAGGGAAGTTGCACTGAACACTATTATATTCATGGGGAGAGTGGCTAATCCTTGTGTGAACTAA
AATATTCTTAATCTTTGCACCTTTTCCTACTTTGGTGTTTGTGAATAGAAGTAAAAATAAATACGACTGC
CACCTCACGAGAATGGACTTTTCCACTTGAAGACGAGAGACTGGAGTACAGATGCTACACCACTTTTGGG
CAAGTGAAGGGGGAGCAGCCAGCCACGGTGGCACAAACCTATATCCTGGTGCTTTTGAAGGTAGAAGCAG
GGCGGTCAGGAGTTAAGGCCAGTTGAGGCTGGGCTGCAGAGTGAAAGACCATGTCTCAAGATGGTCTTTC
TCCTCCCCAAAGTAGAAAAGAAAACCATAAAAACAAGAGGTAAATATATTACTATTTCATCTTAGAGGAT
AGCAGGCATCTTGAAAGGGTAGAGGGACCTTAAATTCTCATTATTGCCCCCATACTACAAACTAAAAAAC
AAACCCGAATCAATCTCCCATAAAGACAGAGATTCAAATAAGAGTATTAAACGTTTTATTTCTCAAACCA
CTCACATGCATAATGTTCTTATACACAGTGTCAAAATAAAGAGAAATGCATTTTTATACAAAAAAAAAAA
A

Figure 30C

SEQ ID NO:4
>gi|58865629|ref|NM_001012027.1| Rattus norvegicus serpin peptidase inhibitor, clade C (antithrombin), member 1 (Serpinc1), mRNA
CGGAGGGATTGCTCAGCACTGTCTCCACGGCTTCTCTGCAGAAGCGTCCACCATGTATTCCCGGGAATA
GGAAGTGCGGTTGCTGGAGAGAGGAAGCTTTGTCTCCTCTCTCTGCTACTCATTGGTGCCTTGGGCTGTG
CTGTCTGTCATGGAAACCCTGTGGACGACATCTGCATAGCGAAGCCCCGAGACATCCCCGTGAACCCCAT
GTGCATTTACCGCTCCCCTGCGAAGAAGGCCACGGAGGAGGATGTCCTAGAGCAGAAGGTTCCGGAAGCC
ACCAACCGGCGGGTCTGGGAACTGTCCAAGGCCAATTCTCGATTTGCCACTAACTTCTATCAGCACCTGG
CAGACTCCAAGAACGACAACGACAACATTTTCCTGTCACCCTTGAGCATCTCCACGGCGTTTGCTATGAC
CAAGCTGGGTGCTTGTAATAACACCCTCAAGCAGCTGATGGAGGTTTTTAAATTTGATACCATCTCCGAG
AAGACATCCGACCAGATCCACTTCTTCTTTGCCAAACTGAACTGCCGACTCTATCGAAAAGCCAACAAGT
CCTCTAACTTGGTGTCAGCCAACCGCCTTTTTGGAGACAAATCCCTTACCTTCAATGAGAGCTATCAAGA
CGTTAGTGAGATTGTCTATGGAGCCAAGCTTCAGCCCCTGGACTTCAAGGAGAATCCGGAGCAATCCAGA
GTGACCATCAACAACTGGGTAGCTAATAAGACTGAAGGCCGCATCAAAGACGTCATCCCCCAAGGAGCCA
TTGATGAGCTCACTGCCCTGGTGCTGGTTAACACCATTTACTTCAAGGGCCTGTGGAAGTCAAAGTTCAG
CCCTGAGAACACAAGGAAGGAACCATTCCACAAAGTTGATGGGCAGTCATGCCTGGTGCCCATGATGTAC
CAGGAAGGCAAATTCAAATACAGGCGTGTGGGAGAGGGTACCCAGGTGCTAGAGATGCCCTTCAAGGGGG
ACGACATCACCATGGTGCTCATCCTGCCCAAGCCTGAGAAGAGCCTGGCTAAGGTGGAGCAGGAACTCAC
CCCGGAGCTGCTGCAGGAGTGGCTGGATGAGCTGTCGGAGGTCATGCTTGTGGTCCACGTGCCCCGCTTC
CGCATCGAGGACAGCTTCAGTCTGAAGGAGCAGCTGCAAGACATGGGCCTTGTTGATCTCTTCAGCCCTG
AGAAGTCCCAACTCCCAGGGATCATTGCTGAAGGCAGGGACGACCTCTTTGTCTCCGATGCATTCCACAA
AGCGTTTCTTGAGGTAAATGAGGAAGGCAGTGAAGCAGCAGCGAGTACTTCTGTCGTGATTACTGGCCGG
TCACTGAACCCCAGTAGGGTGACCTTCAAGGCCAACAGGCCCTTCCTGGTTCTTATAAGGGAAGTCGCAC
TGAACACTATTATATTCATGGGGAGAGTGTCTAATCCTTGTGTGAACTAAAATATTCTTAATCTTTGCAC
CTTTTCCTATCTCGGTGTTTGTTAATGGAAGTAAAAATAAATATGACTGCCACCTCAAAAAAAAAAAAAA
AAAAAAAAAAAAAAAAAAAAA

Figure 30D

SEQ ID NO:5 Reverse Complement of SEQ ID NO:1

TAATGTGAGATGGAAGTAGTTTGTATTTATTTTTACTTCTGTTCACAAACCAAAAATAGGAAGAGGTGCAAAGAATAAGAACATTT
TACTTAACACAAGGGTTGGCTACTCTGCCCATGAAGATAATAGTGTTCAGAGGAACTTCTCTTATAAAAACCAGGAAAGGCCTGTT
GGCCTTGAAAGTCACCCTGTTGGGGTTTAGCGAACGGCCAGCAATCACAACAGCGGTACTTGCAGCTGCTTCACTGCCTTCTTCAT
TTACCTCAAGAAATGCCTTATGGAATGCATCTGAGACATAGAGGTCATCTCGGCCTTCTGCAACAATACCTGGGAGTTTGGACTTT
TCAGGGCTGAACAGATCGACAAGGCCCATGTCTTGCAGCTGCTCCTTCAAACTGAAGCCGTCCTCAATGCGGAAGCGGGGCATGTG
GACCACCAGCATCATCTCCTCCAATTCATCCAGCCACTCTTGCAGCACCTCTGGGGTGAGTTCCTTCTCTACCTTGGCCAGGCTCT
TCTCAGGCTTGGGCAAGATGAGGACCATGGTGATGTCATCACCTTTGAAGGGCAACTCAAGCACCTGGGTGCCTTCAGCCACGCGC
CGATAACGGAACTTGCCTTCCTGGTACATCATAGATGCTGAACACGACTCTCCATCAGCCTTGTAGAACAGTTCCTTCCTTGTGTT
CTCAGGGCTGAACTTTGACTTCCACAGGCCCTTGAAGTAAATGGTGTTAACCAGCACCAGAACAGTGAGCTCATTGATGGCTTCCG
AGGGAATGACATCGGTGATTCGGCCTTCGGTCTTATTGGACACCCATTTGTTGATGGCCGCTCTGGATTGCTCTGCATTTTCCTTG
AAGTCCAGGGGCTGGAGCTTGGCTCCATATACCAACTCACTGATGTCCTGGTAGGTCTCATTGAAGGTAAGGGATTTGTCTCCAAA
AAGGCGATTGGCTGATACTAACTTGGAGGATTTGTTGGCTTTTCGATAGAGTCGGCAGTTCAGTTTGGCAAAGAAGAAGTGGATCT
GATCAGATGTTTTCTCAGATATGGTGTCAAACTTAAATACCTCCATCAGTTGCTGGAGGGTGTCATTACAGGCACCCAGCTTGGTC
ATAGCAAAAGCCGTGGAGATACTCAGGGGTGACAGGAAAATGTTATCATTGTCATTCTTGGAATCTGCCAGGTGCTGATAGAAAGT
GGTAGCAAAGCGGGAATTGGCCTTGGACAGTTCCCAGACACGCCGGTTGGTGGCCTCCGGGATCTTCTGTTCTGAGCCCTCATCCT
CAGTTGCCTTCTTCTCCGGGGAGCGGTAAATGCACATGGGATTCATGGGAATGTCCCGCGGCTTGGCTGTGCAGATGTCCACAGGG
CTCCCGTGACAGGTCACGCAGTCCCAGAAGCCAATGAGCAGCAAGGACAAAAGATAAACCTTCCTTTTTCCAGAGGTTACAGTTCC
TATCACATTGGAATACATGGCCGCTAATCTTCCACAGGGCTGGGCAAGTGGAGATAGTGTGATCTGAGGCAATCCGCCTGAAAACT
GGTTCTTTCCTCTAAATCTCGCAGAGGTTCCAGAGGACAGGGTGGGGCAGA

Figure 30E

SEQ ID NO:6 Reverse Complement of SEQ ID NO:2

TTTTTTTTTTTTTTTTTTTAATGTAAGATGGGAGTAGTTGTATTTATTTTTACTTCTATTCACAAACCAAAATAGGAAGAGGTACA
AAGAATAAGAACAGTTTAGCTCACACAAGGGTTGGCTACTCTGCCCATGAAGATAATAGTGTTCAGAGGAACTTCTCTTATAAAAA
CCAGGAAAGGCCTGTTGGCCTTGAAGGTCACCCTGTTGGGGTTTAGCGAACGGCCAGCAATCCCAATGGCGGTACTTGCAGCTGCT
TCACTGCCTTCTTCATTTACCTCAAGAAATGCCTTATGGAATGCATCGGAGACATAGAGGTCATCCCGGCCTTCTGCAACAATACC
TGGGAGTTTGGACTTTTCAGGGCTGAACAGATCGACAAGGCCCATGTCTTGCAGCTGCTCCTTCAAACTGAAGCCGTCCTCAATGC
GGAAGCGGGGCATGTGAACCACCAGCATCATCTCCTCCAACTCATCCAGCCACTCCTGCAGCACCTCTGGGGTGAGTTCCTGCTCC
ACCTTGGTCAGGCTCTTCTCAGGCTTGGGCAGGATGAGCACCATGGTGATGTCATCACCCTTGAAGGGCAACTCAAGCACCTGGGT
GCCTTCAGCCACGCGCCGATAACAGAACTTGCCTTCCTGGTACATCATAGACGCTGAACACGACTCTCCATCAGCCTTGTAGAACG
GTTCCATCCTTGTGTTCTCAGGGCTAAACTTTGACTTCCACAGGCCCTTGAAGTAAATGGTGTTAACCAGCACCAGAACAGTGAGC
TCGTTGATGGCTTCCGGGGGAATGACATCGGTGATTCGGCCTTCGGTCTTATTGGACACCCATTTGTTGATGGCCGCTCTGGATTG
CTCTGCATTTTCCTTGAAGTCCAGGGGCTGGAGCTTGGCTCCGTATACCAACTCACTGATGTCCTGGTAGGTCTCATTGAAGGTAA
GGGATTTGTCTCCAAAAAGGCGATTGGCTGATACTAACTTGGAGGATTTGTTGGCTTTTCGATAGAGTCGGCAGTTCAGTTTGGCA
AAGAAGAAGTGGATCTGATCAGATGTTTTCTCAGATATGGTGTCAAACTTAAATACCTCCATCAGTTGCTTGAGGGTGTCATTACA
GGCACCCAGCTTGGTCATAGCAAAAGCCGTGGAGACACTCAGGGGTGACAGGAAAATGTTATCCTTGTCGTTCTTGGAATCTGCCA
GGTGCTGATAGAAAGTGGTAGCAAAGCGGGAATTGGCCTTGGACAGTTCCCAGACGCGCCGGTTGGTGGCCTCGGGGATCTTCTGT
TCTGAGCCCTCATCCTCAGTTGCCTTCTTCTCCGGGGAGCGGTAAATGCACATGGGATTCATGGGAATGTCCCGCGGCTTGGCTGT
GCAGATGTCCACAGGGCTCCCGTGACAGGTCATACAGTCCCAGAGGCCAATGAGCAGCAAGGACAGAAGATAAACCTTCCTTTTTC
CAGAGGCTACGGTTCCTATCACATTGGAATACATGGTCGCTAATCTTCCACAGGGCTGGGCAAGTGGAGATGGTCCTCGTGCC

Figure 30F

SEQ ID NO:7 Reverse Complement of SEQ ID NO:3

TTTTTTTTTTTTGTATAAAAATGCATTTCTCTTTATTTTGACACTGTGTATAAGAACATTATGCATGTGAGTGGTTTGAGAAATAA
AACGTTTAATACTCTTATTTGAATCTCTGTCTTTATGGGAGATTGATTCGGGTTTGTTTTTTAGTTTGTAGTATGGGGGCAATAAT
GAGAATTTAAGGTCCCTCTACCCTTTCAAGATGCCTGCTATCCTCTAAGATGAAATAGTAATATATTTACCTCTTGTTTTTATGGT
TTTCTTTTCTACTTTGGGGAGGAGAAAGACCATCTTGAGACATGGTCTTTCACTCTGCAGCCCAGCCTCAACTGGCCTTAACTCCT
GACCGCCCTGCTTCTACCTTCAAAAGCACCAGGATATAGGTTTGTGCCACCGTGGCTGGCTGCTCCCCCTTCACTTGCCCAAAAGT
GGTGTAGCATCTGTACTCCAGTCTCTCGTCTTCAAGTGGAAAAGTCCATTCTCGTGAGGTGGCAGTCGTATTTATTTTTACTTCTA
TTCACAAACACCAAAGTAGGAAAAGGTGCAAAGATTAAGAATATTTTAGTTCACACAAGGATTAGCCACTCTCCCCATGAATATAA
TAGTGTTCAGTGCAACTTCCCTTATAAGAACCAGGAAGGGCCTGTTGGCCTTGAAGGTCACCCTATTGGGGTTCAGTGACCGGCCA
GTAATCACGACAGAAGTACTCGCTGCTGCTTCACTGCCTTCCTCATTTACCTCAAGAAATGCTTTGTGGAATGCGTCGGAGACATA
GAGGTCGTCCCTGCCTCCAGCAACGATCCCTGGGAGTTGGGACTTTTCAGGGCTGAAGAGATCAATGAGGCCCATGTCTTGCAGCT
GCTCCTTCAGACTGAAGCCATCCTCGGTGCGGAAGCGGGGCATGTGGACCACAAGCATAGTCTCTGACAGCTCATCCAGCCACTCC
TGCAGCAGCTCTGGGGTGAGCTCCTGCTCCACCTTGGCCAGGCTCTTCTCAGGCTTGGGCAGGATGAGCACCATGGTGATGTCATC
CCCCTTGAAGGGCAGCTCTAGCACCTGGGTGCCCTCTGCCACGCGCCGGTATTTGAATTTGCCTTCCTGGTACATCATAGGCACTG
GGCATGACTGCCCATCGACCTTATAGAACGGTTCCTTCCTTGTGTTCTCAGGGCTGAACTTTGACTTCCACAGGCCCTTGAAGTAA
ATGGTGTTAACCAGAACCAGGGCAGTGAGCTCGTTAATGGCGCCCTGTGGGATGACATCTTTGATGCGGCCTTCAGTCTTATTAGC
TACCCAGTTGTTGATGGTCACTCTGGATTGCTCCGGATTCTCCTTGAAGTCCAGGGGCTGGAGCTTGGCTCCATAGACAACCTCAC
TAACATCTTGATAGCTCTCGTTGAAGGTGAGGGATTTGTCTCCAAAAAGGCGGTTGGCTGATACCAAGTCAGAGGACTTGTTGGCT
TTTCGATAGAGTCGGCAGTTCAGTTTGGCAAAGAAGAAGTGGATCTGGTCGGATGTCTTCTCGGAGATGGTATCAAATTTAAAAAC
CTCCATCAGCTGCTTGAGAGTGTCGTTACAGGCACCCAGCTTGGTCATAGCAAAAGCAGTGGAGATGCTCAAGGGTGACAGGAAAA
TGTTGTCGTTGTCATTCTTGGAGTCTGCCAGGTGCTGGTAGAAGTTAGTGGCAAATCGCGAATTGGCCTTGGACAGTTCCCAGACC
CGCCGGTTGGTGGCTTCTGGAACCTTCTGCTCTGAGCCATCCTCCTCGGTGGCCTTCTTCCCAGGGGAGCGGTAAATGCACAAGGG
ATTCACGGGGATGTCTCGGGGCTTCGCTATGCAGATGTCGTCCACAGGGTTTCCGTGACAGATAGCACAGCCCAAGGCACCGATGA
GGAGCAGAGAGAGGAGACAAAGCTTCCTCTCACCAGCAGCCCCACTTCCTGCCCCAGGGGAATACATGGCCGATGCTCCTACAGAG
ATGGTGCTGACTGAGACGATCACTCCGAAAACTGGTTCTTTCCCCTAAATCTGAGAGGTCCAGAGGCCAGGTGGGGGAGGGAGCTC
TCCCCTTAAAGTCTTCAGGTAGATATGTCTTCTGATTATGTCTTATATCTCACCACTTCACTAAAATGTCTCAGATACAAATCAGA
TCTATTTCTAAAATTACCTAT

Figure 30G

SEQ ID NO:8 Reverse Complement of SEQ ID NO:4

TTTTTTTTTTTTTTTTTTTTTTTTTTTTTTTTTTTGAGGTGGCAGTCATATTTATTTTTACTTCCATTAACAAACACCGAGATAGG
AAAAGGTGCAAAGATTAAGAATATTTTAGTTCACACAAGGATTAGACACTCTCCCCATGAATATAATAGTGTTCAGTGCGACTTCC
CTTATAAGAACCAGGAAGGGCCTGTTGGCCTTGAAGGTCACCCTACTGGGGTTCAGTGACCGGCCAGTAATCACGACAGAAGTACT
CGCTGCTGCTTCACTGCCTTCCTCATTTACCTCAAGAAACGCTTTGTGGAATGCATCGGAGACAAAGAGGTCGTCCCTGCCTTCAG
CAATGATCCCTGGGAGTTGGGACTTCTCAGGGCTGAAGAGATCAACAAGGCCCATGTCTTGCAGCTGCTCCTTCAGACTGAAGCTG
TCCTCGATGCGGAAGCGGGGCACGTGGACCACAAGCATGACCTCCGACAGCTCATCCAGCCACTCCTGCAGCAGCTCCGGGGTGAG
TTCCTGCTCCACCTTAGCCAGGCTCTTCTCAGGCTTGGGCAGGATGAGCACCATGGTGATGTCGTCCCCCTTGAAGGGCATCTCTA
GCACCTGGGTACCCTCTCCCACACGCCTGTATTTGAATTTGCCTTCCTGGTACATCATGGGCACCAGGCATGACTGCCCATCAACT
TTGTGGAATGGTTCCTTCCTTGTGTTCTCAGGGCTGAACTTTGACTTCCACAGGCCCTTGAAGTAAATGGTGTTAACCAGCACCAG
GGCAGTGAGCTCATCAATGGCTCCTTGGGGGATGACGTCTTTGATGCGGCCTTCAGTCTTATTAGCTACCCAGTTGTTGATGGTCA
CTCTGGATTGCTCCGGATTCTCCTTGAAGTCCAGGGGCTGAAGCTTGGCTCCATAGACAATCTCACTAACGTCTTGATAGCTCTCA
TTGAAGGTAAGGGATTTGTCTCCAAAAAGGCGGTTGGCTGACACCAAGTTAGAGGACTTGTTGGCTTTTCGATAGAGTCGGCAGTT
CAGTTTGGCAAAGAAGAAGTGGATCTGGTCGGATGTCTTCTCGGAGATGGTATCAAATTTAAAAACCTCCATCAGCTGCTTGAGGG
TGTTATTACAAGCACCCAGCTTGGTCATAGCAAACGCCGTGGAGATGCTCAAGGGTGACAGGAAAATGTTGTCGTTGTCGTTCTTG
GAGTCTGCCAGGTGCTGATAGAAGTTAGTGGCAAATCGAGAATTGGCCTTGGACAGTTCCCAGACCCGCCGGTTGGTGGCTTCCGG
AACCTTCTGCTCTAGGACATCCTCCTCCGTGGCCTTCTTCGCAGGGGAGCGGTAAATGCACATGGGGTTCACGGGGATGTCTCGGG
GCTTCGCTATGCAGATGTCGTCCACAGGGTTTCCATGACAGACAGCACAGCCCAAGGCACCAATGAGTAGCAGAGAGAGGAGACAA
AGCTTCCTCTCTCCAGCAACCGCACTTCCTATTCCCGGGGAATACATGGTGGACGCTTCTGCAGAGAAGCCGTGGAGACAGTGCTG
AGCAATCCCTCCG

Figure 30H

SEQ ID NO: 9

AAVALLPAVLLALLAP

SEQ ID NO: 10

AALLPVLLAAP

SEQ ID NO: 11 HIV Tat peptide

GRKKRRQRRRPPQ

SEQ ID NO: 12 Drosophila Antennapedia peptide

RQIKIWFQNRRMKWKK

Peptide-based Cleavable Linking Group

NHCHRAC(O)NHCHRBC(O)-

Figure 30I

Serpinc1 iRNA COMPOSITIONS AND METHODS OF USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application claims priority to U.S. Provisional Application No. 61/638,952, filed on Apr. 26, 2012, to U.S. Provisional Application No. 61/669,249, filed on Jul. 9, 2012, and to U.S. Provisional Application No. 61/734,573, filed on Dec. 7, 2012. The entire contents of each of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 26, 2013, is named 12130100204SeqList.txt and is 458,189 bytes in size.

BACKGROUND OF THE INVENTION

Serpinc1 is a member of the serine proteinase inhibitor (serpin) superfamily. Serpinc1 is a plasma protease inhibitor that inhibits thrombin as well as other activated serine proteases of the coagulation system, such as factors X, IX, XI, XII and VII and, thus, regulates the blood coagulation cascade (see, e.g., FIG. 1). The anticoagulant activity of Serpinc1 is enhanced by the presence of heparin and other related glycosaminoglycans which catalyze the formation of a thrombin:antithrombin (TAT) complexes.

Bleeding disorders, either inherited or acquired, are conditions in which there is inadequate blood clotting. For example, hemophilia is a group of hereditary genetic bleeding disorders that impair the body's ability to control blood clotting or coagulation. Hemophilia A is a recessive X-linked genetic disorder involving a lack of functional clotting Factor VIII and represents 80% of hemophilia cases. Hemophilia B is a recessive X-linked genetic disorder involving a lack of functional clotting Factor IX. It comprises approximately 20% of haemophilia cases. Hemophilia C is an autosomal genetic disorder involving a lack of functional clotting Factor XI. Hemophilia C is not completely recessive, as heterozygous individuals also show increased bleeding.

Although, at present there is no cure for hemophilia, it can be controlled with regular infusions of the deficient clotting factor, e.g., factor VIII in hemophilia A. However, some hemophiliacs develop antibodies (inhibitors) against the replacement factors given to them and, thus, become refractory to replacement coagulation factor. Accordingly, bleeds in such subjects cannot be properly controlled.

The development of high-titer inhibitors to, for example, factor VIII and other coagulation factors, is the most serious complication of hemophilia therapy and makes treatment of bleeds very challenging. Currently, the only strategies to stop bleeds in such subjects are the use of "bypassing agents" such as factor eight inhibitor bypass activity (FEIBA) and activated recombinant factor VII (rFVIIa), plasmapheresis, continuous factor replacement, and immune tolerance therapy, none of which are completely effective. Accordingly, there is a need in the art for alternative treatments for subjects having a bleeding disorder, such as hemophilia.

SUMMARY OF THE INVENTION

The present invention provides iRNA compositions which effect the RNA-induced silencing complex (RISC)-mediated cleavage of RNA transcripts of a Serpinc1 gene. The Serpinc1 gene may be within a cell, e.g., a cell within a subject, such as a human. The present invention also provides methods of using and uses of the iRNA compositions of the invention for inhibiting the expression of a Serpinc1 gene and/or for treating a subject having a disorder that would benefit from inhibiting or reducing the expression of a Serpinc1 gene, e.g., a bleeding disorder, such as hemophilia.

Accordingly, in one aspect, the present invention provides double-stranded ribonucleic acids (dsRNAs) for inhibiting expression of Serpinc1. The dsRNAs comprise a sense strand and an antisense strand, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5.

In another aspect, the present invention provides double-stranded ribonucleic acids (dsRNAs) for inhibiting expression of Serpinc1. The dsRNAs comprise a sense strand and an antisense strand, the antisense strand comprising a region of complementarity which comprises at least 15 contiguous nucleotides differing by no more than 3 nucleotides from any one of the antisense sequences listed in any one of Tables 3, 4, 8, 11, 12, 14, 15, 20, and 21.

In one embodiment, the sense and antisense strands comprise sequences selected from the group consisting of AD-50487.1, AD-50477.1, AD-50483.1, AD-50475.1, AD-50495.1, AD-50476.1, AD-50499.1, AD-50478.1, AD-50489.1, AD-50501.1, AD-50507.1, AD-50484.1, AD-50515.1, AD-50540.1, AD-50528.1, AD-50549.1, AD-50539.1, AD-50534.1, AD-50527.1, AD-50514.1, AD-50509.1, AD-50529.1, AD-54944, AD-56813, AD-57205, AD-57214, and AD-57213 of any one of Tables 3, 4, 8, 11, 12, 14, 15, 20, and 21. In certain embodiments of the invention, the dsRNAs comprise at least one modified nucleotide. In one embodiment, at least one of the modified nucleotides is selected from the group consisting of a 2'-O-methyl modified nucleotide, a nucleotide comprising a 5'-phosphorothioate group, and a terminal nucleotide linked to a cholesteryl derivative or a dodecanoic acid bisdecylamide group. In another embodiment, the modified nucleotide is selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity of the dsRNAs may be at least 17 nucleotides in length, between 19 and 21 nucleotides in length, or 19 nucleotides in length.

In one embodiment, each strand of a dsRNA is no more than 30 nucleotides in length.

At least one strand of a dsRNA may comprise a 3' overhang of at least 1 nucleotide or at least 2 nucleotides.

In certain embodiments, a dsRNA further comprises a ligand. In one embodiment, the ligand is conjugated to the 3' end of the sense strand of the dsRNA.

In some embodiments, the ligand is one or more N-acetylgalactosamine (GalNAc) derivatives attached through a bivalent or trivalent branched linker. In particular embodiments, the ligand is

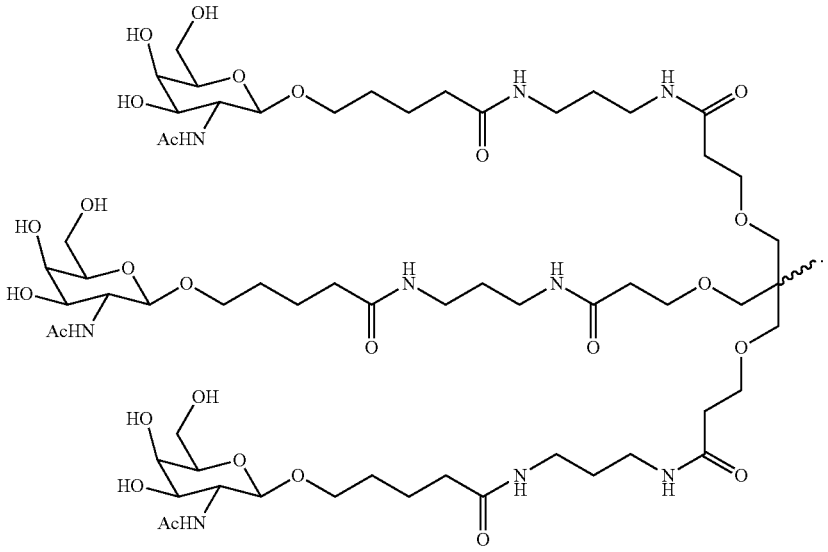

In some embodiments, the RNAi agent is conjugated to the ligand as shown in the following schematic

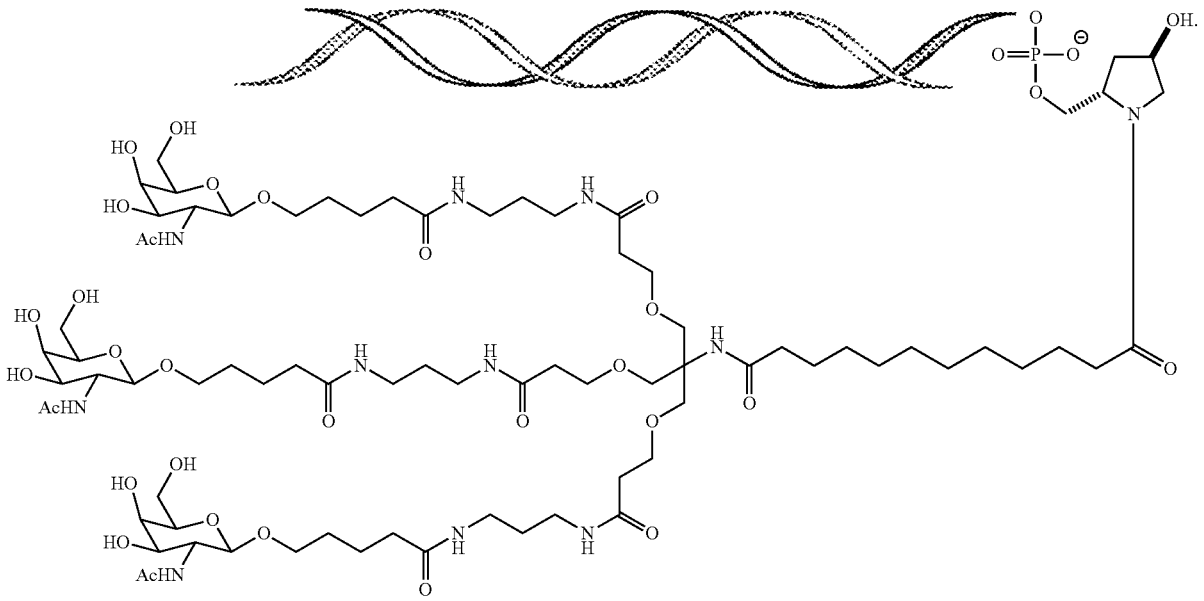

In another embodiment, the RNAi agent is conjugated to the ligand as shown in the following schematic, wherein X is O or S.

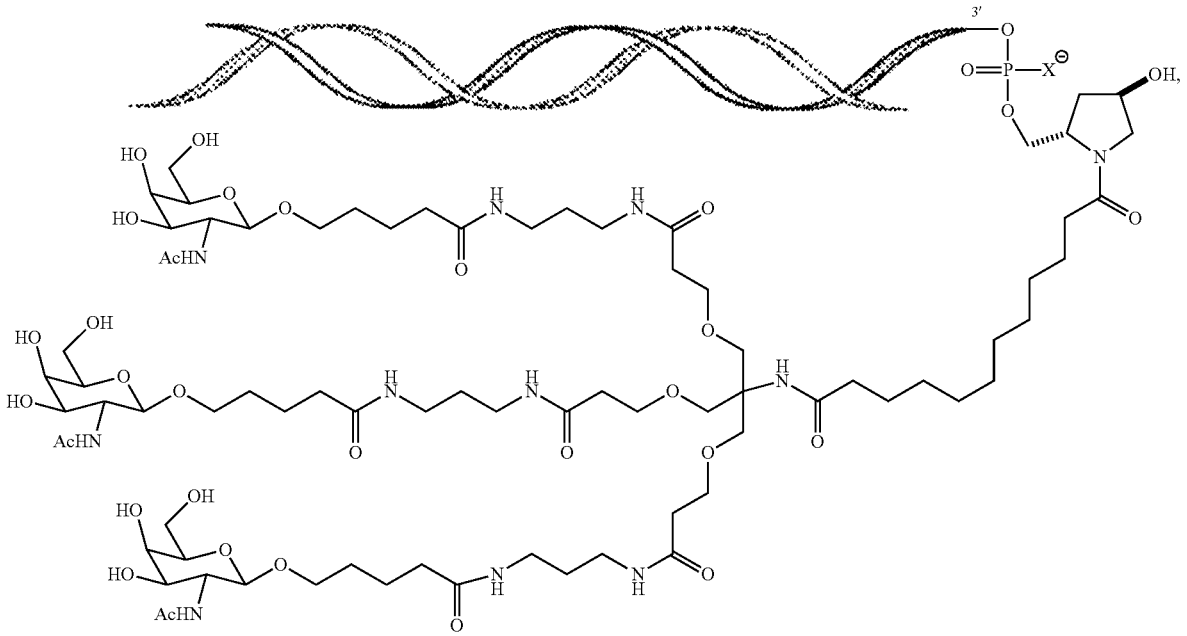

In one embodiment, the region of complementarity of a dsRNA consists of one of the antisense sequences of any one of Tables 3, 4, 8, 11, 12, 14, 15, 20, and 21.

In another embodiment, a dsRNA comprises a sense strand consisting of a sense strand sequence selected from the sequences of any one of Tables 3, 4, 8, 11, 12, 14, 15, 20, and 21, and an antisense strand consisting of an antisense sequence selected from the sequences of any one of Tables 3, 4, 8, 11, 12, 14, 15, 20, and 21.

In another aspect, the present invention provides a cell containing a dsRNA of the invention.

In yet another aspect, the present invention provides a vector encoding at least one strand of a dsRNA, wherein the dsRNA comprises a region of complementarity to at least a part of an mRNA encoding Serpinc1, wherein the dsRNA is 30 base pairs or less in length, and wherein the dsRNA targets the mRNA for cleavage.

The region of complementarity may be least 15 nucleotides in length or 19 to 21 nucleotides in length.

In a further aspect, the present invention provides a cell comprising a vector encoding at least one strand of a dsRNA, wherein the dsRNA comprises a region of complementarity to at least a part of an mRNA encoding Serpinc1, wherein the dsRNA is 30 base pairs or less in length, and wherein the dsRNA targets the mRNA for cleavage.

In one aspect, the present invention provides a pharmaceutical composition for inhibiting expression of a Serpinc1 gene comprising a dsRNA or vector of the invention.

In one embodiment, the pharmaceutical composition further comprises a lipid formulation, such as an MC3, SNALP, or XTC formulation.

In another aspect, the present invention provides methods of inhibiting Serpinc1 expression in a cell. The methods include contacting the cell with the dsRNA or a vector of the invention, and maintaining the cell produced for a time sufficient to obtain degradation of the mRNA transcript of a Serpinc1 gene, thereby inhibiting expression of the Serpinc1 gene in the cell.

The cell may be within a subject, such as a human subject, for example a human subject suffering from a bleeding disorder, e.g., a hemophilia.

In one embodiment of the methods of the invention, Serpinc1 expression is inhibited by at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

In another aspect, the present invention provides methods of treating a subject having a disorder that would benefit from reduction in Serpinc1 expression, e.g., a bleeding disorder, such as a hemophilia. The methods include administering to the subject a therapeutically effective amount of the dsRNA or vector of the invention, thereby treating the subject.

In one aspect, the invention provides methods of preventing at least one symptom, e.g., bleeding, in a subject having a disorder that would benefit from reduction in Serpinc1 expression, e.g., hemophilia. The methods include administering to the subject a therapeutically effective amount of the RNA, e.g., dsRNA, or vector of the invention, thereby preventing at least one symptom in the subject having a disorder that would benefit from reduction in Serpinc1 expression.

The disorder may be a bleeding disorder, such as a hemophilia.

In one embodiment, the administration of the dsRNA to the subject causes an increase in blood clotting and/or a decrease in Serpinc1 protein expression and/or accumulation.

In one embodiment, the dsRNA is conjugated to a ligand, e.g., at the 3'-end of the sense strand of the dsRNA. In one embodiment the ligand is an N-acetylgalactosamine (GalNAc) derivative.

In one embodiment, the dsRNA is administered at a dose of about 0.01 mg/kg to about 10 mg/kg, e.g., about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 [mg/mg] *mg/kg*, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 [mg/mg] *mg/kg*, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 [mg/mg] *mg/kg*, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 [mg/mg] *mg/kg*, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 [mg/mg] *mg/kg*, about 1.5 to about 20 [mg/kb] *mg/kg*, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The dsRNA, e.g., conjugated to a ligand, may be administered to the subject once a week or twice a month.

In another aspect, the present invention provides methods of inhibiting the expression of Serpinc1 in a subject. The methods include administering to the subject a therapeutically effective amount of the dsRNA or a vector of the invention, thereby inhibiting the expression of Serpinc1 in the subject.

In one embodiment, the dsRNA is conjugated to a ligand, e.g., at the 3'-end of the sense strand of the dsRNA. In one embodiment the ligand is an N-acetylgalactosamine (GalNAc) derivative.

In one embodiment, the dsRNA is administered at a dose of about 0.01 mg/kg to about 10 mg/kg, e.g., about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 [mg/mg] *mg/kg*, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 [mg/mg] *mg/kg*, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 [mg/mg] *mg/kg*, about 1.5 to about 20 [mg/kb] *mg/kg*, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The dsRNA, e.g., conjugated to a ligand, may be administered to the subject once a week or twice a month.

In yet another aspect, the invention provides kits for performing the methods of the invention. In one embodiment, the invention provides a kit for performing a method of inhibiting expression of Serpinc1 in a cell by contacting a cell with a double stranded RNAi agent in an amount effective to inhibit expression of the Serpinc1 gene in the cell. The kit comprises an RNAi agent and instructions for use and, optionally, means for administering the RNAi agent to a subject.

BRIEF DESCRIPTION OF THE DRAWINGS

FIG. 30A shows the nucleotide sequence of Homo sapiens serpin peptidase inhibitor, Glade C (antithrombin), member 1 (SERPINC1) (SEQ ID NO:1); FIG. 30B shows the nucleotide sequence of Macaca mulatta serpin peptidase inhibitor, Glade C (antithrombin), member 1 (SERPINC1) (SEQ ID NO:2); FIG. 30C shows the nucleotide sequence of Mus musculus serine (or cysteine) peptidase inhibitor, Glade C (antithrombin), member 1 (Serpinc1) (SEQ ID NO:3); FIG. 30D shows the nucleotide sequence of Rattus norvegicus serpin peptidase inhibitor, Glade C (antithrombin), member 1 (Serpinc1) (SEQ ID NO:4); FIG. 30E shows the reverse complement of SEQ ID NO:1 (SEQ ID NO:5); FIG. 30F shows the reverse complement of SEQ ID NO:2 (SEQ ID NO:6); FIG. 30G shows the reverse complement of SEQ ID NO:3 (SEQ ID NO:7); FIG. 30H shows the reverse complement of SEQ ID NO:4 (SEQ ID NO:8); and FIG. 30I shows the amino acid sequence of an exemplary hydrophobic MTS-containing peptide, RFGF (SEQ ID NO: 9); the amino acid sequence of an exemplary RFGF analogue (SEQ ID NO: 10); the amino acid sequence of the HIV Tat protein (SEQ ID NO: 11); the amino acid sequence of the Drosophila Antennapedia protein (SEQ ID NO: 12); and the amino acid sequence of an exemplary Peptide-based Cleavable Linking Group.

DETAILED DESCRIPTION OF THE INVENTION

Figure 1:
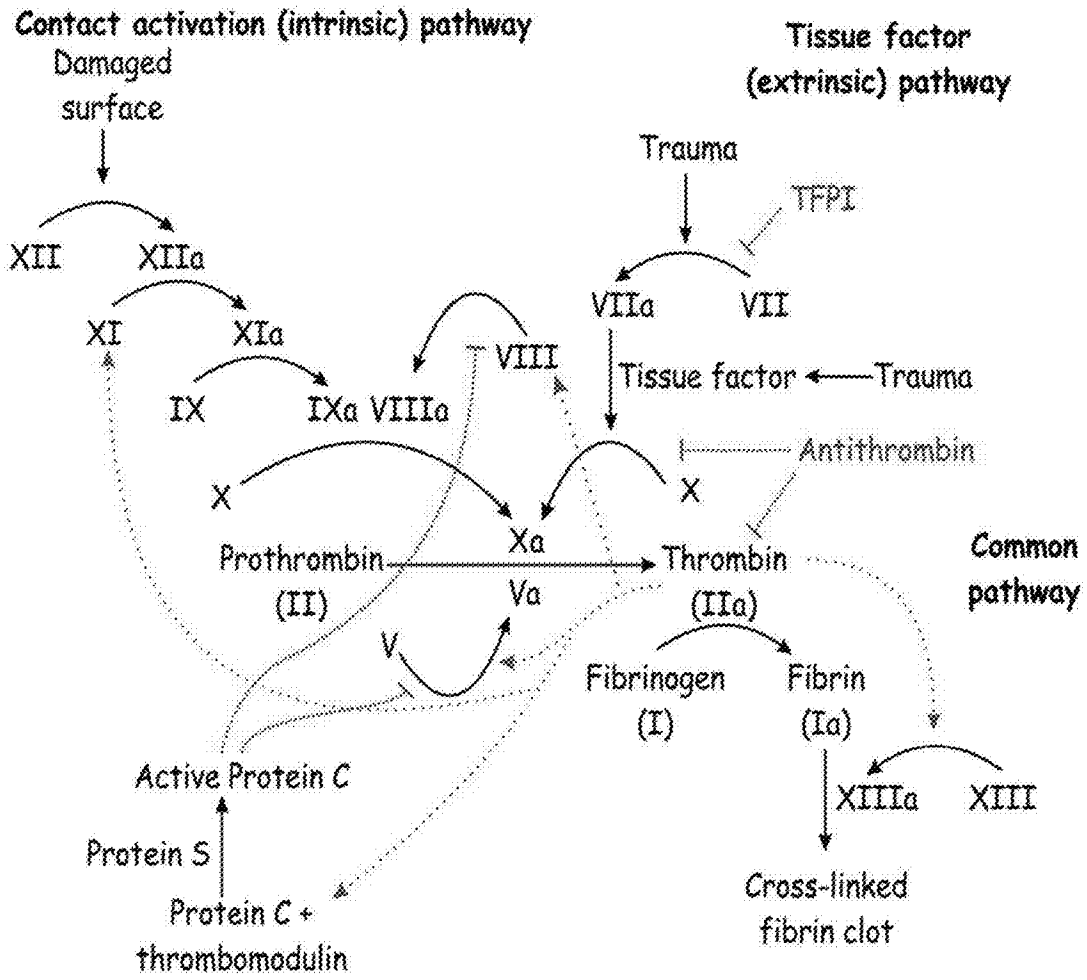
FIG. 1 is a schematic of the blood coagulation cascade.

The present invention provides iRNA compositions which effect the RNA-induced silencing complex (RISC)-mediated cleavage of RNA transcripts of a Serpinc1 gene. The Serpinc1 gene may be within a cell, e.g., a cell within a subject, such as a human. The present invention also provides methods of using the iRNA compositions of the invention for inhibiting the expression of a Serpinc1 gene and/or for treating a subject having a disorder that would benefit from inhibiting or reducing the expression of a Serpinc1 gene, e.g., a bleeding disorder, such as hemophilia. The present invention further provides methods for preventing at least one symptom, e.g., bleeding, in a subject having a disorder that would benefit from inhibiting or reducing the expression of a Serpinc1 gene, e.g., a bleeding disorder, such as hemophilia.

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a Serpinc1 gene. The use of these iRNAs enables the targeted degradation of mRNAs of a Serpinc1 gene in mammals. Very low dosages of Serpinc1 iRNAs, in particular, can specifically and efficiently mediate RNA interference (RNAi), resulting in significant inhibition of expression of a Serpinc1 gene. The present inventors have demonstrated that iRNAs targeting Serpinc1 can mediate RNAi in vitro and in vivo, resulting in significant inhibition of expression of a Serpinc1 gene. Thus, methods and compositions including these iRNAs are useful for treating a subject who would benefit by a reduction in the levels and/or activity of a Serpinc1 protein, such as a subject having a bleeding disorder, e.g., hemophilia.

The following detailed description discloses how to make and use compositions containing iRNAs to inhibit the expression of a Serpinc1 gene, as well as compositions, uses, and methods for treating subjects having diseases and disorders that would benefit from inhibition and/or reduction of the expression of this gene.

I. DEFINITIONS

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Serpinc1" refers to a particular polypeptide expressed in a cell. Serpinc1 is also known as serpin peptidase inhibitor, Glade C (antithrombin), member 1; antithrombin III; AT3; antithrombin; and heparin cofactor 1. The sequence of a human Serpinc1 mRNA transcript can be found at, for example, GenBank Accession No. GI:254588059 (NM_000488; SEQ ID NO:1). The sequence of rhesus Serpinc1 mRNA can be found at, for example, GenBank Accession No. GI:157167169 (NM_001104583; SEQ ID NO:2). The sequence of mouse Serpinc1 mRNA can be found at, for example, GenBank Accession No. GI:237874216 (NM_080844; SEQ ID NO:3). The sequence of rat Serpinc1 mRNA can be found at, for example, GenBank Accession No. GI:58865629 (NM_001012027; SEQ ID NO:4).

The term"Serpinc1" as used herein also refers to a particular polypeptide expressed in a cell by naturally occurring DNA sequence variations of the Serpinc1 gene, such as a single nucleotide polymorphism in the Serpinc1 gene. Numerous SNPs within the Serpinc1 gene have been identified and may be found at, for example, NCBI dbSNP (see, e.g., www.ncbi.nlm.nih.gov/snp). Non-limiting examples of SNPs within the Serpinc1 gene may be found at, NCBI dbSNP Accession Nos. rs677; rs5877; rs5878; rs5879; rs941988; rs941989; rs1799876; rs19637711; rs2008946; and rs2227586. As used herein, "target sequence" refers to a contiguous portion of the nucleotide sequence of an mRNA molecule formed during the transcription of a Serpinc1 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a Serpinc1 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Serpinc1 in a cell, e.g., a cell within a subject, such as a mammalian subject.

In one embodiment, an RNAi agent of the invention includes a single stranded RNA that interacts with a target RNA sequence, e.g., a Serpinc1 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the invention relates to a single stranded RNA (siRNA) generated within a cell and which promotes the formation of a RISC complex to effect silencing of the target gene, i.e., a Serpinc1 gene. Accordingly, the term "siRNA" is also used herein to refer to an RNAi as described above.

In another embodiment, the RNAi agent may be a single-stranded siRNA that is introduced into a cell or organism to inhibit a target mRNA. The single-stranded siRNAs are generally 15-30 nucleotides and are chemically modified.

The design and testing of single-stranded siRNAs are described in U.S. Pat. No. 8,101,348 and in Lima et al., (2012) Cell 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150; 883-894.

In another aspect, the agent is a single-stranded antisense RNA molecule that inhibits a target via an antisense inhibition mechanism. The single-stranded antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. Alternatively, the single-stranded antisense RNA molecule inhibits a target mRNA by hydridizing to the target and cleaving the target through an RNaseH cleavage event. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences in any one of Tables 3, 4, 8, 11, 12, 14, 15, 20, and 21.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a Serpinc1 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, and 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence, e.g., a Serpinc1 mRNA. As used herein, the term "region of complementarity" refers to the region on the antisense strand that is substantially complementary to a sequence, for example a target sequence, e.g., a Serpinc1 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand," or "passenger strand" as used herein, refers to the strand of an iRNA that includes a region that is substantially complementary to a region of the antisense strand as that term is defined herein.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Serpinc1). For example, a polynucleotide is complementary to at least a part of a Serpinc1 mRNA if the sequence is substantially complementary to a non-interrupted portion of an mRNA encoding Serpinc1.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

The term "inhibiting," as used herein, is used interchangeably with "reducing," "silencing," "downregulating," "suppressing" and other similar terms, and includes any level of inhibition.

The phrase "inhibiting expression of a Serpinc1," as used herein, includes inhibition of expression of any Serpinc1 gene (such as, e.g., a mouse Serpinc1 gene, a rat Serpinc1 gene, a monkey Serpinc1 gene, or a human Serpinc1 gene) as well as variants or mutants of a Serpinc1 gene that encodes a Serpinc1 protein.

"Inhibiting expression of a Serpinc1 gene" includes any level of inhibition of a Serpinc1 gene, e.g., at least partial suppression of the expression of a Serpinc1 gene, such as an inhibition by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a Serpinc1 gene may be assessed based on the level of any variable associated with Serpinc1 gene expression, e.g., Serpinc1 mRNA level, Serpinc1 protein level, or, for example, thrombin:antithrombin complex levels as a measure of thrombin generation potential, bleeding time, prothrombin time (PT), platelet count, and/or activated partial thromboplastin time (aPTT). Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of a Serpinc1 gene, is assessed by a reduction of the amount of Serpinc1 mRNA which can be isolated from or detected in a first cell or group of cells in which a Serpinc1 gene is transcribed and which has or have been treated such that the expression of a Serpinc1 gene is inhibited, as compared to a second cell or group of cells substantially identical to the first cell or group of cells but which has or have not been so treated (control cells). The degree of inhibition may be expressed in terms of $$\frac{(\text{mRNA in control cells}) - (\text{mRNA in treated cells})}{(\text{mRNA in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

The term "SNALP" refers to a stable nucleic acid-lipid particle. A SNALP is a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817, the entire contents of which are hereby incorporated herein by reference. Examples of "SNALP" formulations are described below.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in Serpinc1 expression; a human at risk for a disease, disorder or condition that would benefit from reduction in Serpinc1 expression; a human having a disease, disorder or condition that would benefit from reduction in Serpinc1 expression; and/or human being treated for a disease, disorder or condition that would benefit from reduction in Serpinc1 expression as described herein. As used herein, the terms "treating" or "treatment" refer to a beneficial or desired result including, but not limited to, alleviation or amelioration of one or more symptoms, diminishing the extent of bleeding, stabilized (i.e., not worsening) state of bleeding, amelioration or palliation of the bleeding, whether detectable or undetectable. "Treatment" can also mean prolonging survival as compared to expected survival in the absence of treatment.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, "prevention" or "preventing," when used in reference to a disease, disorder or condition thereof, that would benefit from a reduction in expression of a Serpinc1 gene, refers to a reduction in the likelihood that a subject will develop a symptom associated with a such a disease, disorder, or condition, e.g., a symptom such as a bleed. The likelihood of developing a bleed is reduced, for example, when an individual having one or more risk factors for a bleed either fails to develop a bleed or develops a bleed with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "bleeding disorder" is a disease or disorder that results in poor blood clotting and/or excessive bleeding. A bleeding disorder may be an inherited disorder, such as a hemophilia or von Willebrand's disease, or an acquired disorder, associated with, for example, disseminated intravascular coagulation, pregnancy-associated eclampsia, vitamin K deficiency, an autoimmune disorder, inflammatory bowel disease, ulcerative colitis, a dermatologic disorder (e.g., psoriasis, pemphigus), a respiratory disease (e.g., asthma, chronic obstructive pulmonary disease), an allergic drug reaction, e.g., the result of medications, such as aspirin, heparin, and warfarin, diabetes, acute hepatitis B infection, acute hepatitis C infection, a malignancy or solid tumor (e.g., prostate, lung, colon, pancreas, stomach, bile duct, head and neck, cervix, breast, melanoma, kidney, and/or a hematologic malignancy). In one embodiment, an inherited bleeding disorder is a hemophilia, e.g., hemophilia A, B, or C. In one embodiment, a subject having an inherited bleeding disorder, e.g., a hemophilia, has developed inhibitors, e.g., alloantibody inhibitors, to replacement coagulation therapies and is referred to herein as an "inhibitor subject." In one embodiment, the inhibitor subject has hemophilia A. In another embodiment, the inhibitor subject has hemophilia B. In yet another embodiment, the inhibitor subject has hemophilia C.

"Therapeutically effective amount," as used herein, is intended to include the amount of an RNAi agent that, when administered to a subject having a bleeding disorder and bleeding, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a bleeding disorder but not bleeding, e.g., a subject having a bleeding disorder and scheduled for surgery, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs OF THE INVENTION

Described herein are iRNAs which inhibit the expression of a Serpinc1 gene. In one embodiment, the iRNA agent includes double-stranded ribonucleic acid (dsRNA) molecules for inhibiting the expression of a Serpinc1 gene in a cell, such as a cell within a subject, e.g., a mammal, such as a human having a bleeding disorder, e.g., an inherited bleeding disorder. The dsRNA includes an antisense strand having a region of complementarity which is complementary to at least a part of an mRNA formed in the expression of a Serpinc1 gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the Serpinc1 gene, the iRNA inhibits the expression of the Serpinc1 gene (e.g., a human, a primate, a non-primate, or a bird Serpinc1 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a Serpinc1 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 20 nucleotides in length, or between about 25 and about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target Serpinc1 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in any one of Tables 3, 4, 8, 11, 12, 14, 15, 20, and 21, and the corresponding antisense strand of the sense strand is selected from the group of sequences of any one of Tables 3, 4, 8, 11, 12, 14, 15, 20, and 21. In this aspect, one of the two sequences is complementary to the other of the two sequences, with one of the sequences being substantially complementary to a sequence of an mRNA generated in the expression of a Serpinc1 gene. As such, in this aspect, a dsRNA will include two oligonucleotides, where one oligonucleotide is described as the sense strand in any one of Tables 3, 4, 8, 11, 12, 14, 15, 20, and 21, and the second oligonucleotide is described as the corresponding antisense strand of the sense strand in any one of Tables 3, 4, 8, 11, 12, 14, 15, 20, and 21. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 3, 4, 8, 11, 12, 14, 15, 20, and 21 are described as modified and/or conjugated sequences, the RNA of the iRNA of the invention e.g., a dsRNA of the invention, may comprise any one of the sequences set forth in Tables 3, 4, 8, 11, 12, 14, 15, 20, and 21 that is un-modified, unconjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., EMBO 2001, 20:6877-6888). However, others have found that shorter or longer RNA duplex structures can also be effective (Chu and Rana (2007) RNA 14:1714-1719; Kim et al. (2005) Nat Biotech 23:222-226). In the embodiments described above, by virtue of the nature of the oligonucleotide sequences provided in any one of Tables 3, 4, 8, 11, 12, 14, 15, 20, and 21, dsRNAs described herein can include at least one strand of a length of minimally 21 nucleotides. It can be reasonably expected that shorter duplexes having one of the sequences of any one of Tables 3, 4, 8, 11, 12, 14, 15, 20, and 21 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3, 4, 8, 11, 12, 14, 15, 20, and 21, and differing in their ability to inhibit the expression of a Serpinc1 gene by not more than about 5, 10, 15, 20, 25, or 30% inhibition from a dsRNA comprising the full sequence, are contemplated to be within the scope of the present invention.

In addition, the RNAs provided in any one of Tables 3, 4, 8, 11, 12, 14, 15, 20, and 21 identify a site(s) in a Serpinc1 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 3, 4, 8, 11, 12, 14, 15, 20, and 21 coupled to additional nucleotide sequences taken from the region contiguous to the selected sequence in a Serpinc1 gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 3, 4, 8, 11, 12, 14, 15, 20, and 21 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 3, 4, 8, 11, 12, 14, 15, 20, and 21, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of a Serpinc1 gene, generally does not contain any mismatch within the central 13 nucleotides. The methods described herein or methods known in the art can be used to determine whether an iRNA containing a mismatch to a target sequence is effective in inhibiting the expression of a Serpinc1 gene. Consideration of the efficacy of iRNAs with mismatches in inhibiting expression of a Serpinc1 gene is important, especially if the particular region of complementarity in a Serpinc1 gene is known to have polymorphic sequence variation within the population.

III. MODIFIED iRNAs OF THE INVENTION

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160, 109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene(methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nO[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy(2'-$OCH_3$), 2'-aminopropoxy(2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley &

Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

IV. iRNAs CONJUGATED TO LIGANDS

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVLLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the Drosophila Antennapedia protein (RQIKIWFQNRRMKWKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as Formula II

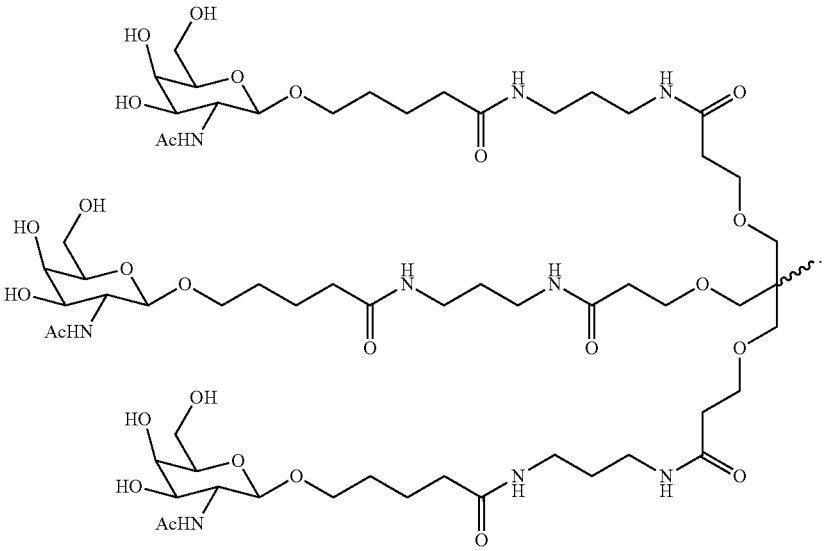

In another embodiment, a carbohydrate conjugate for use in the compositions and methods of the invention is selected from the group consisting of:
Formula II
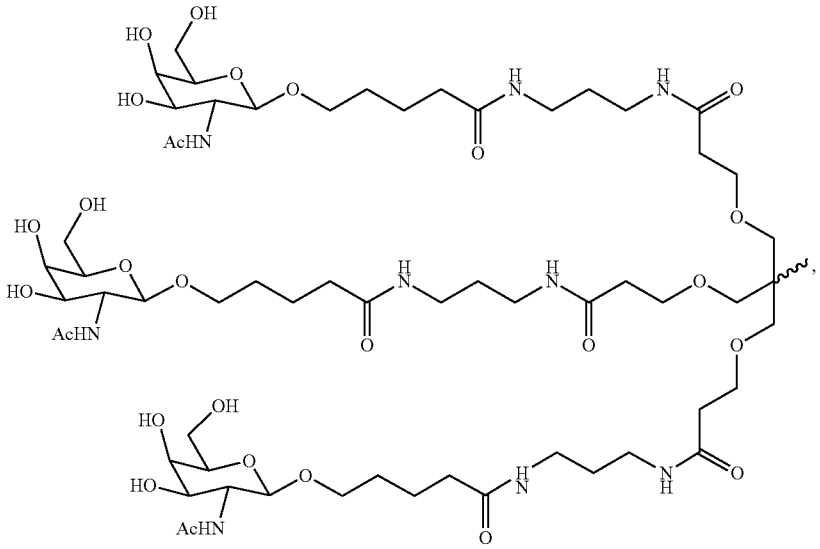
Formula III
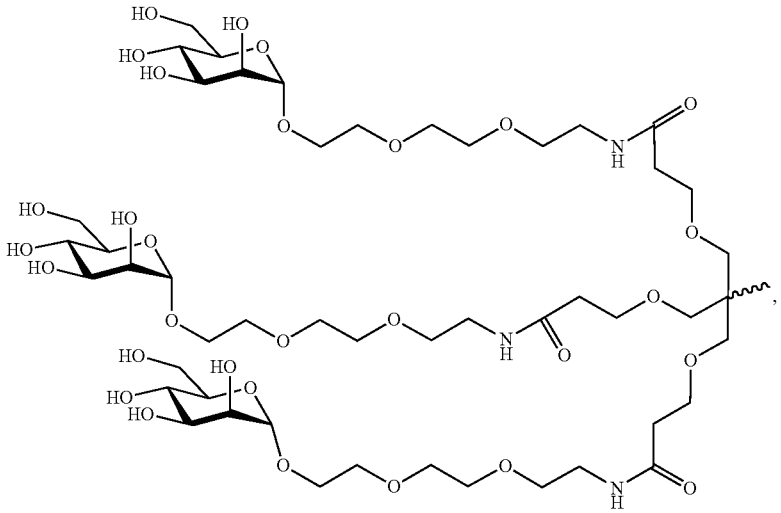
Formula IV
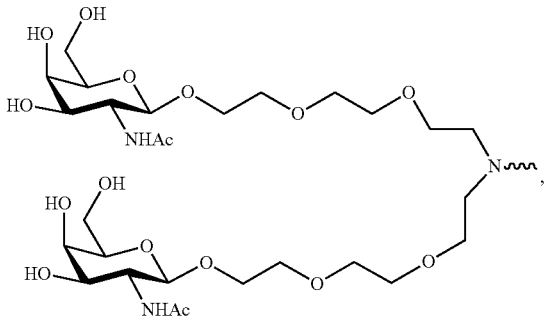
Formula V
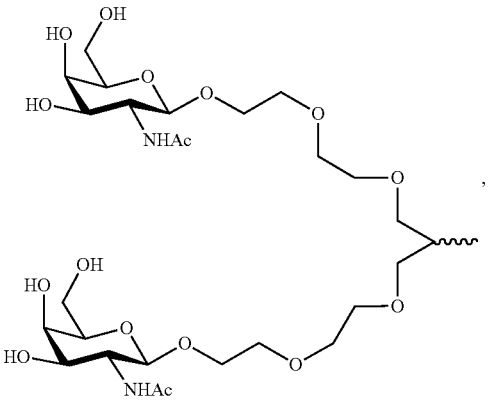

-continued
Formula VI
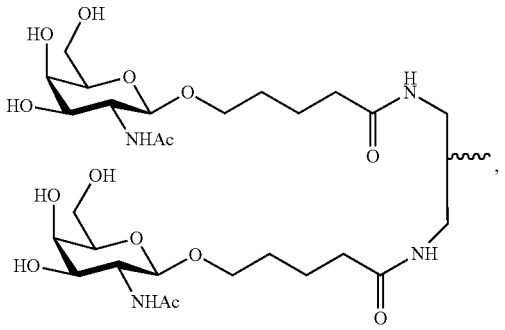
Formula VII
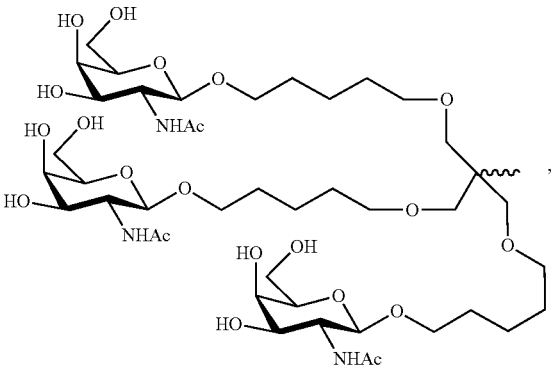
Formula VIII
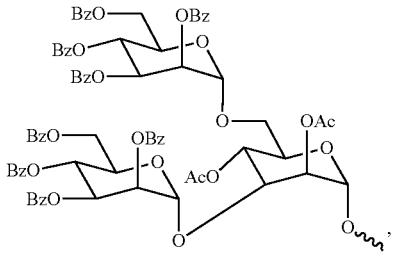
Formula IX
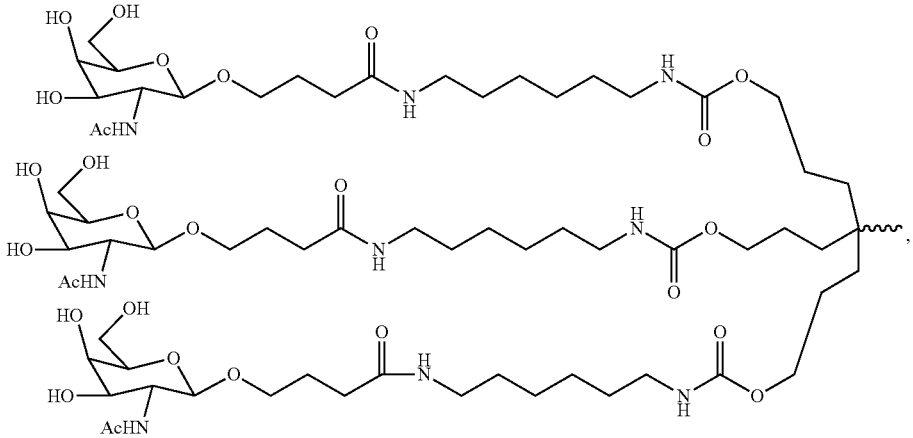
Formula X
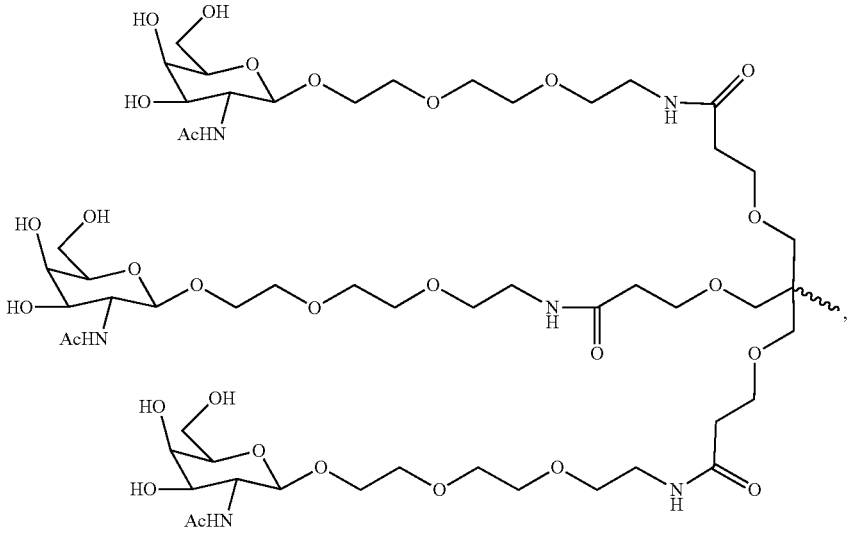

-continued
Formula XI
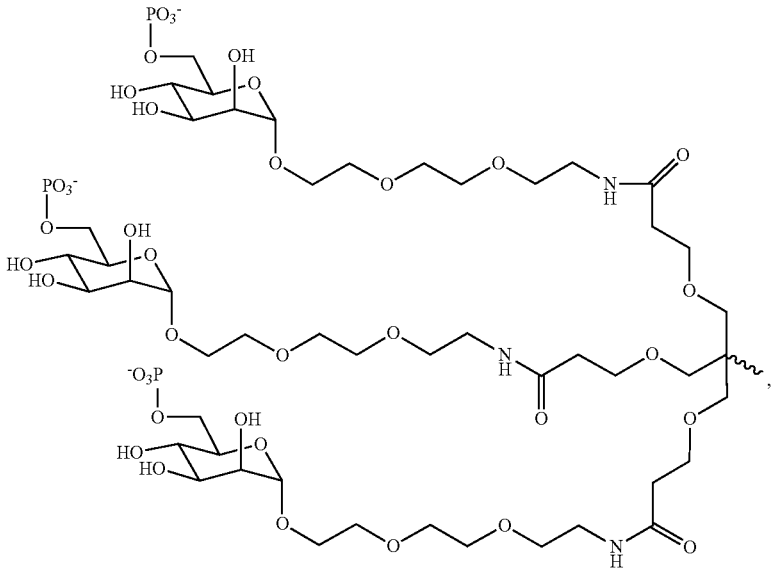
Formula XII
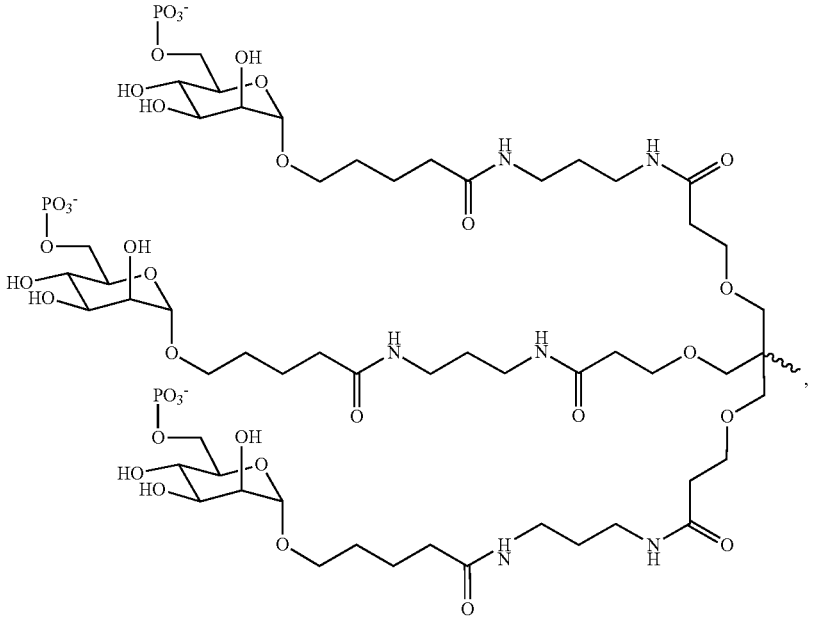
Formula XIII
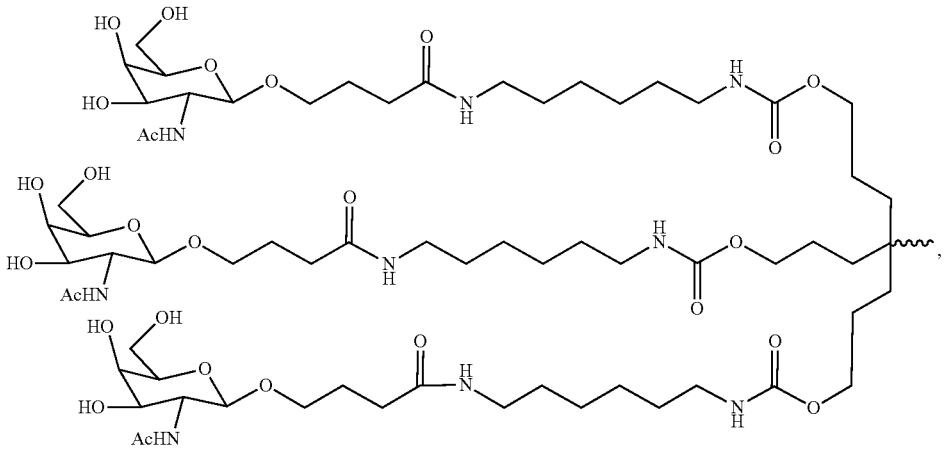

-continued
Formula XIV
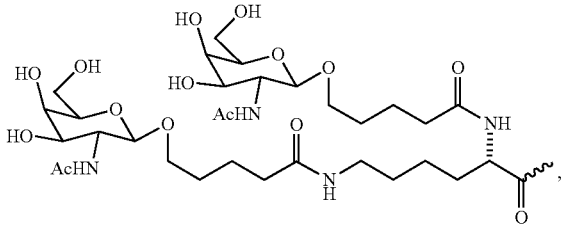
Formula XV
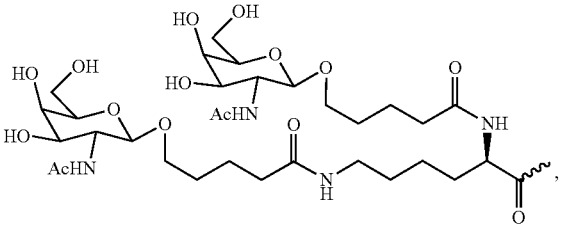
Formula XVI
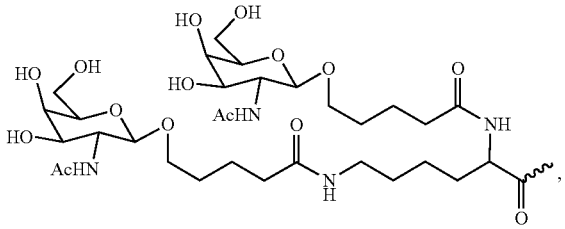
Formula XVII
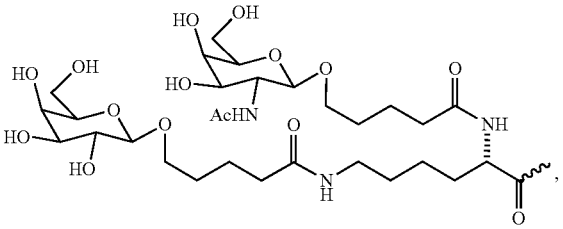
Formula XVIII
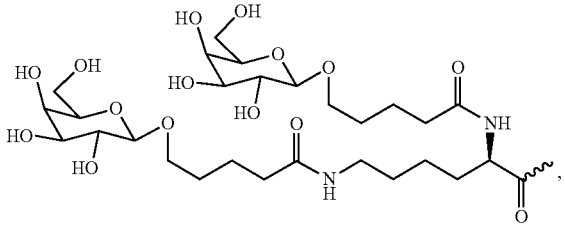
Formula XIX
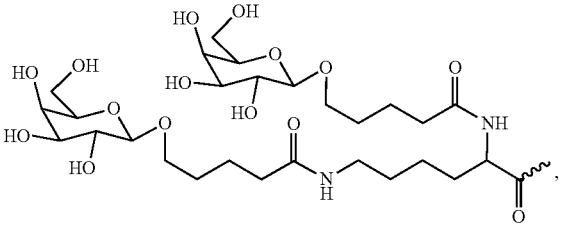
Formula XX
Formula XXI
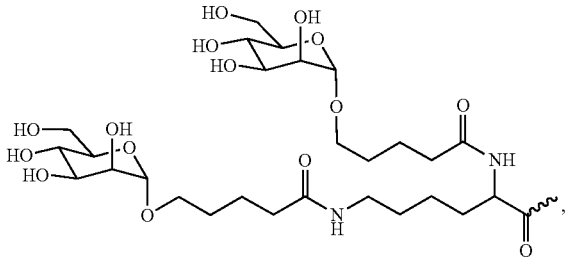
Formula XXII
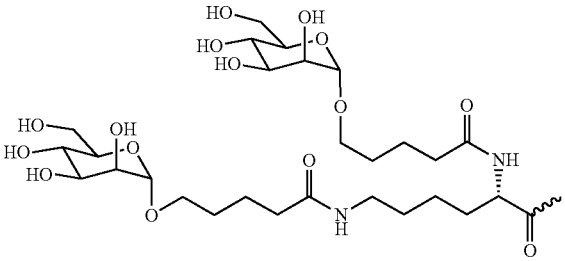
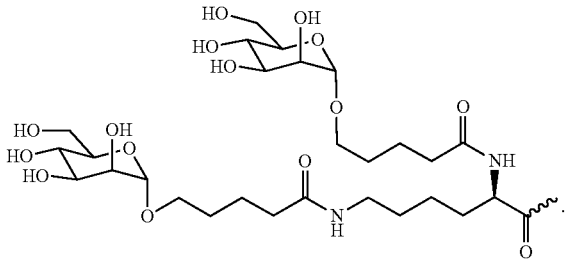
Another representative carbohydrate conjugate for use in the embodiments described herein includes, but is not limited to,

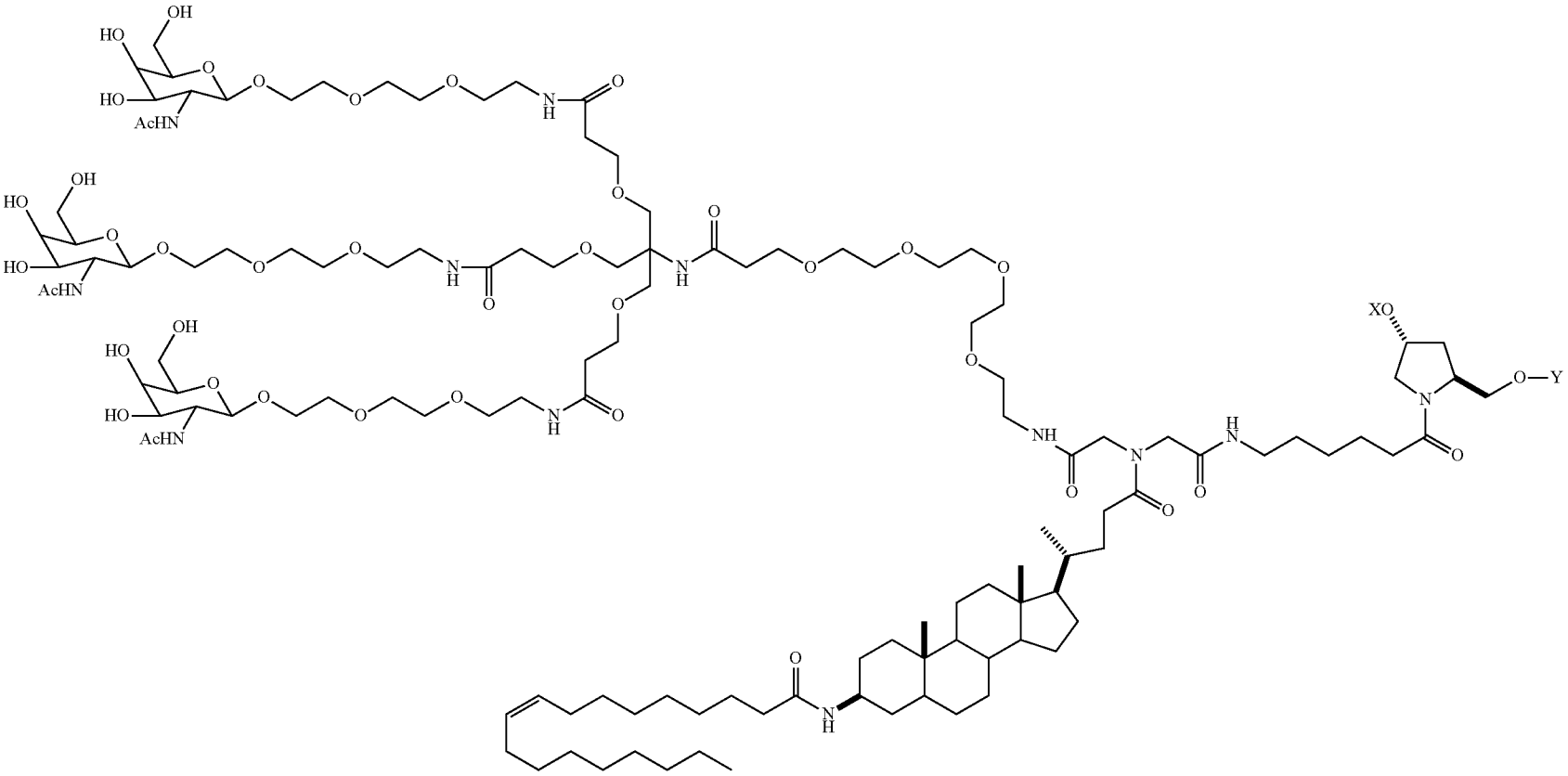

(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O), where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

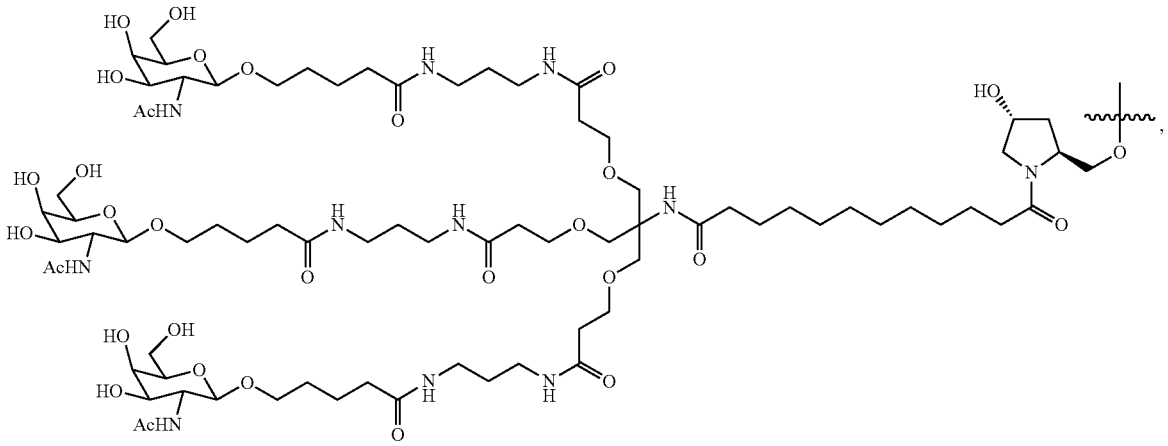

-continued
(Formula XXV)
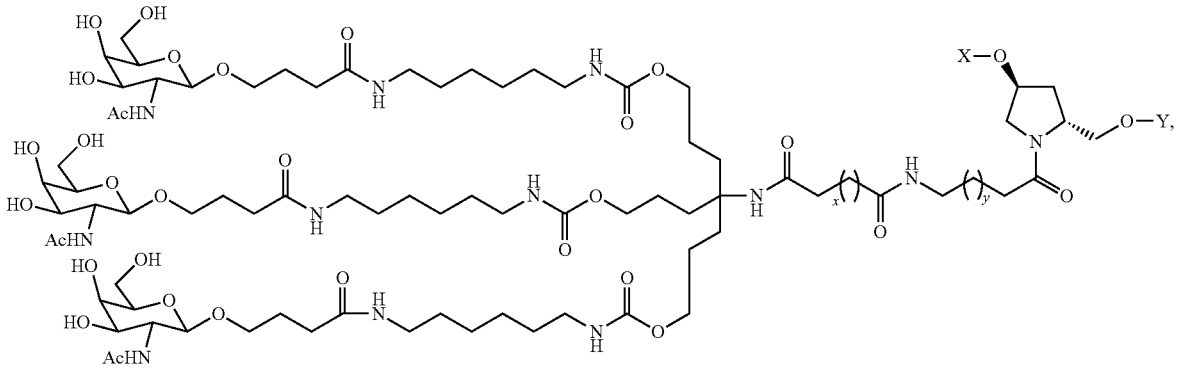
x = 1-30
y = 1-15
(Formula XXVI)
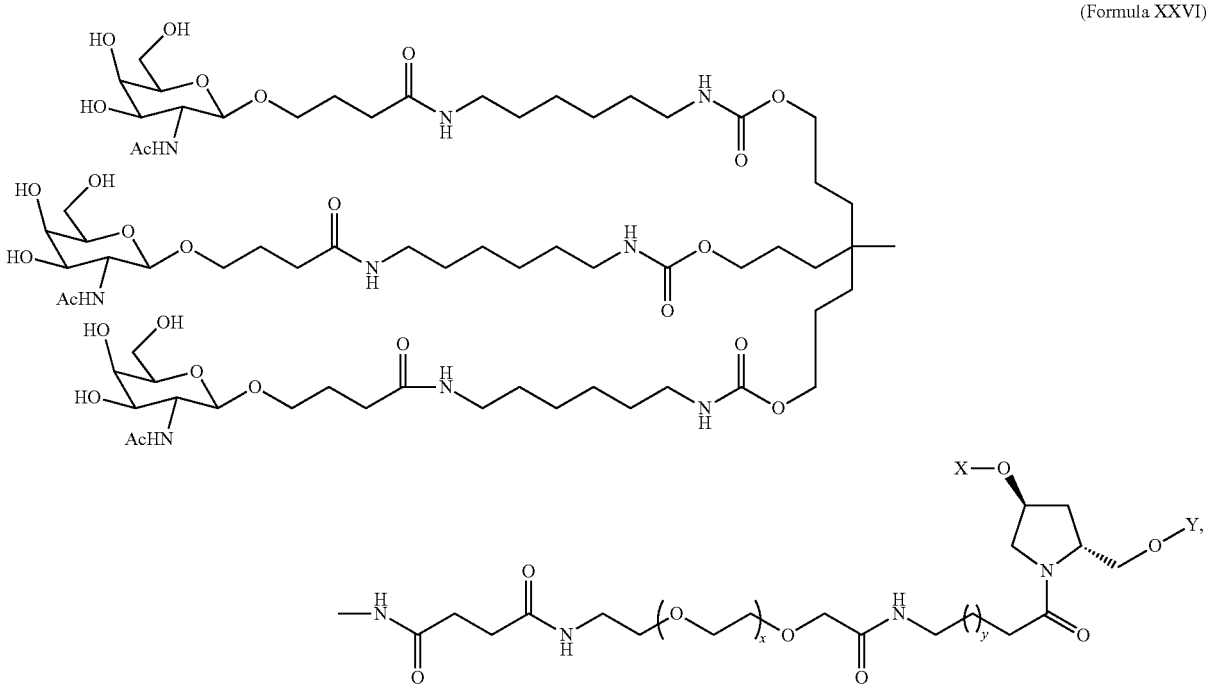
x = 1-30
y = 1-15
(Formula XXVII)
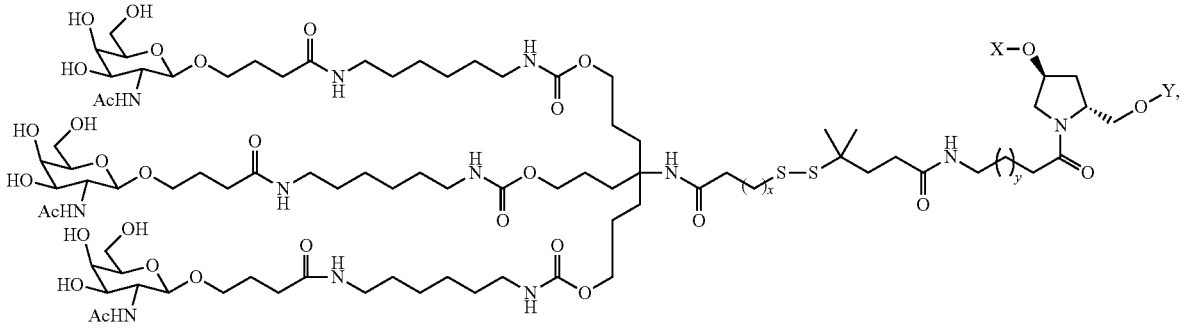
x = 0-30
y = 1-15

-continued
(Formula XXVIII)
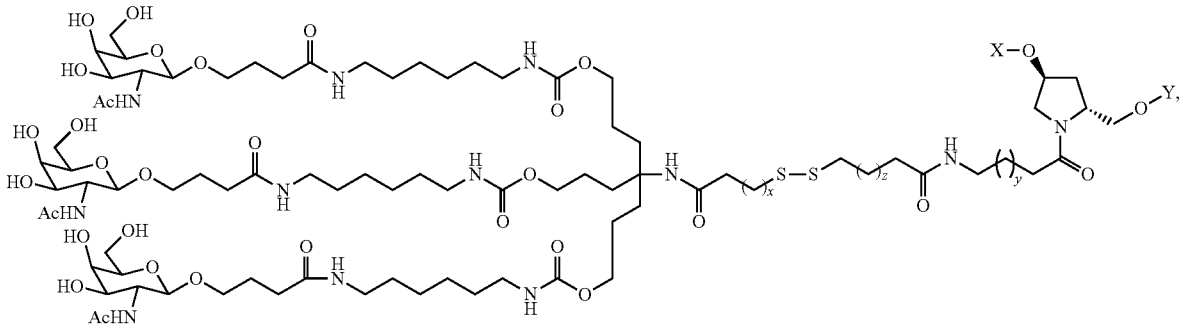
x = 0-30
y = 1-15
z = 1-20
(Formula XXIX)
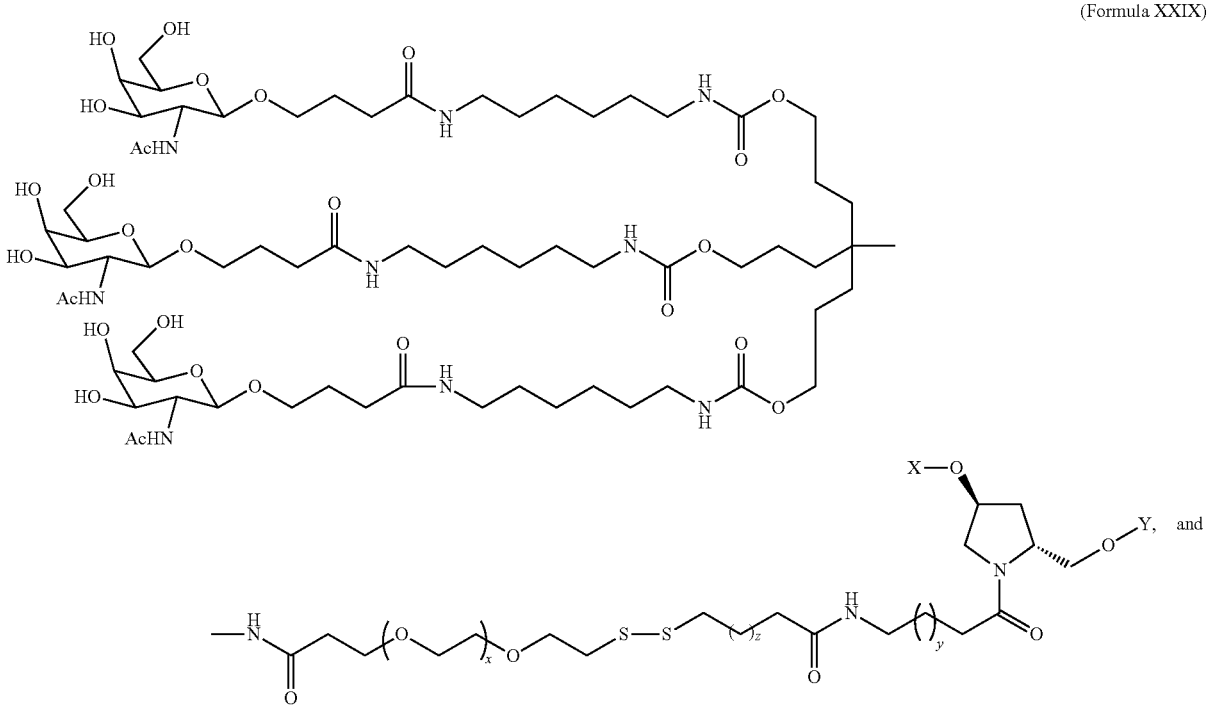
x = 1-30
y = 1-15
z = 1-20
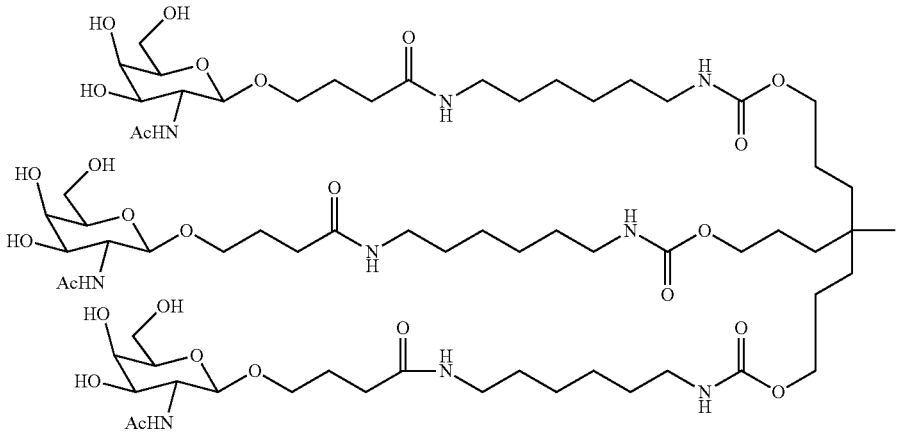

-continued

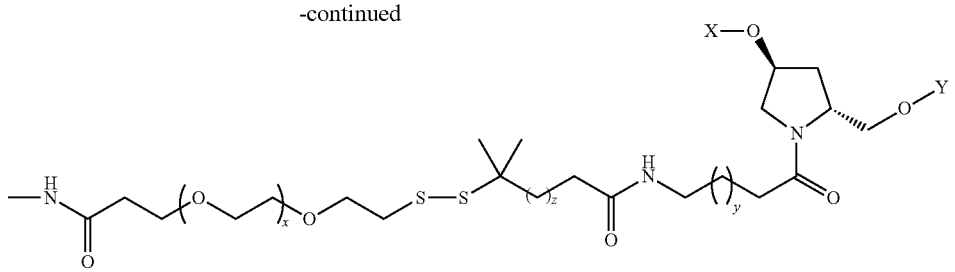

x = 1-30
y = 1-15
z = 1-20

(Formula XXX), when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXI)-(XXXIV):

Formula XXXI

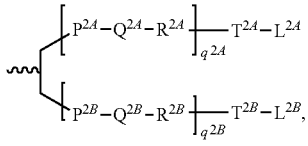

Formula XXXII

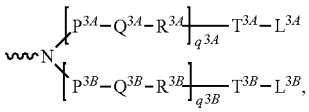

Formula XXXIII

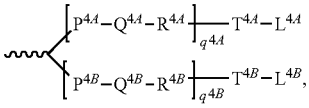

Formula XXXIV

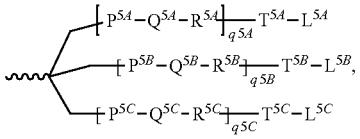

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')═C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—$CH(R^a)$—NH—, CO, CH═N—O,

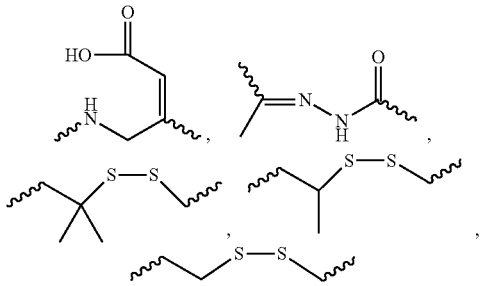

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

Formula XXXV

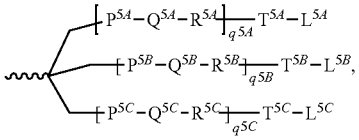

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245, 022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. DELIVERY OF AN iRNA OF THE INVENTION

The delivery of an iRNA of the invention to a cell e.g., a cell within a subject, such as a human subject (e.g., a subject in need thereof, such as a subject having a bleeding disorder) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S, and Julian R L. (1992) Trends Cell. Biol. 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol. 327: 761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the Serpinc1 gene can be expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), Nat. Biotech. 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. PHARMACEUTICAL COMPOSITIONS OF THE INVENTION

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a Serpinc1 gene, e.g. a bleeding disorder. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a Serpinc1 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 [mg/mg] *mg/kg*, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 [mg/mg] *mg/kg*, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 [mg/mg] *mg/kg*, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 [mg/mg] *mg/kg*, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 [mg/mg] *mg/kg*, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 [mg/mg] *mg/kg*, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 [mg/mg] *mg/kg*, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered a therapeutic amount of iRNA, such as about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a bleeding disorder that would benefit from reduction in the expression of Serpinc1. Such models can be used for in vivo testing of iRNA, as well as for determining a therapeutically effective dose. Suitable mouse models are known in the art and include, for example, Hemophilia A mouse models and Hemophilia B mouse models, e.g., mice containing a knock-out of a clotting factor gene, such as those described in Bolliger, et al. (2010) Thromb Haemost 103: 1233-1238, Bi L, et al. (1995) Nat Genet. 10: 119-21, Lin et al. (1997) Blood 90: 3962-6, Kundu et al. (1998) Blood 92: 168-74, Wang et al. (1997) Proc Natl Acad Sci USA 94: 11563-6, and Jin, et al. (2004) Blood 104:1733.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The iRNA can be delivered in a manner to target a particular tissue, such as the liver (e.g., the hepatocytes of the liver). Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., Proc. Natl. Acad. Sci., USA 8:7413-7417, 1987; U.S. Pat. No. 4,897,355; U.S. Pat. No. 5,171,678; Bangham, et al. M. Mol. Biol. 23:238, 1965; Olson, et al. Biochim. Biophys. Acta 557:9, 1979; Szoka, et al. Proc. Natl. Acad. Sci. 75: 4194, 1978; Mayhew, et al. Biochim. Biophys. Acta 775:169, 1984; Kim, et al. Biochim. Biophys. Acta 728:339, 1983; and Fukunaga, et al. Endocrinol. 115:757, 1984. Commonly used techniques for preparing lipid aggregates of appropriate size for use as delivery vehicles include sonication and freeze-thaw plus extrusion (see, e.g., Mayer, et al. Biochim. Biophys. Acta 858:161, 1986). Microfluidization can be used when consistently small (50 to 200 nm) and relatively uniform aggregates are desired (Mayhew, et al. Biochim. Biophys. Acta 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, J. Biol. Chem. 269:2550, 1994; Nabel, Proc. Natl. Acad. Sci. 90:11307, 1993; Nabel, Human Gene Ther. 3:649, 1992; Gershon, Biochem. 32:7143, 1993; and Strauss EMBO J. 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. S.T.P. Pharma. Sci., 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Choi") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. Nos. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure.

Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, e.g., to form a SPLP, pSPLP, SNALP, or other nucleic acid-lipid particle.

As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N, N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

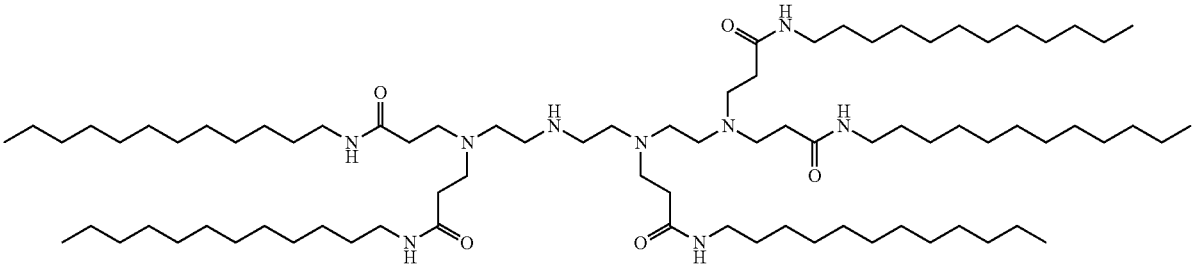

ND98 Isomer 1

LNP01 formulations are described, e.g., in International Application Publication No. WO 2008/042973, which is hereby incorporated by reference.

Additional exemplary lipid-dsRNA formulations are described in Table 1.

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |

TABLE 1-continued

| | Ionizable/Cationic Lipid | cationic lipid/non-cationic lipid/cholesterol/PEG-lipid conjugate Lipid:siRNA ratio |
|---|---|---|
| LNP19 | MC3 | MC3/DSPC/Chol/PEG-DMG<br>50/10/35/5<br>Lipid:siRNA: 8:1 |
| LNP20 | MC3 | MC3/DSPC/Chol/PEG-DPG<br>50/10/38.5/1.5<br>Lipid:siRNA: 10:1 |
| LNP21 | C12-200 | C12-200/DSPC/Chol/PEG-DSG<br>50/10/38.5/1.5<br>Lipid:siRNA: 7:1 |
| LNP22 | XTC | XTC/DSPC/Chol/PEG-DSG<br>50/10/38.5/1.5<br>Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —ORx, —NRxRy, —NRxC(═O)Ry, —NRxSO2Ry, —C(═O)Rx, —C(═O)ORx, —C(═O)NRxRy, —SOnRx and —SOnNR xRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NR xRy, —NRxC(═O)Ry, —NRxSO2Ry, —C(═O)Rx, —C(═O)ORx, —C(═O)NRxRy, —S OnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

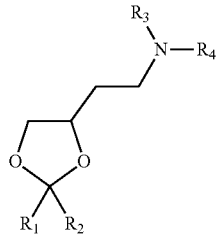

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

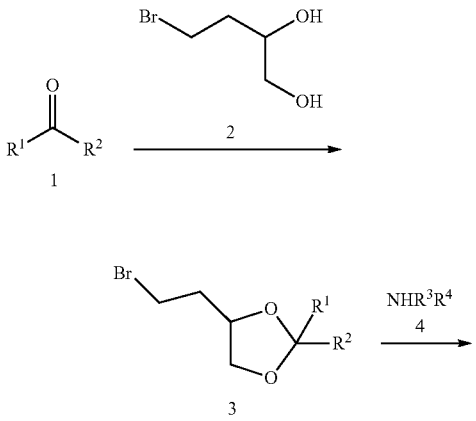

-continued

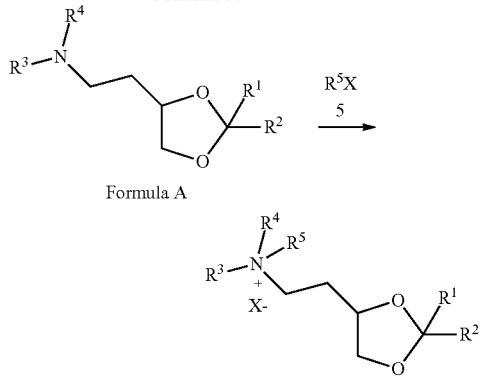

Formula A

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

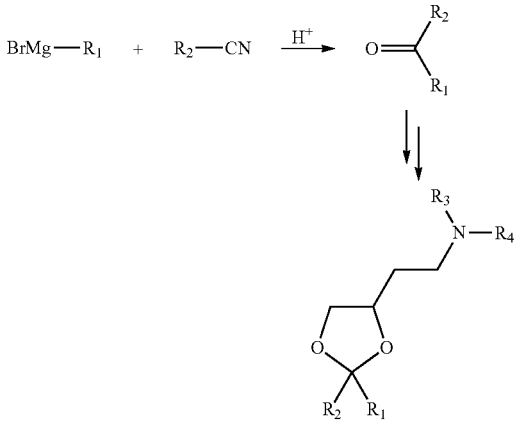

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

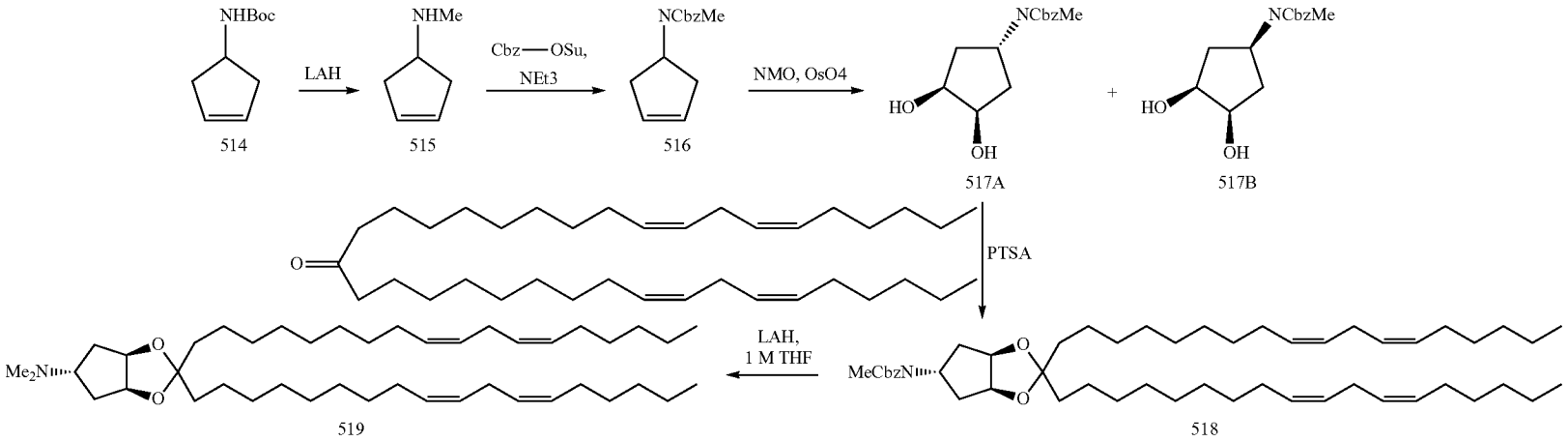
NHBoc
514
LAH
NHMe
515
Cbz—OSu,
NEt3
NCbzMe
516
NMO, OsO4
NCbzMe
HO
OH
517A
+
NCbzMe
HO
OH
517B
PTSA
O
O
O
MeCbzNu
518
LAH,
1 M THF
O
O
O
Me2Nu
519

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g $^1$H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). $^1$H-NMR ($CDCl_3$, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517E

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1× 50 mL). Organic phase was dried over an .Na2SO4 and solvent was removed in vacuum. Silica gel column chromatographic purification of the crude material was afforded a mixture of diastereomers, which were separated by prep HPLC. Yield: −6 g crude 517A—Peak-1 (white solid), 5.13 g (96%). $^1$H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. $^1$H-NMR ($CDCl_3$, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. $^{13}$C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6. Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.;

Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, MA, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by Serpinc1 expression. In any event, the administering physician can adjust the amount and timing of iRNA administration on the basis of results observed using standard measures of efficacy known in the art or described herein.

VI. Methods of the Invention

The present invention also provides methods of using an iRNA of the invention and/or a composition containing an iRNA of the invention to reduce and/or inhibit Serpinc1 expression in a cell. In other aspects, the present invention provides an iRNA of the invention and/or a composition comprising an iRNA of the invention for use in reducing and/or inhibiting Serpinc1 expression in a cell. In yet other aspects, use of an iRNA of the invention and/or a composition comprising an iRNA of the invention for the manufacture of a medicament for reducing and/or inhibiting Serpinc1 expression in a cell are provided.

The methods and uses include contacting the cell with an iRNA, e.g., a dsRNA, of the invention and maintaining the cell for a time sufficient to obtain degradation of the mRNA transcript of a Serpinc1 gene, thereby inhibiting expression of the Serpinc1 gene in the cell.

Reduction in gene expression can be assessed by any methods known in the art. For example, a reduction in the expression of Serpinc1 may be determined by determining the mRNA expression level of Serpinc1 using methods routine to one of ordinary skill in the art, e.g., Northern blotting, qRT-PCR, by determining the protein level of Serpinc1 using methods routine to one of ordinary skill in the art, such as Western blotting, immunological techniques, and/or by determining a biological activity of Serpinc1, such as affecting one or more molecules associated with the cellular blood clotting mechanism (or in an in vivo setting, blood clotting itself).

In the methods and uses of the invention the cell may be contacted in vitro or in vivo, i.e., the cell may be within a subject.

A cell suitable for treatment using the methods of the invention may be any cell that expresses a Serpinc1 gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

Serpinc1 expression may be inhibited in the cell by at least about 5, 6, 7, 8, 9, 10, 11, 12, 13, 14, 15, 16, 17, 18, 19, 20, and 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%.

The in vivo methods and uses of the invention may include administering to a subject a composition containing an iRNA, where the iRNA includes a nucleotide sequence that is complementary to at least a part of an RNA transcript of the Serpinc1 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of Serpinc1, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of a Serpinc1 gene in a mammal, e.g., a human. The present invention also provides a composition comprising an iRNA, e.g., a dsRNA, that targets a Serpinc1 gene in a cell of a mammal for use in inhibiting expression of the Serpinc1 gene in the mammal. In another aspect, the present invention provides use of an iRNA, e.g., a dsRNA, that targets a Serpinc1 gene in a cell of a mammal in the manufacture of a medicament for inhibiting expression of the Serpinc1 gene in the mammal.

The methods and uses include administering to the mammal, e.g., a human, a composition comprising an iRNA, e.g., a dsRNA, that targets a Serpinc1 gene in a cell of the mammal and maintaining the mammal for a time sufficient to obtain degradation of the mRNA transcript of the Serpinc1 gene, thereby inhibiting expression of the Serpinc1 gene in the mammal.

Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a puncture liver biopsy sample serves as the tissue material for monitoring the reduction in Serpinc1 gene and/or protein expression. In another embodiment, a blood sample serves as the tissue material for monitoring the reduction in Serpinc1 gene and/or protein expression. In other embodiments, inhibition of the expression of a Serpinc1 gene is monitored indirectly by, for example, determining the expression and/or activity of a gene in a Serpinc1 pathway (see, e.g., FIG. 1). For example, the activity of factor Xa may be monitored to determine the inhibition of expression of a Serpinc1 gene. Antithrombin levels, clot formation, and/or endogenous thrombin potential, in a sample, e.g., a blood or liver sample, may also be measured. Suitable assays are further described in the Examples section below.

The present invention further provides methods of treating a subject having a disorder that would benefit from reduction in Serpinc1 expression, e.g., hemophilia. The treatment methods (and uses) of the invention include administering to the subject, e.g., a human, a therapeutically effective amount of an iRNA targeting a Serpinc1 gene or a pharmaceutical composition comprising an iRNA targeting a Serpinc1 gene, thereby treating the subject having a disorder that would benefit from reduction in Serpinc1 expression.

In one aspect, the invention provides methods of preventing at least one symptom in a subject having a disorder that would benefit from reduction in Serpinc1 expression. The methods include administering to the subject a therapeutically effective amount of the iRNA, e.g., dsRNA, or vector of the invention, thereby preventing at least one symptom in the subject having a disorder that would benefit from reduction in Serpinc1 expression. For example, the invention provides methods for preventing bleeding in a subject suffering from a disorder that would benefit from reduction in Serpinc1 expression, e.g., a hemophilia In another aspect, the present invention provides use of a therapeutically effective amount of an iRNA of the invention for treating a subject, e.g., a subject that would benefit from a reduction and/or inhibition of Serpinc1 expression. The iRNA includes iRNA targeting a Serpinc1 gene or a pharmaceutical composition comprising an iRNA targeting a Serpinc1 gene.

In yet another aspect, the present invention provides use of an iRNA of the invention targeting a Serpinc1 gene or a pharmaceutical composition comprising an iRNA targeting a Serpinc1 gene in the manufacture of a medicament for treating a subject, e.g., a subject that would benefit from a reduction and/or inhibition of Serpinc1 expression.

In another aspect, the invention provides uses of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia.

In a further aspect, the present invention provides uses of an iRNA of the invention in the manufacture of a medicament for preventing at least one symptom in a subject suffering from a disorder that would benefit from a reduction and/or inhibition of Serpinc1 expression, such as a bleeding disorder, e.g., a hemophilia. An iRNA of the invention may be administered in "naked" form, or as a "free iRNA." A naked iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of Serpinc1 gene expression are those having a bleeding disorder, e.g., an inherited bleeding disorder or an acquired bleeding disorder as described herein. In one embodiment, a subject having an inherited bleeding disorder has a hemophilia, e.g., hemophilia A, B, or C. In one embodiment, a subject having an inherited bleeding disorder, e.g., a hemophilia, is an inhibitor subject. In one embodiment, the inhibitor subject has hemophilia A. In another embodiment, the inhibitor subject has hemophilia B. In yet another embodiment, the inhibitor subject has hemophilia C. Treatment of a subject that would benefit from a reduction and/or inhibition of Serpinc1 gene expression includes therapeutic (e.g., on-demand, e.g., the subject is bleeding (spontaneous bleeding or bleeding as a result of trauma) and failing to clot) and prophylactic (e.g., the subject is not bleeding and/or is to undergo surgery) treatment.

The invention further provides methods and uses for the use of an iRNA or a pharmaceutical composition thereof, e.g., for treating a subject that would benefit from reduction and/or inhibition of Serpinc1 expression, e.g., a subject having a bleeding disorder, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting Serpinc1 is administered in combination with, e.g., an agent useful in treating a bleeding disorder as described elsewhere herein. For example, additional therapeutics and therapeutic methods suitable for treating a subject that would benefit from reduction in Serpinc1 expression, e.g., a subject having a bleeding disorder, include fresh-frozen plasma (FFP); recombinant FVIIa; recombinant FIX; FXI concentrates; virus-inactivated, vWF-containing FVIII concentrates; desensitization therapy which may include large doses of FVIII or FIX, along with steroids or intravenous immunoglobulin (IVIG) and cyclophosphamide; plasmapheresis in conjunction with immunosuppression and infusion of FVIII or FIX, with or without antifibrinolytic therapy; immune tolerance induction (ITI), with or without immunosuppressive therapy (e.g., cyclophosphamide, prednisone, and/or anti-CD20); desmopressin acetate [DDAVP]; antifibrinolytics, such as aminocaproic acid and tranexamic acid; activated prothrombin complex concentrate (PCC); antihemophilic agents; corticosteroids; immunosuppressive agents; and estrogens. The iRNA and an additional therapeutic agent and/or treatment may be administered at the same time and/or in the same combination, e.g., parenterally, or the additional therapeutic agent can be administered as part of a separate composition or at separate times and/or by another method known in the art or described herein.

In one embodiment, the methods and uses include administering a composition featured herein such that expression of the target Serpinc1 gene is decreased, such as for about 1, 2, 3, 4, 5, 6, 7, 8, 12, 16, 18, 24, 28, 32, 36, 40, 44, 48, 52, 56, 60, 64, 68, 72, 76, or about 80 hours. In one embodiment, expression of the target Serpinc1 gene is decreased for an extended duration, e.g., at least about two, three, four, five, six, seven days or more, e.g., about one week, two weeks, three weeks, or about four weeks or longer.

Preferably, the iRNAs useful for the methods, uses, and compositions featured herein specifically target RNAs (primary or processed) of the target Serpinc1 gene. Compositions, uses, and methods for inhibiting the expression of these genes using iRNAs can be prepared and performed as described herein.

Administration of the dsRNA according to the methods and uses of the invention may result in a reduction of the severity, signs, symptoms, and/or markers of such diseases or disorders in a patient with a bleeding disorder. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, frequency of bleeds, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a bleeding disorder may be assessed, for example, by periodic monitoring of thrombin: anti-thrombin levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting Serpinc1 or pharmaceutical composition thereof, "effective against" a bleeding disorder indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating bleeding disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). Any positive change resulting in e.g., lessening of severity of disease measured using the appropriate scale, represents adequate treatment using an iRNA or iRNA formulation as described herein.

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 [mg/mg] *mg/kg*, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 [mg/mg] *mg/kg*, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 [mg/mg] *mg/kg*, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 [mg/mg] *mg/kg*, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 [mg/mg] *mg/kg*, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The iRNA can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

In one embodiment, the present invention provides methods for treating a subject suffering from a bleeding disorder, e.g., a hemophilia, by subcutaneously administering to said subject compound AD-57213 at a cumulative weekly dose of about 0.5 mg/kg to about 5 mg/kg, or about 1 mg/kg to about 3 mg/kg.

In one embodiment, the methods may include subcutaneously administering to the subject a cumulative weekly dose of about 0.5 mg/kg. For example, in one embodiment, the methods may include administering to the subject a cumulative weekly dose of about 0.5 mg/kg as 0.5 .mg/kg every week. In another embodiment, the methods may include administering to the subject a cumulative weekly dose of about 0.5 mg/kg as 1 mg/kg every two weeks.

In another embodiment, the methods may include subcutaneously administering to the subject a cumulative weekly dose of about 1.5 mg/kg. For example, in one embodiment, the methods may include administering to the subject a cumulative weekly dose of about 1.5 mg/kg as 1.5 .mg/kg every week. In another embodiment, the methods may include administering to the subject a cumulative weekly dose of about 1.5 mg/kg as 3 mg/kg every two weeks.

In another embodiment, the methods may include subcutaneously administering to the subject a cumulative weekly dose of about 2 mg/kg. For example, in one embodiment, the methods may include administering to the subject a cumulative weekly dose of about 2 mg/kg as 2 mg/kg every week. In another embodiment, the methods may include administering to the subject a cumulative weekly dose of about 2 mg/kg as 4 mg/kg every two weeks.

In yet another embodiment, the methods may include subcutaneously administering to the subject a cumulative weekly dose of about 3 mg/kg. For example, in one embodiment, the methods may include administering to the subject a cumulative weekly dose of about 3 mg/kg as 3 mg/kg every week. In another embodiment, the methods may include administering to the subject a cumulative weekly dose of about 3 mg/kg as 6 mg/kg every two weeks.

In another embodiment, the present invention provides methods for preventing in a subject at least one symptom of a bleeding disorder, e.g., a hemophilia, by subcutaneously administering to the subject compound AD-57213 at a cumulative weekly dose of about 0.5 mg/kg to about 5 mg/kgor about 1 mg/kg to about 3 mg/kg.

In one embodiment, the methods may include subcutaneously administering to the subject a cumulative weekly dose of about 0.5 mg/kg. For example, in one embodiment, the methods may include administering to the subject a cumulative weekly dose of about 0.5 mg/kg as 0.5 .mg/kg every week. In another embodiment, the methods may include administering to the subject a cumulative weekly dose of about 0.5 mg/kg as 1 mg/kg every two weeks.

In another embodiment, the methods may include subcutaneously administering to the subject a cumulative weekly dose of about 1.5 mg/kg. For example, in one embodiment, the methods may include administering to the subject a cumulative weekly dose of about 1.5 mg/kg as 1.5 .mg/kg every week. In another embodiment, the methods may include administering to the subject a cumulative weekly dose of about 1.5 mg/kg as 3 mg/kg every two weeks.

In another embodiment, the methods may include subcutaneously administering to the subject a cumulative weekly dose of about 2 mg/kg. For example, in one embodiment, the methods may include administering to the subject a cumulative weekly dose of about 2 mg/kg as 2 mg/kg every week. In another embodiment, the methods may include administering to the subject a cumulative weekly dose of about 2 mg/kg as 4 mg/kg every two weeks.

In yet another embodiment, the methods may include subcutaneously administering to the subject a cumulative weekly dose of about 3 mg/kg. For example, in one embodiment, the methods may include administering to the subject a cumulative weekly dose of about 3 mg/kg as 3 mg/kg every week. In another embodiment, the methods may include administering to the subject a cumulative weekly dose of about 3 mg/kg as 6 mg/kg every two weeks.

Administration of the iRNA can reduce Serpinc1 levels, e.g., in a cell, tissue, blood, urine or other compartment of the patient by at least about 5%, 6, 7, 8, 9, 10, 11, 12, 13, 14, 15, 16, 17, 18, 19, 20, and 21, 22, 23, 24, 25, 26, 27, 28, 29, 30, 31, 32, 33, 34, 35, 36, 37, 38, 39, 40, 41, 42, 43, 44, 45, 46, 47, 48, 39, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or at least about 99% or more.

In one embodiment, the treatment and/or preventive methods include subcutaneously administering to a subject compound AD-57213 at a dose sufficient to inhibit reduce Serpinc1 levels, e.g., in a cell, tissue, blood, urine or other compartment of the patient by at least about by about 40, 41, 42, 43, 44, 45, 46, 47, 48, 49, 50, 51, 52, 53, 54, 55, 56, 57, 58, 69, 60, 61, 62, 63, 64, 65, 66, 67, 68, 69, 70, 71, 72, 73, 74, 75, 76, 77, 78, 79, or about 80%.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on Serpinc1 expression, a composition according to the invention or a pharmaceutical composition prepared therefrom can enhance the quality of life.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 iRNA Synthesis

Source of Reagents

Where the source of a reagent is not specifically given herein, such reagent can be obtained from any supplier of reagents for molecular biology at a quality/purity standard for application in molecular biology.

Transcripts siRNA design was carried out to identify siRNAs targeting human, rhesus (Macaca mulatta), dog, mouse, and rat SERPINC1 transcripts annotated in the NCBI Gene database (http://www.ncbi.nlm.nih.gov/gene/). Design used the following transcripts from the NCBI RefSeq collection: Human—NM_000488.2, NM_000488.3; Rhesus—NM_001104583.1; Dog—XM_856414.1; Mouse—NM_080844.4; Rat—NM_001012027.1. Due to high primate/canine/rodent sequence divergence, siRNA duplexes were designed in several separate batches, including but not limited to batches containing duplexes matching human and rhesus transcripts only; human, rhesus, and dog transcripts only; human, rhesus, mouse, and rat transcripts only; and mouse and rat transcripts only. All siRNA duplexes were designed that shared 100% identity the listed human transcript and other species transcripts considered in each design batch (above).

siRNA Design, Specificity, and Efficacy Prediction

The predicted specificity of all possible 19mers was predicted from each sequence. Candidate 19mers were then selected that lacked repeats longer than 7 nucleotides. These 874 candidate human/rhesus, 67 human/rhesus/dog, 103 human/rhesus/mouse/rat, and 569 mouse/rat siRNAs were used in comprehensive searches against the appropriate transcriptomes (defined as the set of NM_ and XM_ records within the human, rhesus, dog, mouse, or rat NCBI Refseq sets) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5'-end of the molecule.

Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octamer. 'Heptamer1' was created by adding a 3'-A to the hexamer; heptamer2 was created by adding a 5'-A to the hexamer; the octomer was created by adding an A to both 5'- and 3'-ends of the hexamer. The frequency of octamers and heptamers in the human, rhesus, mouse, or rat 3'-UTRome (defined as the subsequence of the transcriptome from NCBI's Refseq database where the end of the coding region, the 'CDS', is clearly defined) was pre-calculated. The octamer frequency was normalized to the heptamer frequency using the median value from the range of octamer frequencies. A 'mirSeedScore' was then calculated by calculating the sum of ((3× normalized octamer count)+(2×heptamer2 count)+(1×heptamer1 count)).

Both siRNAs strands were assigned to a category of specificity according to the calculated scores: a score above 3 qualifies as highly specific, equal to 3 as specific and between 2.2 and 2.8 as moderately specific. The duplexes were sorted by the specificity of the antisense strand and those duplexes whose antisense oligos lacked GC at the first position, lacked G at both positions 13 and 14, and had 3 or more Us or As in the seed region were selected.

siRNA Sequence Selection

A total of 66 sense and 66 antisense derived human/rhesus, 6 sense and 6 antisense derived human/rhesus/mouse, 12 human/rhesus/mouse/rat, and 21 sense and 21 antisense derived mouse/rat siRNA oligos were synthesized and formed into duplexes. A detailed list of Serpinc1 sense and antisense strand sequences is shown in Tables 3 and 4.

siRNA Synthesis

I. General Small and Medium Scale RNA Synthesis Procedure

RNA oligonucleotides were synthesized at scales between 0.2-500 μmol using commercially available 5'-O-(4,4'-dimethoxytrityl)-2'-O-t-butyldimethylsilyl-3'-O-(2-cyanoethyl-N,N-diisopropyl)phosphoramidite monomers of uridine, 4-N-acetylcytidine, 6-N-benzoyladenosine and 2-N-isobutyrylguanosine and the corresponding 2'-O-methyl and 2'-fluoro phosphoramidites according to standard solid phase oligonucleotide synthesis protocols. The amidite solutions were prepared at 0.1-0.15 M concentration and 5-ethylthio-1H-tetrazole (0.25-0.6 M in acetonitrile) was used as the activator. Phosphorothioate backbone modifications were introduced during synthesis using 0.2 M phenylacetyl disulfide (PADS) in lutidine:acetonitrile (1:1) (v; v) or 0.1 M 3-(dimethylaminomethylene)amino-3H-1,2,4-dithiazole-5-thione (DDTT) in pyridine for the oxidation step. After completion of synthesis, the sequences were cleaved from the solid support and deprotected using methylamine followed by triethylamine. 3HF to remove any 2'-O-t-butyldimethylsilyl protecting groups present.

For synthesis scales between 5-500 μmol and fully 2' modified sequences (2'-fluoro and/or 2'-O-methyl or combinations thereof) the oligonucleotides where deprotected using 3:1 (v/v) ethanol and concentrated (28-32%) aqueous ammonia either at 35° C. 16 h or 55° C. for 5.5 h. Prior to ammonia deprotection the oligonucleotides where treated with 0.5 M piperidine in acetonitrile for 20 min on the solid support. The crude oligonucleotides were analyzed by LC-MS and anion-exchange HPLC (IEX-HPLC). Purification of the oligonucleotides was carried out by IEX HPLC using: 20 mM phosphate, 10%-15% ACN, pH=8.5 (buffer A) and 20 mM phosphate, 10%-15% ACN, 1 M NaBr, pH=8.5 (buffer B). Fractions were analyzed for purity by analytical HPLC. The product-containing fractions with suitable purity were pooled and concentrated on a rotary evaporator prior to desalting. The samples were desalted by size exclusion chromatography and lyophilized to dryness. Equal molar amounts of sense and antisense strands were annealed in 1×PBS buffer to prepare the corresponding siRNA duplexes.

For small scales (0.2-1 μmol), synthesis was performed on a MerMade 192 synthesizer in a 96 well format. In case of fully 2'-modified sequences (2'-fluoro and/or 2'-O-methyl or combinations thereof) the oligonucleotides where deprotected using methylamine at room temperature for 30-60 min followed by incubation at 60° C. for 30 min or using 3:1 (v/v) ethanol and concentrated (28-32%) aqueous ammonia at room temperature for 30-60 min followed by incubation at 40° C. for 1.5 hours. The crude oligonucleotides were then precipitated in a solution of acetonitrile:acetone (9:1) and isolated by centrifugation and decanting the supernatant. The crude oligonucleotide pellet was re-suspended in 20 mM NaOAc buffer and analyzed by LC-MS and anion exchange HPLC. The crude oligonucleotide sequences were desalted in 96 deep well plates on a 5 mL HiTrap Sephadex G25 column (GE Healthcare). In each well about 1.5 mL samples corresponding to an individual sequence was collected. These purified desalted oligonucleotides were analyzed by LC-MS and anion exchange chromatography. Duplexes were prepared by annealing equimolar amounts of sense and antisense sequences on a Tecan robot. Concentration of duplexes was adjusted to 10 μM in 1×PBS buffer.

II. Synthesis of GalNAc-Conjugated Oligonucleotides for In Vivo Analysis

Oligonucleotides conjugated with GalNAc ligand at their 3'-terminus were synthesized at scales between 0.2-500 μmol using a solid support pre-loaded with a Y-shaped linker bearing a 4,4'-dimethoxytrityl (DMT)-protected primary hydroxy group for oligonucleotide synthesis and a GalNAc ligand attached through a tether.

For synthesis of GalNAc conjugates in the scales between 5-500 μmol, the above synthesis protocol for RNA was followed with the following adaptions: For polystyrene-based synthesis supports 5% dichloroacetic acid in toluene was used for DMT-cleavage during synthesis. Cleavage from the support and deprotection was performed as described above. Phosphorothioate-rich sequences (usually >5 phorphorothioates) were synthesized without removing the final 5'-DMT group ("DMT-on") and, after cleavage and deprotection as described above, purified by reverse phase HPLC using 50 mM ammonium acetate in water (buffer A) and 50 mM ammoniumacetate in 80% acetonitrile (buffer B). Fractions were analyzed for purity by analytical HPLC and/or LC-MS. The product-containing fractions with suitable purity were pooled and concentrated on a rotary evaporator. The DMT-group was removed using 20%-25% acetic acid in water until completion. The samples were desalted by size exclusion chromatography and lyophilized to dryness. Equal molar amounts of sense and antisense strands were annealed in 1×PBS buffer to prepare the corresponding siRNA duplexes.

For small scale synthesis of GalNAc conjugates (0.2-1 μmol), including sequences with multiple phosphorothioate linkages, the protocols described above for synthesis of RNA or fully 2'-F/2'-OMe-containing sequences on MerMade platform were applied. Synthesis was performed on pre-packed columns containing GalNAc-functionalized controlled pore glass support.

Example 2

In Vitro Screening

Cell Culture and Transfections

Figure 2A:
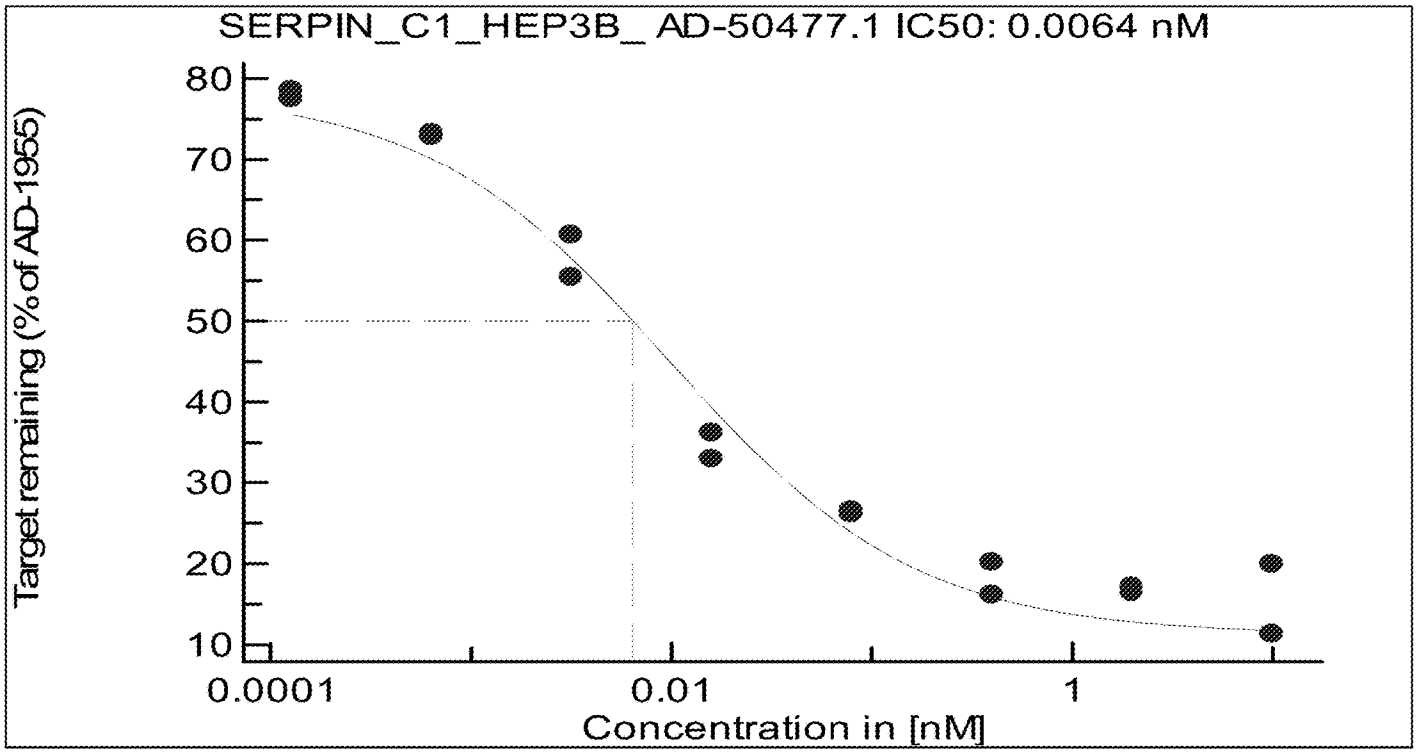
FIGS. 2A and 2B are graphs showing the inhibition of Serpinc1 expression in Hep3B cells following a single dose of the indicated iRNAs.
Figure 2B:
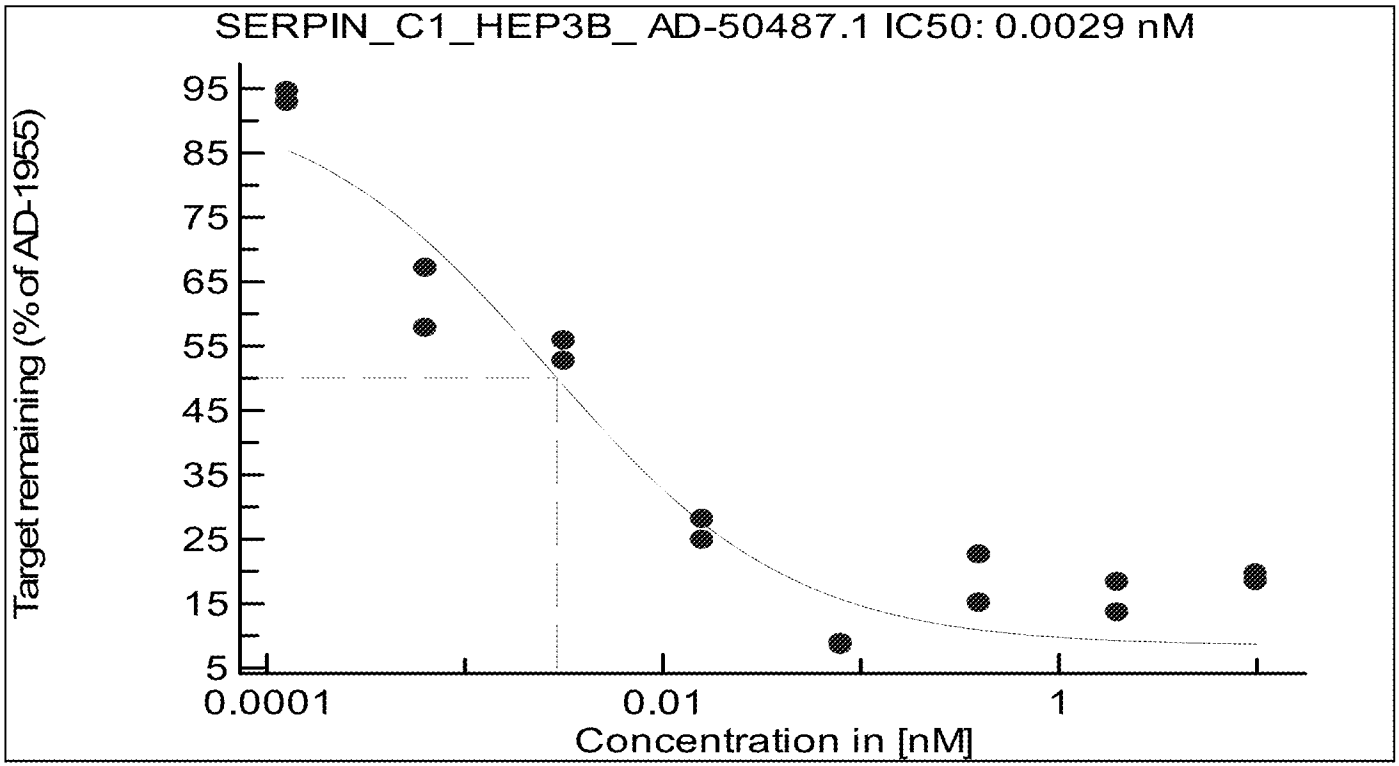

Hep3B cells (ATCC, Manassas, Va.) were grown to near confluence at 37° C. in an atmosphere of 5% CO2 in Eagle's Minimum Essential Medium (ATCC) supplemented with 10% FBS, streptomycin, and glutamine (ATCC) before being released from the plate by trypsinization. For mouse cross reactive duplexes, primary mouse hepatocytes (PMH) were freshly isolated less than 1 hour prior to transfections and grown in primary hepatocyte media. For both Hep3B and PMH, transfection was carried out by adding 14.8 μl of Opti-MEM plus 0.2 μl of Lipofectamine RNAiMax per well (Invitrogen, Carlsbad Calif. cat #13778-150) to 5 μl of each siRNA duplex to an individual well in a 96-well plate. The mixture was then incubated at room temperature for 15 minutes. Eighty μl of complete growth media without antibiotic containing ~$2\times10^4$ Hep3B cells were then added to the siRNA mixture. Cells were incubated for 24 hours prior to RNA purification. Single dose experiments were performed at 10 nM and 0.1 nM final duplex concentration and dose response experiments were done using 8×5-fold serial dilutions over the range of 10 nM to 128 pM (see FIGS. 2A and 2B).

Free Uptake Transfection

Five μl of each GalNac conjugated siRNA in PBS was combined with $4\times10^4$ freshly thawed cryopreserved Cynomolgus monkey hepatocytes resuspended in 95 μl of In Vitro Gro CP media (In Vitro Technologies-Celsis, Baltimore, Md.) in each well of a 96 well plate. The mixture was incubated for about 24 hrs at 37° C. in an atmosphere of 5% $CO_2$. siRNAs were tested at final concentrations of 100 nM, 10 nM and 0.1 nM for efficacy free uptake assays.

Total RNA Isolation using DYNABEADS mRNA Isolation Kit (Invitrogen, Part #: 610-12)

Cells were harvested and lysed in 150 μl of Lysis/Binding Buffer then mixed for 5 minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using a magnetic stand and the supernatant was removed without disturbing the beads. After removing the supernatant, the lysed cells were added to the remaining beads and mixed for 5 minutes. After removing the supernatant, magnetic beads were washed 2 times with 150 Wash Buffer A and mixed for 1 minute. The beads were capturedagain and the supernatant was removed. The beads were then washed with 150 μl Wash Buffer B, captured and the supernatant was removed. The beads were next washed with 150 μl Elution Buffer, captured and the supernatant removed. Finally, the beads were allowed to dry for 2 minutes. After drying, 50 μl of Elution Buffer was added and mixed for 5 minutes at 70° C. The beads were captured on magnet for 5 minutes. 40 μl of supernatant was removed and added to another 96 well plate.

cDNA Synthesis Using ABI High Capacity cDNA Reverse Transcription Kit (Applied Biosystems, Foster City, Calif., Cat #4368813)

A master mix of 2 μl 10× Buffer, 0.8 μl 25×dNTPs, 2 μl Random primers, 1 μl Reverse Transcriptase, 1 μl RNase inhibitor and 3.2 μl of H2O per reaction were added into 10 μl total RNA. cDNA was generated using a Bio-Rad C-1000 or S-1000 thermal cycler (Hercules, Calif.) through the following steps: 25° C. for 10 minutes, 37° C. for 120 minutes, 85° C. for 5 seconds, and 4° C. hold.

Real Time PCR

Two μl of cDNA were added to a master mix containing 0.5 μl human GAPDH TaqMan Probe (Applied Biosystems Cat #4326317E), 0.5 μl human SERPINC1 TaqMan probe (Applied Biosystems cat #Hs00892758_ml) for human cells or 0.5 μl mouse GAPDH TaqMan Probe (Applied Biosystems Cat #4308313), 0.5 μl mouse SERPINC1 TaqMan probe (Applied Biosystems cat #Mm00446573_ml) for mouse cells and 50 Lightcycler 480 probe master mix (Roche Cat #04887301001) per well in a 384 well plates. Real time PCR was done in an ABI 7900HT Real Time PCR system (Applied Biosystems) using the ΔΔCt(RQ) assay. Each duplex was tested in two independent transfections and each transfection was assayed in duplicate, unless otherwise noted in the summary tables.

To calculate relative fold change in Serpinc1 mRNA levels, real time data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 over the same dose range, or to its own lowest dose. Table 5 shows the results of a single dose screen in Hep3B cells and PMH cells transfected with the indicated iRNAs. Table 6 shows the results of dose response of the indicated iRNAs transfected into Hep3B and PMH cells.

The sense and antisense sequences of AD-1955 are:

SENSE:

cuuAcGcuGAGuAcuucGAdTsdT (SEQ ID NO: 13)

ANTISENSE:

UCGAAGuACUcAGCGuAAGdTsdT. (SEQ ID NO: 14)

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| (Chd) | 2'-O-hexadecyl-cytidine-3'-phosphate |
| (Chds) | 2'-O-hexadecyl-cytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tb | beta-L-thymidine-3'-phosphate |
| Tbs | beta-L-thymidine-3'-phosphorothioate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Ub | beta-L-uridine-3'-phosphate |
| Ubs | beta-L-uridine-3'-phosphorothioate |
| Uf | 2'-fluorouridine-3'-phosphate |
| Ufs | 2'-fluorouridine-3'-phosphorothioate |
| (Uhd) | 2'-O-hexadecyl-uridine-3'-phosphate |
| (Uhds) | 2'-O-hexadecyl-uridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |

TABLE 3

Unmodified Sense and antisense strand sequences of Serpinc1 dsRNAs (The "Sense Sequence" column sequences are disclosed as SEQ ID NOS 15-71, respectively, in order of appearance, and the "Antisense Sequence" column sequences are disclosed as SEQ ID NOS 72-128, respectively, in order of appearance)

| Duplex Name | Sense Name | Sense Sequence | Antisense Name | Antisense Sequence |
|---|---|---|---|---|
| AD-50475.1-UM | A-104633.1 | CCCUGUGGACAUCUGCACA | A-104634.1 | UGUGCAGAUGUCCACAGGG |
| AD-50476.1-UM | A-104649.1 | CUACCACUUUCUAUCAGCA | A-104650.1 | UGCUGAUAGAAAGUGGUAG |
| AD-50477.1-UM | A-104665.1 | CUAUCGAAAAGCCAACAAA | A-104666.1 | UUUGUUGGCUUUUCGAUAG |
| AD-50478.1-UM | A-104681.1 | GGACUUCAAGGAAAAUGCA | A-104682.1 | UGCAUUUUCCUUGAAGUCC |
| AD-50479.1-UM | A-104697.1 | GUUAACACCAUUUACUUCA | A-104698.1 | UGAAGUAAAUGGUGUUAAC |
| AD-50480.1-UM | A-104713.1 | CCUGGUUUUUAUAAGAGAA | A-104714.1 | UUCUCUUAUAAAAACCAGG |
| AD-50481.1-UM | A-104635.1 | GACAUUCCCAUGAAUCCCA | A-104636.1 | UGGGAUUCAUGGGAAUGUC |
| AD-50482.1-UM | A-104651.1 | CACCUGGCAGAUUCCAAGA | A-104652.1 | UCUUGGAAUCUGCCAGGUG |
| AD-50483.1-UM | A-104667.1 | CGAAAAGCCAACAAAUCCU | A-104668.1 | AGGAUUUGUUGGCUUUUCG |
| AD-50484.1-UM | A-104683.1 | GAAAAUGCAGAGCAAUCCA | A-104684.1 | UGGAUUGCUCUGCAUUUUC |
| AD-50485.1-UM | A-104699.1 | GGCCUGUGGAAGUCAAAGU | A-104700.1 | ACUUUGACUUCCACAGGCC |
| AD-50486.1-UM | A-104715.1 | GAAGUUCCUCUGAACACUA | A-104716.1 | UAGUGUUCAGAGGAACUUC |
| AD-50487.1-UM | A-104637.1 | CCAUGAAUCCCAUGUGCAU | A-104638.1 | AUGCACAUGGGAUUCAUGG |
| AD-50488.1-UM | A-104653.1 | CAACUGAUGGAGGUAUUUA | A-104654.1 | UAAAUACCUCCAUCAGUUG |
| AD-50489.1-UM | A-104669.1 | CCAAGUUAGUAUCAGCCAA | A-104670.1 | UUGGCUGAUACUAACUUGG |
| AD-50490.1-UM | A-104685.1 | CGGCCAUCAACAAAUGGGU | A-104686.1 | ACCCAUUUGUUGAUGGCCG |
| AD-50491.1-UM | A-104701.1 | GAGGACGGCUUCAGUUUGA | A-104702.1 | UCAAACUGAAGCCGUCCUC |
| AD-50492.1-UM | A-104717.1 | CCUCUGAACACUAUUAUCU | A-104718.1 | AGAUAAUAGUGUUCAGAGG |
| AD-50493.1-UM | A-104639.1 | CAUGAAUCCCAUGUGCAUU | A-104640.1 | AAUGCACAUGGGAUUCAUG |
| AD-50494.1-UM | A-104655.1 | GAUGGAGGUAUUUAAGUUU | A-104656.1 | AAACUUAAAUACCUCCAUC |
| AD-50495.1 UM | A-104671.1 | GUAUCAGCCAAUCGCCUUU | A-104672.1 | AAAGGCGAUUGGCUGAUAC |
| AD-50496.1-UM | A-104687.1 | GGGUGUCCAAUAAGACCGA | A-104688.1 | UCGGUCUUAUUGGACACCC |
| AD-50497.1-UM | A-104703.1 | CAGCCCUGAAAAGUCCAAA | A-104704.1 | UUUGGACUUUUCAGGGCUG |
| AD-50498.1-UM | A-104641.1 | CCCAUGUGCAUUUACCGCU | A-104642.1 | AGCGGUAAAUGCACAUGGG |
| AD-50499.1-UM | A-104657.1 | GUAUUUAAGUUUGACACCA | A-104658.1 | UGGUGUCAAACUUAAAUAC |
| AD-50500.1-UM | A-104673.1 | GACAAAUCCCUUACCUUCA | A-104674.1 | UGAAGGUAAGGGAUUUGUC |
| AD-50501.1-UM | A-104689.1 | CUGUUCUGGUGCUGGUUAA | A-104690.1 | UUAACCAGCACCAGAACAG |
| AD-50502.1 UM | A-104705.1 | CCAAACUCCCAGGUAUUGU | A-104706.1 | ACAAUACCUGGGAGUUUGG |
| AD-50503.1-UM | A-104643.1 | CCCGCUUUGCUACCACUUU | A-104644.1 | AAAGUGGUAGCAAAGCGGG |
| AD-50505.1-UM | A-104675.1 | CUUACCUUCAAUGAGACCU | A-104676.1 | AGGUCUCAUUGAAGGUAAG |
| AD-50506.1-UM | A-104691.1 | CUGGUGCUGGUUAACACCA | A-104692.1 | UGGUGUUAACCAGCACCAG |
| AD-50507.1-UM | A-104707.1 | CAAACUCCCAGGUAUUGUU | A-104708.1 | AACAAUACCUGGGAGUUUG |
| AD-50508.1-UM | A-104645.1 | GCUUUGCUACCACUUUCUA | A-104646.1 | UAGAAAGUGGUAGCAAAGC |
| AD-50510.1-UM | A-104677.1 | CCUACCAGGACAUCAGUGA | A-104678.1 | UCACUGAUGUCCUGGUAGG |
| AD-50511.1-UM | A-104693.1 | GGUGCUGGUUAACACCAUU | A-104694.1 | AAUGGUGUUAACCAGCACC |
| AD-50512.1-UM | A-104709.1 | GCCGUUCGCUAAACCCCAA | A-104710.1 | UUGGGGUUUAGCGAACGGC |

TABLE 3-continued

Unmodified Sense and antisense strand sequences of Serpinc1 dsRNAs (The "Sense Sequence" column sequences are disclosed as SEQ ID NOS 15-71, respectively, in order of appearance, and the "Antisense Sequence" column sequences are disclosed as SEQ ID NOS 72-128, respectively, in order of appearance)

| Duplex Name | Sense Name | Sense Sequence | Antisense Name | Antisense Sequence |
|---|---|---|---|---|
| AD-50515.1-UM | A-104679.1 | GGACAUCAGUGAGUUGGUA | A-104680.1 | UACCAACUCACUGAUGUCC |
| AD-50516.1-UM | A-104695.1 | GUGCUGGUUAACACCAUUU | A-104696.1 | AAAUGGUGUUAACCAGCAC |
| AD-50517.1-UM | A-104711.1 | GCCUUUCCUGGUUUUUAUA | A-104712.1 | UAUAAAAACCAGGAAAGGC |
| AD-50518.1-UM | A-104719.1 | CUUUUGCUAUGACCAAGCU | A-104720.1 | AGCUUGGUCAUAGCAAAAG |
| AD-50523.1-UM | A-104721.1 | UGUACCAGGAAGGCAAGUU | A-104722.1 | AACUUGCCUUCCUGGUACA |
| AD-50528.1-UM | A-104723.1 | ACUAUUAUCUUCAUGGGCA | A-104724.1 | UGCCCAUGAAGAUAAUAGU |
| AD-50540.1-UM | A-104729.1 | UCAUGGGCAGAGUAGCCAA | A-104730.1 | UUGGCUACUCUGCCCAUGA |
| AD-50539.1-UM | A-104785.1 | CCAUUUACUUCAAGGGCCU | A-104786.1 | AGGCCCUUGAAGUAAAUGG |
| AD-50544.1-UM | A-104787.1 | UACUUCAAGGGCCUGUGGA | A-104788.1 | UCCACAGGCCCUUGAAGUA |
| AD-50549.1-UM | A-104789.1 | ACUUCAAGGGCCUGUGGAA | A-104790.1 | UUCCACAGGCCCUUGAAGU |
| AD-50514.1-UM | A-104663.1 | CGACUCUAUCGAAAAGCCA | A-104664.1 | UGGCUUUUCGAUAGAGUCG |
| AD-50522.1-UM | A-104779.1 | AACUGCCGACUCUAUCGAA | A-104780.1 | UUCGAUAGAGUCGGCAGUU |
| AD-50527.1-UM | A-104781.1 | ACUGCCGACUCUAUCGAAA | A-104782.1 | UUUCGAUAGAGUCGGCAGU |
| AD-50531.1-UM | A-104739.1 | GACUCUAUCGAAAAGCCAA | A-104740.1 | UUGGCUUUUCGAUAGAGUC |
| AD-50534.1-UM | A-104769.1 | UCUUCUUUGCCAAACUGAA | A-104770.1 | UUCAGUUUGGCAAAGAAGA |
| AD-50538.1-UM | A-104771.1 | UGCCAAACUGAACUGCCGA | A-104772.1 | UCGGCAGUUCAGUUUGGCA |
| AD-50543.1-UM | A-104773.1 | CCAAACUGAACUGCCGACU | A-104774.1 | AGUCGGCAGUUCAGUUUGG |
| AD-50553.1-UM | A-104777.1 | ACUGAACUGCCGACUCUAU | A-104778.1 | AUAGAGUCGGCAGUUCAGU |
| AD-50504.1-UM | A-104659.1 | GAACUGCCGACUCUAUCGA | A-104660.1 | UCGAUAGAGUCGGCAGUUC |
| AD-50509.1-UM | A-104661.1 | CUGCCGACUCUAUCGAAAA | A-104662.1 | UUUUCGAUAGAGUCGGCAG |
| AD-50529.1-UM | A-104751.1 | CUGGUUAACACCAUUUACU | A-104752.1 | AGUAAAUGGUGUUAACCAG |

TABLE 4

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50475.1 | A-104633.1 | cccuGuGGAcAucuGcAcAdTsdT | A-104634.1 | UGUGcAGAUGUCcAcAGGGdTsdT |
| AD-50476.1 | A-104649.1 | cuAccAcuuucuAucAGcAdTsdT | A-104650.1 | UGCUGAuAGAAAGUGGuAGdTsdT |
| AD-50477.1 | A-104665.1 | cuAucGAAAAGccAAcAAAdTsdT | A-104666.1 | UUUGUUGGCUUUUCGAuAGdTsdT |
| AD-50478.1 | A-104681.1 | GGAcuucAAGGAAAAuGcAdTsdT | A-104682.1 | UGcAUUUUCCUUGAAGUCCdTsdT |
| AD-50479.1 | A-104697.1 | GuuAAcAccAuuuAcuucAdTsdT | A-104698.1 | UGAAGuAAAUGGUGUuAACdTsdT |
| AD-50480.1 | A-104713.1 | ccuGGuuuuuAuAAGAGAAdTsdT | A-104714.1 | UUCUCUuAuAAAAACcAGGdTsdT |
| AD-50481.1 | A-104635.1 | GAcAuucccAuGAAucccAdTsdT | A-104636.1 | UGGGAUUcAUGGGAAUGUCdTsdT |
| AD-50482.1 | A-104651.1 | cAccuGGcAGAuuccAAGAdTsdT | A-104652.1 | UCUUGGAAUCUGCcAGGUGdTsdT |
| AD-50483.1 | A-104667.1 | cGAAAAGccAAcAAAuccudTsdT | A-104668.1 | AGGAUUUGUUGGCUUUUCGdTsdT |

TABLE 4-continued

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50484.1 | A-104683.1 | GAAAAuGcAGAGcAAuccAdTsdT | A-104684.1 | UGGAUUGCUCUGcAUUUUCdTsdT |
| AD-50485.1 | A-104699.1 | GGccuGuGGAAGucAAAGudTsdT | A-104700.1 | ACUUUGACUUCcAcAGGCCdTsdT |
| AD-50486.1 | A-104715.1 | GAAGuuccucuGAAcAcuAdTsdT | A-104716.1 | uAGUGUUcAGAGGAACUUCdTsdT |
| AD-50487.1 | A-104637.1 | ccAuGAAucccAuGuGcAudTsdT | A-104638.1 | AUGcAcAUGGGAUUcAUGGdTsdT |
| AD-50488.1 | A-104653.1 | cAAcuGAuGGAGGuAuuuAdTsdT | A-104654.1 | uAAAuACCUCcAUcAGUUGdTsdT |
| AD-50489.1 | A-104669.1 | ccAAGuuAGuAucAGccAAdTsdT | A-104670.1 | UUGGCUGAuACuAACUUGGdTsdT |
| AD-50490.1 | A-104685.1 | cGGccAucAAcAAAuGGGudTsdT | A-104686.1 | ACCcAUUUGUUGAUGGCCGdTsdT |
| AD-50491.1 | A-104701.1 | GAGGAcGGcuucAGuuuGAdTsdT | A-104702.1 | UcAAACUGAAGCCGUCCUCdTsdT |
| AD-50492.1 | A-104717.1 | ccucuGAAcAcuAuuAucudTsdT | A-104718.1 | AGAuAAuAGUGUUcAGAGGdTsdT |
| AD-50493.1 | A-104639.1 | cAuGAAucccAuGuGcAuudTsdT | A-104640.1 | AAUGcAcAUGGGAUUcAUGdTsdT |
| AD-50494.1 | A-104655.1 | GAuGGAGGuAuuuAAGuuudTsdT | A-104656.1 | AAACUuAAAuACCUCcAUCdTsdT |
| AD-50495.1 | A-104671.1 | GuAucAGccAAucGccuuudTsdT | A-104672.1 | AAAGGCGAUUGGCUGAuACdTsdT |
| AD-50496.1 | A-104687.1 | GGGuGuccAAuAAGAccGAdTsdT | A-104688.1 | UCGGUCUuAUUGGAcACCCdTsdT |
| AD-50497.1 | A-104703.1 | cAGcccuGAAAAGuccAAAdTsdT | A-104704.1 | UUUGGACUUUUcAGGGCUGdTsdT |
| AD-50498.1 | A-104641.1 | cccAuGuGcAuuuAccGcudTsdT | A-104642.1 | AGCGGuAAAUGcAcAUGGGdTsdT |
| AD-50499.1 | A-104657.1 | GuAuuuAAGuuuGAcAccAdTsdT | A-104658.1 | UGGUGUcAAACUuAAAuACdTsdT |
| AD-50500.1 | A-104673.1 | GAcAAAucccuuAccuucAdTsdT | A-104674.1 | UGAAGGuAAGGGAUUUGUCdTsdT |
| AD-50501.1 | A-104689.1 | cuGuucuGGuGcuGGuuAAdTsdT | A-104690.1 | UuAACcAGcACcAGAAcAGdTsdT |
| AD-50502.1 | A-104705.1 | ccAAAcucccAGGuAuuGudTsdT | A-104706.1 | AcAAuACCUGGGAGUUUGGdTsdT |
| AD-50503.1 | A-104643.1 | cccGcuuuGcuAccAcuuudTsdT | A-104644.1 | AAAGUGGuAGcAAAGCGGGdTsdT |
| AD-50505.1 | A-104675.1 | cuuAccuucAAuGAGAccudTsdT | A-104676.1 | AGGUCUcAUUGAAGGuAAGdTsdT |
| AD-50506.1 | A-104691.1 | cuGGuGcuGGuuAAcAccAdTsdT | A-104692.1 | UGGUGUuAACcAGcACcAGdTsdT |
| AD-50507.1 | A-104707.1 | cAAAcucccAGGuAuuGuudTsdT | A-104708.1 | AAcAAuACCUGGGAGUUUGdTsdT |
| AD-50508.1 | A-104645.1 | GcuuuGcuAccAcuuucuAdTsdT | A-104646.1 | uAGAAAGUGGuAGcAAAGCdTsdT |
| AD-50510.1 | A-104677.1 | ccuAccAGGAcAucAGuGAdTsdT | A-104678.1 | UcACUGAUGUCCUGGuAGGdTsdT |
| AD-50511.1 | A-104693.1 | GGuGcuGGuuAAcAccAuudTsdT | A-104694.1 | AAUGGUGUuAACcAGcACCdTsdT |
| AD-50512.1 | A-104709.1 | GccGuucGcuAAAccccAAdTsdT | A-104710.1 | UUGGGGUUuAGCGAACGGCdTsdT |
| AD-50515.1 | A-104679.1 | GGAcAucAGuGAGuuGGuAdTsdT | A-104680.1 | uACcAACUcACUGAUGUCCdTsdT |
| AD-50516.1 | A-104695.1 | GuGcuGGuuAAcAccAuuudTsdT | A-104696.1 | AAAUGGUGUuAACcAGcACdTsdT |
| AD-50517.1 | A-104711.1 | GccuuuccuGGuuuuuAuAdTsdT | A-104712.1 | uAuAAAAACcAGGAAAGGCdTsdT |
| AD-50518.1 | A-104719.1 | cuuuuGcuAuGAccAAGcudTsdT | A-104720.1 | AGCUUGGUcAuAGcAAAAGdTsdT |
| AD-50523.1 | A-104721.1 | uGuAccAGGAAGGcAAGuudTsdT | A-104722.1 | AACUUGCCUUCCUGGuAcAdTsdT |
| AD-50528.1 | A-104723.1 | AcuAuuAucuucAuGGGcAdTsdT | A-104724.1 | UGCCcAUGAAGAuAAuAGUdTsdT |
| AD-50540.1 | A-104729.1 | ucAuGGGcAGAGuAGccAAdTsdT | A-104730.1 | UUGGCuACUCUGCCcAUGAdTsdT |
| AD-50539.1 | A-104785.1 | ccAuuuAcuucAAGGGccudTsdT | A-104786.1 | AGGCCCUUGAAGuAAAUGGdTsdT |
| AD-50544.1 | A-104787.1 | uAcuucAAGGGccuGuGGAdTsdT | A-104788.1 | UCcAcAGGCCCUUGAAGuAdTsdT |

TABLE 4-continued

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50549.1 | A-104789.1 | AcuucAAGGGccuGuGGAAdTsdT | A-104790.1 | UUCcAcAGGCCCUUGAAGUdTsdT |
| AD-50514.1 | A-104663.1 | cGAcucuAucGAAAAGccAdTsdT | A-104664.1 | UGGCUUUUCGAuAGAGUCGdTsdT |
| AD-50522.1 | A-104779.1 | AAcuGccGAcucuAucGAAdTsdT | A-104780.1 | UUCGAuAGAGUCGGcAGUUdTsdT |
| AD-50527.1 | A-104781.1 | AcuGccGAcucuAucGAAAdTsdT | A-104782.1 | UUUCGAuAGAGUCGGcAGUdTsdT |
| AD-50531.1 | A-104739.1 | GAcucuAucGAAAAGccAAdTsdT | A-104740.1 | UUGGCUUUUCGAuAGAGUCdTsdT |
| AD-50534.1 | A-104769.1 | ucuucuuuGccAAAcuGAAdTsdT | A-104770.1 | UUcAGUUUGGcAAAGAAGAdTsdT |
| AD-50538.1 | A-104771.1 | uGccAAAcuGAAcuGccGAdTsdT | A-104772.1 | UCGGcAGUUcAGUUUGGcAdTsdT |
| AD-50543.1 | A-104773.1 | ccAAAcuGAAcuGccGAcudTsdT | A-104774.1 | AGUCGGcAGUUcAGUUUGGdTsdT |
| AD-50553.1 | A-104777.1 | AcuGAAcuGccGAcucuAudTsdT | A-104778.1 | AuAGAGUCGGcAGUUcAGUdTsdT |
| AD-50504.1 | A-104659.1 | GAAcuGccGAcucuAucGAdTsdT | A-104660.1 | UCGAuAGAGUCGGcAGUUCdTsdT |
| AD-50509.1 | A-104661.1 | cuGccGAcucuAucGAAAAdTsdT | A-104662.1 | UUUUCGAuAGAGUCGGcAGdTsdT |
| AD-50529.1 | A-104751.1 | cuGGuuAAcAccAuuuAcudTsdT | A-104752.1 | AGuAAAUGGUGUuAACcAGdTsdT |

TABLE 5[1]

Serpinc1 single dose screen

| | Human (Hep3B) | | Mouse (PMH) | |
|---|---|---|---|---|
| Duplex Name | 10 nM Ave | 0.1 nM Ave | 10 nM Ave | 0.1 nM Ave |
| AD-50475.1 | 0.11 | 0.21 | | |
| AD-50476.1 | 0.08 | 0.43 | | |
| AD-50477.1 | 0.10 | 0.10 | | |
| AD-50478.1 | 0.12 | 0.36 | | |
| AD-50479.1 | 0.24 | 0.84 | | |
| AD-50480.1 | 0.31 | 0.73 | | |
| AD-50481.1 | 0.74 | 1.12 | | |
| AD-50482.1 | 0.61 | 0.89 | | |
| AD-50483.1 | 0.07 | 0.14 | | |
| AD-50484.1 | 0.12 | 0.33 | | |
| AD-50485.1 | 0.58 | 1.18 | | |
| AD-50486.1 | 0.79 | 0.94 | | |
| AD-50487.1 | 0.05 | 0.09 | | |
| AD-50488.1 | 0.83 | 1.07 | | |
| AD-50489.1 | 0.09 | 0.28 | | |
| AD-50490.1 | 0.04 | 0.78 | | |
| AD-50491.1 | 0.19 | 0.77 | | |
| AD-50492.1 | 0.16 | 0.84 | | |
| AD-50493.1 | 0.17 | 0.55 | | |
| AD-50494.1 | 0.16 | 0.59 | | |
| AD-50495.1 | 0.08 | 0.13 | | |
| AD-50496.1 | 0.57 | 0.94 | | |
| AD-50497.1 | 0.85 | 1.15 | | |
| AD-50498.1 | 0.16 | 1.02 | | |
| AD-50499.1 | 0.10 | 0.21 | | |
| AD-50500.1 | 0.22 | 0.58 | | |
| AD-50501.1 | 0.10 | 0.32 | | |
| AD-50502.1 | 0.76 | 1.07 | | |
| AD-50503.1 | 0.08 | 0.47 | | |
| AD-50505.1 | 0.74 | 0.77 | | |
| AD-50506.1 | 0.85 | 0.89 | | |
| AD-50507.1 | 0.03 | 0.37 | | |
| AD-50508.1 | 0.16 | 0.97 | | |
| AD-50510.1 | 0.09 | 0.89 | | |
| AD-50511.1 | 0.15 | 0.71 | | |
| AD-50512.1 | 0.88 | 1.19 | | |

TABLE 5[1]-continued

Serpinc1 single dose screen

| | Human (Hep3B) | | Mouse (PMH) | |
|---|---|---|---|---|
| Duplex Name | 10 nM Ave | 0.1 nM Ave | 10 nM Ave | 0.1 nM Ave |
| AD-50515.1 | 0.13 | 0.49 | | |
| AD-50516.1 | 0.85 | 0.95 | | |
| AD-50517.1 | 0.14 | 0.59 | | |
| AD-50518.1 | 0.36 | 1.05 | | |
| AD-50523.1 | 0.03 | 0.66 | | |
| AD-50528.1 | 0.04 | 0.27 | | |
| AD-50540.1 | 0.14 | 0.37 | | |
| AD-50539.1 | 0.09 | 0.46 | 0.39 | 1.10 |
| AD-50544.1 | 0.23 | 0.75 | 0.36 | 1.07 |
| AD-50549.1 | 0.10 | 0.19 | 0.17 | 0.71 |
| AD-50514.1 | 0.12 | 0.48 | 0.19 | 0.95 |
| AD-50522.1 | 0.61 | 1.02 | 0.46 | 1.32 |
| AD-50527.1 | 0.06 | 0.15 | 0.08 | 0.45 |
| AD-50531.1 | 0.09 | 0.47 | 0.24 | 1.04 |
| AD-50534.1 | 0.05 | 0.10 | 0.11 | 0.55 |
| AD-50538.1 | 0.61 | 0.86 | 0.79 | 1.23 |
| AD-50543.1 | 0.40 | 1.04 | 0.49 | 1.23 |
| AD-50553.1 | 0.40 | 0.93 | 0.72 | 1.25 |
| AD-50504.1 | ND | ND | 0.92 | 1.25 |
| AD-50509.1 | ND | ND | 0.12 | 0.37 |
| AD-50529.1 | ND | ND | 0.23 | 0.47 |

[1]Modified.

TABLE 6

Serpinc1 $IC_{50}$ Data

| Duplex Name | Hep3B $IC_{50}$ (nM) | PMH $IC_{50}$ (nM) |
|---|---|---|
| AD-50487.1 | 0.003 | — |
| AD-50477.1 | 0.006 | — |
| AD-50483.1 | 0.011 | — |
| AD-50475.1 | 0.011 | — |

TABLE 6-continued

| Serpinc1 $IC_{50}$ Data | | |
|---|---|---|
| Duplex Name | Hep3B $IC_{50}$ (nM) | PMH $IC_{50}$ (nM) |
| AD-50495.1 | 0.017 | — |
| AD-50476.1 | 0.026 | — |
| AD-50499.1 | 0.027 | — |
| AD-50478.1 | 0.028 | — |
| AD-50489.1 | 0.029 | — |
| AD-50501.1 | 0.045 | — |
| AD-50507.1 | 0.052 | — |
| AD-50484.1 | 0.081 | — |
| AD-50515.1 | 0.185 | — |
| AD-50540.1 | 0.023 | — |
| AD-50528.1 | 0.056 | — |
| AD-50549.1 | 0.053 | ND |
| AD-50539.1 | 0.170 | ND |
| AD-50534.1 | 0.007 | ND |
| AD-50527.1 | 0.028 | ND |
| AD-50514.1 | 0.085 | ND |
| AD-50527.1 | ND | 0.019 |
| AD-50534.1 | ND | 0.011 |
| AD-50509.1 | ND | 0.006 |
| AD-50529.1 | ND | 0.021 |

A subset of siRNAs were also synthesized with 2'-OMe modifications, and duplexes of these siRNAs in lipofectamine formulations were used to transfect Hep3B cells. The results of the single dose screen of the modified duplexes are shown in Table 7.

TABLE 7

| Lead Optimization (2'-OMe variants) | | | | |
|---|---|---|---|---|
| Parent | Duplex ID | Ave 1 nM | Ave 0.1 nM | Ave 0.01 nM |
| AD-50477 | AD-50477.1 | 0.22 | 0.33 | 0.53 |
| AD-50477 | AD-55025.1 | 0.29 | 0.68 | 0.86 |
| AD-50477 | AD-55031.1 | 0.42 | 0.74 | 0.93 |
| AD-50477 | AD-55037.1 | 0.52 | 0.73 | 0.95 |
| AD-50477 | AD-55043.1 | 0.45 | 0.70 | 0.94 |
| AD-50477 | AD-55049.1 | 0.24 | 0.47 | 0.95 |
| AD-50477 | AD-55055.1 | 0.37 | 0.68 | 0.99 |
| AD-50477 | AD-55061.1 | 0.43 | 0.66 | 0.85 |
| AD-50477 | AD-55067.1 | 0.56 | 0.72 | 0.92 |
| AD-50477 | AD-55026.1 | 0.28 | 0.59 | 0.87 |
| AD-50477 | AD-55032.1 | 0.49 | 0.76 | 0.86 |
| AD-50477 | AD-55038.1 | 0.52 | 0.75 | 0.93 |
| AD-50477 | AD-55044.1 | 0.84 | 0.77 | 1.06 |

TABLE 7-continued

| Lead Optimization (2'-OMe variants) | | | | |
|---|---|---|---|---|
| Parent | Duplex ID | Ave 1 nM | Ave 0.1 nM | Ave 0.01 nM |
| AD-50487 | AD-50487.1 | 0.21 | 0.50 | 0.76 |
| AD-50487 | AD-55050.1 | 0.24 | 0.53 | 0.75 |
| AD-50487 | AD-55056.1 | 0.27 | 0.50 | 0.84 |
| AD-50487 | AD-55062.1 | 0.30 | 0.61 | 0.84 |
| AD-50487 | AD-55068.1 | 0.20 | 0.37 | 0.66 |
| AD-50487 | AD-55027.1 | 0.18 | 0.36 | 0.67 |
| AD-50487 | AD-55033.1 | 0.22 | 0.43 | 0.70 |
| AD-50487 | AD-55039.1 | 0.19 | 0.38 | 0.67 |
| AD-50487 | AD-55045.1 | 0.18 | 0.29 | 0.57 |
| AD-50487 | AD-55051.1 | 0.17 | 0.29 | 0.60 |
| AD-50487 | AD-55057.1 | 0.21 | 0.37 | 0.65 |
| AD-50487 | AD-55063.1 | 0.19 | 0.33 | 0.63 |
| AD-50487 | AD-55069.1 | 0.16 | 0.26 | 0.51 |
| AD-50509 | AD-50509.1 | 0.15 | 0.31 | 0.57 |
| AD-50509 | AD-55029.1 | 0.17 | 0.26 | 0.49 |
| AD-50509 | AD-55028.1 | 0.17 | 0.35 | 0.54 |
| AD-50509 | AD-55052.1 | 0.21 | 0.32 | 0.59 |
| AD-50509 | AD-55035.1 | 0.19 | 0.31 | 0.62 |
| AD-50509 | AD-55047.1 | 0.19 | 0.35 | 0.66 |
| AD-50509 | AD-55058.1 | 0.21 | 0.40 | 0.66 |
| AD-50509 | AD-55046.1 | 0.18 | 0.37 | 0.66 |
| AD-50509 | AD-55070.1 | 0.17 | 0.40 | 0.68 |
| AD-50509 | AD-55034.1 | 0.19 | 0.37 | 0.69 |
| AD-50509 | AD-55041.1 | 0.20 | 0.28 | 0.63 |
| AD-50509 | AD-55064.1 | 0.19 | 0.34 | 0.65 |
| AD-50509 | AD-55040.1 | 0.18 | 0.34 | 0.69 |
| AD-50534 | AD-50534.1 | 0.19 | 0.42 | 0.83 |
| AD-50534 | AD-55053.1 | 0.24 | 0.38 | 0.59 |
| AD-50534 | AD-55030.1 | 0.15 | 0.33 | 0.64 |
| AD-50534 | AD-55054.1 | 0.18 | 0.40 | 0.69 |
| AD-50534 | AD-55059.1 | 0.18 | 0.33 | 0.56 |
| AD-50534 | AD-55036.1 | 0.22 | 0.37 | 0.61 |
| AD-50534 | AD-55060.1 | 0.19 | 0.42 | 0.62 |
| AD-50534 | AD-55071.1 | 0.29 | 0.56 | 0.81 |
| AD-50534 | AD-55048.1 | 0.26 | 0.56 | 0.83 |
| AD-50534 | AD-55066.1 | 0.30 | 0.49 | 0.76 |
| AD-50534 | AD-55042.1 | 0.25 | 0.47 | 0.79 |
| AD-50534 | AD-55065.1 | 0.24 | 0.50 | 0.83 |

Examples 3-4

Lead Optimization and In Vivo Testing

Table 8 is a detailed list of sequences of duplex siRNAs targeting Serpinc1 that were formulated as a lipid nanoparticle (LNP) (i.e., with MC3) or conjugated to GalNAc for lead optimization and in vivo delivery.

TABLE 8

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-50477.1 | A-104665.1 | cuAucGAAAAGccAAcAAAdTsdT | A-104666.1 | UUUGUUGGCUUUUCGAuAGdTsdT |
| AD-55025.1 | A-113301.1 | cuAucGAAAAGccAAcAAAdTdT | A-113302.1 | UUUGUUGGCUUUUcGAuAGdTdT |
| AD-5503.1 | A-113301.2 | cuAucGAAAAGccAAcAAAdTdT | A-113303.1 | UUUGUUGGCUUuUcGAuAGdTdT |
| AD-55037.1 | A-113301.3 | cuAucGAAAAGccAAcAAAdTdT | A-113304.1 | UUUGUUGGcUUuUcGAuAGdTdT |
| AD-55043.1 | A-113301.4 | cuAucGAAAAGccAAcAAAdTdT | A-113305.1 | UUUGuUGGcUUuUcGAuAGdTdT |
| AD-55049.1 | A-113306.1 | cuAucGAAAAGcCAAcAAAdTdT | A-113302.2 | UUUGUUGGCUUUUcGAuAGdTdT |
| AD-55055.1 | A-113306.2 | cuAucGAAAAGcCAAcAAAdTdT | A-113303.2 | UUUGUUGGCUUuUcGAuAGdTdT |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-55061.1 | A-113306.3 | cuAucGAAAAGcCAAcAAAdTdT | A-113304.2 | UUUGUUGGcUUuUcGAuAGdTdT |
| AD-55067.1 | A-113306.4 | cuAucGAAAAGcCAAcAAAdTdT | A-113305.2 | UUUGuUGGcUUuUcGAuAGdTdT |
| AD-55026.1 | A-113307.1 | cuAucGAAAAGcCAACAAAdTdT | A-113302.3 | UUUGUUGGCUUUUcGAuAGdTdT |
| AD-55032.1 | A-113307.2 | cuAucGAAAAGcCAACAAAdTdT | A-113303.3 | UUUGUUGGCUUuUcGAuAGdTdT |
| AD-55038.1 | A-113307.3 | cuAucGAAAAGcCAACAAAdTdT | A-113304.3 | UUUGUUGGcUUuUcGAuAGdTdT |
| AD-55044.1 | A-113307.4 | cuAucGAAAAGcCAACAAAdTdT | A-113305.3 | UUUGuUGGcUUuUcGAuAGdTdT |
| AD-50487.1 | A-104637.1 | ccAuGAAucccAuGuGcAudTsdT | A-104638.1 | AUGcAcAUGGGAUUcAUGGdTsdT |
| AD-55050.1 | A-113308.1 | ccAuGAAucccAuGuGcAudTdT | A-113309.1 | AUGcAcAUGGGAUUcAuGGdTdT |
| AD-55056.1 | A-113308.2 | ccAuGAAucccAuGuGcAudTdT | A-113310.1 | AUGCAcAUGGGAUUcAuGGdTdT |
| AD-55062.1 | A-113308.3 | ccAuGAAucccAuGuGcAudTdT | A-113311.1 | AUGCAcAUGGGAuUcAuGGdTdT |
| AD-55068.1 | A-113308.4 | ccAuGAAucccAuGuGcAudTdT | A-113312.1 | AUGCACAUGGGAuUcAuGgdTdT |
| AD-55027.1 | A-113313.1 | ccAuGAAucccAuGUGcAUdTdT | A-113309.2 | AUGcAcAUGGGAUUcAuGGdTdT |
| AD-55033.1 | A-113313.2 | ccAuGAAucccAuGUGcAUdTdT | A-113310.2 | AUGCAcAUGGGAUUcAuGGdTdT |
| AD-55039.1 | A-113313.3 | ccAuGAAucccAuGUGcAUdTdT | A-113311.2 | AUGCAcAUGGGAuUcAuGGdTdT |
| AD-55045.1 | A-113313.4 | ccAuGAAucccAuGUGcAUdTdT | A-113312.2 | AUGCACAUGGGAuUcAuGgdTdT |
| AD-55055.1 | A-113314.1 | ccAuGAAucCcAuGUGcAUdTdT | A-113309.3 | AUGcAcAUGGGAUUcAuGGdTdT |
| AD-55057.1 | A-113341.2 | ccAuGAAucCcAuGUGcAUdTdT | A-113310.3 | AUGCAcAUGGGAUUcAuGGdTdT |
| AD-55063.1 | A-113314.3 | ccAuGAAucCcAuGUGcAUdTdT | A-113311.3 | AUGCAcAUGGGAuUcAuGGdTdT |
| AD-55069.1 | A-113314.4 | ccAuGAAucCcAuGUGcAUdTdT | A-113312.3 | AUGCACAUGGGAuUcAuGgdTdT |
| AD-50509.1 | A-104661.1 | cuGccGAcucuAucGAAAAdTsdT | A-104662.1 | UUUUCGAuAGAGUCGGcAGdTsdT |
| AD-55029.1 | A-113321.1 | cuGccGAcuCuAuCGAaAAdTdT | A-113316.3 | UUUUCGAuAGAGUCGGcAgdTdT |
| AD-55028.1 | A-113315.1 | cuGccGAcucuAucGAAAAdTdT | A-113316.1 | UUUUCGAuAGAGUCGGcAgdTdT |
| AD-55052.1 | A-113320.1 | cuGccGAcuCuAuCGAAAAdTdT | A-113316.2 | UUUUCGAuAGAGUCGGcAgdTdT |
| AD-55035.1 | A-113321.2 | cuGccGAcuCuAuCGAaAAdTdT | A-113317.3 | UUUUCGAuAGAGUCgGcAgdTdT |
| AD-55047.1 | A-113321.4 | cuGccGAcuCuAuCGAaAAdTdT | A-113319.3 | UUuUCGAUAGAGUCgGcAgdTdT |
| AD-55058.1 | A-113320.2 | ccGccGAcuCuAuCGAAAAdTdT | A-113317.2 | UUUUCGAuAGAGUCgGcAgdTdT |
| AD-55046.1 | A-113315.4 | cuGccGAcucuAucGAAAAdTdT | A-113319.1 | UUuUCGAUAGAGUCgGcAgdTdT |
| AD-55070.1 | A-113320.4 | cuGccGAcuCuAuCGAAAAdTdT | A-113319.2 | UUuUCGAUAGAGUCgGcAgdTdT |
| AD-55034.1 | A-113315.2 | cuGccGAcucuAucGAAAAdTdT | A-113317.1 | UUUUCGAuAGAGUCgGcAgdTdT |
| AD-55041.1 | A-113321.3 | cuGccGAcuCuAuCGAaAAdTdT | A-113318.3 | UUuUCGAuAGAGUCgGcAgdTdT |
| AD-55064.1 | A-113320.3 | cuGccGAcuCuAuCGAAAAdTdT | A-113318.2 | UUuUCGAuAGAGUCgGcAgdTdT |
| AD-55040.1 | A-113315.3 | cuGccGAcucuAucGAAAAdTdT | A-113318.1 | UUuUCGAuAGAGUCgGcAgdTdT |
| AD-50534.1 | A-104769.1 | ucuucuuuGccAAAcuGAAdTsdT | A-104770.1 | UUcAGUUUGGcAAAGAAGAdTsdT |
| AD-55053.1 | A-113322.1 | ucuucuuuGccAAAcuGAAdTdT | A-113323.1 | UUcAGUUUGGcAAAGAAGadTdT |
| AD-55030.1 | A-113327.1 | ucuucuuuGcCAAACuGAAdTdT | A-113323.2 | UUcAGUUUGGcAAAGAAGadTdT |
| AD-55054.1 | A-113327.5 | ucuucuuuGcCAAACuGAAdTdT | A-113328.1 | UUCAGUUuGGcAAAGAAGadTdT |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-55059.1 | A-113322.2 | ucuucuuuGccAAAcuGAAdTdT | A-113324.1 | UUcAGUUUGGcAAAgAAGadTdT |
| AD-55036.1 | A-113327.2 | ucuucuuuGcCAAACuGAAdTdT | A-113324.2 | UUcAGUUUGGcAAAgAAGadTdT |
| AD-55060.1 | A-113327.6 | ucuucuuuGcCAAACuGAAdTdT | A-113329.1 | UUCAGUUuGGcAAAgAAGadTdT |
| AD-55071.1 | A-113322.4 | ucuucuuuGccAAAcuGAAdTdT | A-113326.1 | UUcAGUUUGGCaAAgAAGadTdT |
| AD-55048.1 | A-113327.4 | ucuucuuuGcCAAACuGAAdTdT | A-113326.2 | UUcAGUUUGGCaAAgAAGadTdT |
| AD-55066.1 | A-113327.7 | ucuucuuuGcCAAACuGAAdTdT | A-113330.1 | UUCAGUUuGGcaAAgAAGadTdT |
| AD-55042.1 | A-113327.3 | ucuucuuuGcCAAACuGAAdTdT | A-113325.2 | UUcAGUUUGGcaAAgAAGadTdT |
| AD-55065.1 | A-113322.3 | ucuucuuuGccAAAcuGAAdTdT | A-113325.1 | UUcAGUUUGGcaAAgAAGadTdT |
| AD-54944.1 | A-113073.1 | GfgUfuAfaCfaCfCfAfuUfuAfcUfuCfaAf L96 | A-113074.1 | uUfgAfaGfuAfaAfuggUfgUfuAfaCfcsAfsg |
| AD-54951.1 | A-112997.1 | UfaGfuAfuCfaGfCfCfaAfuCfgCfcUfuUf L96 | A-112998.1 | aAfaGfgCfgAfuUfggcUfgAfuAfcUfasAfsc |
| AD-54942.1 | A-113041.1 | CfgCfuUfuGfcUfAfCfcAfcUfuUfcUfaUf L96 | A-113042.1 | aUfaGfaAfaGfuGfguaGfcAfaAfgCfgsGfsg |
| AD-54948.1 | A-113043.1 | CfuUfuGfcUfaCfCfAfcUfuUfcUfaUfcAf L96 | A-113044.1 | uGfaUfaGfaAfaGfuggUfaGfcAfaAfgsCfsg |
| AD-54957.1 | A-112999.1 | AfuCfgAfaAfaGfCfCfaAfcAfaAfuCfcUf L96 | A-113000.1 | aGfgAfuUfuGfuUfggcUfuUfuCfgAfusAfsg |
| AD-54933.1 | A-112991.1 | UfcCfcAfuGfaAfUfCfcCfaUfgUfgCfaUf L96 | A-112992.1 | aUfgCfaCfaUfgGfgauUfcAfuGfgGfasAfsu |
| AD-54962.1 | A-113079.1 | UfaAfgGfcAfuUfUfCfuUfgAfgGfuAfaAf L96 | A-113080.1 | uUfuAfcCfuCfaAfgaaAfuGfcCfuUfasUfsg |
| AD-54972.1 | A-113051.1 | GfcAfaCfuGfaUfGfGfaGfgUfaUfuUfaAf L96 | A-113052.1 | uUfaAfaUfaCfcUfccaufcAfgufuGfcsUfsg |
| AD-54949.1 | A-113059.1 | UfuUfaAfgUfuUfGfAfcAfcCfaUfaUfcUf L96 | A-113060.1 | aGfaUfaUfgGfuGfucaAfaCfuUfaAfasUfsa |
| AD-54936.1 | A-113039.1 | CfcAfuGfaAfuCfCfCfaUfgUfgCfaUfuUf L96 | A-113040.1 | aAfaUfgCfaCfaUfgggAfuUfcAfuGfgsGfsa |
| AD-54971.1 | A-113035.1 | UfgCfuGfgUfuAfAfCfaCfcAfuUfuAfcUf L96 | A-113036.1 | aGfuAfaAfuGfgUfguuAfaCfcAfgCfasCfsc |
| AD-54955.1 | A-113061.1 | UfcUfaUfcGfaAfAfAfgCfcAfaCfaAfaUf L96 | A-113062.1 | aUfuUfgUfuGfgCfuuuUfcGfaUfaGfasGfsu |
| AD-54953.1 | A-113029.1 | UfuCfcCfgCfuUfUfGfcUfaCfcAfcUfuUf L96 | A-113030.1 | aAfaGfuGfgUfaGfcaaAfgCfgGfgAfasUfsu |
| AD-54937.1 | A-113055.1 | GfaUfgGfaGfgUfAfUfuUfaAfgUfuUfgAf L96 | A-113056.1 | uCfaAfaCfuUfaAfauaCfcUfcCfaUfcsAfsg |
| AD-54967.1 | A-113065.1 | AfgAfcAfaAfuCfCfCfuUfaCfcUfuCfaAf L96 | A-113066.1 | uUfgAfaGfgUfaAfgggAfuUfuGfuCfusCfsc |
| AD-54935.1 | A-113023.1 | UfgCfuAfcCfaCfUfUfuCfuAfuCfaGfcAf L96 | A-113024.1 | uGfcUfgAfuAfgAfaagUfgGfuAfgCfasAfsa |
| AD-54976.1 | A-113037.1 | UfgUfaUfuCfcAfAfUfgUfgAfuAfgGfaAf L96 | A-113038.1 | uUfcCfuAfuCfaCfauuGfgAfaUfaCfasUfsg |
| AD-54965.1 | A-113033.1 | AfaCfuGfcCfgAfCfUfcUfaUfcGfaAfaAf L96 | A-113034.1 | uUfuUfcGfaUfaGfaguCfgGfcAfgUfusCfsa |
| AD-54959.1 | A-113031.1 | GfcCfgAfcUfcUfAfUfcGfaAfaAfgCfcAf L96 | A-113032.1 | uGfgCfuUfuUfcGfauaGfaGfuCfgGfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-54943.1 | A-113057.1 | UfaUfuUfaAfgUfUfUfgAfcAfcCfaUfaUf L96 | A-113058.1 | aUfaUfgGfuGfuCfaaaCfuUfaAfaUfasCfsc |
| AD-54956.1 | A-113077.1 | UfgGfgCfcUfuGfUfCfgAfuCfuGfuUfcAf L96 | A-113078.1 | uGfaAfcAfgAfuCfgacAfaGfgCfcCfasUfsg |
| AD-54973.1 | A-113067.1 | CfaAfaUfcCfcUfUfAfcCfuUfcAfaUfgAf L96 | A-113068.1 | uCfaUfuGfaAfgGfuaaGfgGfaUfuUfgsUfsc |
| AD-54975.1 | A-113021.1 | UfcCfaAfaCfuCfCfCfaGfgUfaUfuGfuUf L96 | A-113022.1 | aAfcAfaUfaCfcUfgggAfgUfuUfgGfasCfsu |
| AD-54963.1 | A-113001.1 | GfaAfcUfgCfcGfAfCfuCfuAfuCfgAfaAf L96 | A-113002.1 | uUfuCfgAfuAfgAfgucGfgCfaGfuUfcsAfsg |
| AD-54978.1 | A-113069.1 | UfcAfaCfaAfaUfGfGfgUfgUfcCfaAfuAf L96 | A-113070.1 | uAfuUfgGfaCfaCfccaufuUfgUfuGfasUfsg |
| AD-54952.1 | A-113013.1 | CfaCfuGfuUfcUfGfGfuGfcUfgGfuUfaAf L96 | A-113014.1 | uUfaAfcCfaGfcAfccaGfaAfcAfgUfgsAfsg |
| AD-54950.1 | A-113075.1 | GfgAfcGfgCfuUfCfAfgUfuUfgAfaGfgAf L96 | A-113076.1 | uCfcUfuCfaAfaCfugaAfgCfcGfuCfcsUfsc |
| AD-54964.1 | A-113017.1 | CfuGfgAfcUfuCfAfAfgGfaAfaAfuGfcAf L96 | A-113018.1 | uGfcAfuUfuUfcCfuugAfaGfuCfcAfgsGfsg |
| AD-54974.1 | A-113005.1 | AfgGfuAfuUfuAfAfGfuUfuGfaCfaCfcAf L96 | A-113006.1 | uGfgUfgUfcAfaAfcuuAfaAfuAfcCfusCfsc |
| AD-54969.1 | A-113003.1 | UfuAfcUfuCfaAfGfGfgCfcUfgUfgGfaAf L96 | A-113004.1 | uUfcCfaCfaGfgCfccuUfgAfaGfuAfasAfsu |
| AD-54961.1 | A-113063.1 | UfuUfuUfgGfaGfAfCfaAfaUfcCfcUfuAf L96 | A-113064.1 | uAfaGfgGfaUfuUfgucUfcCfaAfaAfasGfsg |
| AD-54968.1 | A-113081.1 | GfaUfuGfcUfgGfCfCfgUfuCfgCfuAfaAf L96 | A-113082.1 | uUfuAfgCfgAfaCfggcCfaGfcAfaUfcsAfsc |
| AD-54947.1 | A-113027.1 | CfcGfaCfuCfuAfUfCfgAfaAfaGfcCfaAf L96 | A-113028.1 | uUfgGfcUfuUfuCfgauAfgAfgUfcGfgsCfsa |
| AD-54941.1 | A-113025.1 | CfaCfcAfuufuAfCfUfuCfaAfgGfgCfcUf L96 | A-113026.1 | aGfgCfcCfuUfgAfaguAfaAfuGfgUfgsUfsu |
| AD-54966.1 | A-113049.1 | CfaAfgCfuGfgGfUfGgcCfuGfuAfaUfgAf L96 | A-113050.1 | uCfaUfuAfcAfgGfcacCfcAfgCfuUfgsGfsu |
| AD-54940.1 | A-113009.1 | AfcAfcUfaUfuAfUfCfuUfcAfuGfgGfcAf L96 | A-113010.1 | uGfcCfcAfuGfaAfgauAfaUfaGfuGfusUfsc |
| AD-54958.1 | A-113015.1 | AfgGfaAfaAfuGfCfAfgAfgCfaAfuCfcAf L96 | A-113016.1 | uGfgAfuUfgCfuCfugcAfuUfuUfcCfusUfsg |
| AD-54938.1 | A-113071.1 | UfcUfgGfuGfcUfGfGfuUfaAfcAfcCfaUf L96 | A-113072.1 | aUfgGfuGfuUfaAfccaGfcAfcCfaGfasAfsc |
| AD-54934.1 | A-113007.1 | AfgCfcCfuGfuGfGfAfcAfuCfuGfcAfcAf L96 | A-113008.1 | uGfuGfcAfgAfuGfuccAfcAfgGfgCfusCfsc |
| AD-54939.1 | A-112993.1 | CfuUfcUfuCfuUfUfGfcCfaAfaCfuGfaAf L96 | A-112994.1 | uUfcAfgUfuUfgGfcaaAfgAfaGfaAfgsUfsg |
| AD-54960.1 | A-113047.1 | UfcUfcCfaCfgGfCfUfuUfuGfcUfaUfgAf L96 | A-113048.1 | uCfaUfaGfcAfaAfagcCfgUfgGfaGfasUfsa |
| AD-54954.1 | A-113045.1 | GfcAfcCfuGfgCfAfGfaUfuCfcAfaGfaAf L96 | A-113046.1 | uUfcUfuGfgAfaUfcugCfcAfgGfuGfcsUfsg |
| AD-54970.1 | A-113019.1 | CfuUfcAfuGfgGfCfAfgAfgUfaGfcCfaAf L96 | A-113020.1 | uUfgGfcUfaCfuCfugcCfcAfuGfaAfgsAfsu |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-54946.1 | A-113011.1 | CfuCfcAfaGfuUfAfGfuAfuCfaGfcCfaAf L96 | A-113012.1 | uUfgGfcUfgAfuAfcuaAfcUfuGfgAfgsGfsa |
| AD-56331.1 | A-113073.4 | GfgUfuAfaCfaCfCfAfuUfuAfcUfuCfaAf L96 | A-115852.1 | UUfgAfaGfuAfaAfuggUfgUfuAfaCfcsAfsg |
| AD-56337.1 | A-115853.1 | GfguuAfaCfaCfCfAfuUfuAfcUfuCfaAf L96 | A-113074.4 | uUfgAfaGfuAfaAfuggUfgUfuAfaCfcsAfsg |
| AD-56343.1 | A-115854.1 | GfguuAfaCfaCfCfAfuUfuAfcUfuCfaa L96 | A-113074.5 | uUfgAfaGfuAfaAfuggUfgUfuAfaCfcsAfsg |
| AD-56349.1 | A-115855.1 | GfguuAfaCfaCfCfAfuUfuacUfuCfaaL96 | A-113074.6 | uUfgAfaGfuAfaAfuggUfgUfuAfaCfcsAfsg |
| AD-56355.1 | A-115856.1 | GfguuAfaCfaCfCfAfuUfuAfcuucaaL96 | A-113074.7 | uUfgAfaGfuAfaAfuggUfgUfuAfaCfcsAfsg |
| AD-56361.1 | A-115857.1 | GfguuAfacaCfCfAfuUfuacUfucaaL96 | A-113074.8 | uUfgAfaGfuAfaAfuggUfgUfuAfaCfcsAfsg |
| AD-56367.1 | A-115858.1 | GfguuAfacaCfCfAfuuuacUfucaaL96 | A-113074.9 | uUfgAfaGfuAfaAfuggUfgUfuAfaCfcsAfsg |
| AD-56326.1 | A-115859.1 | GfguuAfacaCfCfAfuuuacuucaaL96 | A-113074.10 | uUfgAfaGfuAfaAfuggUfgUfuAfaCfcsAfsg |
| AD-56321.1 | A-115860.1 | GfguuaacaCfCfAfuuuacuucaaL96 | A-113074.11 | uUfgAfaGfuAfaAfuggUfgUfuAfaCfcsAfsg |
| AD-56338.1 | A-113073.5 | GfgUfuAfaCfaCfCfAfuUfuAfcUfuCfaAf L96 | A-115861.1 | uUfgaaGfuAfaAfuggUfgUfuAfaCfcsasg |
| AD-56344.1 | A-115853.2 | GfguuAfaCfaCfCfAfuUfuAfcUfuCfaAf L96 | A-115861.2 | uUfgaaGfuAfaAfuggUfgUfuAfaCfcsasg |
| AD-56350.1 | A-115854.2 | GfguuAfaCfaCfCfAfuUfuAfcUfuCfaa L96 | A-115861.3 | uUfgaaGfuAfaAfuggUfgUfuAfaCfcsasg |
| AD-56356.1 | A-115855.2 | GfguuAfaCfaCfCfAfuUfuacUfuCfaaL96 | A-115861.4 | uUfgaaGfuAfaAfuggUfgUfuAfaCfcsasg |
| AD-56362.1 | A-115856.2 | GfguuAfaCfaCfCfAfuUfuAfcuucaaL96 | A-115861.5 | uUfgaaGfuAfaAfuggUfgUfuAfaCfcsasg |
| AD-56368.1 | A-115857.2 | GfguuAfacaCfCfAfuUfuacUfucaaL96 | A-115861.6 | uUfgaaGfuAfaAfuggUfgUfuAfaCfcsasg |
| AD-56327.1 | A-115858.2 | GfguuAfacaCfCfAfuuuacUfucaaL96 | A-115861.7 | uUfgaaGfuAfaAfuggUfgUfuAfaCfcsasg |
| AD-56333.1 | A-115859.2 | GfguuAfacaCfCfAfuuuacuucaaL96 | A-115861.8 | uUfgaaGfuAfaAfuggUfgUfuAfaCfcsasg |
| AD-56339.1 | A-115860.2 | GfguuaacaCfCfAfuuuacuucaaL96 | A-115861.9 | uUfgaaGfuAfaAfuggUfgUfuAfaCfcsasg |
| AD-56345.1 | A-113073.6 | GfgUfuAfaCfaCfCfAfuUfuAfcUfuCfaAf L96 | A-115862.1 | uUfgaaGfuAfaAfuggUfguuAfaCfcsasg |
| AD-56351.1 | A-115853.3 | GfguuAfaCfaCfCfAfuUfuAfcUfuCfaAf L96 | A-115862.2 | uUfgaaGfuAfaAfuggUfguuAfaCfcsasg |
| AD-56357.1 | A-115854.3 | GfguuAfaCfaCfCfAfuUfuAfcUfuCfaa L96 | A-115862.3 | uUfgaaGfuAfaAfuggUfguuAfaCfcsasg |
| AD-56363.1 | A-115855.3 | GfguuAfaCfaCfCfAfuUfuacUfuCfaaL96 | A-115862.4 | uUfgaaGfuAfaAfuggUfguuAfaCfcsasg |
| AD-56369.1 | A-115856.3 | GfguuAfaCfaCfCfAfuUfuAfcuucaaL96 | A-115862.5 | uUfgaaGfuAfaAfuggUfguuAfaCfcsasg |
| AD-56328.1 | A-115857.3 | GfguuAfacaCfCfAfuUfuacUfucaaL96 | A-115862.6 | uUfgaaGfuAfaAfuggUfguuAfaCfcsasg |
| AD-56334.1 | A-115858.3 | GfguuAfacaCfCfAfuuuacUfucaaL96 | A-115862.7 | uUfgaaGfuAfaAfuggUfguuAfaCfcsasg |
| AD-56340.1 | A-115859.3 | GfguuAfacaCfCfAfuuuacuucaaL96 | A-115862.8 | uUfgaaGfuAfaAfuggUfguuAfaCfcsasg |
| AD-56346.1 | A-115860.3 | GfguuaacaCfCfAfuuuacuucaaL96 | A-115862.9 | uUfgaaGfuAfaAfuggUfguuAfaCfcsasg |
| AD-56352.1 | A-115863.1 | GfgUfUfAfaCfaCfCfAfuUfuAfcUfuCfaAf L96 | A-113074.12 | uUfgAfaGfuAfaAfuggUfgUfuAfaCfcsAfsg |
| AD-56358.1 | A-115864.1 | GfgUfUfAfaCfaCfCfAfUfUfAfcUfuCfaAf L96 | A-113074.13 | uUfgAfaGfuAfaAfuggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56364.1 | A-115865.1 | GfgUfUfAfaCfaCfCfAfuUfUfAfcUfUfCfaAfL96 | A-113074.14 | uUfgAfaGfuAfaAfuggUfgUfuAfaCfcsAfsg |
| AD-56370.1 | A-115866.1 | GfgUfUfAfAfCfaCfCfAfuUfUfAfcUfUfCfAfAfL96 | A-113074.15 | uUfgAfaGfuAfaAfuggUfgUfuAfaCfcsAfsg |
| AD-56329.1 | A-115867.1 | GfGfUfUfAfAfCfaCfCfAfuUfUfAfcUfUfCfAfAfL96 | A-113074.16 | uUfgAfaGfuAfaAfuggUfgUfuAfaCfcsAfsg |
| AD-56335.1 | A-115868.1 | GfGfUfUfAfAfCfaCfCfAfuUfUfAfCfUfUfCfAfAfL96 | A-113074.17 | uUfgAfaGfuAfaAfuggUfgUfuAfaCfcsAfsg |
| AD-56341.1 | A-115869.1 | GfGfUfUfAfAfCfAfCfCfAfuUfUfAfCfUfUfAfCfAfAfL96 | A-113074.18 | uUfgAfaGfuAfaAfuggUfgUfuAfaCfcsAfsg |
| AD-56347.1 | A-115868.2 | GfGfUfUfAfAfCfaCfCfAfuUfUfAfCfUfUfCfAfAfL96 | A-115870.1 | uUfgaaGfuAfaAfuggUfgUfuaaCfcsasg |
| AD-56353.1 | A-115868.3 | GfGfUfUfAfAfCfaCfCfAfuUfUfAfCfUfUfCfAfAfL96 | A-115871.1 | uUfgAaGfuAfaAfuggUfgUfuaaCfcsasg |
| AD-56359.1 | A-115868.4 | GfGfUfUfAfAfCfaCfCfAfuUfUfAfCfUfUfCfAfAfL96 | A-115872.1 | uUfgAaGfuaaAfuggUfgUfuaaCfcsasg |
| AD-56365.1 | A-115868.5 | GfGfUfUfAfAfCfaCfCfAfuUfUfAfCfUfUfCfAfAfL96 | A-115873.1 | uUfgAaGfuAaAfuggUfgUfuaaCfcsasg |
| AD-56371.1 | A-115868.6 | GfGfUfUfAfAfCfaCfCfAfuUfUfAfCfUfUfCfAfAfL96 | A-115874.1 | uUfgAaguAaAfuggUfgUfuaaCfcsasg |
| AD-56330.1 | A-115868.7 | GfGfUfUfAfAfCfaCfCfAfuUfUfAfCfUfUfCfAfAfL96 | A-115875.1 | uUfgAaGuAaAfuggUfgUfuaaCfcsasg |
| AD-56336.1 | A-115868.8 | GfGfUfUfAfAfCfaCfCfAfuUfUfAfCfUfUfCfAfAfL96 | A-115876.1 | uUgAaguAaAfuggUfgUfuaaCfcsasg |
| AD-56342.1 | A-115868.9 | GfGfUfUfAfAfCfaCfCfAfuUfUfAfCfUfUfCfAfAfL96 | A-115877.1 | uUgAaGuAaAfuggUfgUfuaaCfcsasg |
| AD-56348.1 | A-115868.10 | GfGfUfUfAfAfCfaCfCfAfuUfUfAfCfUfUfCfAfAfL96 | A-115861.10 | uUfgaaGfuAfaAfuggUfgUfuAfaCfcsasg |
| AD-56354.1 | A-115868.11 | GfGfUfUfAfAfCfaCfCfAfuUfUfAfCfUfUfCfAfAfL96 | A-115878.1 | uUfgAaGfuAfaAfuggUfgUfuAfaCfcsasg |
| AD-56360.1 | A-115868.12 | GfGfUfUfAfAfCfaCfCfAfuUfUfAfCfUfUfCfAfAfL96 | A-115879.1 | uUfgAaGfuaaAfuggUfgUfuAfaCfcsasg |
| AD-56366.1 | A-115868.13 | GfGfUfUfAfAfCfaCfCfAfuUfUfAfCfUfUfCfAfAfL96 | A-115880.1 | uUfgAaGfuAaAfuggUfgUfuAfaCfcsasg |
| AD-56372.1 | A-115868.14 | GfGfUfUfAfAfCfaCfCfAfuUfUfAfCfUfUfCfAfAfL96 | A-115881.1 | uUfgAaguAaAfuggUfgUfuAfaCfcsasg |
| AD-56378.1 | A-115868.15 | GfGfUfUfAfAfCfaCfCfAfuUfUfAfCfUfUfCfAfAfL96 | A-115882.1 | uUfgAaGuAaAfuggUfgUfuAfaCfcsasg |
| AD-56384.1 | A-115868.16 | GfGfUfUfAfAfCfaCfCfAfuUfUfAfCfUfUfCfAfAfL96 | A-115883.1 | uUgAaGuAaAfuggUfgUfuAfaCfcsasg |
| AD-56390.1 | A-115868.17 | GfGfUfUfAfAfCfaCfCfAfuUfUfAfCfUfUfCfAfAfL96 | A-115884.1 | uUgaAguAaAfuggUfgUfuAfaCfcsasg |
| AD-56396.1 | A-113073.7 | GfgUfuAfaCfaCfCfAfuUfuAfcUfuCfaAfL96 | A-115885.1 | uUfgAfAfGfuAfaAfuggUfgUfUfAfaCfcsAfsg |
| AD-56402.1 | A-115863.2 | GfgUfUfAfaCfaCfCfAfuUfuAfcUfuCfaAfL96 | A-115885.2 | uUfgAfAfGfuAfaAfuggUfgUfUfAfaCfcsAfsg |
| AD-56408.1 | A-115864.2 | GfgUfUfAfaCfaCfCfAfuUfUfAfcUfuCfaAfL96 | A-115885.3 | uUfgAfAfGfuAfaAfuggUfgUfUfAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56414.1 | A-115865.2 | GfgufUfAfaCfaCfCfAfuUfUfAfcUfUfCfaAfL96 | A-115885.4 | uUfgAfAfGfuAfaAfuggUfgUfUfAfaCfcsAfsg |
| AD-56373.1 | A-115886.1 | GfgUfUfAfaCfaCfCfAfuUfUfAfcUfUfCfAfAfL96 | A-115885.5 | uUfgAfAfGfuAfaAfuggUfgUfUfAfaCfcsAfsg |
| AD-56379.1 | A-115866.2 | GfgufUfAfAfCfaCfCfAfuUfUfAfcUfUfCfAfAfL96 | A-115885.6 | uUfgAfAfGfuAfaAfuggUfgUfUfAfaCfcsAfsg |
| AD-56385.1 | A-115867.2 | GfGfUfUfAfAfCfaCfCfAfuUfUfAfcUfUfCfAfAfL96 | A-115885.7 | uUfgAfAfGfuAfaAfuggUfgUfUfAfaCfcsAfsg |
| AD-56391.1 | A-115868.18 | GfGfUfUfAfAfCfaCfCfAfuUfUfAfCfUfUfCfAfAfL96 | A-115885.8 | uUfgAfAfGfuAfaAfuggUfgUfUfAfaCfcsAfsg |
| AD-56397.1 | A-115869.2 | GfGfUfUfAfAfCfAfCfCfAfuUfUfAfCfUfUfCfAfAfL96 | A-115885.9 | uUfgAfAfGfuAfaAfuggUfgUfUfAfaCfcsAfsg |
| AD-56403.1 | A-113073.8 | GfgUfuAfaCfaCfCfAfuUfuAfcUfuCfaAfL96 | A-115887.1 | uUfgAfAfGfUfAfaAfuggUfgUfUfAfaCfcsAfsg |
| AD-56409.1 | A-115863.3 | GfgUfUfAfaCfaCfCfAfuUfuAfcUfuCfaAfL96 | A-115887.2 | uUfgAfAfGfUfAfaAfuggUfgUfUfAfaCfcsAfsg |
| AD-56415.1 | A-115864.3 | GfgufUfAfaCfaCfCfAfuUfUfAfcUfuCfaAfL96 | A-115887.3 | uUfgAfAfGfUfAfaAfuggUfgUfUfAfaCfcsAfsg |
| AD-56374.1 | A-115865.3 | GfgUfUfAfaCfaCfCfAfuUfUfAfcUfUfCfaAfL96 | A-115887.4 | uUfgAfAfGfUfAfaAfuggUfgUfUfAfaCfcsAfsg |
| AD-56380.1 | A-115886.2 | GfgUfUfAfaCfaCfCfAfuUfUfAfcUfUfCfAfAfL96 | A-115887.5 | uUfgAfAfGfUfAfaAfuggUfgUfUfAfaCfcsAfsg |
| AD-56386.1 | A-115866.3 | GfgUfUfAfAfCfaCfCfAfuUfUfAfcUfUfCfAfAfL96 | A-115887.6 | uUfgAfAfGfUfAfaAfuggUfgUfUfAfaCfcsAfsg |
| AD-56392.1 | A-115867.3 | GfGfUfUfAfAfCfaCfCfAfuUfUfAfcUfUfCfAfAfL96 | A-115887.7 | uUfgAfAfGfUfAfaAfuggUfgUfUfAfaCfcsAfsg |
| AD-56398.1 | A-115868.19 | GfGfUfUfAfAfCfaCfCfAfuUfUfAfCfUfUfCfAfAfL96 | A-115887.8 | uUfgAfAfGfUfAfaAfuggUfgUfUfAfaCfcsAfsg |
| AD-56404.1 | A-115869.3 | GfGfUfUfAfAfCfAfCfCaAfuUfUfAfCfUfUfCfAfAfL96 | A-115887.9 | uUfgAfAfGfUfAfaAfuggUfgUfUfAfaCfcsAfsg |
| AD-56410.1 | A-115881.1 | GfgUfuAfaCfaCfCfAfuUfuAfcUfUfCfAfAfL96 | A-113074.19 | uUfgAfaGfuAfaAfuggUfgUfuAfaCfcsAfsg |
| AD-56416.1 | A-115889.1 | GfgUfuAfaCfaCfCfAfuUfuAfCfUfUfCfaAfL96 | A-113074.20 | uUfgAfaGfuAfaAfuggUfgUfuAfaCfcsAfsg |
| AD-56375.1 | A-115890.1 | GfgUfuAfaCfaCfCfAfuUfUfAfCfUfuCfaAfL96 | A-113074.21 | uUfgAfaGfuAfaAfuggUfgUfuAfaCfcsAfsg |
| AD-56381.1 | A-115891.1 | GfgUfuAfaCfaCfCfAfUfUfUfAfcUfuCfaAfL96 | A-113074.22 | uUfgAfaGfuAfaAfuggUfgUfuAfaCfcsAfsg |
| AD-56387.1 | A-115892.1 | GfgUfuAfaCfAfCfCfAfUfUfuAfcUfuCfaAfL96 | A-113074.23 | uUfgAfaGfuAfaAfuggUfgUfuAfaCfcsAfsg |
| AD-56393.1 | A-115893.1 | GfgUfuAfAfCfAfCfCfAfuUfuAfcUfuCfaAfL96 | A-113074.24 | uUfgAfaGfuAfaAfuggUfgUfuAfaCfcsAfsg |
| AD-56399.1 | A-115894.1 | GfgUfUfAfAfCfaCfCfAfuUfuAfcUfuCfaAfL96 | A-113074.25 | uUfgAfaGfuAfaAfuggUfgUfuAfaCfcsAfsg |
| AD-56405.1 | A-115895.1 | GfGfUfUfAfaCfaCfCfAfuUfuAfcUfuCfaAfL96 | A-113074.26 | uUfgAfaGfuAfaAfuggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56411.1 | A-115896.1 | GfgUfuAfaCfaCfCfAfuUfuAfcUfucaaL96 | A-113074.27 | uUfgAfaGfuAfaAfuggUfgUfuAfaCfcsAfsg |
| AD-56417.1 | A-115897.1 | GfgUfuAfaCfaCfCfAfuUfuAfcuucaAfL96 | A-113074.28 | uUfgAfaGfuAfaAfuggUfgUfuAfaCfcsAfsg |
| AD-56376.1 | A-115898.1 | GfgUfuAfaCfaCfCfAfuUfuacuuCfaAfL96 | A-113074.29 | uUfgAfaGfuAfaAfuggUfgUfuAfaCfcsAfsg |
| AD-56382.1 | A-115899.1 | GfgUfuAfaCfaCfCfAfuuuacufuCfaAfL96 | A-113074.30 | uUfgAfaGfuAfaAfuggUfgUfuAfaCfcsAfsg |
| AD-56388.1 | A-115900.1 | GfgUfuAfaCfaCfcauuuAfcUfuCfaAfL96 | A-113074.31 | uUfgAfaGfuAfaAfuggUfgUfuAfaCfcsAfsg |
| AD-56394.1 | A-115901.1 | gfgUfuAfaCfaccauUfuAfcUfuCfaAfL96 | A-113074.32 | uUfgAfaGfuAfaAfuggUfgUfuAfaCfcsAfsg |
| AD-56400.1 | A-115902.1 | GfgUfuAfacaccAfuUfuAfcufuCfaAfL96 | A-113074.33 | uUfgAfaGfuAfaAfuggUfgUfuAfaCfcsAfsg |
| AD-56406.1 | A-115903.1 | GfgUfuAfacaCfCfAfuuuAfcUfuCfaAfL96 | A-113074.34 | uUfgAfaGfuAfaAfuggUfgUfuAfaCfcsAfsg |
| AD-56412.1 | A-115904.1 | GfgUfuaacaCfCfAfuUfuAfcUfuCfaAfL96 | A-113074.35 | uUfgAfaGfuAfaAfuggUfgUfuAfaCfcsAfsg |
| AD-56418.1 | A-115905.1 | GfguuaaCfaCfCfAfuUfuAfcUfuCfaAfL96 | A-113074.36 | uUfgAfaGfuAfaAfuggUfgUfuAfaCfcsAfsg |
| AD-56377.1 | A-115906.1 | gguuAfaCfaCfCfAfuUfuAfcUfuCfaAfL96 | A-113074.37 | uUfgAfaGfuAfaAfuggUfgUfuAfaCfcsAfsg |
| AD-56383.1 | A-113073.9 | GfgUfuAfaCfaCfCfAfuUfuAfcUfuCfaAf L96 | A-115907.1 | UfUfGfAfaGfuAfaAfuggUfgUfuAfaCfcsAf sg |
| AD-56389.1 | A-113073.10 | GfgUfuAfaCfaCfCfAfuUfuAfcUfuCfaAf L96 | A-115908.1 | uUfGfAfAfGfuAfaAfuggUfgUfuAfaCfcsAf sg |
| AD-56395.1 | A-113073.11 | GfgUfuAfaCfaCfCfAfuUfuAfcUfuCfaAf L96 | A-115909.1 | uUfgAfAfGfUfAfaAfuggUfgUfuAfaCfcsAf sg |
| AD-56401.1 | A-113073.12 | GfgUfuAfaCfaCfCfAfuUfuAfcUfuCfaAf L96 | A-115910.1 | uUfgAfaGfUfAfAfAfuggUfgUfuAfaCfcsAf sg |
| AD-56407.1 | A-113073.13 | GfgUfuAfaCfaCfCfAfuUfuAfcUfuCfaAf L96 | A-115911.1 | uUfgAfaGfuAfAfAfUfGfgUfgUfuAfaCfcsA fsg |
| AD-56413.1 | A-113073.14 | GfgUfuAfaCfaCfCfAfuUfuAfcUfuCfaAf L96 | A-115912.1 | uUfgAfaGfuAfaAfUfGfGfUfgUfuAfaCfcsA fsg |
| AD-56419.2 | A-113073.15 | GfgUfuAfaCfaCfCfAfuUfuAfcUfuCfaAf L96 | A-115913.1 | uUfgAfaGfuAfaAfuGfGfUfGfUfuAfaCfcsA fsg |
| AD-56425.2 | A-113073.16 | GfgUfuAfaCfaCfCfAfuUfuAfcUfuCfaAf L96 | A-115914.1 | uUfgAfaGfuAfAfAfuggUfGfUfuAfaCfcsAf sg |
| AD-56431.2 | A-113073.17 | GfgUfuAfaCfaCfCfAfuUfuAfcUfuCfaAf L96 | A-115915.1 | uUfgAfaGfuAfaAfuggUfGfUfUfAfaCfcsAf sg |
| AD-56436.2 | A-113073.18 | GfgUfuAfaCfaCfCfAfuUfuAfcUfuCfaAf L96 | A-115916.1 | uUfgAfaGfuAfaAfuggUfgUfUfAfAfCfcsAf sg |
| AD-56442.2 | A-113073.19 | GfgUfuAfaCfaCfCfAfuUfuAfcUfuCfaAf L96 | A-115917.1 | uUfgAfaGfuAfaAfuggUfgUfuAfAfCfCfsAf sg |
| AD-56448.2 | A-113073.20 | GfgUfuAfaCfaCfCfAfuUfuAfcUfuCfaAf L96 | A-115918.1 | uUfgAfaGfuAfaAfuggUfgUfuAfaCfCfsAfs Gf |
| AD-56454.2 | A-113073.21 | GfgUfuAfaCfaCfCfAfuUfuAfcUfuCfaAf L96 | A-115919.1 | uugaaGfuAfaAfuggUfgUfuAfaCfcsAfsg |
| AD-56460.2 | A-113073.22 | GfgUfuAfaCfaCfCfAfuUfuAfcUfuCfaAf L96 | A-115920.1 | uUfgaaguAfaAfuggUfgUfuAfaCfcsAfsg |
| AD-56420.2 | A-113073.23 | GfgUfuAfaCfaCfCfAfuUfuAfcUfuCfaAf L96 | A-115921.1 | uUfgAfaguaaAfuggUfgUfuAfaCfcsAfsg |
| AD-56426.2 | A-113073.24 | GfgUfuAfaCfaCfCfAfuUfuAfcUfuCfaAf L96 | A-115922.1 | uUfgAfaGfuaaauggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56432.2 | A-113073.25 | GfgUfuAfaCfaCfCfAfuUfuAfcUfuCfaAfL96 | A-115923.1 | uUfgAfaGfuAfaauggugUfuAfaCfcsAfsg |
| AD-56437.2 | A-113073.26 | GfgUfuAfaCfaCfCfAfuUfuAfcUfuCfaAfL96 | A-115924.1 | uUfgAfaGfuAfaAfugguguuAfaCfcsAfsg |
| AD-56443.2 | A-113073.27 | GfgUfuAfaCfaCfCfAfuUfuAfcUfuCfaAfL96 | A-115925.1 | uUfgAfaGfuAfaAfuggUfguuaaCfcsAfsg |
| AD-56449.2 | A-113073.28 | GfgUfuAfaCfaCfCfAfuUfuAfcUfuCfaAfL96 | A-115926.1 | uUfgAfaGfuAfaAfuggUfgUfuaaccsAfsg |
| AD-56455.2 | A-113073.29 | GfgUfuAfaCfaCfCfAfuUfuAfcUfuCfaAfL96 | A-115927.1 | uUfgAfaGfuAfaAfuggUfgUfuAfaccsasg |
| AD-56461.2 | A-115888.2 | GfgUfuAfaCfaCfCfAfuUfuAfcUfUfCfAfAfL96 | A-115919.2 | uugaaGfuAfaAfuggUfgUfuAfaCfcsAfsg |
| AD-56421.2 | A-115889.2 | GfgUfuAfaCfaCfCfAfuUfuAfCfUfUfCfaAfL96 | A-115920.2 | uUfgaaguAfaAfuggUfgUfuAfaCfcsAfsg |
| AD-56427.2 | A-115890.2 | GfgUfuAfaCfaCfCfAfuUfUfAfCfUfuCfaAfL96 | A-115921.2 | uUfgAfaguaaAfuggUfgUfuAfaCfcsAfsg |
| AD-56433.2 | A-115891.2 | GfgUfuAfaCfaCfCfAfUfUfUfAfcUfuCfaAfL96 | A-115922.2 | uUfgAfaGfuaaauggUfgUfuAfaCfcsAfsg |
| AD-56438.2 | A-115892.2 | GfgUfuAfaCfAfCfCfAfUfUfuAfcUfuCfaAfL96 | A-115923.2 | uUfgAfaGfuAfaauggugUfuAfaCfcsAfsg |
| AD-56444.2 | A-115893.2 | GfgUfuAfAfCfAfCfCfAfuUfuAfcUfuCfaAfL96 | A-115924.2 | uUfgAfaGfuAfaAfugguguuAfaCfcsAfsg |
| AD-56450.2 | A-115894.2 | GfgUfUfAfAfCfaCfCfAfuUfuAfcUfuCfaAfL96 | A-115925.2 | uUfgAfaGfuAfaAfuggUfguuaaCfcsAfsg |
| AD-56456.2 | A-115895.2 | GfGfUfUfAfaCfaCfCfAfuUfuAfcUfuCfaAfL96 | A-115926.2 | uUfgAfaGfuAfaAfuggUfgUfuaaccsAfsg |
| AD-56462.2 | A-115896.2 | GfgUfuAfaCfaCfCfAfuUfuAfcUfucaaL96 | A-115907.2 | UfUfGfAfaGfuAfaAfuggUfgUfuAfaCfcsAfsg |
| AD-56422.2 | A-115897.2 | GfgUfuAfaCfaCfCfAfuUfuAfcuucaAfL96 | A-115908.2 | uUfGfAfAfGfuAfaAfuggUfgUfuAfaCfcsAfsg |
| AD-56428.2 | A-115898.2 | GfgUfuAfaCfaCfCfAfuUfuacuuCfaAfL96 | A-115909.2 | uUfgAfAfGfUfAfaAfuggUfgUfuAfaCfcsAfsg |
| AD-56434.2 | A-115899.2 | GfgUfuAfaCfaCfCfAfuuuacUfuCfaAfL96 | A-115910.2 | uUfgAfaGfUfAfAfAfuggUfgUfuAfaCfcsAfsg |
| AD-56439.2 | A-115900.2 | GfgUfuAfaCfaCfcauuuAfcUfuCfaAfL96 | A-115911.2 | uUfgAfaGfuAfAfAfUfGfgUfgUfuAfaCfcsAfsg |
| AD-56445.2 | A-115901.2 | GfgUfuAfaCfaccauUfuAfcUfuCfaAfL96 | A-115912.2 | uUfgAfaGfuAfaAfUfGfGfUfgUfuAfaCfcsAfsg |
| AD-56451.2 | A-115902.2 | GfgUfuAfacaccAfuUfuAfcUfuCfaAfL96 | A-115913.2 | uUfgAfaGfuAfaAfuGfGfUfGfUfuAfaCfcsAfsg |
| AD-56457.2 | A-115903.2 | GfgUfuAfacaCfCfAfuuuAfcUfuCfaAfL96 | A-115914.2 | uUfgAfaGfuAfAfAfuggUfGfUfuAfaCfcsAfsg |
| AD-56463.2 | A-115904.2 | GfgUfuaacaCfCfAfuUfuAfcUfuCfaAfL96 | A-115915.2 | uUfgAfaGfuAfaAfuggUfGfUfUfAfaCfcsAfsg |
| AD-56423.2 | A-115905.2 | GfguuaaCfaCfCfAfuUfuAfcUfuCfaAfL96 | A-115916.2 | uUfgAfaGfuAfaAfuggUfgUfUfAfAfCfcsAfsg |
| AD-56429.2 | A-115906.2 | gguuAfaCfaCfCfAfuUfuAfcUfuCfaAfL96 | A-115917.2 | uUfgAfaGfuAfaAfuggUfgUfuAfAfCfCfsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56440.2 | A-113073.31 | GfgUfuAfaCfaCfCfAfuUfuAfcUfuCfaAfL96 | A-115928.1 | uUfgAfaGfuAfaAfugGfUfgUfuAfaCfcsAfsg |
| AD-56446.2 | A-115929.1 | GfgUfuAfaCfacCfAfuUfuAfcUfuCfaAfL96 | A-115928.2 | uUfgAfaGfuAfaAfugGfUfgUfuAfaCfcsAfsg |
| AD-56452.2 | A-113073.32 | GfgUfuAfaCfaCfCfAfuUfuAfcUfuCfaAfL96 | A-115930.1 | UUfgAfaGfuAfaAfugGfUfgUfuAfaCfcsAfsg |
| AD-56458.2 | A-115929.2 | GfgUfuAfaCfacCfAfuUfuAfcUfuCfaAfL96 | A-115930.2 | UUfgAfaGfuAfaAfugGfUfgUfuAfaCfcsAfsg |
| AD-56464.2 | A-113073.33 | GfgUfuAfaCfaCfCfAfuUfuAfcUfuCfaAfL96 | A-115931.1 | uUfgAfaGfuAfaAfugGUfgUfuAfaCfcsAfsg |
| AD-56424.2 | A-115929.3 | GfgUfuAfaCfacCfAfuUfuAfcUfuCfaAfL96 | A-115931.2 | uUfgAfaGfuAfaAfugGUfgUfuAfaCfcsAfsg |
| AD-56430.2 | A-115932.1 | GfgUfuAfaCfaCCfAfuUfuAfcUfuCfaAfL96 | A-115931.3 | uUfgAfaGfuAfaAfugGUfgUfuAfaCfcsAfsg |
| AD-56435.2 | A-113073.34 | GfgUfuAfaCfaCfCfAfuUfuAfcUfuCfaAfL96 | A-115933.1 | UUfgAfaGfuAfaAfugGUfgUfuAfaCfcsAfsg |
| AD-56441.2 | A-115929.4 | GfgUfuAfaCfacCfAfuUfuAfcUfuCfaAfL96 | A-115933.2 | UUfgAfaGfuAfaAfugGUfgUfuAfaCfcsAfsg |
| AD-56447.2 | A-115932.2 | GfgUfuAfaCfaCCfAfuUfuAfcUfuCfaAfL96 | A-115933.3 | UUfgAfaGfuAfaAfugGUfgUfuAfaCfcsAfsg |
| AD-56453.2 | A-115934.1 | GfgUfuAfaCfaUfCfAfuUfuAfcUfuCfaAfL96 | A-113074.39 | uUfgAfaGfuAfaAfuggUfgUfuAfaCfcsAfsg |
| AD-56459.2 | A-115935.1 | GfgUfuAfaCfaAfCfAfuUfuAfcUfuCfaAfL96 | A-113074.40 | uUfgAfaGfuAfaAfuggUfgUfuAfaCfcsAfsg |
| AD-56465.2 | A-115936.1 | GfgUfuAfaCfaCfUfAfuUfuAfcUfuCfaAfL96 | A-113074.41 | uUfgAfaGfuAfaAfuggUfgUfuAfaCfcsAfsg |
| AD-56471.2 | A-115937.1 | GfgUfuAfaCfaCfAfAfuUfuAfcUfuCfaAfL96 | A-113074.42 | uUfgAfaGfuAfaAfuggUfgUfuAfaCfcsAfsg |
| AD-56477.2 | A-113073.35 | GfgUfuAfaCfaCfCfAfuUfuAfcUfuCfaAfL96 | A-115938.1 | uUfgAfaGfuAfaAfuggUfgUfuAfaCfc |
| AD-56483.3 | A-113073.36 | GfgUfuAfaCfaCfCfAfuUfuAfcUfuCfaAfL96 | A-115939.1 | uUfgAfaGfuAfaAfuggUfgUfuAfaCfsc |
| AD-56488.2 | A-113073.37 | GfgUfuAfaCfaCfCfAfuUfuAfcUfuCfaAfL96 | A-115940.1 | uUfgAfaGfuAfaAfuggUfgUfuAfasCfsc |
| AD-56483.4 | A-113073.38 | GfgUfuAfaCfaCfCfAfuUfuAfcUfuCfaAfL96 | A-115939.2 | uUfgAfaGfuAfaAfuggUfgUfuAfaCfsc |
| AD-56497.2 | A-115941.1 | UfuAfaCfaCfCfAfuUfuAfcUfuCfaAfL96 | A-115940.2 | uUfgAfaGfuAfaAfuggUfgUfuAfasCfsc |
| AD-56502.2 | A-115941.2 | UfuAfaCfaCfCfAfuUfuAfcUfuCfaAfL96 | A-115942.1 | uUfgAfaGfuAfaAfuggUfgUfuAfa |
| AD-56466.2 | A-115941.3 | UfuAfaCfaCfCfAfuUfuAfcUfuCfaAfL96 | A-115943.1 | uUfgAfaGfuAfaAfuggUfgUfuAfsa |
| AD-56472.2 | A-115941.4 | UfuAfaCfaCfCfAfuUfuAfcUfuCfaAfL96 | A-115944.1 | uUfgAfaGfuAfaAfuggUfgUfusAfsa |
| AD-56478.2 | A-115945.1 | AfaCfaCfCfAfuUfuAfcUfuCfaAfL96 | A-115943.2 | uUfgAfaGfuAfaAfuggUfgUfuAfsa |
| AD-56484.2 | A-115945.2 | AfaCfaCfCfAfuUfuAfcUfuCfaAfL96 | A-115944.2 | uUfgAfaGfuAfaAfuggUfgUfusAfsa |
| AD-56493.2 | A-113073.39 | GfgUfuAfaCfaCfCfAfuUfuAfcUfuCfaAfL96 | A-115948.1 | uUfgAf(Aeo)GfuAfaAfuggUfgUfuAfaCfcsAfsg |
| AD-56498.2 | A-113073.40 | GfgUfuAfaCfaCfCfAfuUfuAfcUfuCfaAfL96 | A-115949.1 | uUfgAfa(Geo)uAfaAfuggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56467.2 | A-113073.42 | GfgUfuAfaCfaCfCfAfuUfuAfcUfuCfaAf L96 | A-115951.1 | uUfgAfaGfu(Aeo)aAfuggUfgUfuAf aCfcsAfsg |
| AD-56473.2 | A-113073.43 | GfgUfuAfaCfaCfCfAfuUfuAfcUfuCfaAf L96 | A-115952.1 | uUfgAfaGfuAf(Aeo)AfuggUfgUfuA faCfcsAfsg |
| AD-56479.2 | A-113073.44 | GfgUfuAfaCfaCfCfAfuUfuAfcUfuCfaAf L96 | A-115953.1 | uUfgAfaGfuAfa(Aeo)uggUfgUfuAf aCfcsAfsg |
| AD-56485.2 | A-113073.45 | GfgUfuAfaCfaCfCfAfuUfuAfcUfuCfaAf L96 | A-115954.1 | uUfgAfaGfuAfaAfugg(Teo) gUfuAfaCfcsAfsg |
| AD-56490.2 | A-113073.46 | GfgUfuAfaCfaCfCfAfuUfuAfcUfuCfaAf L96 | A-115955.1 | uUfgAfaGfuAfaAfuggUf(Geo) UfuAfaCfcsAfsg |
| AD-56494.2 | A-113073.47 | GfgUfuAfaCfaCfCfAfuUfuAfcUfuCfaAf L96 | A-115956.1 | uUfgAfaGfuAfaAfuggUfg(Teo) uAfaCfcsAfsg |
| AD-56499.2 | A-113073.48 | GfgUfuAfaCfaCfCfAfuUfuAfcUfuCfaAf L96 | A-115957.1 | uUfgAfaGfuAfaAfuggUfgUf(Teo) AfaCfcsAfsg |
| AD-56504.2 | A-113073.49 | GfgUfuAfaCfaCfCfAfuUfuAfcUfuCfaAf L96 | A-115958.1 | uUfgAfaGfuAfaAfuggUfgUfu(Aeo) aCfcsAfsg |
| AD-56468.2 | A-113073.50 | GfgUfuAfaCfaCfCfAfuUfuAfcUfuCfaAf L96 | A-115959.1 | uUfgAfaGfuAfaAfuggUfgUfuAf(Aeo) CfcsAfsg |
| AD-56474.2 | A-113073.51 | GfgUfuAfaCfaCfCfAfuUfuAfcUfuCfaAf L96 | A-115960.1 | uUfgAfaGfuAfaAfuggUfgUfuAfa (m5Ceo)csAfsg |
| AD-56480.2 | A-113073.52 | GfgUfuAfaCfaCfCfAfuUfuAfcUfuCfaAf L96 | A-115961.1 | uUfgAfaGfuAfaAfuggUfgUfuAfaCf (m5Ceos)Afsg |
| AD-56486.2 | A-113073.53 | GfgUfuAfaCfaCfCfAfuUfuAfcUfuCfaAf L96 | A-115962.1 | uUfgAfaGfuAfaAfuggUfgUfuAfaCfcs (Aeos)(Geo) |
| AD-56491.2 | A-113073.54 | GfgUfuAfaCfaCfCfAfuUfuAfcUfuCfaAf L96 | A-115963.1 | uUfgAfaGfuAfaAf(Teo)(Geo)(Geo)UfgUf usAfsa |
| AD-56495.2 | A-115964.1 | GfgUfuAfaCfaCfCfAfuUfuAfcUf(Teo) Cf(Aeo)AfL96 | A-113074.43 | uUfgAfaGfuAfaAfuggUfgUfuAfaCfcsAfsg |
| AD-56500.2 | A-115965.1 | Gf(Geo)UfuAfaCfaCfCfAfuUfuAfcUf (Teo)Cf(Aeo)AfL96 | A-113074.44 | uUfgAfaGfuAfaAfuggUfgUfuAfaCfcsAfsg |
| AD-56505.2 | A-115966.1 | Gf(Geo)Uf(Teo)AfaCfaCfCfAfuUfuAfcUf (Teo)Cf(Aeo)AfL96 | A-113074.45 | uUfgAfaGfuAfaAfuggUfgUfuAfaCfcsAfsg |
| AD-56469.2 | A-115967.1 | Gf(Geo)Uf(Teo)AfaCfaCfCfAfuUfuAf (m5Ceo)Uf(Teo)Cf(Aeo)AfL96 | A-113074.46 | uUfgAfaGfuAfaAfuggUfgUfuAfaCfcsAfsg |
| AD-56475.2 | A-115968.1 | Gf(Geo)Uf(Teo)AfaCfaCfCfAfuUf(Teo) Af(m5Ceo)Uf(Teo)Cf(Aeo)AfL96 | A-113074.47 | uUfgAfaGfuAfaAfuggUfgUfuAfaCfcsAfsg |
| AD-56481.2 | A-115969.1 | Gf(Geo)Uf(Teo)AfaCfaCfCfAf(Teo)Uf (Teo)Af(m5Ceo)Uf(Teo)Cf(Aeo)AfL96 | A-113074.48 | uUfgAfaGfuAfaAfuggUfgUfuAfaCfcsAfsg |
| AD-56487.2 | A-115970.1 | Gf(Geo)Uf(Teo)Af(Aeo)Cf(Aeo)CfCfAf (Teo)Uf(Teo)Af(m5Ceo)Uf(Teo)Cf (Aeo)AfL96 | A-113074.49 | uUfgAfaGfuAfaAfuggUfgUfuAfaCfcsAfsg |

Example 3

LNP-Mediated Delivery of siRNAs

Figure 3A:
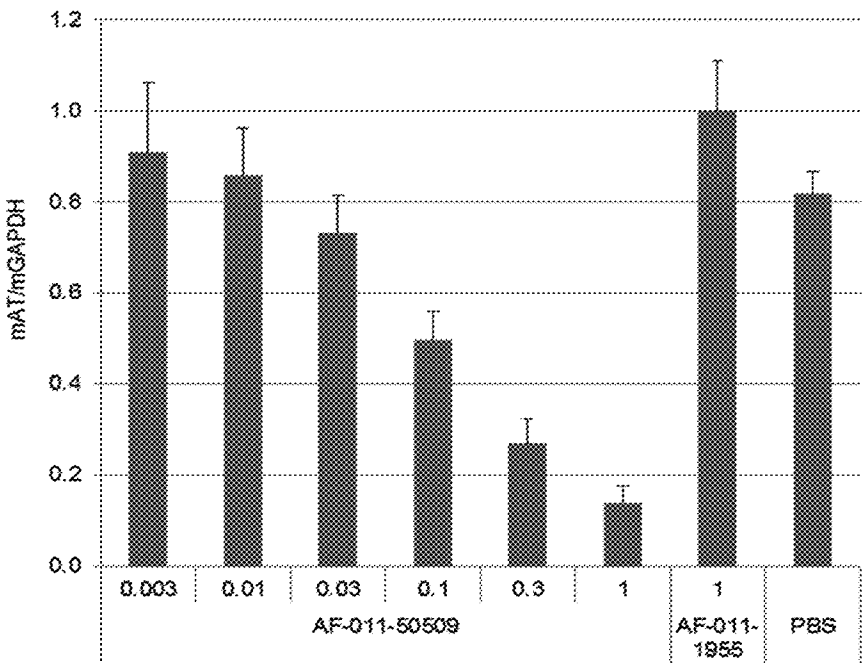
FIGS. 3A and 3B are graphs showing the inhibition of Serpinc1 mRNA (A) and protein (B) expression in CD-1 mice following a single dose, as indicated, of an LNP formulation of AD-50509 or AD-1955.
Figure 3B:
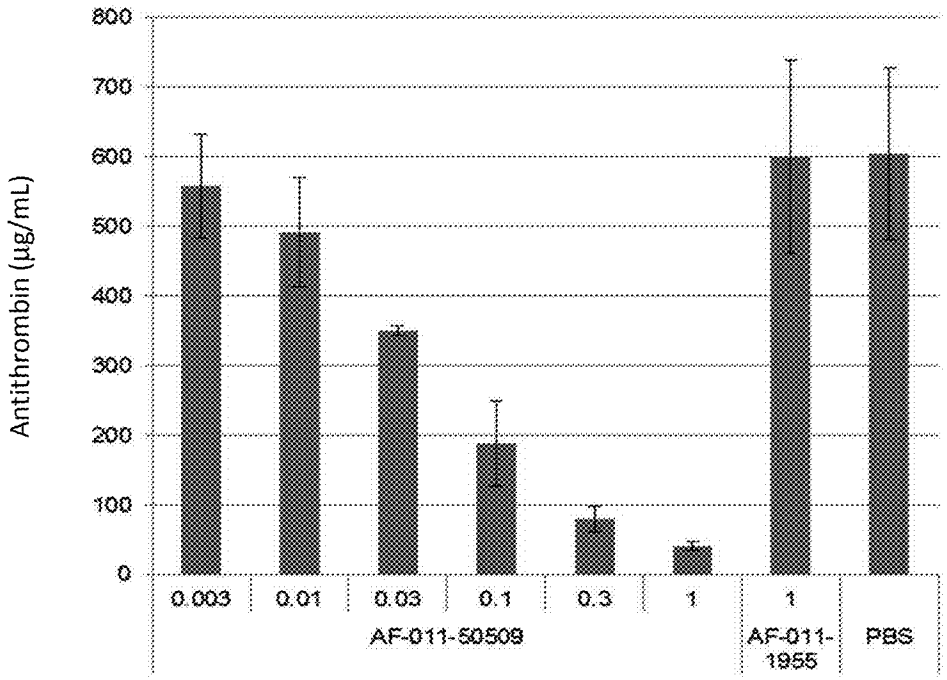

Based on the in vitro single dose and $IC_{50}$ results described above, modified AD-50509 was selected for formulation in a lipid nanoparticle (LNP). In order to determine an effective dose for LNP-mediated delivery of AD-50509, CD1 mice were intravenously injected with a single dose of an LNP formulation (AF-011) of AD-50509 siRNA at 0.003, 0.01, 0.03, 0.1, 0.3, or 1.0 mg/kg. Animals were sacrificied 48 hours later and the level of Serpinc1 mRNA relative to GAPDH and the level of Serpinc1 protein were determined as described herein. As shown in FIGS. 3A and 3B, the maximum Serpinc1 mRNA silencing of 85% with AF-011-AD-50509 was achieved with an $ED_{50}$ of about 0.1 mg/kg (FIG. 3A) and the maximum Serpinc1 protein silencing of 90% was achieved with an $ED_{50}$ of about 0.05 mg/kg (FIG. 3B).

Figure 4A:
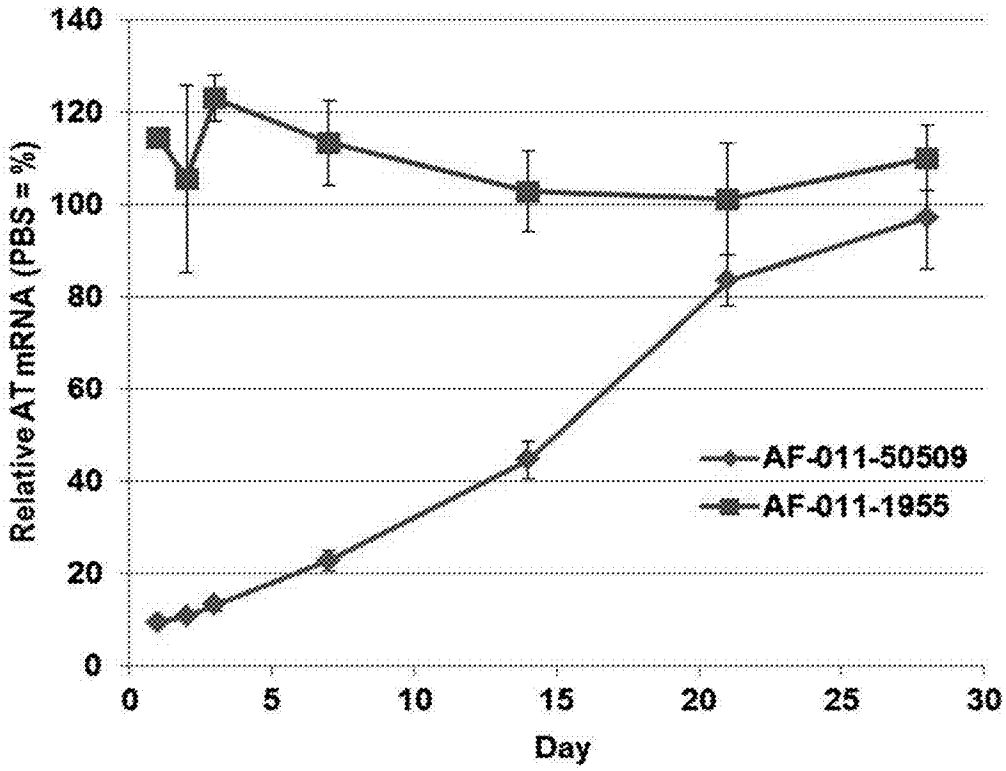
FIGS. 4A and 4B are graphs showing the duration of inhibition of Serpinc1 mRNA (A) and protein (B) expression in CD-1 mice following a single 1 mg/kg dose of an LNP formulation of AD-50509 or AD-1955.
Figure 4B:
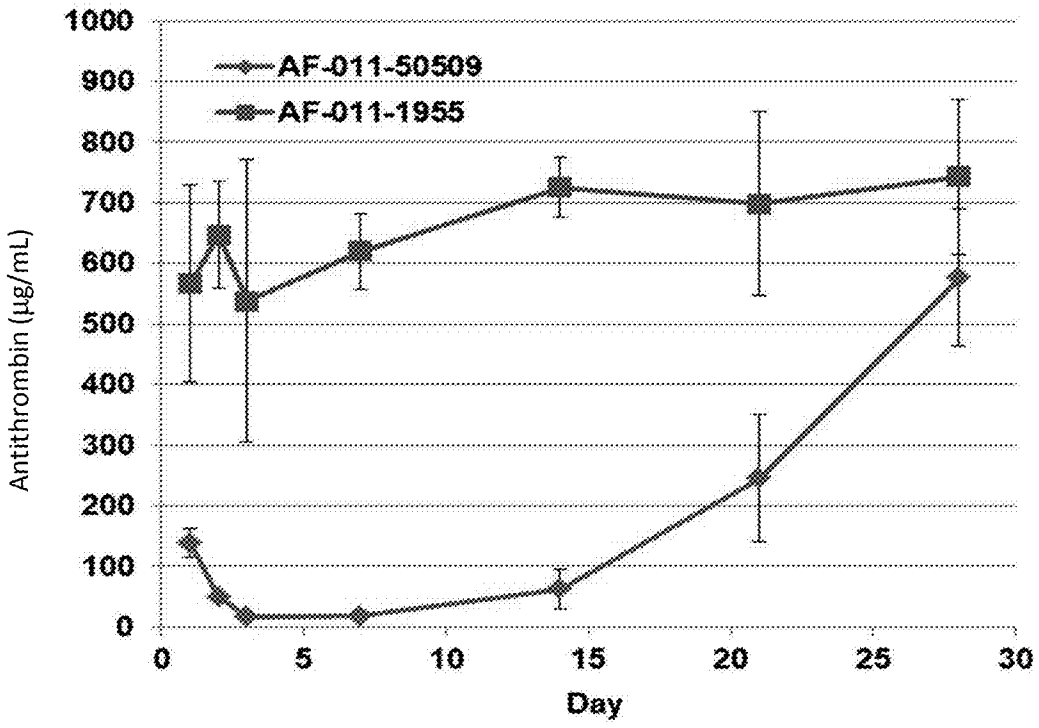
Figure 4C:
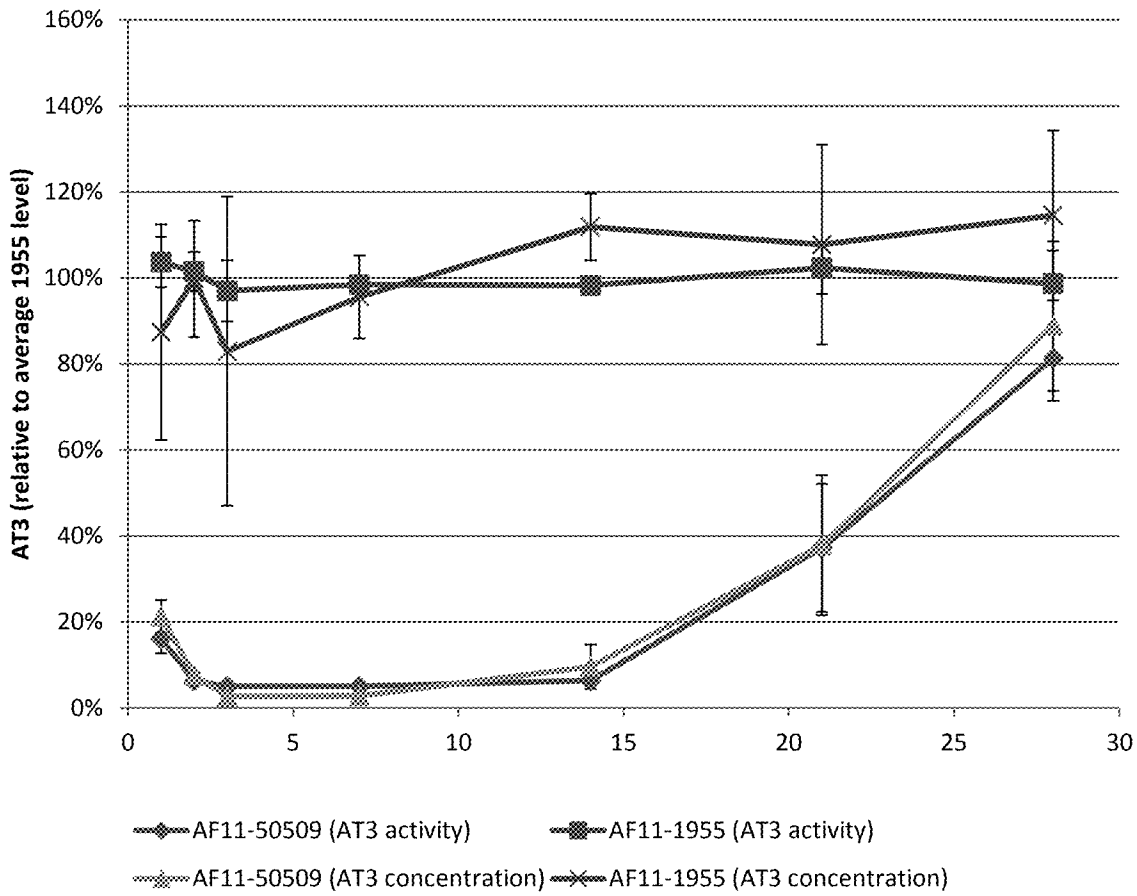
FIG. 4C is a graph showing the inhibition of Serpinc1 activity and Serpinc1 protein expression in CD1 mice following a single 1 mg/kg dose of an LNP formulation of AD-50509 or AD-1955.

The duration of silencing of an LNP formulation of AD-50509 siRNA (AF-011-50509) was determined in CD1 mice following a single 1 mg/kg intravenous injection of the siRNA. Animals were sacrificed at Day 1, 2, 3, 7, 14, 21, or 28 after administration and the relative level of Serpinc1 mRNA and the level of Serpinc1 protein were determined. FIG. 4A demonstrates that AF-011 formulated AD-50509 achieved Serpinc1 mRNA silencing of about 90% within 24 hours of administration and that there was approximately a 50% recovery in the relative amount of Serpinc1 mRNA by about two weeks after administration. FIG. 4B demonstrates that AF-011 formulated AD-50509 achieved Serpinc1 protein silencing of about 90% within about 72 hours of administration and that there was approximately a 50% recovery in the relative amount of Serpinc1 protein by about two weeks after administration. Serpinc1 activity was also determined by measuring Factor Xa activity using a commercially available kit (Aniara) in CD1 mice following a single 1 mg/kg intravenous injection of the LNP formulated AD-50509 siRNA. Animals were sacrificed at Day 1, 2, 3, 7, 14, 21, or 28 after administration and the relative activity level of Serpinc1 protein and the relative Serpinc1 protein level were determined. FIG. 4C shows that there is good correlation between the level of Serpinc1 protein level and Serpinc1 activity.

Example 4

GalNAc-Conjugated siRNAs

Forty-four modified Serpinc1 siRNA duplexes were conjugated with a trivalent GALNAc at the 3-end of the sense strand. These duplexes were assayed for efficacy in single dose free uptake of the conjugated duplexes in Cynomolgus monkey hepatocytes. Table 9 shows the results of these assays.

TABLE 9

| GalNAc Free-Uptake Single Dose | | | |
|---|---|---|---|
| Duplex ID | Ave 100 nM | Ave 10 nM | Ave 0.1 nM |
| AD-54944.1 | 0.4 | 0.53 | 0.94 |
| AD-54951.1 | 0.37 | 0.56 | 1 |
| AD-54942.1 | 0.38 | 0.58 | 1.01 |

TABLE 9-continued

| GalNAc Free-Uptake Single Dose | | | |
|---|---|---|---|
| Duplex ID | Ave 100 nM | Ave 10 nM | Ave 0.1 nM |
| AD-54948.1 | 0.36 | 0.6 | 0.96 |
| AD-54957.1 | 0.47 | 0.61 | 1 |
| AD-54933.1 | 0.51 | 0.65 | 0.96 |
| AD-54962.1 | 0.48 | 0.66 | 0.95 |
| AD-54972.1 | 0.49 | 0.66 | 1.05 |
| AD-54949.1 | 0.49 | 0.71 | 0.96 |
| AD-54936.1 | 0.54 | 0.72 | 1.07 |
| AD-54971.1 | 0.49 | 0.72 | 1 |
| AD-54955.1 | 0.52 | 0.74 | 0.98 |
| AD-54953.1 | 0.63 | 0.76 | 1.07 |
| AD-54937.1 | 0.64 | 0.81 | 0.94 |
| AD-54967.1 | 0.74 | 0.82 | 1.02 |
| AD-54935.1 | 0.68 | 0.83 | 0.99 |
| AD-54976.1 | 0.7 | 0.85 | 1.04 |
| AD-54965.1 | 0.7 | 0.86 | 0.97 |
| AD-54959.1 | 0.79 | 0.86 | 0.95 |
| AD-54943.1 | 0.75 | 0.86 | 0.94 |
| AD-54956.1 | 0.86 | 0.87 | 0.95 |
| AD-54973.1 | 0.96 | 0.89 | 1 |
| AD-54975.1 | 0.67 | 0.89 | 0.99 |
| AD-54963.1 | 0.73 | 0.9 | 0.96 |
| AD-54978.1 | 0.85 | 0.9 | 0.98 |
| AD-54952.1 | 0.59 | 0.91 | 1.11 |
| AD-54950.1 | 0.89 | 0.91 | 0.95 |
| AD-54964.1 | 0.87 | 0.93 | 1.01 |
| AD-54974.1 | 0.83 | 0.93 | 0.96 |
| AD-54969.1 | 0.87 | 0.94 | 0.94 |
| AD-54961.1 | 0.74 | 0.94 | 1.07 |
| AD-54968.1 | 0.89 | 0.95 | 0.91 |
| AD-54947.1 | 0.92 | 0.96 | 0.94 |
| AD-54941.1 | 0.91 | 0.96 | 1 |
| AD-54966.1 | 0.93 | 0.97 | 1.06 |
| AD-54940.1 | 0.86 | 0.99 | 1.03 |
| AD-54958.1 | 0.97 | 0.99 | 1.06 |
| AD-54938.1 | 0.93 | 0.99 | 1.05 |
| AD-54934.1 | 0.92 | 1 | 0.96 |
| AD-54939.1 | 0.84 | 1.02 | 1.02 |
| AD-54960.1 | 0.98 | 1.03 | 1.02 |
| AD-54954.1 | 1.04 | 1.03 | 1.01 |
| AD-54970.1 | 1.03 | 1.06 | 1.01 |
| AD-54946.1 | 0.83 | 1.17 | 1.1 |

These duplexes were also assayed for dose response in free uptake and transfection assays.

Table 10 shows the results of these assays and the rank order of the duplexes for both free uptake and transfection. The 5 duplexes with the best $IC_{50}$ are shaded in light gray and the bottom 5 duplexes are shaded in dark gray. The $IC_{50}$ rank order of the duplexes is well conserved between free uptake and transfection-mediated uptake of GalNAc conjugates.

TABLE 10

Dose Response of GalNAc-conjugated duplexes: Free uptake and Transfection

| | Free Uptake (nM) | Free Uptake Rank | Transfection (nM) | Transfection Rank |
|---|---|---|---|---|
| AD-54948.1 | 8.2 | 1 | 0.0018 | 3 |
| AD-54951.1 | 10.1 | 2 | 0.009 | 1 |
| AD-54942.1 | 10.8 | 3 | 0.024 | 6 |
| AD-54957.1 | 17.8 | 4 | 0.012 | 2 |
| AD-54944.1 | 19.3 | 5 | 0.019 | 4 |
| AD-54933.1 | 33.2 | 6 | 0.031 | 7 |
| AD-54936.1 | 43.2 | 7 | **0.032** | **9** |
| AD-54971.1 | 44.7 | 8 | **0.041** | **11** |
| AD-54962.1 | **80.2** | **9** | 0.032 | 8 |
| AD-54972.1 | **101.4** | **10** | **0.035** | **10** |
| AD-54955.1 | **148.1** | **11** | 0.022 | 5 |
| AD-54949.1 | **No IC50** | **12** | **0.302** | **13** |
| AD-54953.1 | **No IC50** | **13** | **0.058** | **12** |

Example 5

AD-54944 Optimization

As described in Example 4 above, AD-54944 was among the most active GalNAc-conjugated siRNA duplex as determined by both free uptake and transfection assays and was, thus, selected for further optimization and in vivo testing.

Figure 5:
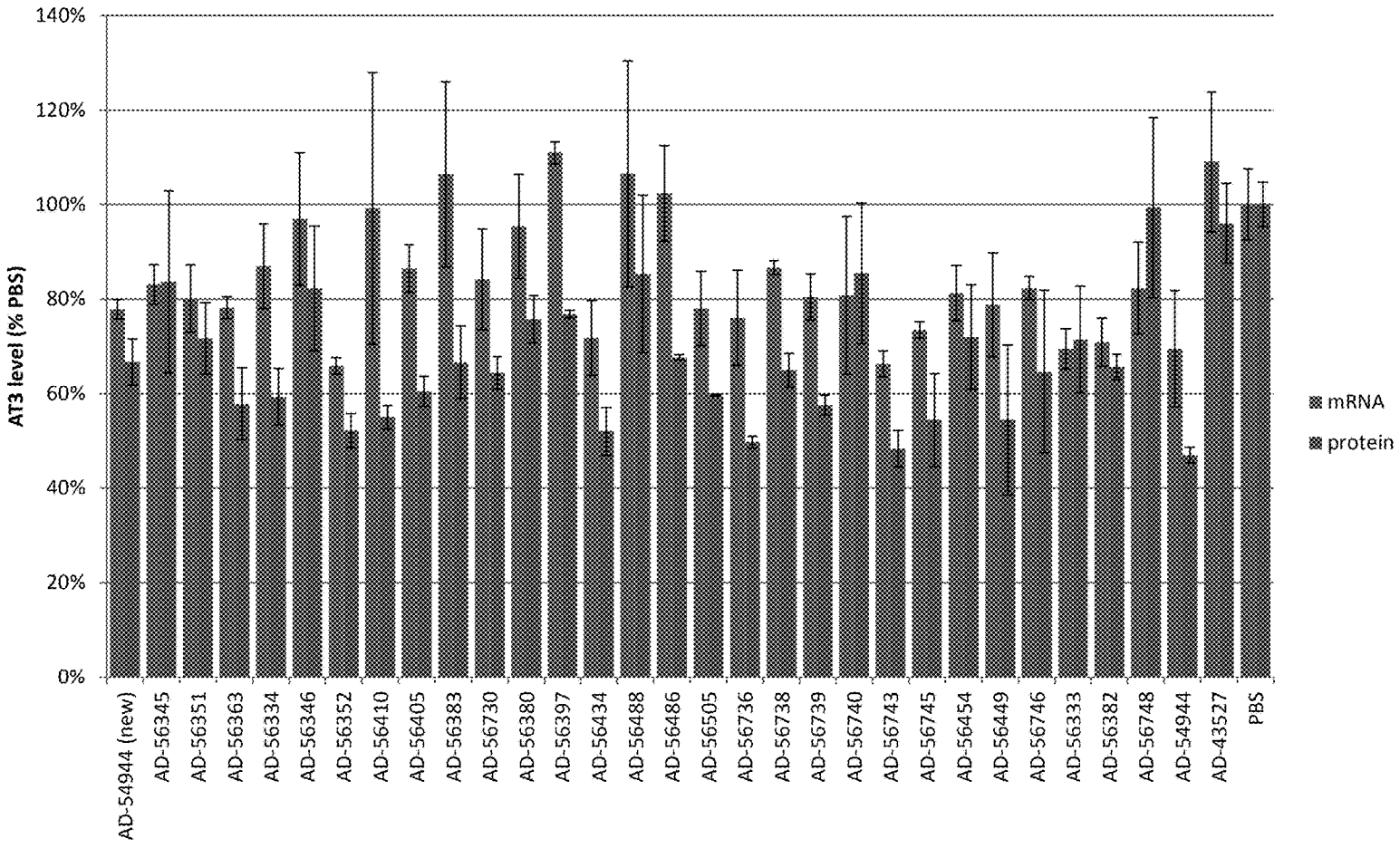
FIG. 5 is a graph showing the percent knock-down of Serpinc1 mRNA and protein levels following a single 10 mg/kg dose of the indicated iRNA conjugated to GalNAc.

Twenty-nine compounds were prepared based on the same AD-54944 parent sequence and screened for in vivo efficacy using a single 10 mg/kg dose. Animals (C57BL/6) were injected subcutaneously at Day 0 and sacrificed at Day 3. Serum Serpinc1 protein levels were determined by ELISA assay and the level of Serpinc1 mRNA was determined by QRT-PCR using liver samples from the animals. Tables 11 and 12 show the sequences of the duplexes and the results of the single dose screen with these duplexes as a percent knock-down of Serpinc1 protein levels from PBS. FIG. 5 shows the results of the single dose screen as a percent knock-down of Serpince mRNA and protein levels from PBS.

TABLE 11

AD-54944 optimized sequences and protein levels. (The "Sense Sequence" column sequences are disclosed as SEQ ID NOS 779-808, respectively, in order of appearance, and the "Antisense Sequence" column sequences are disclosed as SEQ ID NOS 809-838, respectively, in order of appearance)

| Duplex Name | Sense Sequence | Antisense Sequence | % PBS | Std Dev |
|---|---|---|---|---|
| AD-54944 (new) | GfgUfuAfaCfaCfCfAfuUfuAfcUfuCfaAfL96 | uUfgAfaGfuAfaAfuggUfgUfuAfaCfcsAfsg | 66.8 | 4.8 |
| AD-56345 | GfgUfuAfaCfaCfCfAfuUfuAfcUfuCfaAfL96 | uUfgaaGfuAfaAfuggUfguuAfaCfcsasg | 83.6 | 19.2 |
| AD-56351 | GfguuAfaCfaCfCfAfuUfuAfcUfuCfaAfL96 | uUfgaaGfuAfaAfuggUfguuAfaCfcsasg | 71.7 | 7.5 |
| AD-56363 | GfguuAfaCfaCfCfAfuUfuacUfuCfaaL96 | uUfgaaGfuAfaAfuggUfguuAfaCfcsasg | 57.9 | 7.6 |
| AD-56334 | GfguuAfacaCfCfAfuuuacUfucaaL96 | uUfgaaGfuAfaAfuggUfguuAfaCfcsasg | 59.4 | 6.0 |
| AD-56346 | GfguuaacaCfCfAfuuuacuucaaL96 | uUfgaaGfuAfaAfuggUfguuAfaCfcsasg | 82.3 | 13.2 |
| AD-56352 | GfgUfUfAfaCfaCfCfAfuUfuAfcUfuCfaAf L96 | uUfgAfaGfuAfaAfuggUfgUfuAfaCfcsAfsg | 52.2 | 3.6 |
| AD-56410 | GfgUfuAfaCfaCfCfAfuUfuAfcUfUfCfAfA fL96 | uUfgAfaGfuAfaAfuggUfgUfuAfaCfcsAfsg | 55.0 | 2.5 |
| AD-56405 | GfGfUfUfAfaCfaCfCfAfuUfuAfcUfuCfaA fL96 | uUfgAfaGfuAfaAfuggUfgUfuAfaCfcsAfsg | 60.6 | 3.1 |

TABLE 11-continued

AD-54944 optimized sequences and protein levels. (The "Sense Sequence" column sequences are disclosed as SEQ ID NOS 779-808, respectively, in order of appearance, and the "Antisense Sequence" column sequences are disclosed as SEQ ID NOS 809-838, respectively, in order of appearance)

| Duplex Name | Sense Sequence | Antisense Sequence | % PBS | Std Dev |
|---|---|---|---|---|
| AD-56383 | GfgUfuAfaCfaCfCfAfuUfuAfcUfuCfaAfL96 | UfUfGfAfaGfuAfaAfuggUfgUfuAfaCfcsAfsg | 66.7 | 7.6 |
| AD-56730 | GfgUfuAfaCfaCfCfAfuUfuAfcUfUfCfAfAfL96 | uUfgAfaGfuAfaAfuggUfgUfuAfaCfCfsAfsGf | 64.4 | 3.4 |
| AD-56380 | GfgUfUfAfaCfaCfCfAfuUfUfAfcUfUfCfAfAfL96 | uUfgAfAfGfUfAfaAfuggUfgUfUfAfaCfcsAfsg | 75.7 | 5.0 |
| AD-56397 | GfGfUfUfAfAfCfAfCfCfAfuUfUfAfCfUfUfCfAfAfL96 | uUfgAfAfGfuAfaAfuggUfgUfUfAfaCfcsAfsg | 76.9 | 0.8 |
| AD-56434 | GfgUfuAfaCfaCfCfAfuuuacUfuCfaAfL96 | uUfgAfaGfUfAfAfAfuggUfgUfuAfaCfcsAfsg | 52.0 | 5.1 |
| AD-56488 | GfgUfuAfaCfaCfCfAfuUfuAfcUfuCfaAfL96 | uUfgAfaGfuAfaAfuggUfgUfuAfasCfsc | 85.3 | 16.6 |
| AD-56486 | GfgUfuAfaCfaCfCfAfuUfuAfcUfuCfaAfL96 | uUfgAfaGfuAfaAfuggUfgUfuAfaCfcs(Aeos)(Geo) | 67.7 | 0.5 |
| AD-56505 | Gf(Geo)Uf(Teo)AfaCfaCfCfAfuUfuAfcUf(Teo)Cf(Aeo)AfL96 | uUfgAfaGfuAfaAfuggUfgUfuAfaCfcsAfsg | 59.7 | 0.2 |
| AD-56736 | Gf(Geo)Uf(Teo)AfaCfaCfCfAfuUf(Teo)Af(m5Ceo)Uf(Teo)Cf(Aeo)AfL96 | uUfgAfaGfuAfaAfuggUf(Geo)UfuA-faCfcsAfsg | 49.7 | 1.2 |
| AD-56738 | Gf(Geo)Uf(Teo)AfaCfaCfCfAfuUfuAfcUf(Teo)Cf(Aeo)AfL96 | uUfgaaGfuAfaAfuggUfguuAfaCfcsasg | 65.0 | 3.6 |
| AD-56739 | Gf(Geo)Uf(Teo)AfaCfaCfCfAfuUf(Teo)Af(m5Ceo)Uf(Teo)Cf(Aeo)AfL96 | uUfgaaGfuAfaAfuggUfguuAfaCfcsasg | 57.6 | 2.1 |
| AD-56740 | Gf(Geo)Uf(Teo)AfaCfaCfCfAfuUfuAfcUf(Teo)Cf(Aeo)AfL96 | uUfgaaGfuAfaAfuggUfgUfuAfaCfcsasg | 85.5 | 14.8 |
| AD-56743 | Gf(Geo)UfuAfaCfaCfCfAfuUfuAfcUf(Teo)Cf(Aeo)AfL96 | uUfgaaGfuAfaAfuggUfgUfuAfaCfcsasg | 48.3 | 3.9 |
| AD-56745 | Gf(Geo)Uf(Teo)AfaCfaCfCfAfuUfuAf(m5Ceo)Uf(Teo)Cf(Aeo)AfL96 | uUfgaaGfuAfaAfuggUfgUfuAfaCfcsasg | 54.4 | 9.9 |
| AD-56454 | GfgUfuAfaCfaCfCfAfuUfuAfcUfuCfaAfL96 | uugaaGfuAfaAfuggUfgUfuAfaCfcsAfsg | 72.0 | 11.0 |
| AD-56449 | GfgUfuAfaCfaCfCfAfuUfuAfcUfuCfaAfL96 | uUfgAfaGfuAfaAfuggUfgUfuaaccsAfsg | 54.4 | 15.9 |
| AD-56746 | Gf(Geo)UfuAfaCfaCfCfAfuUfuAfcUf(Teo)Cf(Aeo)AfL96 | uUfgAfaGfuAfaAfuggUfgUfuaaccsAfsg | 64.7 | 17.2 |
| AD-56333 | GfguuAfacaCfCfAfuuuacuucaaL96 | uUfgaaGfuAfaAfuggUfgUfuAfaCfcsasg | 71.5 | 11.3 |
| AD-56382 | GfgUfuAfaCfaCfCfAfuuuacUfuCfaAfL96 | uUfgAfaGfuAfaAfuggUfgUfuAfaCfcsAfsg | 65.7 | 2.7 |
| AD-56748 | GfgUfuAfaCfaCfCfAfuuuacUfuCfaAfL96 | uUfgaaGfuAfaAfuggUfguuAfaCfcsasg | 99.4 | 19.1 |
| AD-54944 (original) | GfgUfuAfaCfaCfCfAfuUfuAfcUfuCfaAfL96 | uUfgAfaGfuAfaAfuggUfgUfuAfaCfcsAfsg | 46.9 | 1.7 |
| control | | | 96.0 | 8.5 |
| PBS | | | 100.0 | 4.7 |

TABLE 12

AD-54944 optimized sequences and protein levels. (The "Sense Sequence" column sequences are disclosed as SEQ ID NOS 839-868, respectively, in order of appearance, and the "Antisense Sequence" column sequences are disclosed as SEQ ID NOS 869-898, respectively, in order of appearance)

| Duplex Name | Sense Sequence | Antisense Sequence | % PBS | Std Dev |
|---|---|---|---|---|
| AD-54944 (original) | GfgUfuAfaCfaCfCfAfuUfuAfcUfuCfaAfL96 | uUfgAfaGfuAfaAfuggUfgUfuAfaCfcsAfsg | 46.9 | 1.7 |
| AD-56743 | Gf(Geo)UfuAfaCfaCfCfAfuUfuAfcUf(Teo)Cf(Aeo)AfL96 | uUfgaaGfuAfaAfuggUfgUfuAfaCfcsasg | 48.3 | 3.9 |
| AD-56736 | Gf(Geo)Uf(Teo)AfaCfaCfCfAfuUf(Teo)Af(m5Ceo)Uf(Teo)Cf(Aeo)AfL96 | uUfgAfaGfuAfaAfuggUf(Geo)UfuAfaCfcsAfsg | 49.7 | 1.2 |
| AD-56434 | GfgUfuAfaCfaCfCfAfuuuacUfuCfaAfL96 | uUfgAfaGfUfAfAfAfuggUfgUfuAfaCfcsAfsg | 52.0 | 5.1 |
| AD-56352 | GfgUfUfAfaCfaCfCfAfuUfuAfcUfuCfaAfL96 | uUfgAfaGfuAfaAfuggUfgUfuAfaCfcsAfsg | 52.2 | 3.6 |
| AD-56745 | Gf(Geo)Uf(Teo)AfaCfaCfCfAfuUfuAf(m5Ceo)Uf(Teo)Cf(Aeo)AfL96 | uUfgaaGfuAfaAfuggUfgUfuAfaCfcsasg | 54.4 | 9.9 |
| AD-56449 | GfgUfuAfaCfaCfCfAfuUfuAfcUfuCfaAfL96 | uUfgAfaGfuAfaAfuggUfgUfuaaccsAfsg | 54.4 | 15.9 |
| AD-56410 | GfgUfuAfaCfaCfCfAfuUfuAfcUfUfCfAfAfL96 | uUfgAfaGfuAfaAfuggUfgUfuAfaCfcsAfsg | 55.0 | 2.5 |
| AD-56739 | Gf(Geo)Uf(Teo)AfaCfaCfCfAfuUf(Teo)Af(m5Ceo)Uf(Teo)Cf(Aeo)AfL96 | uUfgaaGfuAfaAfuggUfguuAfaCfcsasg | 57.6 | 2.1 |
| AD-56363 | GfguuAfaCfaCfCfAfuUfuacUfuCfaaL96 | uUfgaaGfuAfaAfuggUfguuAfaCfcsasg | 57.9 | 7.6 |
| AD-56334 | GfguuAfacaCfCfAfuuuacUfucaaL96 | uUfgaaGfuAfaAfuggUfguuAfaCfcsasg | 59.4 | 6.0 |
| AD-56505 | Gf(Geo)Uf(Teo)AfaCfaCfCfAfuUfuAfcUf(Teo)Cf(Aeo)AfL96 | uUfgAfaGfuAfaAfuggUfgUfuAfaCfcsAfsg | 59.7 | 0.2 |
| AD-56405 | GfGfUfUfAfaCfaCfCfAfuUfuAfcUfuCfaAfL96 | uUfgAfaGfuAfaAfuggUfgUfuAfaCfcsAfsg | 60.6 | 3.1 |
| AD-56730 | GfgUfuAfaCfaCfCfAfuUfuAfcUfUfCfAfAfL96 | uUfgAfaGfuAfaAfuggUfgUfuAfaCfCfsAfsGf | 64.4 | 3.4 |
| AD-56746 | Gf(Geo)UfuAfaCfaCfCfAfuUfuAfcUf(Teo)Cf(Aeo)AfL96 | uUfgAfaGfuAfaAfuggUfgUfuaaccsAfsg | 64.7 | 17.2 |
| AD-56738 | Gf(Geo)Uf(Teo)AfaCfaCfCfAfuUfuAfcUf(Teo)Cf(Aeo)AfL96 | uUfgaaGfuAfaAfuggUfguuAfaCfcsasg | 65.0 | 3.6 |
| AD-56382 | GfgUfuAfaCfaCfCfAfuuuacUfuCfaAfL96 | uUfgAfaGfuAfaAfuggUfgUfuAfaCfcsAfsg | 65.7 | 2.7 |
| AD-56383 | GfgUfuAfaCfaCfCfAfuUfuAfcUfuCfaAfL96 | UfUfGfAfaGfuAfaAfuggUfgUfuAfaCfcsAfsg | 66.7 | 7.6 |
| AD-54944 (new) | GfgUfuAfaCfaCfCfAfuUfuAfcUfuCfaAfL96 | uUfgAfaGfuAfaAfuggUfgUfuAfaCfcsAfsg | 66.8 | 4.8 |
| AD-56486 | GfgUfuAfaCfaCfCfAfuUfuAfcUfuCfaAfL96 | uUfgAfaGfuAfaAfuggUfgUfuAfaCfcs(Aeos)(Geo) | 67.7 | 0.5 |
| AD-56333 | GfguuAfacaCfCfAfuuuacuucaaL96 | uUfgaaGfuAfaAfuggUfgUfuAfaCfcsasg | 71.5 | 11.3 |
| AD-56351 | GfguuAfaCfaCfCfAfuUfuAfcUfuCfaAfL96 | uUfgaaGfuAfaAfuggUfguuAfaCfcsasg | 71.7 | 7.5 |
| AD-56454 | GfgUfuAfaCfaCfCfAfuUfuAfcUfuCfaAfL96 | uugaaGfuAfaAfuggUfgUfuAfaCfcsAfsg | 72.0 | 11.0 |
| AD-56380 | GfgUfUfAfaCfaCfCfAfuUfUfAfcUfUfCfAfAfL96 | uUfgAfAfGfUfAfaAfuggUfgUfUfAfaCfcsAfsg | 75.7 | 5.0 |
| AD-56397 | GfGfUfUfAfAfCfAfCfCfAfuUfUfAfCfUfUfCfAfAfL96 | uUfgAfAfGfuAfaAfuggUfgUfUfAfaCfcsAfsg | 76.9 | 0.8 |
| AD-56346 | GfguuaacaCfCfAfuuuacuucaaL96 | uUfgaaGfuAfaAfuggUfguuAfaCfcsasg | 82.3 | 13.2 |
| AD-56345 | GfgUfuAfaCfaCfCfAfuUfuAfcUfuCfaAfL96 | uUfgaaGfuAfaAfuggUfguuAfaCfcsasg | 83.6 | 19.2 |
| AD-56488 | GfgUfuAfaCfaCfCfAfuUfuAfcUfuCfaAfL96 | uUfgAfaGfuAfaAfuggUfgUfuAfasCfsc | 85.3 | 16.6 |

TABLE 12-continued

AD-54944 optimized sequences and protein levels. (The "Sense Sequence" column sequences are disclosed as SEQ ID NOS 839-868, respectively, in order of appearance, and the "Antisense Sequence" column sequences are disclosed as SEQ ID NOS 869-898, respectively, in order of appearance)

| Duplex Name | Sense Sequence | Antisense Sequence | % PBS | Std Dev |
|---|---|---|---|---|
| AD-56740 | Gf(Geo)Uf(Teo)AfaCfaCfCfAfuUfuAfcUf(Teo)Cf(Aeo)AfL96 | uUfgaaGfuAfaAfuggUfgUfuAfaCfcsasg | 85.5 | 14.8 |
| | | | 96.0 | 8.5 |
| AD-56748 | GfgUfuAfaCfaCfCfAfuuuacUfuCfaAfL96 | uUfgaaGfuAfaAfuggUfguuAfaCfcsasg | 99.4 | 19.1 |
| PBS | | | 100.0 | 4.7 |

The in vivo dose response of AD-54944 conjugated to GalNAc was determined by administering a single subcutaneous dose to C57BL/6J mice (n=5). AD-54944 conjugated to GalNAc was also administered subcutaneously as a repeat daily dose of 5 mg/kg to C57BL/6J mice (n=5) over a 5 day period. Animals were sacrificed 72 hours after administration and Serpinc1 protein and activity levels were determined in liver and serum samples as described above.

Figure 6:
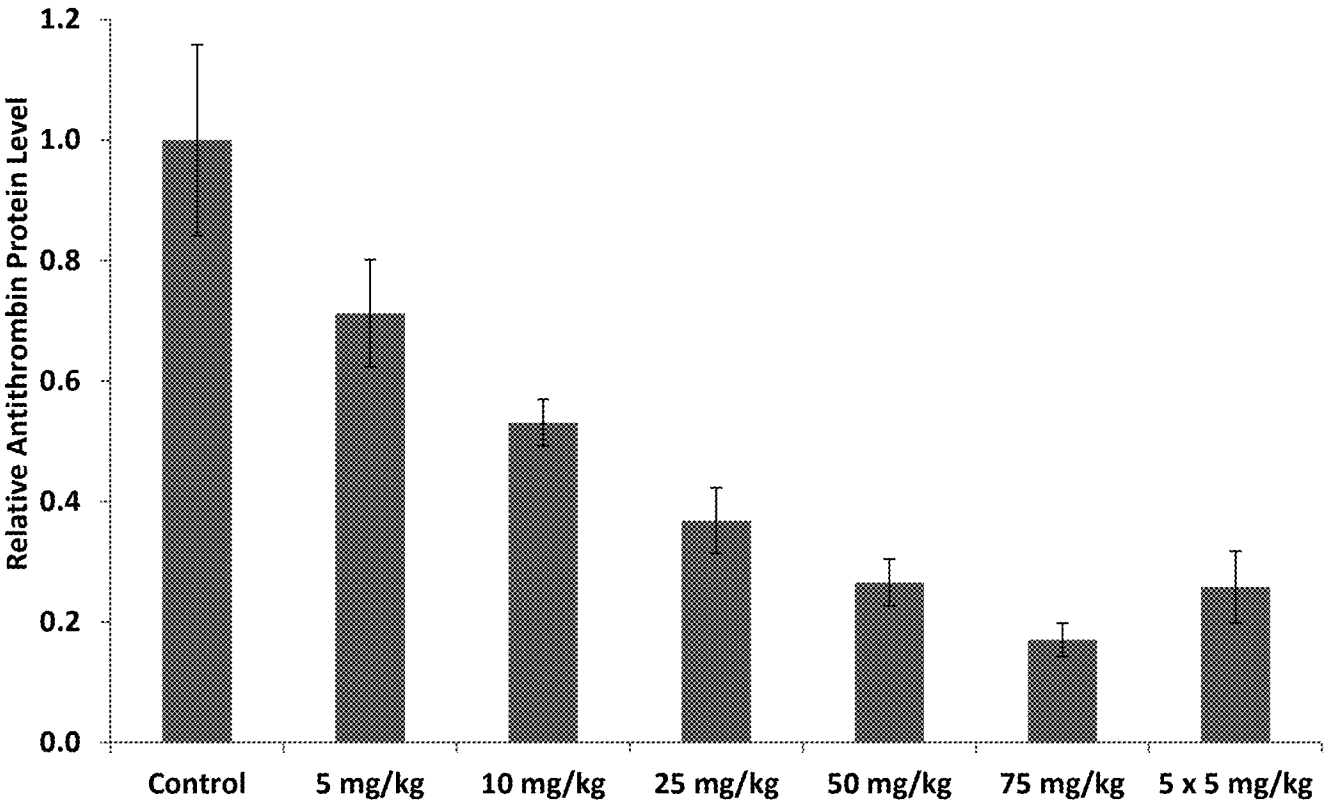
FIG. 6 is a graph showing the inhibition of Serpinc1 protein expression in C57BL/6 mice following a single 5 mg/kg, 10 mg/kg, 25 mg/kg, 50 mg/kg, and 75 mg/kg, and a repeat dose of 5×5 mg/kg of AD-54944 conjugated to GalNAc.

As shown in FIG. 6, a single subcutaneous dose of AD-54944 conjugated to GalNAc resulted in a protein $EC_{50}$ of about 10 mg/kg and a 5×5 mg/kg daily, repeat dose resulted in about a 75% protein silencing.

Figure 7A:
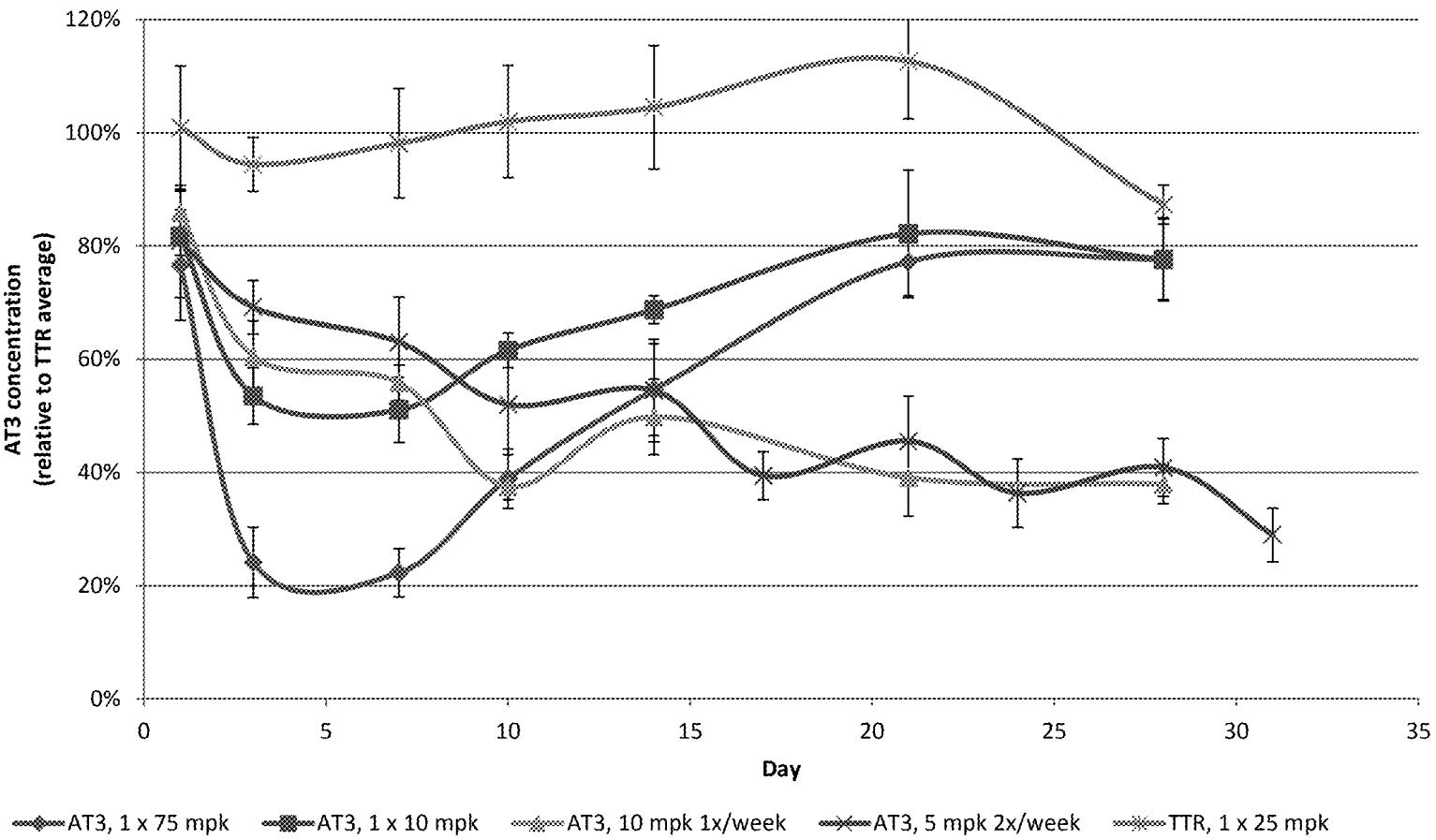
FIGS. 7A and 7B are graphs showing the effect of repeat-dosing on the duration of inhibition of Serpinc1 protein expression in C57BL/6 mice of GalNAc conjugated AD-54944.
Figure 7B:
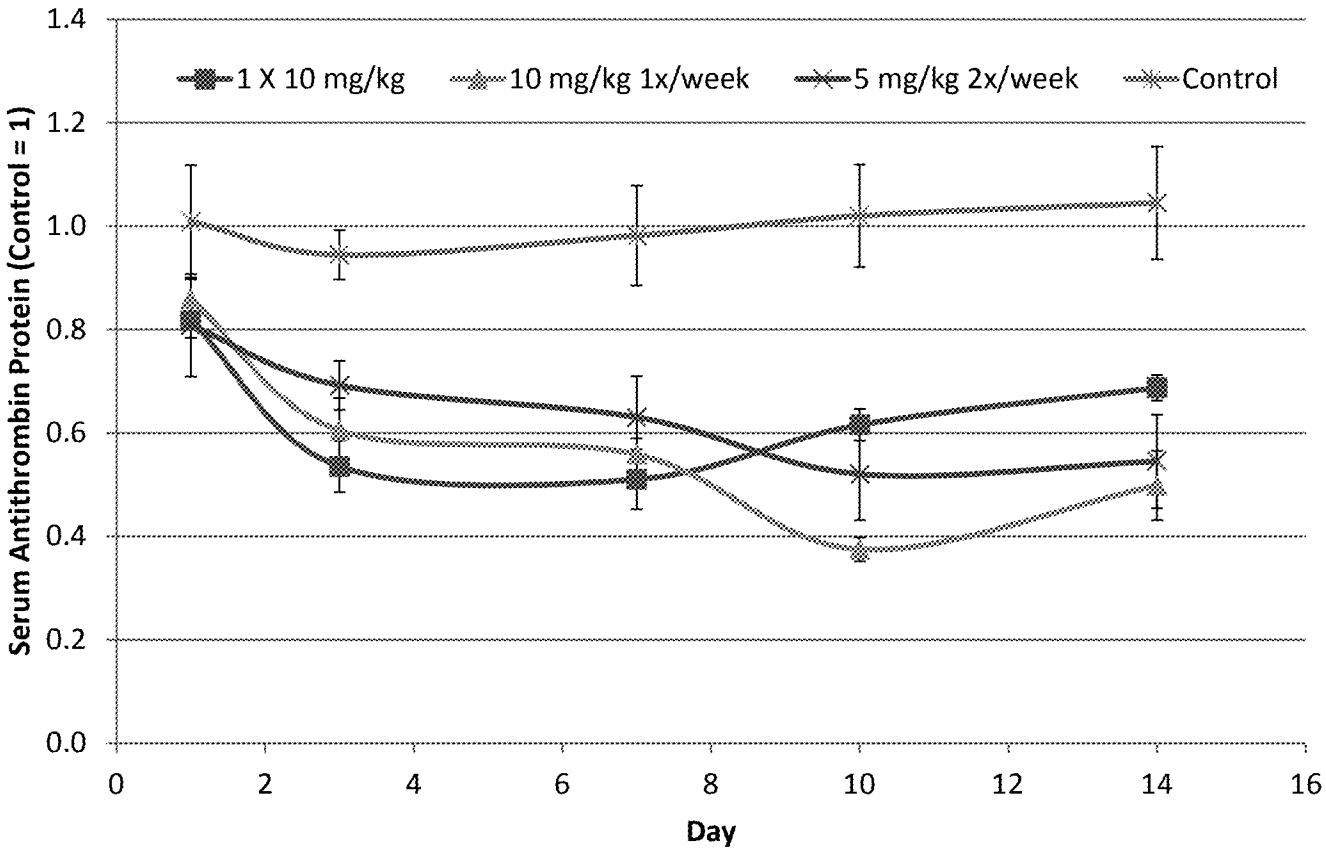

Additional repeat-dosing of AD-54944 conjugated to GalNAc in C57BL/6J mice was also performed over an 8 week period to determine the efficacy and duration of silencing. FIGS. 7A and 7B show the results of these studies.

Example 6

Dose Duration of a Split-Dose of AD-54944

In order to further evaluate compound AD-54944 knock-down of Serpinc1 expression and activity, a split-dosing experiment was performed. C57BL/6 mice were subcutaneously administered GalNAc-conjugated AD-54944 and the effect of a 3 times per week, ⅓ dose of AD-54944 was compared to the effect of a 1 time per week fully concentrated dose of AD-54944. A summary of the study design is presented in Table 13. Serum Serpinc1 protein levels were determined at Days 0, 3, 7, 10, 14, 17, 21, 24, 29, 31, and 35.

TABLE 13

Study Design of Split-Dosing Experiment

| Group | Test compound | Dose (mg/kg) | Frequency |
|---|---|---|---|
| 1 | AD-54944 | 1.25 | 3x/week (M,W, |
| 2 | | 2.5 | F) |
| 3 | | 5 | |
| 4 | | 10 | 1x/week |
| 5 | | 3.75 | (Monday) |
| 6 | | 7.5 | |
| 7 | | 15 | |
| 8 | | 30 | |
| 9 | PBS | — | |

Figure 8:
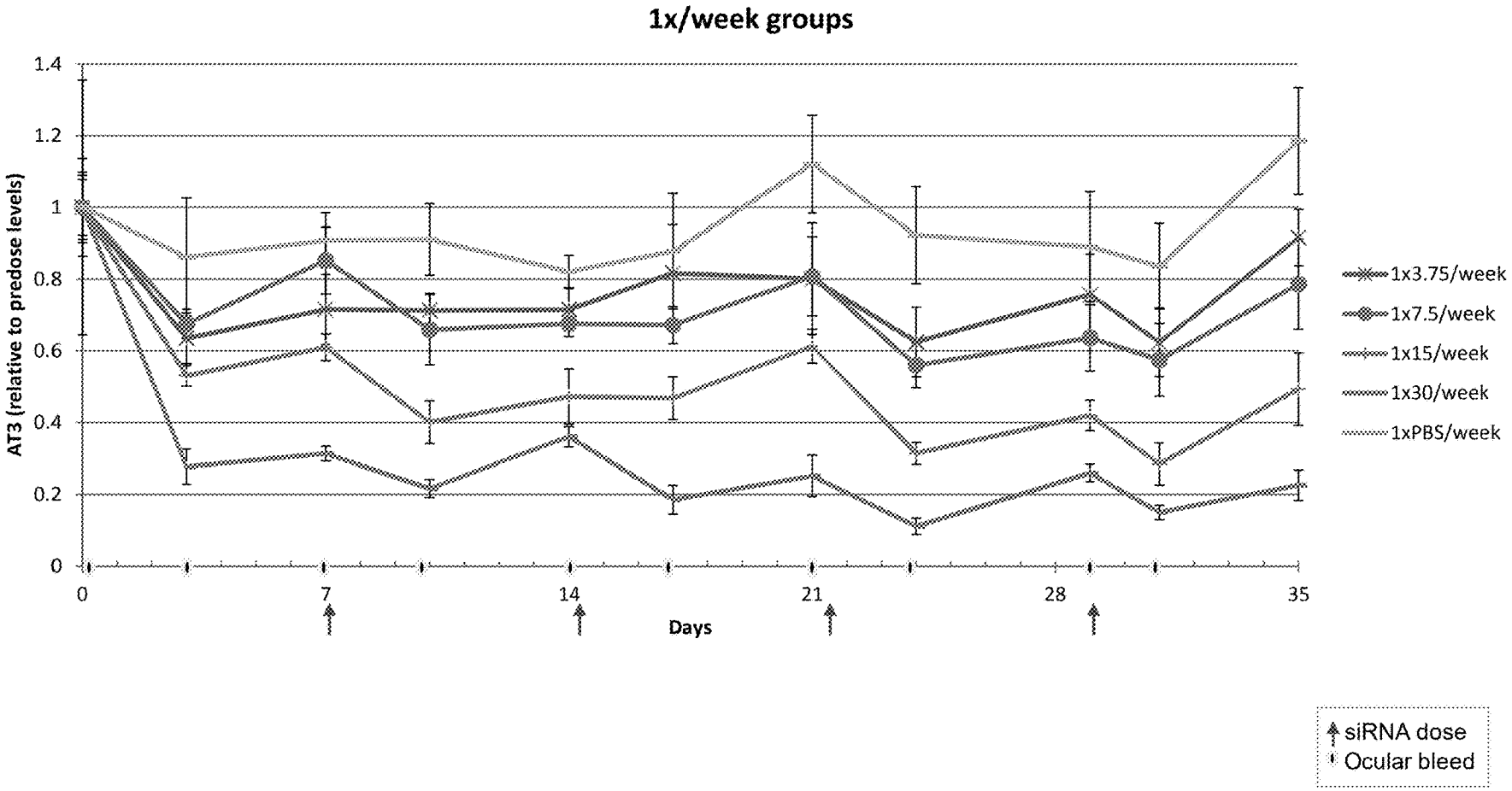
FIGS. 8 and 9 are graphs showing the effects of the indicated split-dosing regimens on the duration of silencing of Serpinc1 protein expression in C57BL/6 mice administered GalNAc conjugated AD-54944.
Figure 9:
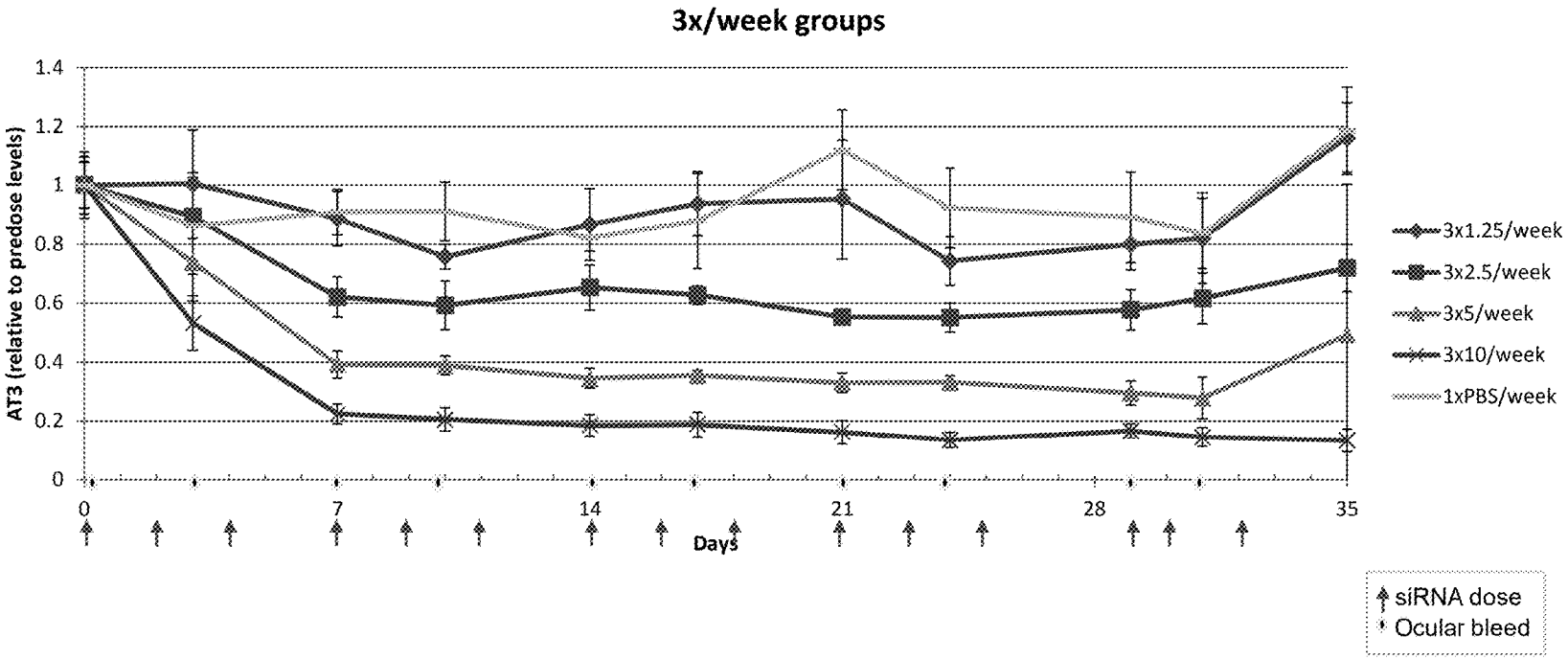

The results of the one-time per week split-dose screen as a percent knock-down of Serpinc1 protein levels from pre-dose levels are shown in FIG. 8 and the results of the three-time per week screen as a percent knock-down of Serpinc1 protein levels from pre-dose levels are shown in FIG. 9. The results demonstrate that there is a dose response effect with AD-54944 conjugated to GalNAc in both groups and that dosages at both 30 mg/kg one time per week and at 10 mg/kg three times per week lead to long-term silencing of Serpinc1.

Example 7

Further Optimization of AD-54944

In order to further improve the efficacy of AD-54944, additional compounds were prepared based on the AD-54944 parent sequence. In general, the modifications included the addition of phosphorothiate linkages, C16 (hexadecyl) modifications, 5'-end-caps, and 2'-methyls. The new compounds were screened for in vivo efficacy using both a single 3 [mg/mg] *mg/kg* dose and a single 10 mg/kg dose. Animals (C57BL/6) were injected subcutaneously at Day 0 and sacrificed at Day 3. Serum Serpinc1 protein levels were determined by ELISA assay. The ELISA assay was performed using an Antithrombin III Mouse ELISA kit purchased from Abcam. Briefly, serum was diluted (e.g., about 1:10,000) and used accordingly to manufacturers instructions. The plates were read at 450 nm at the end of the assay.

Figure 10:
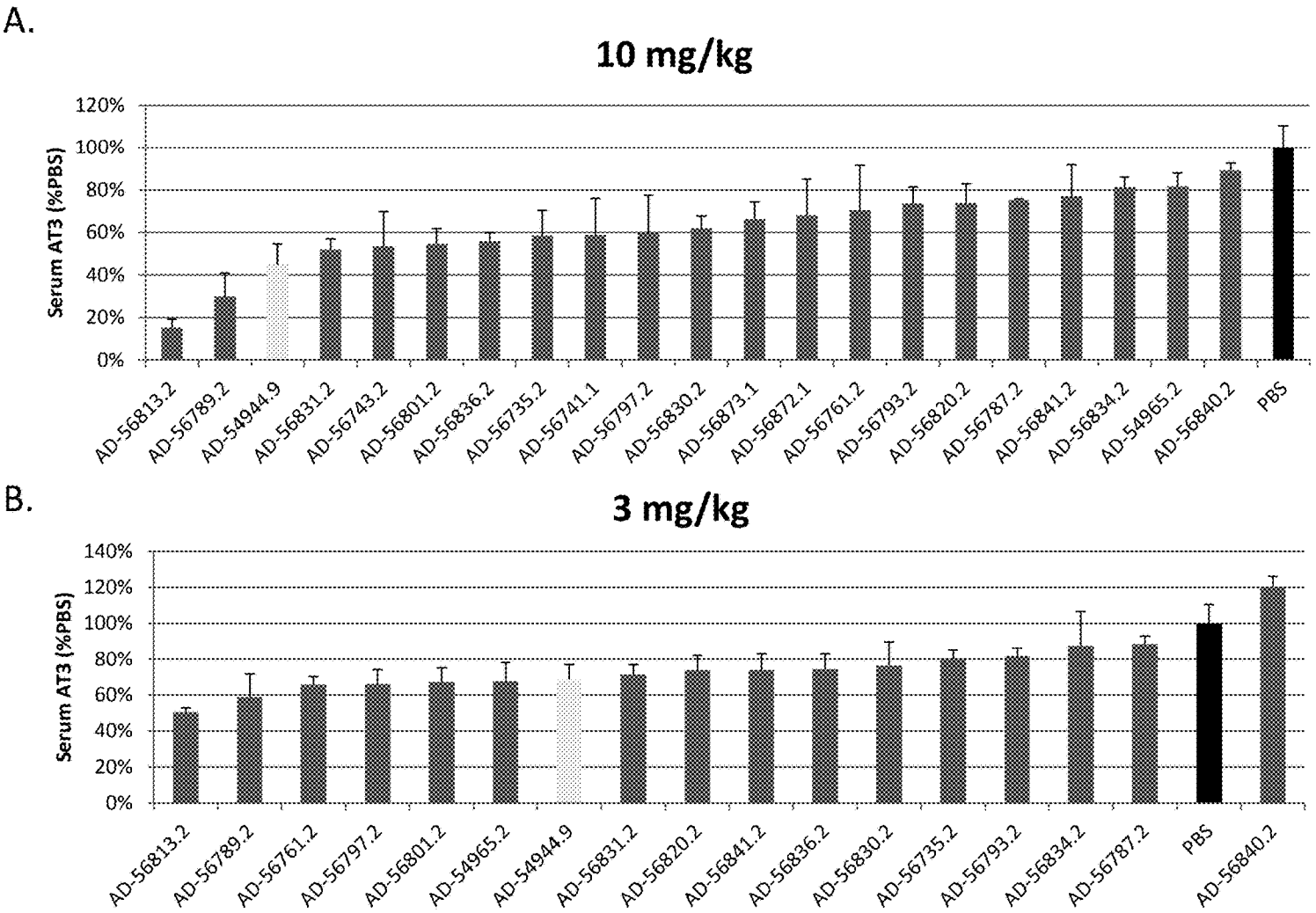
FIGS. 10A and 10B are graphs showing the percent knock-down of Serpinc1 protein levels following a single 10 mg/kg (A) or 3 mg/kg (B) dose of the indicated iRNA conjugated to GalNAc.

Table 14 shows the sequences of the duplexes and the results of the single dose screens with these duplexes as a percent knock-down of Serpinc1 protein levels from PBS. FIGS. 10A and 10B show the results of the single dose screen as a percent knock-down of Serpinc1 protein levels from PBS. As can be seen in Table 14 and FIG. 10, compound AD-56813 emerged as a new lead based on the level of knock-down of Serpinc1 protein levels.

Further compounds were prepared based on the AD-56813 parent sequence in which the number of 2'-methoxyethyl and phosphorothioate linkages were reduced in order to determine the minimum chemical modifications required for stability of the compounds which maintained activity of the compounds. The new compounds were screened for in vivo efficacy using both a single 3 [mg/mg] *mg/kg* dose and a single 10 mg/kg dose. Animals (C57BL/6) were injected subcutaneously at Day 0 and sacrificed at Day 3. Serpinc1 (AT3) activity and serum Serpinc1 protein levels were determined by ELISA assay. The ELISA assay was performed as described above. Serpinc1 activity was determined using a BIOPHEN (anti-Factor Xa) activity assay kit. Briefly, serum samples were diluted from about 1:20 to about 1:60 and processed according to the manufacturers' instructions. The plates were read at 450 nm at the end of the assay.

Figure 11:
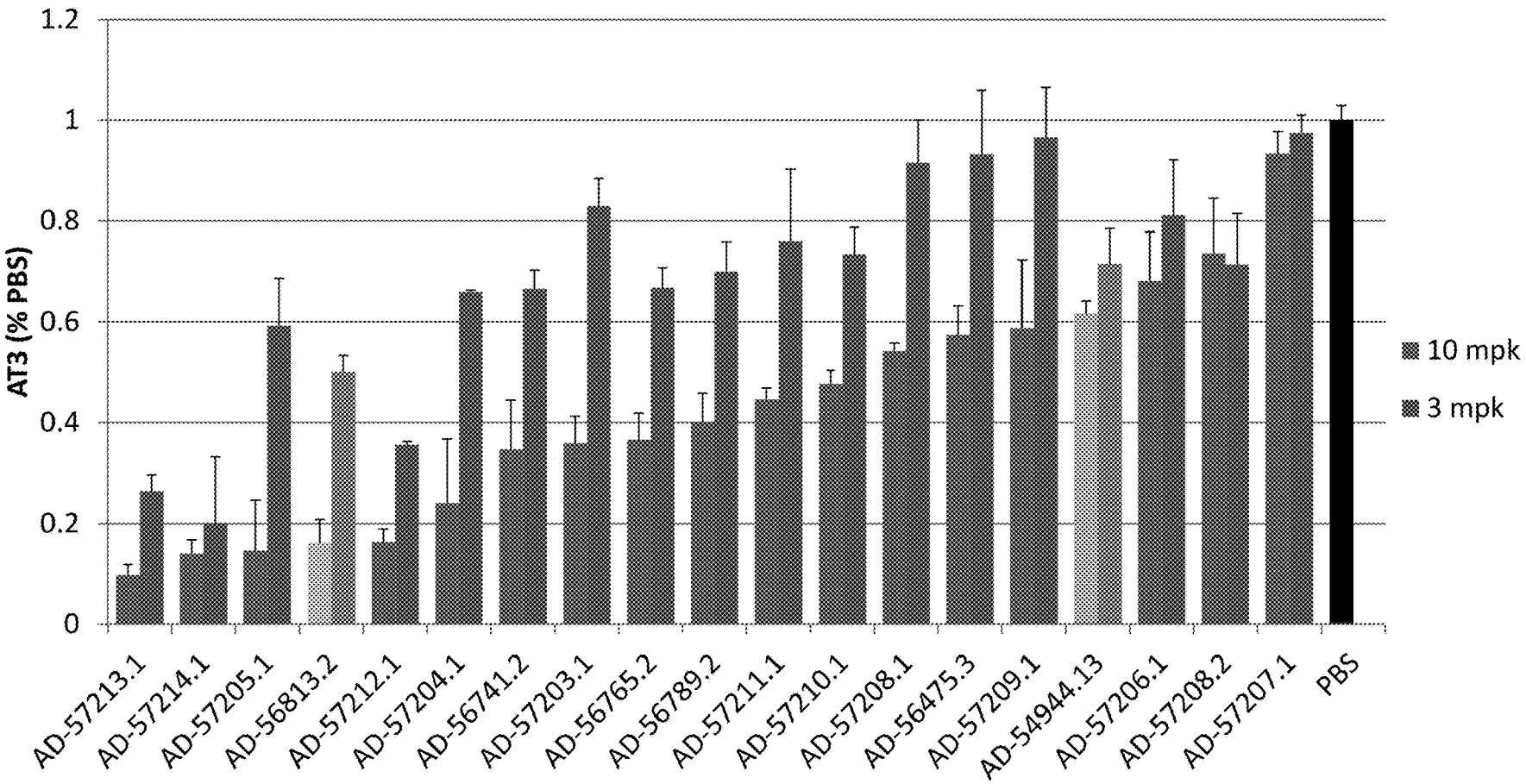
FIG. 11 is a graph showing the percent knock-down of Serpinc1 protein levels following a single 10 mg/kg or 3 mg/kg dose of the indicated iRNA conjugated to GalNAc.

The sequences of the duplexes that were newly prepared and the results of the single dose screens with these duplexes as a percent knock-down of Serpinc1 protein levels from PBS are shown in Table 15. FIG. 11 shows the results of the single dose screen as a percent knock-down of Serpinc1 protein levels from PBS and FIG. 12 shows the results of the single dose screen as a percent knock-down of Serpinc1 activity from PBS.

Figure 12:
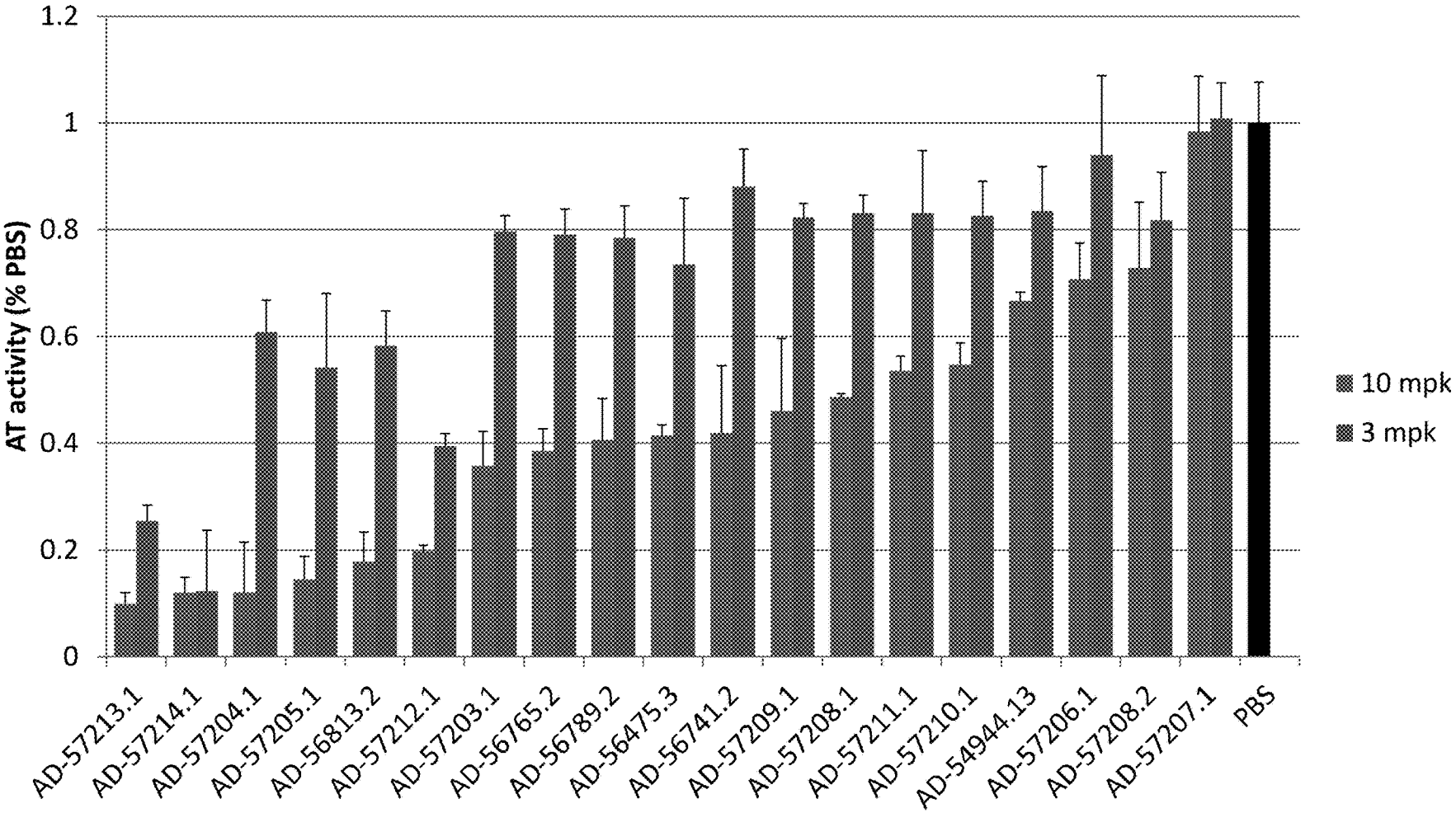
FIG. 12 is a graph showing the percent knock-down of Serpinc1 activity following a single 10 mg/kg or 3 mg/kg dose of the indicated iRNA conjugated to GalNAc.

As can be seen in Table 15 and FIGS. 11 and 12, although the number of modifications to the compound was dramatically reduced, compound AD-57213 maintained knockdown of Serpinc1 expression and activity and, thus, emerged as a new lead. A single 10 mg/kg dose of AD-57213 led to an $ED_{90}$ and a single 3 mg/kg dose led to an $ED_{50}$.

TABLE 14

AD-54944 optimized sequences and protein levels. (The "Sense Sequence" column sequences are disclosed as SEQ ID NOS 899-919, respectively, in order of appearance, and the "Antisense Sequence" column sequences are disclosed as SEQ ID NOS 920-940, respectively, in order of appearance)

| | | | | | 3 mpk | | 10 mpk | |
|---|---|---|---|---|---|---|---|---|
| Duplex ID | Sense strand | Sense sequence | Antisense | Antisense sequence | % PBS | stdev | % PBS | stdev |
| AD-56813.2 | A-116280.6 | Gfs(Geo)UfsuAfaCfsaCfsCfsAfuUfsuAfcUfsuCfs(Aeo)AfL96 | A-116278.6 | usUfsgAfaGfuAfaAfuggUfsgUfsuAfaCfscs(Aeos)(Geo) | 0.62 | 0.04 | 0.26 | 0.04 |
| AD-56789.2 | A-116276.12 | GfgUfsuAfaCfsaCfsCfsAfuUfsuAfcUfsuCfsaAfL96 | A-116275.7 | uUfsgAfaGfuAfaAfuggUfsgUfsuAfaCfscsAfsg | 0.74 | 0.11 | 0.44 | 0.11 |
| AD-56741 | A-115968.11 | Gf(Geo)Uf(Teo)AfaCfaCfCfAfuUf(Teo)Af(m5Ceo)Uf(Teo)Cf(Aeo)AfL96 | A-115861.11 | uUfgaaGfuAfaAfuggUfgUfuAfaCfcsasg | | | 0.52 | 0.09 |
| AD-54944/parent | A-113073.1 | GfgUfuAfaCfaCfCfAfuUfuAfcUfuCfaAfL96 | A-113074.1 | uUfgAfaGfuAfaAfuggUfgUfuAfaCfcsAfsg | 0.93 | 0.10 | 0.63 | 0.10 |
| AD-56743 | A-115965.5 | Gf(Geo)UfuAfaCfaCfCfAfuUfuAfcUf(Teo)Cf(Aeo)AfL96 | A-115861.11 | uUfgaaGfuAfaAfuggUfgUfuAfaCfcsasg | | | 0.71 | 0.24 |
| AD-56836.2 | A-115966.25 | Gf(Geo)Uf(Teo)AfaCfaCfCfAfuUfuAfcUf(Teo)Cf(Aeo)AfL96 | A-116284.3 | uUfgAfaGf(Uhd)AfaAfuggUfgUfuAfaCfcsasg | 1.01 | 0.11 | 0.73 | 0.11 |
| AD-56797.2 | A-115968.8 | Gf(Geo)Uf(Teo)AfaCfaCfCfAfuUf(Teo)Af(m5Ceo)Uf(Teo)Cf(Aeo)AfL96 | A-116250.6 | uUfgAfaGfuAfaAfuggUf(Geo)UfuAfaCfcs(Aeos)(Geo) | 0.87 | 0.25 | 0.74 | 0.25 |
| AD-56801.2 | A-116277.6 | Gf(Geo)UfsuAfaCfsaCfsCfsAfuUfsuAfcUfsuCfs(Aeo)AfL96 | A-116279.9 | uUfsgAfaGfuAfaAfuggUfsgUfsuAfaCfscs(Aeos)(Geo) | 0.83 | 0.08 | 0.77 | 0.08 |
| AD-56831.2 | A-116290.3 | Gf(Geo)Uf(Teo)AfaCfaCfCfAfuUf(Uhd)AfcUf(Teo)Cf(Aeo)AfL96 | A-115962.21 | uUfgAfaGfuAfaAfuggUfgUfuAfaCfcs(Aeos)(Geo) | 1.11 | 0.09 | 0.78 | 0.09 |
| AD-56830.2 | A-116283.3 | Gfs(Geo)UfsuAfaCfsaCfCfAfuUfsuAfcUfsuCfs(Aeo)AfL96 | A-116279.12 | uUfsgAfaGfuAfaAfuggUfsgUfsGuAfaCfscs(Aeos)(eo) | 1.01 | 0.13 | 0.79 | 0.13 |
| AD-56761.2 | A-116247.13 | gguuaacaCfCfAfuuuacu(Uhd)caaL96 | A-116244.6 | uUfgaaGfuAfaAfuggUfguuaaccsasg | 0.82 | 0.26 | 0.83 | 0.26 |
| AD-56735.2 | A-115966.29 | Gf(Geo)Uf(Teo)AfaCfaCfCfAfuUfuAfcUf(Teo)Cf(Aeo)AfL96 | A-115962.18 | uUfgAfaGfuAfaAfuggUfgUfuAfaCfcs(Aeos)(Geo) | 1.20 | 0.15 | 0.90 | 0.15 |
| AD-56872 | A-115965.5 | Gf(Geo)UfuAfaCfaCfCfAfuUfuAfcUf(Teo)Cf(Aeo)AfL96 | A-116392.1 | uUfgaaGfuAfaAfuggUfguuAfaCfcs(Aeos)(Geo) | | | 0.93 | 0.24 |
| AD-56820.2 | A-116317.4 | gUf(Uhd)AfaCfaCfCfAfuUfuAfcUfuCfaAfL96 | A-116297.10 | uUfgAfaGfuAfaAfuggUfgUfuAfaCfs(m5Ceos)(Aeo) | 1.05 | 0.10 | 0.94 | 0.10 |
| AD-56793.2 | A-116382.1 | gdGuudAdAcadCdCauudTdAcu(Uhd)dCadAL96 | A-1116373.1 | udTdGadAgdTadAdAuggdTdGuudAdAcdCsasg | 0.98 | 0.08 | 0.99 | 0.08 |
| PBS/Control | | | | | 1.00 | 0.04 | 1.00 | 0.04 |
| AD-56873 | A-115968.11 | Gf(Geo)Uf(Teo)AfaCfaCfCfAfuUf(Teo)Af(m5Ceo)Uf(Teo)Cf(Aeo)AfL96 | A-116392.1 | uUfgaaGfuAfaAfuggUfguuAfaCfcs(Aeos)(Geo) | | | 1.01 | 0.18 |

TABLE 14-continued

AD-54944 optimized sequences and protein levels. (The "Sense Sequence" column sequences are disclosed as SEQ ID NOS 899-919, respectively, in order of appearance, and the "Antisense Sequence" column sequences are disclosed as SEQ ID NOS 920-940, respectively, in order of appearance)

| | | | | | 3 mpk | | 10 mpk | |
|---|---|---|---|---|---|---|---|---|
| Duplex ID | Sense strand | Sense sequence | Antisense | Antisense sequence | % PBS | stdev | % PBS | stdev |
| AD-54965 | A-113033.1 | AfaCfuGfcCfgAfCfUfcUfaUfcGfaAfaAfL96 | A-113034.1 | uUfuUfcGfaUfaGfaguCfgGfcAfgUfusCfsa | 0.89 | 0.07 | 1.03 | 0.07 |
| AD-56787.2 | A-116381.1 | gguuaacaccdAudTudAcdT(Uhd)dCasaL96 | A-116373.10 | udTdGadAgdTadAdAuggdTdGuudAdAcdCsasg | 1.03 | 0.18 | 1.04 | 0.18 |
| AD-56840.2 | A-116317.5 | gUf(Uhd)AfaCfaCfCfAfuUfuAfcUfuCfaAfL96 | A-116344.5 | uUfgAfaGfuAfaAfuggUfgUfuAfaCfs(Chds)(Aeo) | 1.38 | 0.14 | 1.05 | 0.14 |
| AD-56834.2 | A-116333.3 | GbguuAfaCfaCfCfAfuUfuAfcUfuCfaAfL96 | A-116334.3 | uUfgaaGfuAfaAfuggUfguuAfaCfcsasGb | 1.17 | 0.14 | 1.06 | 0.14 |
| AD-56841.2 | A-115966.26 | Gf(Geo)Uf(Teo)AfaCfaCfCfAfuUfuAfcUf(Teo)Cf(Aeo)AfL96 | A-116285.3 | uUfgAfaGf(Uhd)AfaAfuggUfgUfuAfaCfcs(Aeos)(Geo) | 1.15 | 0.21 | 1.09 | 0.21 |

TABLE 15

AD-56813 optimized sequences and protein and activity levels. (The "Sense Sequence" column sequences are disclosed as SEQ ID NOS 941-959, respectively, in order of appearance, and the "Antisense Sequence" column sequences are disclosed as SEQ ID NOS 960-978, respectively, in order of appearance)

| | | | | | ELISA | | | | Activity | | | |
|---|---|---|---|---|---|---|---|---|---|---|---|---|
| Duplex | Sense | | | Antisense | 10 mpk | | 3 mpk | | 10 mpk | | 3 mpk | |
| name | ID | Sense (5' to 3') | AS ID | (5' to 3') | Av | SD | Av | SD | Av | SD | Av | SD |
| AD-57213.1 | A-116858.1 | GfsgsUfuAfaCfaCfCfAfuUfuAfcUfuCfaAfL96 | A-116861.1 | usUfsgAfaGfuAfaAfuggUfgUfuAfaCfcsasg | 0.098 | 0.021 | 0.264 | 0.032 | 0.099 | 0.021 | 0.255 | 0.030 |
| AD-57214.1 | A-116859.1 | GfsgsUfuAfaCfaCfCfAfuUf(Uhd)AfcUfuCfaAfL96 | A-116861.1 | usUfsgAfaGfuAfaAfuggUfgUfuAfaCfcsasg | 0.140 | 0.027 | 0.200 | 0.132 | 0.121 | 0.028 | 0.123 | 0.114 |
| AD-57205.1 | A-113073.1 | GfgUfuAfaCfaCfCfAfuUfuAfcUfuCfaAfL96 | A-116861.1 | usUfsgAfaGfuAfaAfuggUfgUfuAfaCfcsasg | 0.147 | 0.100 | 0.592 | 0.094 | 0.145 | 0.043 | 0.542 | 0.139 |
| AD-56813.2 | A-116280.6 | Gfs(Geo)UfsuAfaCfsaCfsCfsAfuUfsuAfcUfsuCfs(Aeo)AfL96 | A-116278.6 | usUfsgAfaGfuAfaAfuggUfgUfsgUfsuAfaCfscs(Aeos)(Geo) | 0.161 | 0.047 | 0.500 | 0.033 | 0.179 | 0.055 | 0.583 | 0.065 |
| AD-57212.1 | A-116276.12 | GfgUfsuAfaCfsaCfsCfsAfuUfsuAfcUfsuCfsaAfL96 | A-116860.1 | usUfsgAfaGfuAfaAfuggUfgUfsgUfsuAfaCfscsasg | 0.164 | 0.026 | 0.355 | 0.007 | 0.198 | 0.011 | 0.395 | 0.023 |
| AD-57204.1 | A-113073.1 | GfgUfuAfaCfaCfCfAfuUfuAfcUfuCfaAfL96 | A-116860.1 | usUfsgAfaGfuAfaAfuggUfgUfsgUfsuAfaCfscsasg | 0.170 | 0.127 | 0.659 | 0.004 | 0.121 | 0.094 | 0.608 | 0.060 |
| AD-56741.2 | A-115968 | Gf(Geo)Uf(Teo)AfaCfaCfCfAfuUf(Teo)Af(m5Ceo)Uf(Teo)Cf(Aeo)AfL96 | A-115861 | uUfgaaGfuAfaAfuggUfgUfuAfaCfcsasg | 0.347 | 0.098 | 0.666 | 0.036 | 0.419 | 0.126 | 0.880 | 0.070 |
| AD-57203.1 | A-113073.1 | GfgUfuAfaCfaCfCfAfuUfuAfcUfuCfaAfL96 | A-116278.6 | usUfsgAfaGfuAfaAfuggUfgUfsgUfsuAfaCfscs(Aeos)(Geo) | 0.359 | 0.053 | 0.829 | 0.056 | 0.358 | 0.064 | 0.796 | 0.030 |

TABLE 15-continued

AD-56813 optimized sequences and protein and activity levels. (The "Sense Sequence" column sequences are disclosed as SEQ ID NOS 941-959, respectively, in order of appearance, and the "Antisense Sequence" column sequences are disclosed as SEQ ID NOS 960-978, respectively, in order of appearance)

| | | | | | ELISA | | | | Activity | | | |
|---|---|---|---|---|---|---|---|---|---|---|---|---|
| Duplex | Sense | | | Antisense | 10 mpk | | 3 mpk | | 10 mpk | | 3 mpk | |
| name | ID | Sense (5' to 3') | AS ID | (5' to 3') | Av | SD | Av | SD | Av | SD | Av | SD |
| AD-56765.2 | A-113073.1 | GfgUfuAfaCfaCfCf fAuUfuAfcUfuCfaA fL96 | A-116275.7 | uUfsgAfaGfuAfaAfug gUfsgUfsuAfaCfscsA fsg | 0.366 | 0.053 | 0.668 | 0.040 | 0.385 | 0.041 | 0.791 | 0.047 |
| AD-56789.2 | A-116276.12 | GfgUfsuAfaCfsaCf sCfsAfuUfsuAfcUf suCfsaAfL96 | A-116275.7 | uUfsgAfaGfuAfaAfug gUfsgUfsuAfaCfscsA fsg | 0.401 | 0.057 | 0.700 | 0.059 | 0.406 | 0.078 | 0.785 | 0.059 |
| AD-57211.1 | A-116858.1 | GfsgsUfuAfaCfaCf CfAfuUfuAfcUfuCf aAfL96 | A-113074.1 | uUfgAfaGfuAfaAfugg UfgUfuAfaCfcsAfsg | 0.446 | 0.023 | 0.760 | 0.142 | 0.536 | 0.027 | 0.831 | 0.117 |
| AD-57210.1 | A-116857.1 | GfsgsUfuAfaCfaCf sCfsAfuUfuAfcUfu CfaAfL96 | A-113074.1 | uUfgAfaGfuAfaAfugg UfgUfuAfaCfcsAfsg | 0.476 | 0.028 | 0.734 | 0.053 | 0.547 | 0.041 | 0.826 | 0.065 |
| AD-57208.1 | A-116276.12 | GfgUfsuAfaCfsaCf sCfsAfuUfsuAfcUf suCfsaAfL96 | A-113074.1 | uUfgAfaGfuAfaAfugg UfgUfuAfaCfcsAfsg | 0.542 | 0.016 | 0.915 | 0.085 | 0.486 | 0.006 | 0.831 | 0.034 |
| AD-56475.3 | A-115968 | Gf(Geo)Uf(Teo)Af aCfaCfCfAfuUf (Teo)Af(m5Ceo) Uf(Teo)Cf(Aeo) AfL96 | A-113074.1 | uUfgAfaGfuAfaAfugg UfgUfuAfaCfcsAfsg | 0.574 | 0.058 | 0.932 | 0.127 | 0.415 | 0.019 | 0.735 | 0.123 |
| AD-57209.1 | A-116280.6 | Gfs(Geo)UfsuAfaC fsaCfsCfsAfuUfsu AfcUfsuCfs(Aeo) AfL96 | A-113074.1 | uUfgAfaGfuAfaAfugg UfgUfuAfaCfcsAfsg | 0.588 | 0.135 | 0.966 | 0.100 | 0.460 | 0.136 | 0.823 | 0.026 |
| AD-54944.13 | A-113073.1 | GfgUfuAfaCfaCfCf AfuUfuAfcUfuCfaA fL96 | A-113074.1 | uUfgAfaGfuAfaAfugg UfgUfuAfaCfcsAfsg | 0.617 | 0.025 | 0.715 | 0.071 | 0.667 | 0.016 | 0.835 | 0.083 |
| AD-57206.1 | A-113073.1 | GfgUfuAfaCfaCfCf AfuUfuAfcUfuCfaA fL96 | A-116870.1 | uUfgAfaGfuAfaAfugg UfgUfuAfaCfcAfsg | 0.681 | 0.097 | 0.811 | 0.110 | 0.707 | 0.068 | 0.940 | 0.149 |
| AD-57208.2 | A-116276.12 | GfgUfsuAfaCfsaCf sCfsAfuUfsuAfcUf suCfsaAfL96 | A-113074.1 | uUfgAfaGfuAfaAfugg UfgUfuAfaCfcsAfsg | 0.736 | 0.109 | 0.714 | 0.101 | 0.729 | 0.122 | 0.817 | 0.090 |
| AD-57207.1 | A-113073.1 | GfgUfuAfaCfaCfCf AfuUfuAfcUfuCfaA fL96 | A-116871.1 | uUfgAfaGfuAfaAfugg UfgUfuAfaCfcAfg | 0.934 | 0.043 | 0.975 | 0.035 | 0.984 | 0.104 | 1.009 | 0.066 |
| | | | | | 1.000 | 0.029 | 1.000 | | 1.000 | 0.077 | 1.000 | |

Example 8

Serpinc1 Knock-Down in Hemophilic Mice

Figure 13:
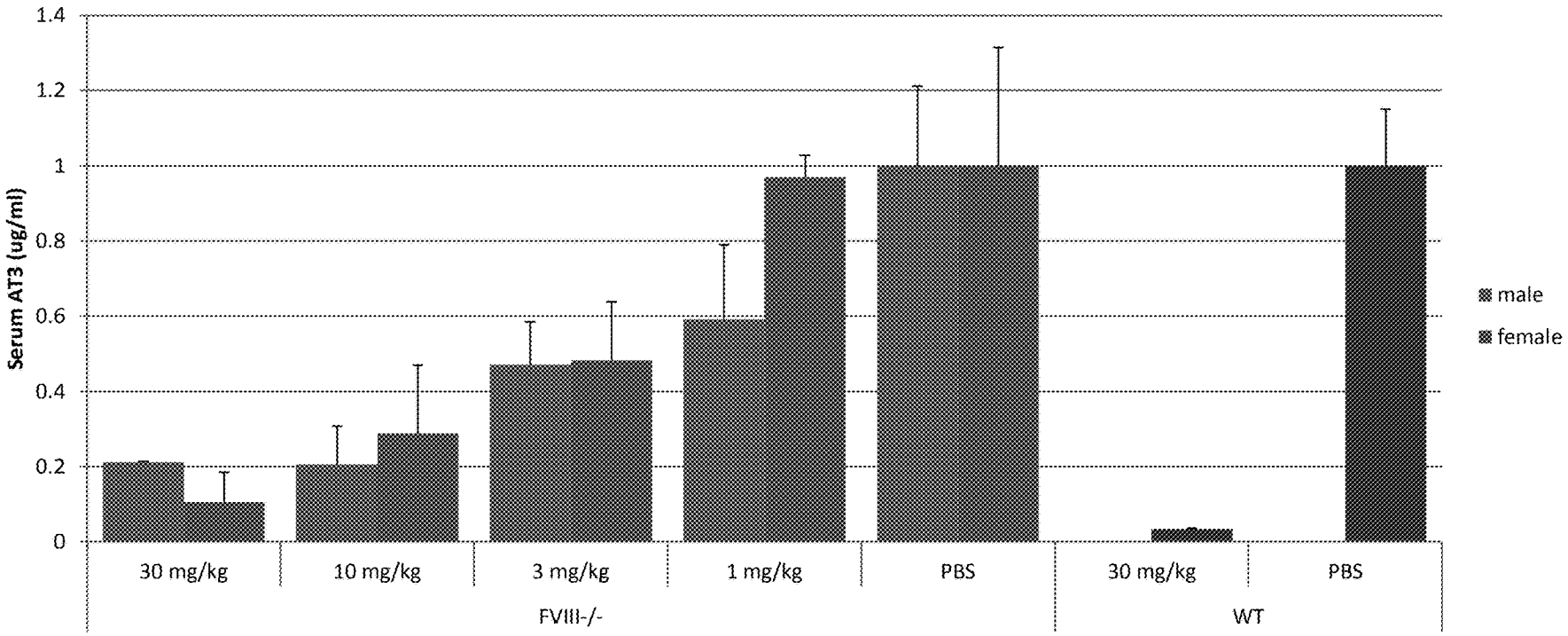
FIG. 13 is a graph showing a dose effect response to a single dose of AD-57213.

Male and female mice having a targeted deletion of Factor VIII (C57BL/6/129 hybrids) and recapitulating the hemophilia A phenotype and control or wild-type (C57BL/6 female) mice were subcutaneously injected with a single dose of compound AD-57213 conjugated to GalNAc at 30 mg/kg, 10 mg/kg, 3 mg/kg, or 1 mg/kg at Day 0, animals were sacrificed at Day 3 and Serpinc1 activity was determined as described above. FIG. 13 shows that, not only does a single dose of AD-57213 effectively knock-down Serpinc1 activity, but there is also a dose response to AD-57213.

Figure 31A:
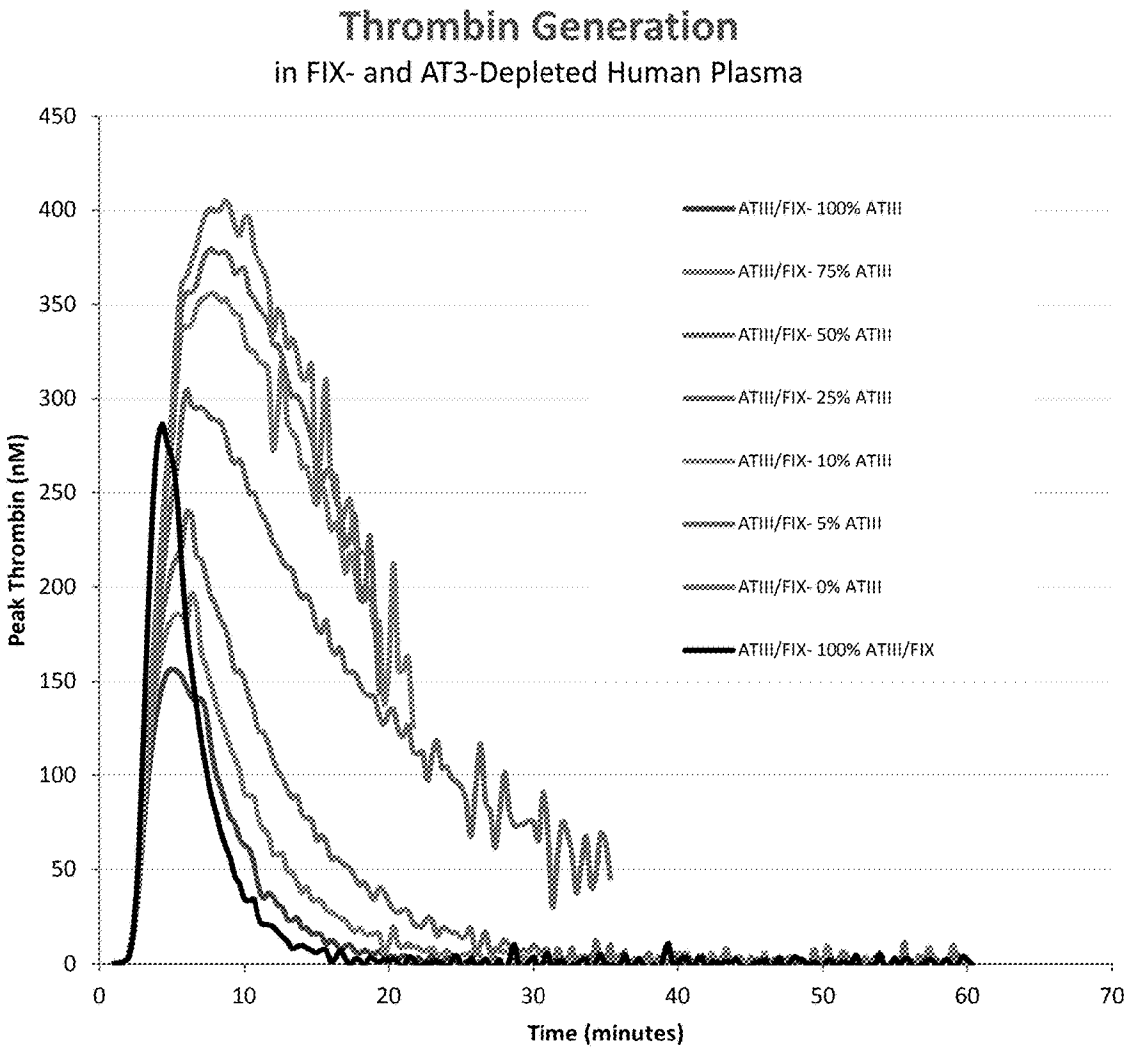
FIGS. 31A and 31B are graphs depicting that antithrombin reduction increases thrombin generation in Factor IX-depleted human plasma in vitro.
Figure 31B:
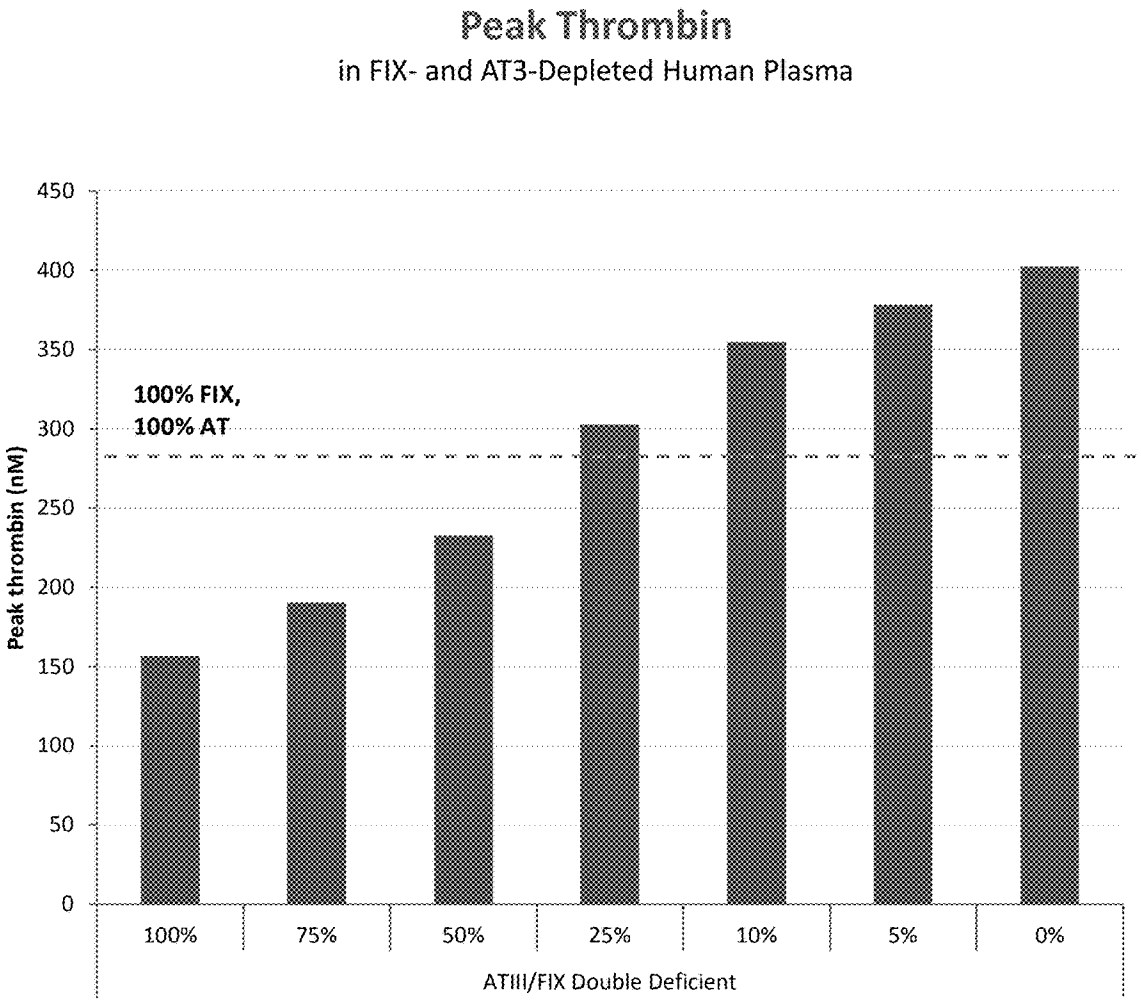

To investigate the impact of antithrombin reduction on thrombin generation in a hemophilia setting, thrombin generation studies were performed on Factor IX (FIX) and Anthithrombin- (AT-) depleted human plasma. FIX depletion recapitulates the hemophilia B phenotype AT was subsequently added back to the plasma samples at various levels (1 IU/ml=100%) to generate FIX-depleted plasma samples with different levels of antithrombin (0-100%). Control plasma was generated by adding back 1 IU/ml antithrombin and 5 μg/ml FIX (100%) to the double-depleted plasma. FIG. 31A depicts thrombin generation in FIX- and AT-depleted human plasma (tissue factor=5 pM). FIG. 31B depicts the peak thrombin in FIX- and AT-depleted human plasma (tissue factor=5 pM). Therefore, antithrombin reduction increases thrombin generation in Factor IX-depleted human plasma in vitro.

Example 9

Dose Duration of AD-57213

Figure 14:
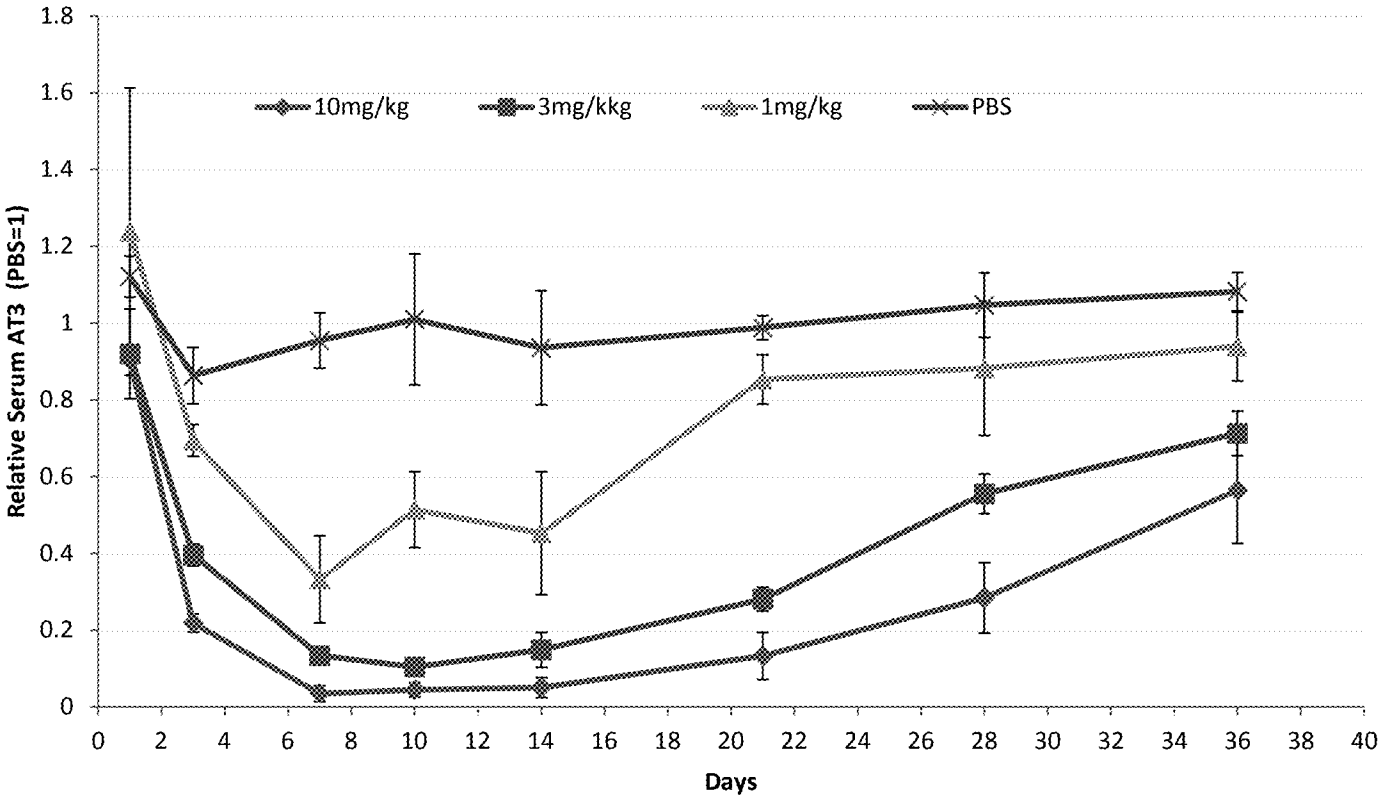
FIG. 14 is a graph showing the duration of silencing of Serpinc1 with AD-57213 following a single dose of 1 mg/kg, 3 mg/kg or 10 mg/kg in Hemophilia A mice.
Figure 16:
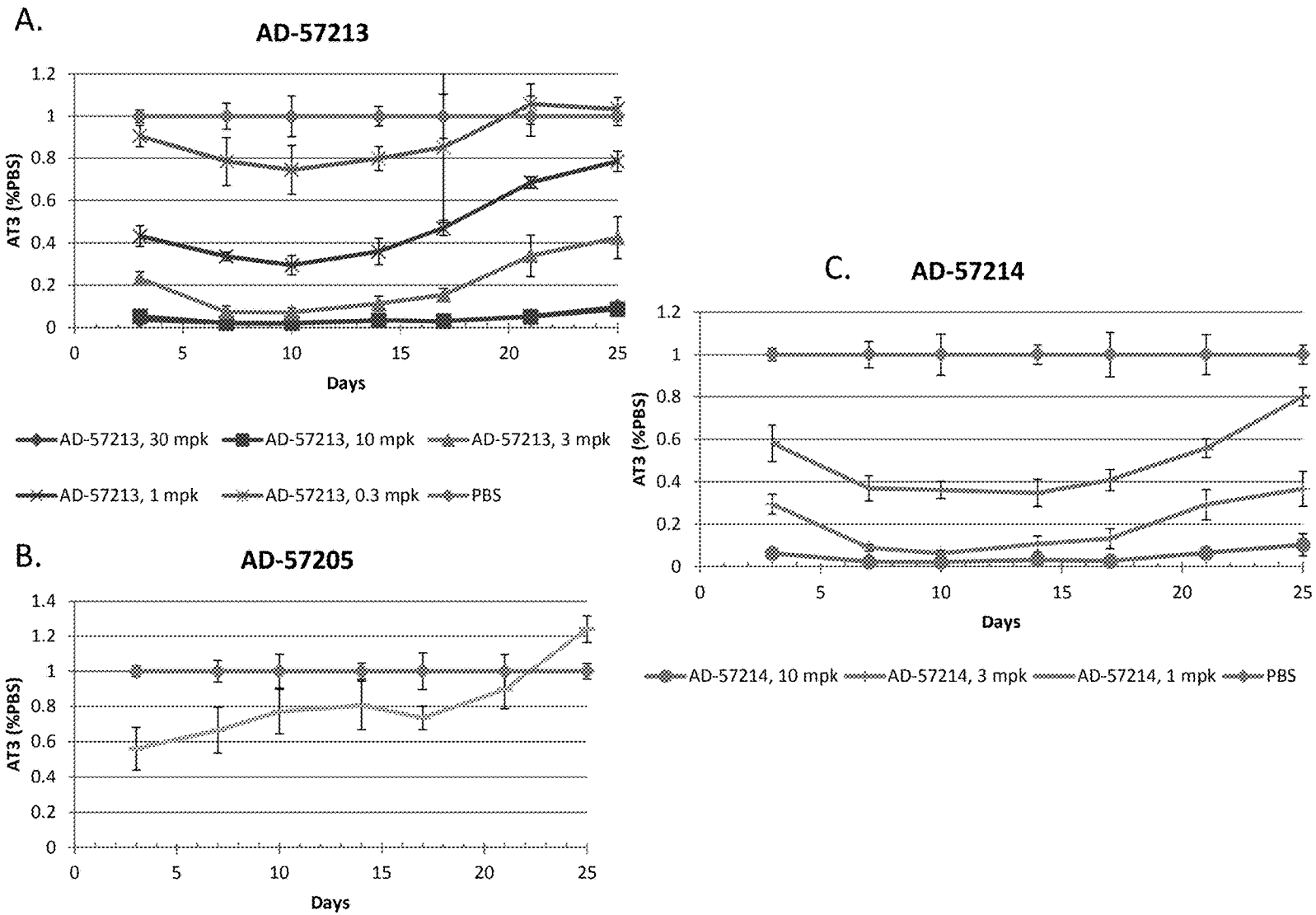
FIGS. 16A-16C are graphs showing the duration of silencing of Serpinc1 with AD-57213 (A), AD-57205 (B), and AD-57214 (C) following a single dose as indicated.

In order to evaluate the duration of anti-thrombin silencing in Hemophilia A mice (B6; 129S4-F8$^{tm1/Kaz/J}$; Jackson Labs) following a single dose of AD-57213 conjugated to GalNAc, mice were subcutaneously injected with compounds AD-57214, AD-57205, or AD-57213 or PBS. Whole blood was collected retroorbitally and assayed for Serpinc1 mRNA levels and Serpinc1 activity. The results of the single dose screen for compound AD-57213 administered at 10 mg/kg, 3 mg/kg, or 1 mg/kg as a percent knock-down of Serpinc1 activity from PBS at Days 3, 7, 10, 14, 17, 21, 28, and 36 are depicted in FIG. 14. FIG. 16 shows the results of the single dose screen for compounds AD-57213, AD-57205, and AD-57214 administered at the doses indicated in the Figures as a percent knock-down of Serpinc1 activity from PBS at Days 3, 7, 10, 14, 17, 21, and 25.

Figure 15:
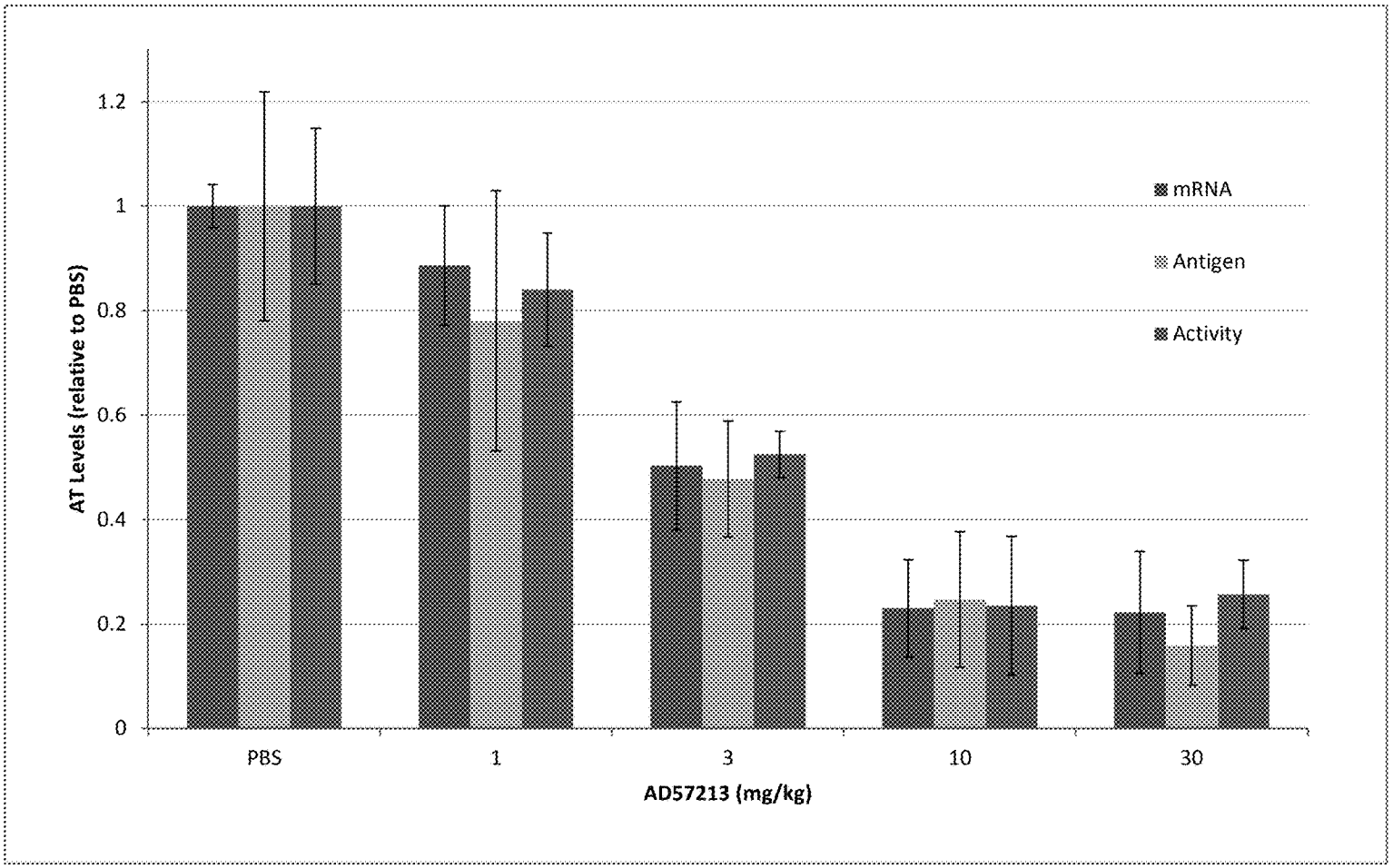
FIG. 15 is a graph showing the inhibition of Serpinc1 mRNA expression in C57BL/6 mice following a single 30 mg/kg, 10 mg/kg, 3 mg/kg, 1 mg/kg, and 0.3 mg/kg dose of AD-57213.

Liver mRNA, AT antigen in serum and AT activity were measured in hemophilia A mice (B6; 129S4-F8$^{tm1/Kaz/J}$; Jackson labs) injected subcutaneously with AD-57213 at a dose of 30 mg/kg, 10 mg/kg, 3 mg/kg, 1 mg/kg, or PBS at Day 0. Animals were sacrificed on Day 3 post-injection as described above. FIG. 15 shows the results of the single dose screen as a percent knock-down of Serpinc1 mRNA levels from PBS, as a percent knock-down of Serpinc1 antigen levels from PBS, and as a percent knock-down of Serpinc1 activity from PBS at Day 3 for AD-57213.

As evidenced by FIGS. 14-16, administration of compound AD-57213 leads to potent, dose-dependent suppression of Serpinc1 in HA mice with a single dose $ED_{50}$ of less than 1 mg/kg on Day 7. Serpinc1 suppression was durable and correlated with the maximal level of antithrombin suppression achieved. A single dose of 1 mg/kg led to the maintenance of 50% suppression for about 15 days, while a dose of 10 mg/kg led to greater than 80% suppression maintained for 28 days.

Example 10

Dose Duration of a Split-Dose of AD-57213

In order to further evaluate compound AD-57213 knock-down of Serpinc1 expression and activity, a split-dosing experiment was performed. C57BL/6 mice were subcutaneously administered GalNAc-conjugated AD-57213 and the effect of a 3 times per week, ⅓ dose of AD-57213 was compared to the effect of a 1 time per week fully concentrated dose of AD-57213. A summary of the study design is presented in Table 16. Serum Serpinc1 protein levels were determined.

TABLE 16

Study Design of Split-Dosing Experiment

| Group | Test compound | Dose (mg/kg) | Frequency |
|---|---|---|---|
| 1 | AD-57213 | 3 | q1w |
| 2 | | 1.5 | (Monday) |
| 3 | | 0.75 | |
| 4 | | 1 | t.i.w. |
| 5 | | 0.5 | (M, W, F) |
| 6 | | 0.25 | |
| 7 | PBS | — | q1w |

(q1w: Once a week)

Figure 17:
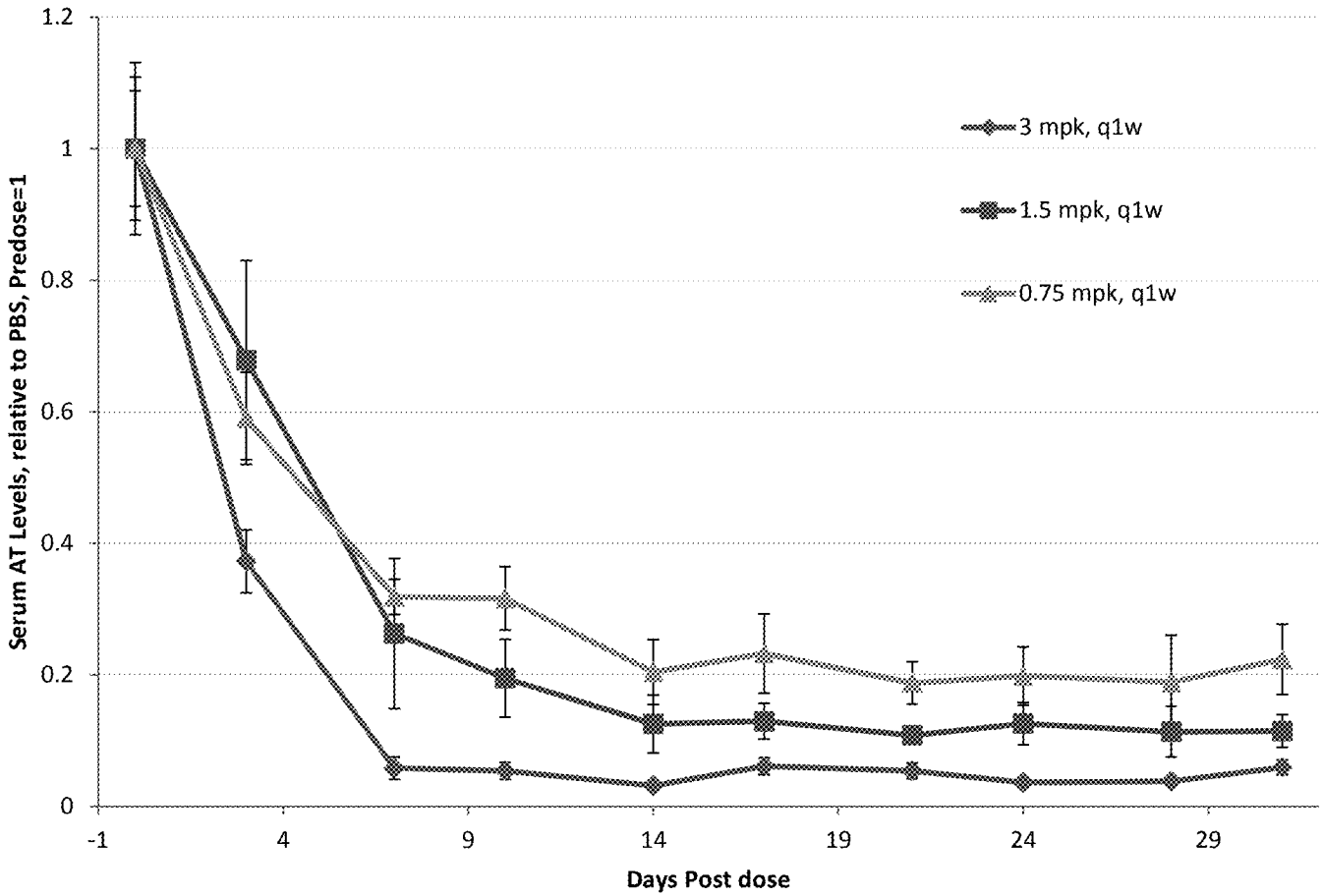
FIGS. 17-19 are graphs showing the effects of the indicated split-dosing regimens on the duration of silencing of Serpinc1 protein expression in C57BL/6 mice administered GalNAc conjugated AD-57213.
Figure 18:
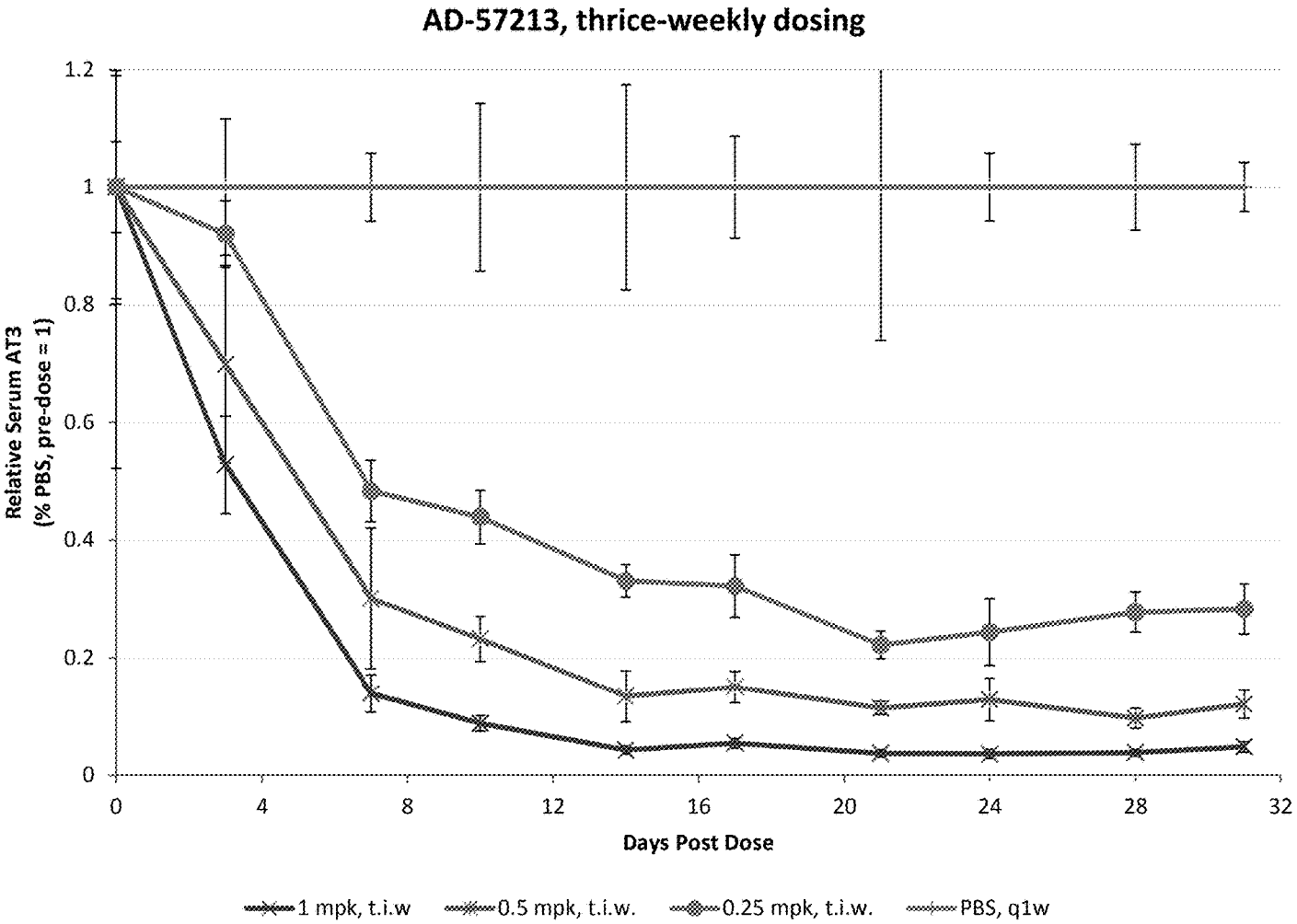

The results of the once a week (q1w) dosing as a percent knock-down of Serpinc1 protein levels from PBS are shown in FIG. 17 and the results of the three-time per week (t.i.w.) dosing as a percent knock-down of Serpinc1 protein levels from PBS are shown in FIG. 18.

Figure 19:
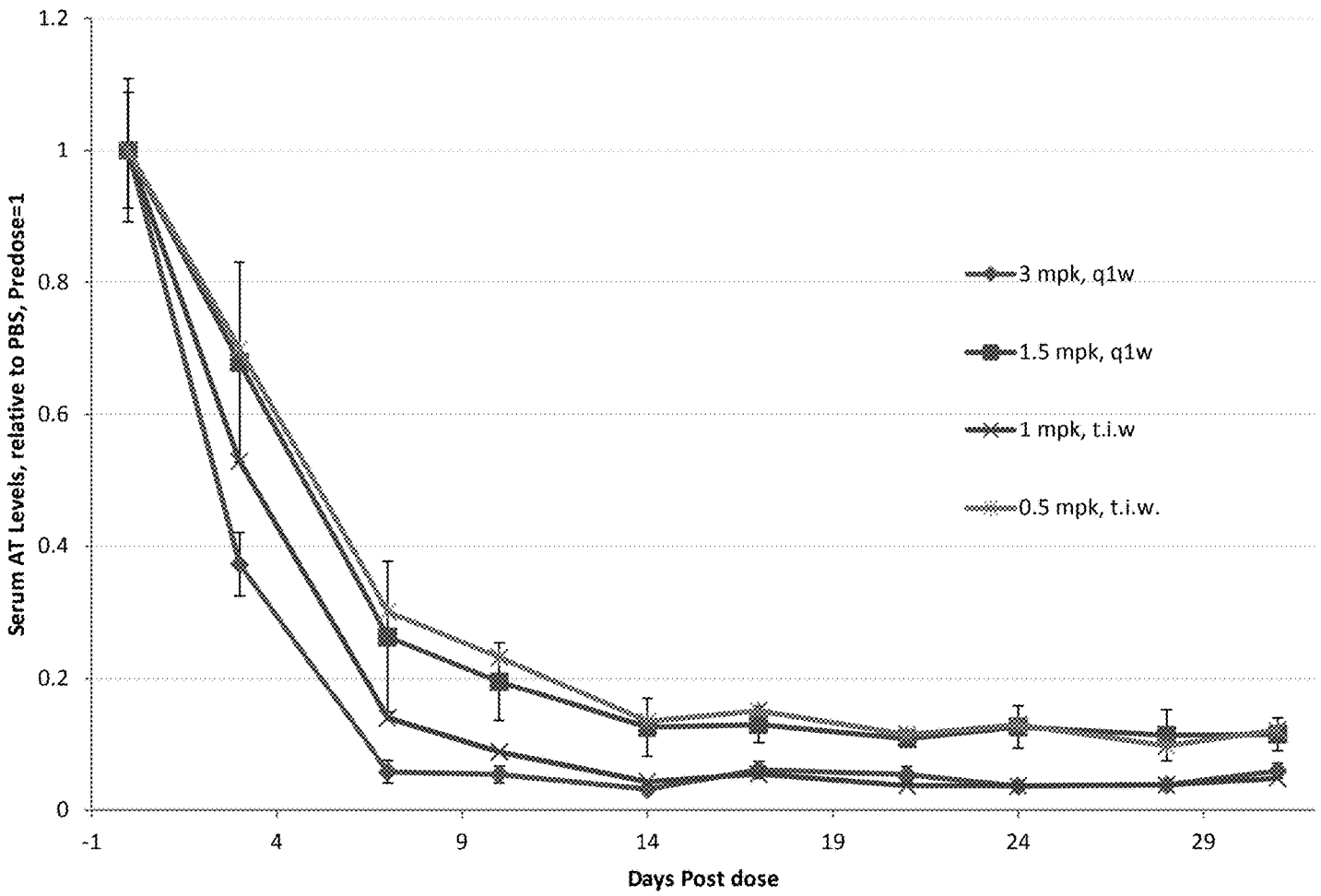

As shown in FIGS. 17 and 18, repeat dosing of compound AD-57213 led to a dose-dependent, durable response, with some additive effect. Animals dosed with 3 mg/kg reached the nadir levels of >95% knock-down after 2 weekly doses whereas the lower two dose groups attained nadir after 3 weekly doses (~90% knock-down for 1.5 mg/kg and ~80% for 0.75 mg/kg). To further study the different dosing regimens, in different groups, the same weekly dose was split and dosed three times a week, e.g., 1.5 mg/kg q1w was compared with 0.5 mg/kg tiw. As shown in FIG. 19, the cumulative weekly dose gave the same level of knock-down. For example, Serpinc1 levels achieved with 1.5 mg/kg (q1w) were equivalent to Serpinc1 levels achieved with 0.5 mg/kg administered three times a week.

Example 11

Non-Human Primate Dosing of Serpinc1 siRNAs

Compound AD-57213 was tested for efficacy in non-human primates as outlined in Table 17. Serum Serpinc1 protein levels were determined at Days −14, −8, −4, Day 1 at 4 hours post-dosing, Days 2, 4, 8, 11, 15, 22, 29, 37, 44, 51, and 58.

TABLE 17

Non-Human Primate Dosing Experiment.

| Test Article | Group Number | n | Dose level (mg/kg) | Route of administration | Rationale | |
|---|---|---|---|---|---|---|
| AD54944 | 1 | 3 | 10 | SC | Parent compound | |
| AD-57213 | 2* | 3 | 30 | SC | Dose response for the lead | Similar to 3 × 10 mpk |
| | 3 | 3 | 10 | SC | | Compare compounds at 10 mpk |

TABLE 17-continued

Non-Human Primate Dosing Experiment.

| Test Article | Group Number | n | Dose level (mg/kg) | Route of administration | Rationale | |
|---|---|---|---|---|---|---|
| | 4 | 3 | 3 | SC | | Dose curve |
| | 5 | 3 | 1 | SC | | |
| AD-57205 | 5 | 3 | 10 | SC | Same potency as 57213 at 10 mpk in mice | Has less PS |
| LNP-55029 | 7 | 3 | 0.3 | IV | Test target | Positive control for target knock-down and assays |

Figure 20:
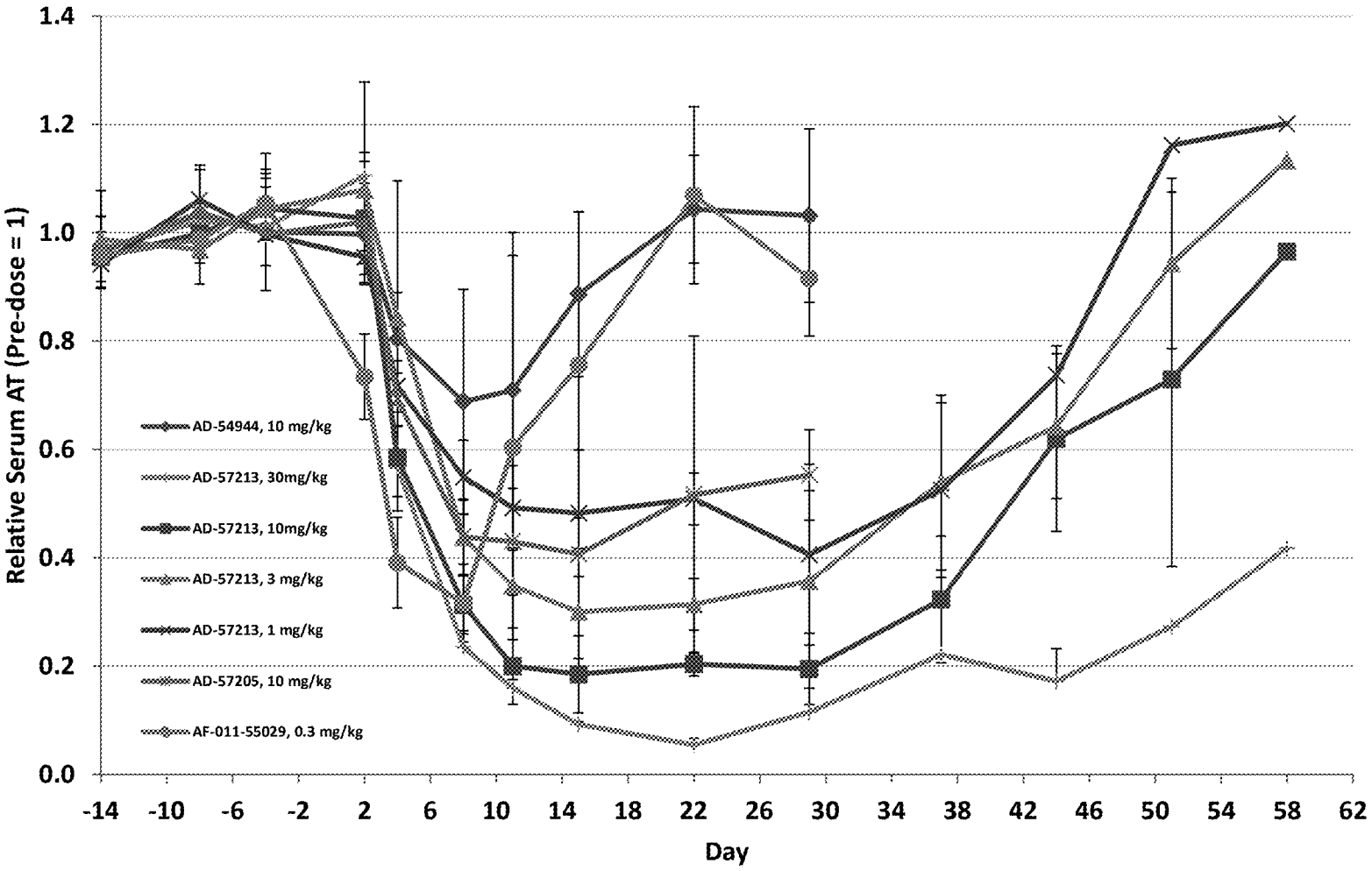
FIG. 20 is a graph showing the effects of the single dose screen of the indicated compounds on the duration of Serpinc1 protein expression in non-human primates.

FIG. 20 shows the results of the single dose screen for all compounds tested as a group average of the relative serum Serpinc1 levels compared to pre-dosing Serpinc1 levels and demonstrates that all of the siRNAs tested effectively knock-down Serpinc1 protein levels.

Figure 21:
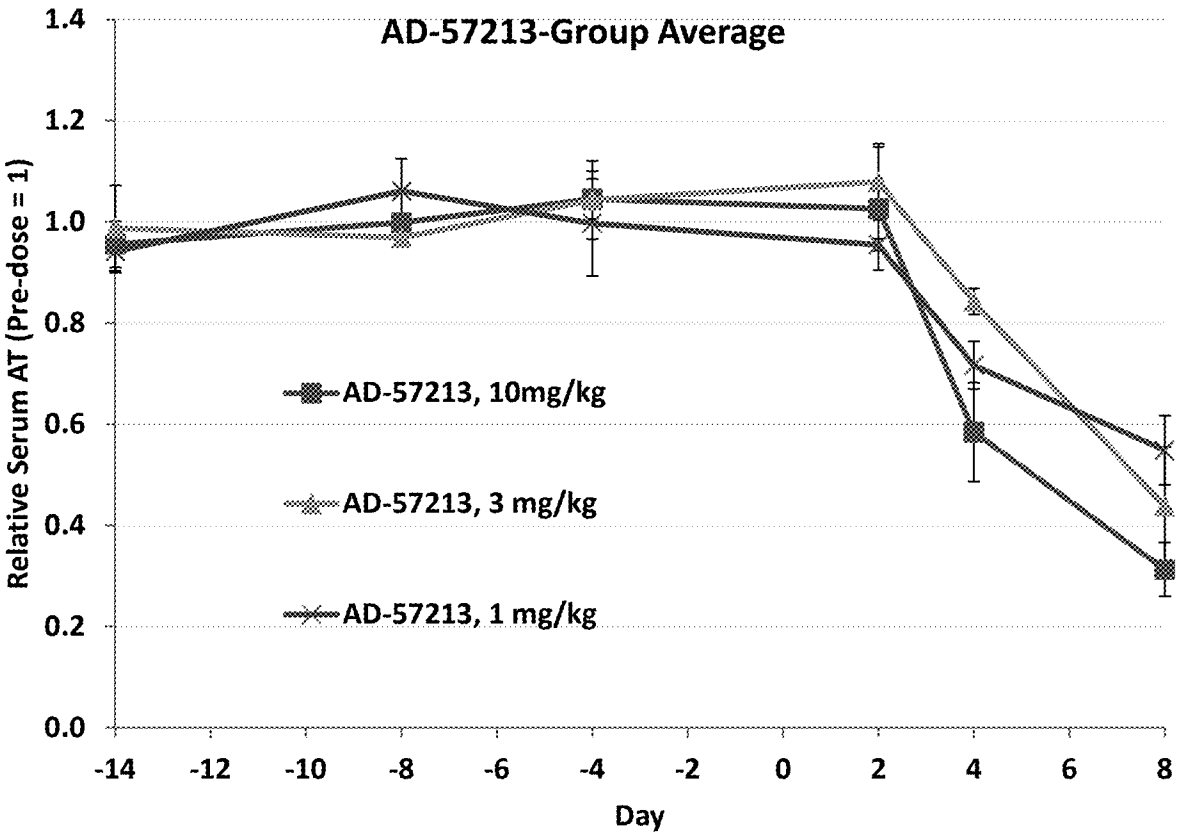
FIG. 21 is a graph showing the effects of the single dose screen of AD-57213 conjugated to GalNAc on the duration of Serpinc1 protein expression in non-human primates.

FIG. 21 shows the results of the single dose screen for compound AD-57213 as a group average of the relative serum Serpinc1 levels compared to pre-dosing Serpinc1 levels.

Figure 22:
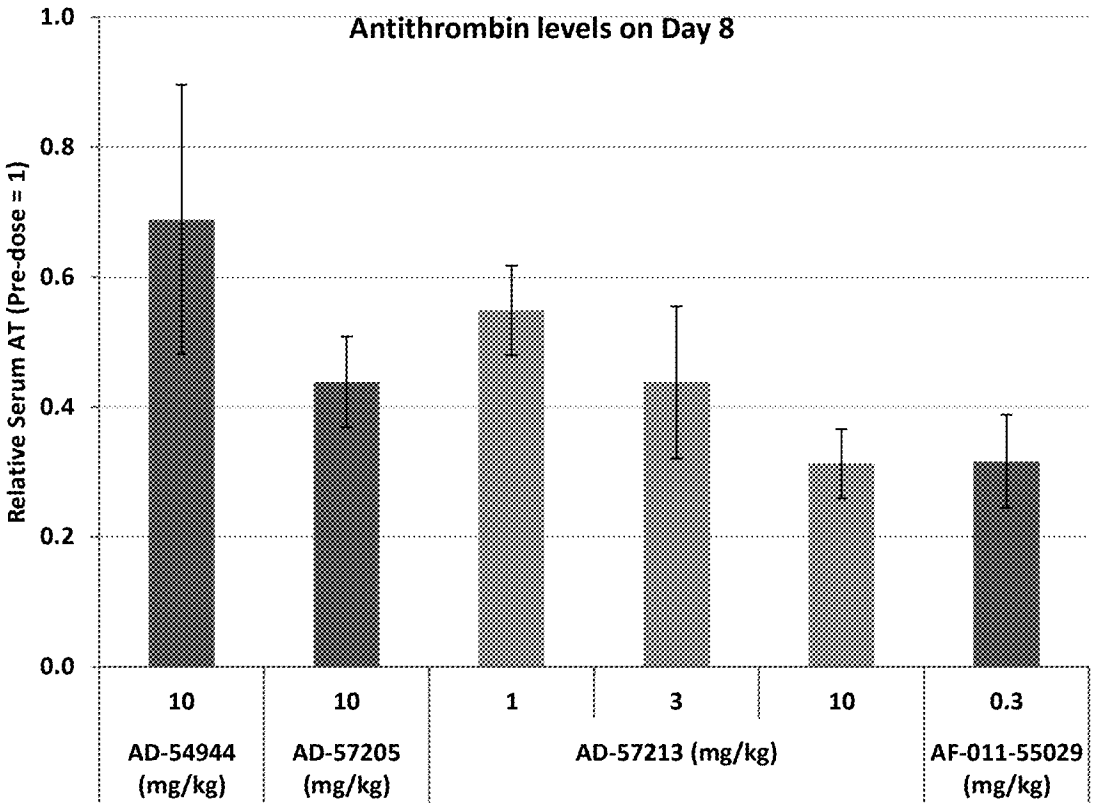
FIG. 22 is a graph showing the effects of the single dose screen of the indicated compounds on the duration of Serpinc1 protein expression in non-human primates.

FIG. 22 shows the results of the single dose screen for all compounds tested as a group average of the relative serum Serpinc1 levels compared to pre-dosing Serpinc1 levels on Day 8.

Overall, the results demonstrate that there is dose-dependent knock-down of Serpinc1 protein levels with AD-57213 in non-human primates and that both AD-57213 and AD-57205 show improved potency over the parent compound AD-52444.

Example 12

Non-Human Primate Dosing of a Therapeutic Serpinc1 siRNA

Compound AD-57213 was tested for efficacy in non-human primates. Cynomolgus monkeys were administered compound AD-57213 as outlined in Table 18 below. Plasma was collected at various time points after administration of AD-57213 and analyzed for antithrombin protein (Serpinc1) levels by ELISA.

TABLE 18

Study Design: AD-57213 pharmacology in nonhuman primates

| Group Number | Test Article | N | Dose Level (mg/kg) | Route of Administration | Sample Collection |
|---|---|---|---|---|---|
| 1 | AD-57213 | 3 | 1 | SC | Plasma for AT protein and thrombin generation |
| 2 | | 3 | 3 | SC | |
| 3 | | 3 | 10 | SC | |
| 4 | | 3 | 30 | SC | |

Figure 23:
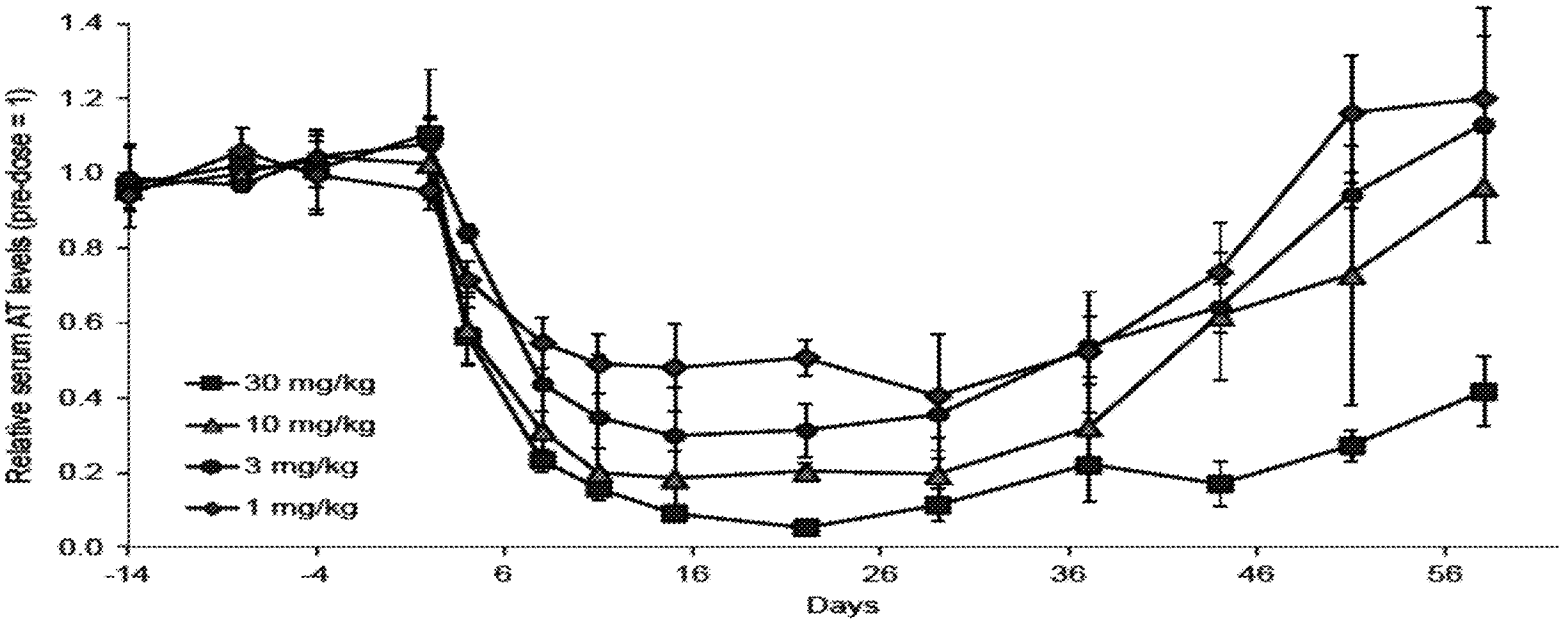
FIG. 23 is a graph showing the effects of the single dose of compound AD-57213 on serum antithrombin (Serpinc1) levels in non-human primates.
Figure 24A:
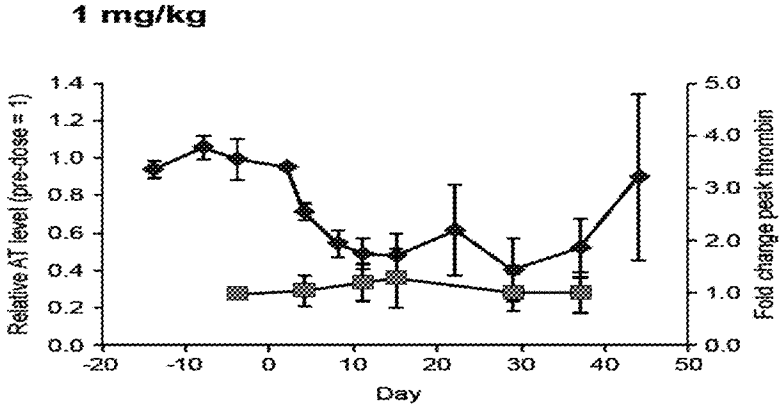
FIGS. 24A-24D are graphs showing the effects of the single dose of compound AD-57213 at A) 1 mg/kg, B) 3 mg/kg, C) 10 mg/kg, and D) 30 mg/kg on the relationship between serum antithrombin (Serpinc1) levels and fold change in peak plasma thrombin levels in non-human primates. Fold change in peak thrombin is depicted on the secondary y-axis (grey) and relative antithrombin level is depicted on the primary y-axis (black).
Figure 24B:
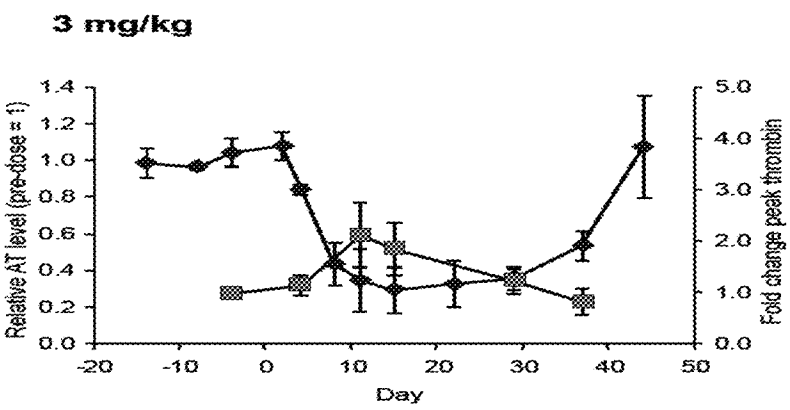
Figure 24C:
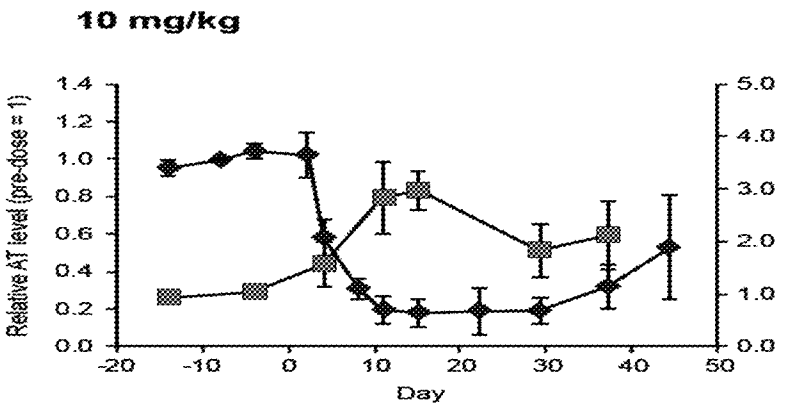
Figure 24D:
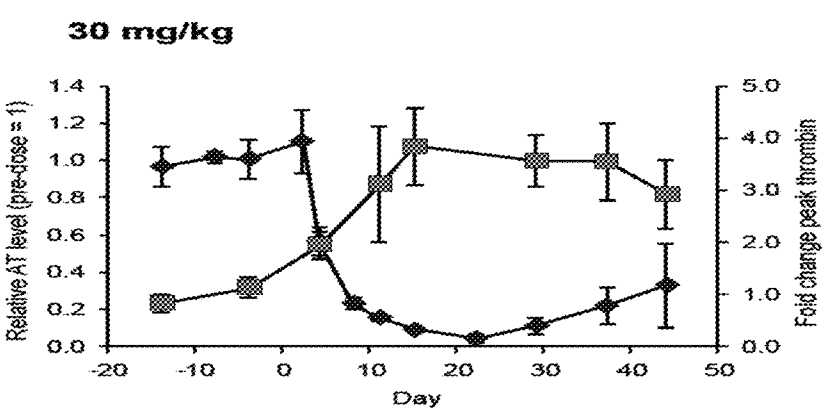

FIG. 23 shows the results of the single dose screen for compound AD-57213 as a group average of the relative serum Serpinc1 levels compared to the average of three pre-dose measurements. The results demonstrate dose dependent Serpinc1 silencing with approximately 50, 70, 80 and >90% silencing at 1, 3, 10 and 30 mg/kg, respectively. Data points represent group mean and error bars represent standard deviation.

Figure 25:
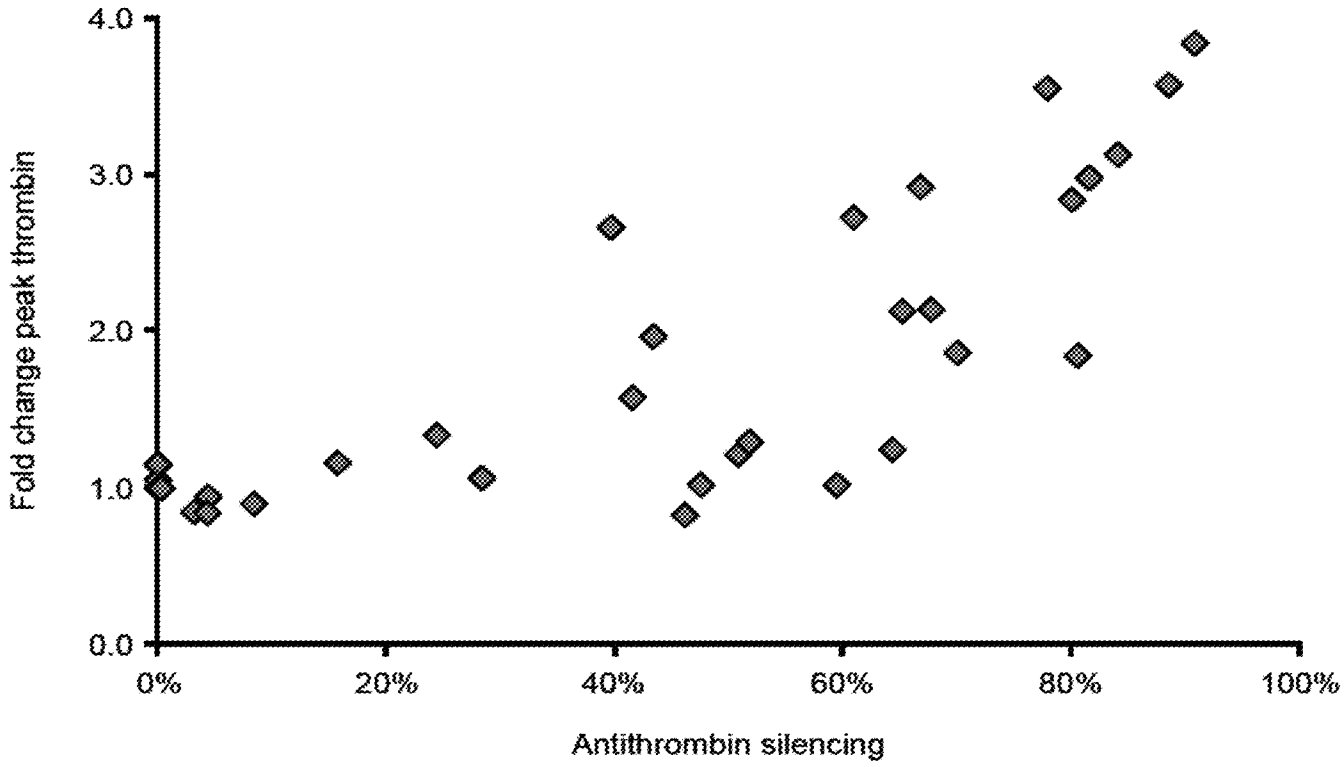
FIG. 25 is a graph showing the effects of AD-57213 as a fold change increase in peak thrombin as a function of relative antithrombin (Serpinc1) silencing.

FIGS. 24A-D show the relationship between relative serum Serpinc1 level and fold change in peak plasma thrombin level at a single A) 1 mg/kg, B) 3 mg/kg, C) 10 mg/kg, and D) 30 mg/kg dose of compound AD57213. Serpinc1 levels are represented relative to the average of three pre-dose measurements. Thrombin generation curves were generated from plasma samples collected at various time points using a Calibrated Automated Thrombinoscope (tissue factor=1 pM). Fold change in peak thrombin was calculated relative to the average peak thrombin value for two pre-dose values for each animal. Data points represent group mean and error bars represent standard deviation. FIG. 25 shows a consolidated scatterplot of fold change increase in peak thrombin as a function of relative Serpinc1 silencing.

Figure 26:
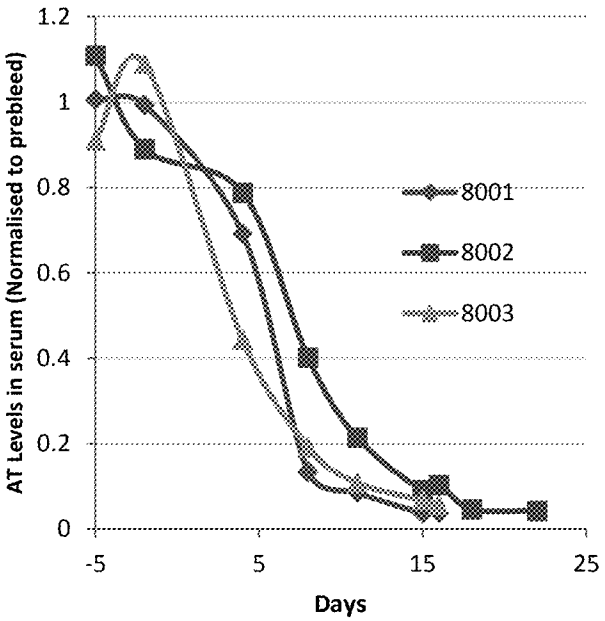
FIGS. 26A and 26B are graphs showing the cumulative effects of Serpinc1 silencing in non-human primates.
Figure 26:
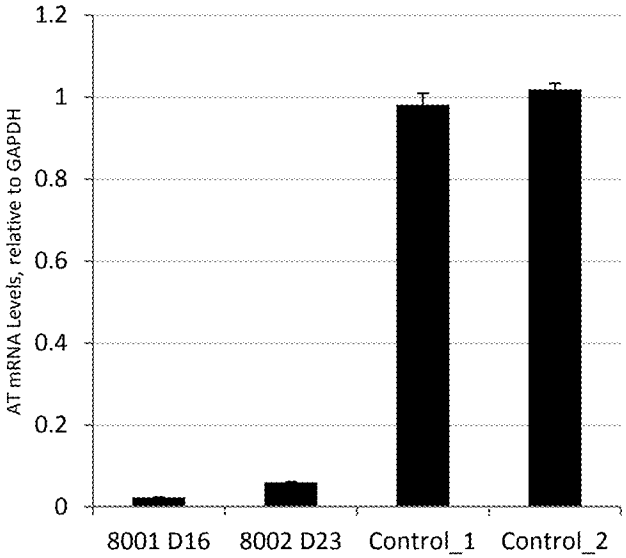

Animals were also administered three weekly AD-57213 doses of 30 mg/kg and the Serpinc1 protein and mRNA levels were determined in blood samples collected from the animals. The results of these studies are presented in FIG. 26A (Serpinc1 protein levels relative to prebleed levels) and 26B (Serpinc1 mRNA levels relative to GAPDH).

Overall, the results demonstrate that there is a durable, dose-dependent inhibition of Serpinc1 protein levels with compound AD-57213 in non-human primates that results in up to a 4-fold increase in thrombin generation.

Example 13

Repeat Administration of a Serpinc1 SiRNA in Non-Human Primate Dosing

Compound AD-57213 was tested for efficacy and to evaluate the cumulative effect of the compound in non-human primates with a repeat administration protocol. Cynomolgus monkeys were administered compound AD-57213 at 0.5 mg/kg q1w; 1 mg/kg q2w (every other week), for 2 months and 1.5 mg/kg q1w; 3 mg/kg q2w for 6 weeks. Serum was collected at various time points as illustrated in FIG. 27 and analyzed for antithrombin protein level (SerpinC1) by ELISA. Antithrombin levels were represented relative to the average of three pre-dose measurements.

Figure 27A:
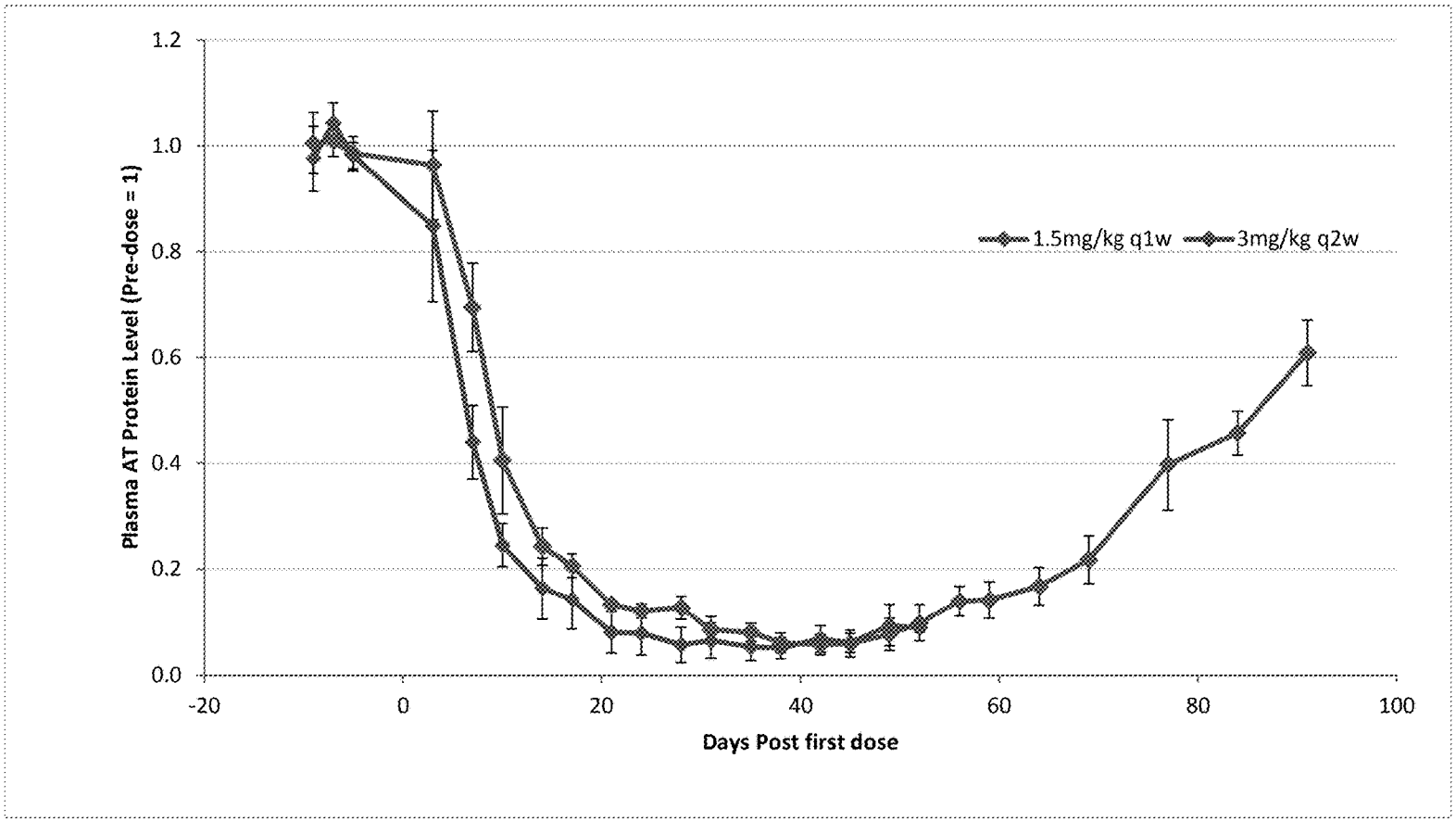
FIGS. 27A and 27B are graphs showing the effects of a multi-dose administration (0.5 mg/kg qw, 1 mg/kg q2w, 1.5 mg/kg qw, 3 mg/kg q2w) of a Serpinc1 siRNA on serum antithrombin levels in non-human primates. Data points represent group mean, error bars represent standard deviation (N=3). (qw=weekly; q2w=every other week).
Figure 27B:
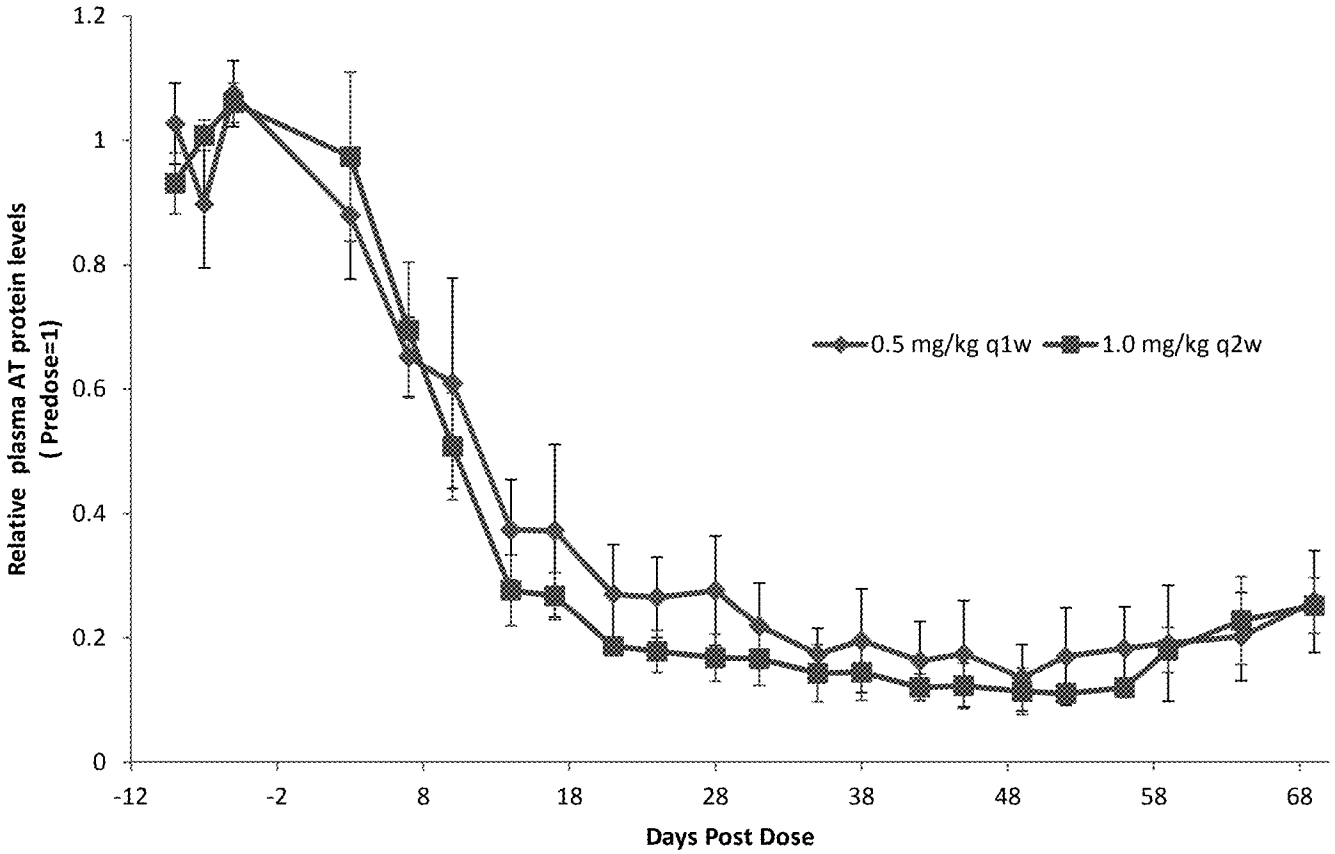

The first two dose groups with 0.5 mg/kg weekly cumulative dose led to 80% decrease in AT levels after 5 weeks. The latter two groups with 1.5 mg/kg the cumulative weekly dose led to >95% maximum knockdown. FIG. 27A shows the data from latter two groups. Animals receiving the 3 mg/kg dose were euthanized on Day 54 and animals receiving the 1.5 mg/kg q1w dose were administered an additional 6th weekly dose on day 36 and are being monitored for recovery to base line levels. FIG. 27B shows AT levels after 0.5 mg/kg cumulative weekly dose.

The data demonstrate that dose dependent antithrombin silencing was observed with all dosing regimens and achieved a steady-state level of suppression by day 25.

Example 14

Figure 28A:
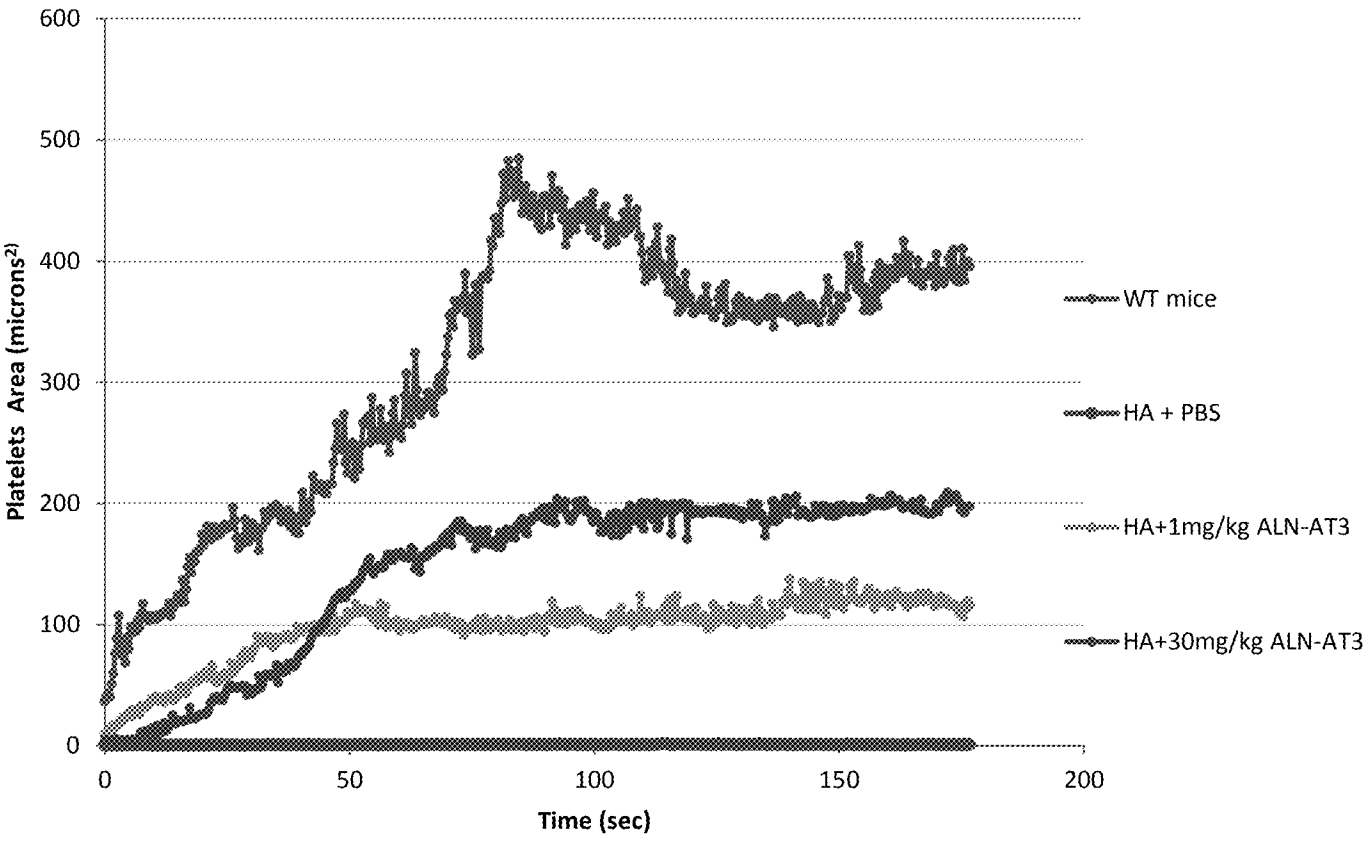
FIG. 28A is a graph showing the effect of Serpinc1 silencing on platelet accumulation following microvessel laser injury. The graph shows the median values from all inflicted [injuriesigure] *injuries. FIG.* 28B is a graph showing the effect of Serpinc1 silencing on fibrin area following microvessel laser injury. The graph shows the median values from all inflicted injuries.
Figure 28B:
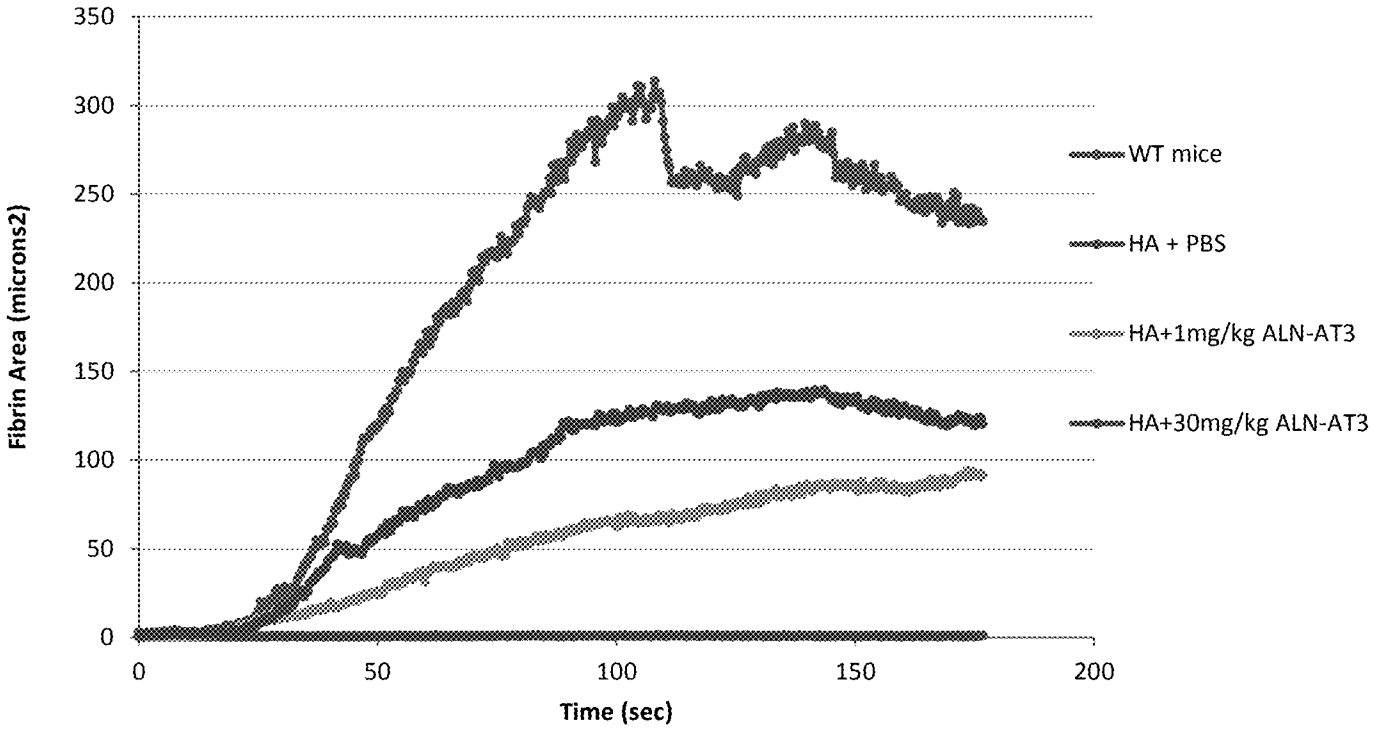

Correction in Hemostasis Following Administration of Compound AD-57213 in Hemophilic Mice Hemophilic animals have less thrombin generation potential and cannot form stable clots. Reduction of antithrombin protein in these animals should help rebalance the hemostasis, increase the endogenous thrombin generating potential, and enable clot formation. This hypothesis was tested in hemophilia A and hemophilia B mice in the microvessel laser injury model accompanied with intravital imaging. Mice were injected with compound AD-57213 and injury was induced 10 days post-treatment. Accumulation of platelets and fibrin at the site of injury were visualized, recorded and quantified. FIG. 28A shows the median values of platelet accumulation over time after laser surgery and FIG. 28B shows the median fibrin values from all inflicted injuries over time after laser surgery. As demonstrated by FIGS. 28A and 28B, compound AD-57213 injected at 1 mg/kg or 30 mg/kg led to platelet and fibrin deposition leading to clot formation in 100% of the injuries. Table 19 summarizes the results from two separate experiments with HA and HB animals.

TABLE 19

| Group | Animals (N) | Injuries (N) | Stable Thrombus (N) | Percent AT mRNA in liver |
|---|---|---|---|---|
| WT | 2 | 10 | 10 | 100% |
| HA + PBS | 2 | 13 | 0 | 100% |
| HA + 1 mg/kg ALN-AT3 | 4 | 20 | 20 | 50% |
| HA + 30 mg/kg ALN-AT3 | 4 | 20 | 20 | 5% |
| HB + PBS | 2 | 6 | 0 | 100% |
| HB + 30 mg/kg ALNAT3 | 2 | 6 | 6 | 5% |

Example 15

In Vivo Efficacy of AD-57213 LNP Formulation

Compounds AD-55029 (unconjugated) and AD-57213 (conjugated to GalNAc) were formulated in a lipid nucleic acid particle (AF-11) and wild-type animals were administered doses of 0.03 mg/kg, 0.1 mg/kg and 0.3 mg/kg of these LNP formulated compounds. Luciferase (AF11-1955) was used as control.

Figure 29:
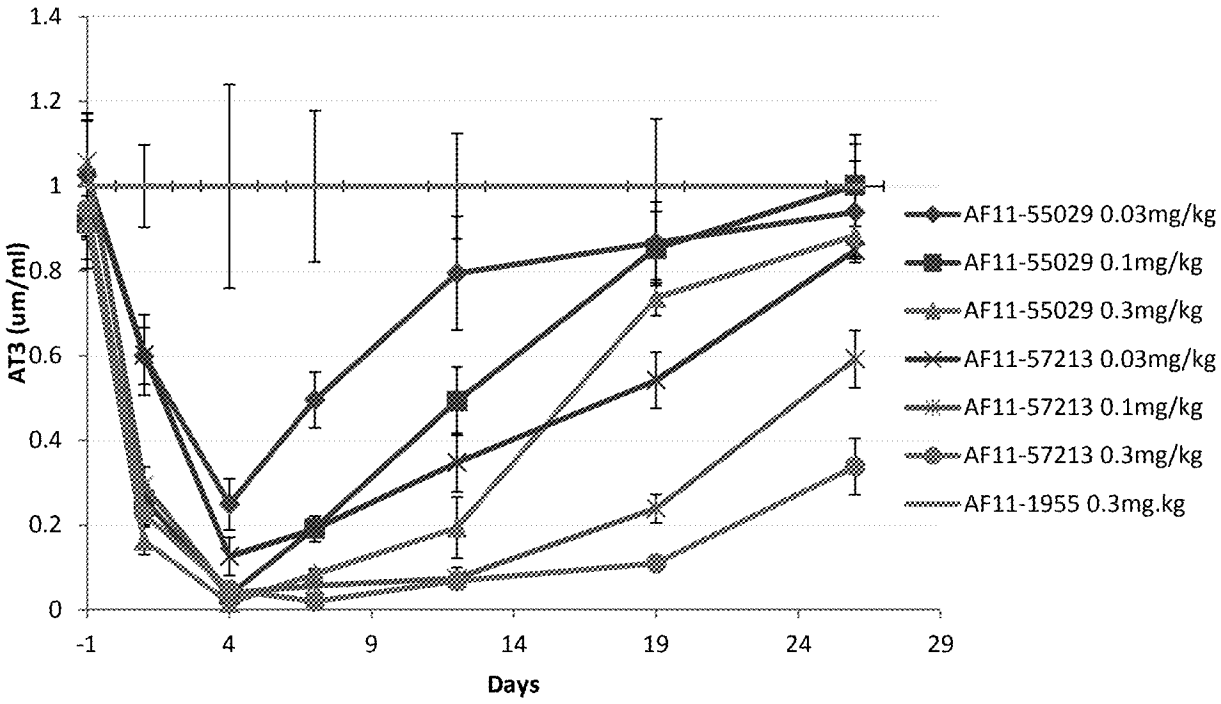
FIG. 29 is a graph showing the duration of silencing of Serpinc1 following administration of compound AD-57213 formulated in a lipid nucleic acid particle.

Both compounds led to >95% knock-down at 0.3 mg/kg but the levels were maintained by AF11-57213 for 15 days versus 8 days by AF11-55029 (see FIG. 29). A similar difference in duration of action between the two compounds was observed at the lower doses.

Example 16

Design, Synthesis, and in Vitro Screening of Additional siRNAs siRNA Design

SiRNA duplexes, 19 nucleotides long for both the sense and antisense strand, were designed using the human SERPINC1 mRNA sequence set forth in GenBank Accession No. NM_000488.3. One thousand five hundred and eighty-one duplexes were initially identified that did not contain repeats longer than 7 nucleotides, spanning the entire 1599 nucleotide transcript. All 1581 duplexes were then scored for predicted efficacy according to a linear model that evaluates the nucleotide pair at each duplex position, and the dose and cell line to be used for screening. The duplexes were also matched against all transcripts in the human RefSeq collection using a custom brute force algorithm, and scored for lowest numbers of mismatches (per strand) to transcripts other than SERPINC1. Duplexes to be synthesized and screened were then selected from the 1581, according to the following scheme: Beginning at the 5' end of the transcript, a duplex was selected within a "window" of every 10±2 nucleotides that 1) had the highest predicted efficacy, 2) had at least one mismatch in both strands to all transcripts other than SERPINC1, 3) had not already been synthesized and screened as part of other duplex sets.

If no duplex could be identified within a given window that satisfied all criteria, that window was skipped. One hundred and sixty-four duplexes were identified that satisfied these criteria.

A detailed list of Serpinc1 sense and antisense strand sequences is shown in Tables 20 and 21.

TABLE 20

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59267.1 | A-120250.1 | GGAGAAGAAGGCAACUGAG | A-120251.1 | CUCAGUUGCCUUCUUCUCC | 293-311 |
| AD-59268.1 | A-120266.1 | UGACCAAGCUGGGUGCCUG | A-120267.1 | CAGGCACCCAGCUUGGUCA | 481-499 |
| AD-59269.1 | A-120282.1 | GGUUAACACCAUUUACUUC | A-120283.1 | GAAGUAAAUGGUGUUAACC | 860-878 |
| AD-59270.1 | A-120298.1 | GCUGGUUAACACCAUUUAC | A-120299.1 | GUAAAUGGUGUUAACCAGC | 857-875 |
| AD-59271.1 | A-120314.1 | UAAUGACACCCUCCAGCAA | A-120315.1 | UUGCUGGAGGGUGUCAUUA | 500-518 |
| AD-59272.1 | A-120330.1 | CGUGUUCAGCAUCUAUGAU | A-120331.1 | AUCAUAGAUGCUGAACACG | 952-970 |
| AD-59273.1 | A-120252.1 | UUGAGGACGGCUUCAGUUU | A-120253.1 | AAACUGAAGCCGUCCUCAA | 1189-1207 |
| AD-59274.1 | A-120268.1 | CGGCGUGUCUGGGAACUGU | A-120269.1 | ACAGUUCCCAGACACGCCG | 351-369 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59275.1 | A-120284.1 | UUAACACCAUUUACUUCAA | A-120285.1 | UUGAAGUAAAUGGUGUUAA | 862-880 |
| AD-59276.1 | A-120300.1 | CCCUGAAAAGUCCAAACUC | A-120301.1 | GAGUUUGGACUUUUCAGGG | 1250-1268 |
| AD-59277.1 | A-120316.1 | CGAGAUGACCUCUAUGUCU | A-120317.1 | AGACAUAGAGGUCAUCUCG | 1290-1308 |
| AD-59278.1 | A-120332.1 | UCUACAAGGCUGAUGGAGA | A-120333.1 | UCUCCAUCAGCCUUGUAGA | 931-949 |
| AD-59279.1 | A-120254.1 | AGCUCACUGUUCUGGUGCU | A-120255.1 | AGCACCAGAACAGUGAGCU | 841-859 |
| AD-59280.1 | A-120270.1 | AGGAGCAGCUGCAAGACAU | A-120271.1 | AUGUCUUGCAGCUGCUCCU | 1210-1228 |
| AD-59281.1 | A-120286.1 | GCCACCAACCGGCGUGUCU | A-120287.1 | AGACACGCCGGUUGGUGGC | 342-360 |
| AD-59282.1 | A-120302.1 | CAGAACAGAAGAUCCCGGA | A-120303.1 | UCCGGGAUCUUCUGUUCUG | 322-340 |
| AD-59283.1 | A-120318.1 | CCUUGUCGAUCUGUUCAGC | A-120319.1 | GCUGAACAGAUCGACAAGG | 1232-1250 |
| AD-59284.1 | A-120334.1 | AGGCAAGUUCCGUUAUCGG | A-120335.1 | CCGAUAACGGAACUUGCCU | 980-998 |
| AD-59285.1 | A-120256.1 | UUUUGUCCUUGCUGCUCAU | A-120257.1 | AUGAGCAGCAAGGACAAAA | 172-190 |
| AD-59286.1 | A-120272.1 | AGACCUACCAGGACAUCAG | A-120273.1 | CUGAUGUCCUGGUAGGUCU | 682-700 |
| AD-59287.1 | A-120288.1 | AACUGAACUGCCGACUCUA | A-120289.1 | UAGAGUCGGCAGUUCAGUU | 589-607 |
| AD-59288.1 | A-120304.1 | CAUUUACUUCAAGGGCCUG | A-120305.1 | CAGGCCCUUGAAGUAAAUG | 869-887 |
| AD-59289.1 | A-120320.1 | CCCUGGACUUCAAGGAAAA | A-120321.1 | UUUUCCUUGAAGUCCAGGG | 730-748 |
| AD-59290.1 | A-120336.1 | AGCUGCAAGUACCGCUGUU | A-120337.1 | AACAGCGGUACUUGCAGCU | 1361-1379 |
| AD-59291.1 | A-120258.1 | ACACAAGGAAGGAACUGUU | A-120259.1 | AACAGUUCCUUCCUUGUGU | 913-931 |
| AD-59292.1 | A-120274.1 | GCAACUGAGGAUGAGGGCU | A-120275.1 | AGCCCUCAUCCUCAGUUGC | 303-321 |
| AD-59293.1 | A-120290.1 | GUAGCCAACCCUUGUGUUA | A-120291.1 | UAACACAAGGGUUGGCUAC | 1491-1509 |
| AD-59294.1 | A-120306.1 | GUUUGUGAACAGAAGUAAA | A-120307.1 | UUUACUUCUGUUCACAAAC | 1550-1568 |
| AD-59295.1 | A-120322.1 | GGGUGACUUUCAAGGCCAA | A-120323.1 | UUGGCCUUGAAAGUCACCC | 1411-1429 |
| AD-59296.1 | A-120338.1 | UUAUCGGCGCGUGGCUGAA | A-120339.1 | UUCAGCCACGCGCCGAUAA | 992-1010 |
| AD-59297.1 | A-120260.1 | CCACUUCUUCUUUGCCAAA | A-120261.1 | UUUGGCAAAGAAGAAGUGG | 572-590 |
| AD-59298.1 | A-120276.1 | AACACCAUUUACUUCAAGG | A-120277.1 | CCUUGAAGUAAAUGGUGUU | 864-882 |
| AD-59299.1 | A-120292.1 | GAUGGAGAGUCGUGUUCAG | A-120293.1 | CUGAACACGACUCUCCAUC | 942-960 |
| AD-59300.1 | A-120308.1 | CACCAUUUACUUCAAGGGC | A-120309.1 | GCCCUUGAAGUAAAUGGUG | 866-884 |
| AD-59301.1 | A-120324.1 | UUUACUUCAAGGGCCUGUG | A-120325.1 | CACAGGCCCUUGAAGUAAA | 871-889 |
| AD-59302.1 | A-120340.1 | UAAGAGAAGUUCCUCUGAA | A-120341.1 | UUCAGAGGAACUUCUCUUA | 1450-1468 |
| AD-59303.1 | A-120262.1 | GCGGGACAUUCCCAUGAAU | A-120263.1 | AUUCAUGGGAAUGUCCCGC | 251-269 |
| AD-59304.1 | A-120278.1 | UGCCCCACCCUGUCCUCUG | A-120279.1 | CAGAGGACAGGGUGGGGCA | 21-Mar |
| AD-59305.1 | A-120294.1 | UGGUUAACACCAUUUACUU | A-120295.1 | AAGUAAAUGGUGUUAACCA | 859-877 |
| AD-59306.1 | A-120310.1 | CGGAUUGCCUCAGAUCACA | A-120311.1 | UGUGAUCUGAGGCAAUCCG | 62-80 |
| AD-59307.1 | A-120326.1 | CCAGGACAUCAGUGAGUUG | A-120327.1 | CAACUCACUGAUGUCCUGG | 689-707 |
| AD-59308.1 | A-120342.1 | CCAGUUUUCAGGCGGAUUG | A-120343.1 | CAAUCCGCCUGAAAACUGG | 50-68 |
| AD-59309.1 | A-120264.1 | CACCAUAUCUGAGAAAACA | A-120265.1 | UGUUUUCUCAGAUAUGGUG | 542-560 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59310.1 | A-120280.1 | AAGUAAAAAUAAAUACAAA | A-120281.1 | UUUGUAUUUAUUUUUACUU | 1562-1580 |
| AD-59311.1 | A-120296.1 | GCACCCAGGUGCUUGAGUU | A-120297.1 | AACUCAAGCACCUGGGUGC | 1012-1030 |
| AD-59312.1 | A-120312.1 | UAACACCAUUUACUUCAAG | A-120313.1 | CUUGAAGUAAAUGGUGUUA | 863-881 |
| AD-59313.1 | A-120328.1 | CCUUCAAAGGUGAUGACAU | A-120329.1 | AUGUCAUCACCUUUGAAGG | 1033-1051 |
| AD-59314.1 | A-120344.1 | CAAGGCCAAUUCCCGCUUU | A-120345.1 | AAAGCGGGAAUUGGCCUUG | 371-389 |
| AD-59315.1 | A-120360.1 | UCAGUUUGAAGGAGCAGCU | A-120361.1 | AGCUGCUCCUUCAAACUGA | 1201-1219 |
| AD-59316.1 | A-120376.1 | GGGACUGCGUGACCUGUCA | A-120377.1 | UGACAGGUCACGCAGUCCC | 199-217 |
| AD-59317.1 | A-120392.1 | UCAGCCAAUCGCCUUUUUG | A-120393.1 | CAAAAAGGCGAUUGGCUGA | 639-657 |
| AD-59318.1 | A-120408.1 | CCUCGGAAGCCAUCAAUGA | A-120409.1 | UCAUUGAUGGCUUCCGAGG | 823-841 |
| AD-59319.1 | A-120424.1 | GACAAUGAUAACAUUUUCC | A-120425.1 | GGAAAAUGUUAUCAUUGUC | 429-447 |
| AD-59320.1 | A-120346.1 | CUUAUUCUUUGCACCUCUU | A-120347.1 | AAGAGGUGCAAAGAAUAAG | 1521-1539 |
| AD-59321.1 | A-120362.1 | AUUGCUGGCCGUUCGCUAA | A-120363.1 | UUAGCGAACGGCCAGCAAU | 1383-1401 |
| AD-59322.1 | A-120378.1 | AAAUGAAGAAGGCAGUGAA | A-120379.1 | UUCACUGCCUUCUUCAUUU | 1340-1358 |
| AD-59323.1 | A-120394.1 | UGAGUUGGUAUAUGGAGCC | A-120395.1 | GGCUCCAUAUACCAACUCA | 701-719 |
| AD-59324.1 | A-120410.1 | UCCAGCAACUGAUGGAGGU | A-120411.1 | ACCUCCAUCAGUUGCUGGA | 511-529 |
| AD-59325.1 | A-120426.1 | AACUGUAACCUCUGGAAAA | A-120427.1 | UUUUCCAGAGGUUACAGUU | 140-158 |
| AD-59326.1 | A-120348.1 | UCAACAAAUGGGUGUCCAA | A-120349.1 | UUGGACACCCAUUUGUUGA | 772-790 |
| AD-59327.1 | A-120364.1 | GAUUAGCGGCCAUGUAUUC | A-120365.1 | GAAUACAUGGCCGCUAAUC | 109-127 |
| AD-59328.1 | A-120380.1 | GUGCUUGAGUUGCCCUUCA | A-120381.1 | UGAAGGGCAACUCAAGCAC | 1020-1038 |
| AD-59329.1 | A-120396.1 | UGCAGAAGGCCGAGAUGAC | A-120397.1 | GUCAUCUCGGCCUUCUGCA | 1280-1298 |
| AD-59330.1 | A-120412.1 | CUAUUUUUGGUUUGUGAAC | A-120413.1 | GUUCACAAACCAAAAAUAG | 1541-1559 |
| AD-59331.1 | A-120428.1 | CAGUGAAGCAGCUGCAAGU | A-120429.1 | ACUUGCAGCUGCUUCACUG | 1352-1370 |
| AD-59332.1 | A-120350.1 | GUGUCCAAUAAGACCGAAG | A-120351.1 | CUUCGGUCUUAUUGGACAC | 783-801 |
| AD-59333.1 | A-120366.1 | AUGAAUUGGAGGAGAUGAU | A-120367.1 | AUCAUCUCCUCCAAUUCAU | 1141-1159 |
| AD-59334.1 | A-120382.1 | AUCUAUGAUGUACCAGGAA | A-120383.1 | UUCCUGGUACAUCAUAGAU | 962-980 |
| AD-59335.1 | A-120398.1 | CCAUAAGGCAUUUCUUGAG | A-120399.1 | CUCAAGAAAUGCCUUAUGG | 1319-1337 |
| AD-59336.1 | A-120414.1 | AUGCAUUCCAUAAGGCAUU | A-120415.1 | AAUGCCUUAUGGAAUGCAU | 1312-1330 |
| AD-59337.1 | A-120430.1 | UGGUGCUGGUUAACACCAU | A-120431.1 | AUGGUGUUAACCAGCACCA | 853-871 |
| AD-59338.1 | A-120352.1 | AUCUGUUCAGCCCUGAAAA | A-120353.1 | UUUUCAGGGCUGAACAGAU | 1240-1258 |
| AD-59339.1 | A-120368.1 | AGAUGAUGCUGGUGGUCCA | A-120369.1 | UGGACCACCAGCAUCAUCU | 1153-1171 |
| AD-59340.1 | A-120384.1 | AUAUGGAGCCAAGCUCCAG | A-120385.1 | CUGGAGCUUGGCUCCAUAU | 710-728 |
| AD-59341.1 | A-120400.1 | CCGAAUCACCGAUGUCAUU | A-120401.1 | AAUGACAUCGGUGAUUCGG | 803-821 |
| AD-59342.1 | A-120416.1 | GCAGAGCAAUCCAGAGCGG | A-120417.1 | CCGCUCUGGAUUGCUCUGC | 750-768 |
| AD-59343.1 | A-120432.1 | ACACCAUUUACUUCAAGGG | A-120433.1 | CCCUUGAAGUAAAUGGUGU | 865-883 |
| AD-59344.1 | A-120354.1 | GUACCAGGAAGGCAAGUUC | A-120355.1 | GAACUUGCCUUCCUGGUAC | 971-989 |
| AD-59345.1 | A-120370.1 | UGCCCAAGCCUGAGAAGAG | A-120371.1 | CUCUUCUCAGGCUUGGGCA | 1069-1087 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59346.1 | A-120386.1 | UUCUUUGCCAAACUGAACU | A-120387.1 | AGUUCAGUUUGGCAAAGAA | 579-597 |
| AD-59347.1 | A-120402.1 | UGGCCAAGGUAGAGAAGGA | A-120403.1 | UCCUUCUCUACCUUGGCCA | 1090-1108 |
| AD-59348.1 | A-120418.1 | UGCUGCAAGAGUGGCUGGA | A-120419.1 | UCCAGCCACUCUUGCAGCA | 1123-1141 |
| AD-59349.1 | A-120434.1 | CCAUGUGCAUUUACCGCUC | A-120435.1 | GAGCGGUAAAUGCACAUGG | 271-289 |
| AD-59350.1 | A-120356.1 | AGACAUGGGCCUUGUCGAU | A-120357.1 | AUCGACAAGGCCCAUGUCU | 1223-1241 |
| AD-59351.1 | A-120372.1 | UUUUGGAGACAAAUCCCUU | A-120373.1 | AAGGGAUUUGUCUCCAAAA | 653-671 |
| AD-59352.1 | A-120388.1 | GGAUGAGGGCUCAGAACAG | A-120389.1 | CUGUUCUGAGCCCUCAUCC | 311-329 |
| AD-59353.1 | A-120404.1 | CGGCUUUUGCUAUGACCAA | A-120405.1 | UUGGUCAUAGCAAAAGCCG | 469-487 |
| AD-59354.1 | A-120420.1 | AGCUCCAGCCCCUGGACUU | A-120421.1 | AAGUCCAGGGGCUGGAGCU | 721-739 |
| AD-59355.1 | A-120436.1 | CUGAUCAGAUCCACUUCUU | A-120437.1 | AAGAAGUGGAUCUGAUCAG | 562-580 |
| AD-59356.1 | A-120358.1 | UGCUGGUGGUCCACAUGCC | A-120359.1 | GGCAUGUGGACCACCAGCA | 1159-1177 |
| AD-59357.1 | A-120374.1 | GCGAGAUUUAGAGGAAAGA | A-120375.1 | UCUUUCCUCUAAAUCUCGC | 30-48 |
| AD-59358.1 | A-120390.1 | CUGCUCAUUGGCUUCUGGG | A-120391.1 | CCCAGAAGCCAAUGAGCAG | 183-201 |
| AD-59359.1 | A-120406.1 | CCUUCAAUGAGACCUACCA | A-120407.1 | UGGUAGGUCUCAUUGAAGG | 673-691 |
| AD-59360.1 | A-120422.1 | ACCAUUUACUUCAAGGGCC | A-120423.1 | GGCCCUUGAAGUAAAUGGU | 867-885 |
| AD-59587.1 | A-120438.1 | GCACCUCUUCCUAUUUUUG | A-120439.1 | CAAAAAUAGGAAGAGGUGC | 1531-1549 |
| AD-59588.1 | A-120454.1 | GUGGCUGAAGGCACCCAGG | A-120455.1 | CCUGGGUGCCUUCAGCCAC | 1002-1020 |
| AD-59589.1 | A-120470.1 | UCCGCAUUGAGGACGGCUU | A-120471.1 | AAGCCGUCCUCAAUGCGGA | 1183-1201 |
| AD-59590.1 | A-120486.1 | UGGACAUCUGCACAGCCAA | A-120487.1 | UUGGCUGUGCAGAUGUCCA | 229-247 |
| AD-59591.1 | A-120502.1 | GUCCAAACUCCCAGGUAUU | A-120503.1 | AAUACCUGGGAGUUUGGAC | 1259-1277 |
| AD-59592.1 | A-120518.1 | AGAAGGAACUCACCCCAGA | A-120519.1 | UCUGGGGUGAGUUCCUUCU | 1102-1120 |
| AD-59593.1 | A-120440.1 | UCUUGAGGUAAAUGAAGAA | A-120441.1 | UUCUUCAUUUACCUCAAGA | 1331-1349 |
| AD-59594.1 | A-120456.1 | AGCCCUGUGGACAUCUGCA | A-120457.1 | UGCAGAUGUCCACAGGGCU | 222-240 |
| AD-59595.1 | A-120472.1 | CAGAGCGGCCAUCAACAAA | A-120473.1 | UUUGUUGAUGGCCGCUCUG | 761-779 |
| AD-59596.1 | A-120488.1 | AUUUAAGUUUGACACCAUA | A-120489.1 | UAUGGUGUCAAACUUAAAU | 530-548 |
| AD-59597.1 | A-120504.1 | UGAGAAGAGCCUGGCCAAG | A-120505.1 | CUUGGCCAGGCUCUUCUCA | 1079-1097 |
| AD-59598.1 | A-120520.1 | UCACCAUGGUCCUCAUCUU | A-120521.1 | AAGAUGAGGACCAUGGUGA | 1051-1069 |
| AD-59599.1 | A-120442.1 | GGAAGGAACUGUUCUACAA | A-120443.1 | UUGUAGAACAGUUCCUUCC | 919-937 |
| AD-59600.1 | A-120458.1 | CUGGUUUUUAUAAGAGAAG | A-120459.1 | CUUCUCUUAUAAAAACCAG | 1440-1458 |
| AD-59601.1 | A-120474.1 | CUGGGUGCCUGUAAUGACA | A-120475.1 | UGUCAUUACAGGCACCCAG | 489-507 |
| AD-59602.1 | A-120490.1 | GUACCGCUGUUGUGAUUGC | A-120491.1 | GCAAUCACAACAGCGGUAC | 1369-1387 |
| AD-59603.1 | A-120506.1 | UCUAUCAGCACCUGGCAGA | A-120507.1 | UCUGCCAGGUGCUGAUAGA | 400-418 |
| AD-59604.1 | A-120522.1 | CUGGCAGAUUCCAAGAAUG | A-120523.1 | CAUUCUUGGAAUCUGCCAG | 411-429 |
| AD-59605.1 | A-120444.1 | CGAUGUCAUUCCCUCGGAA | A-120445.1 | UUCCGAGGGAAUGACAUCG | 812-830 |
| AD-59606.1 | A-120460.1 | GCUUCUGGGACUGCGUGAC | A-120461.1 | GUCACGCAGUCCCAGAAGC | 193-211 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59607.1 | A-120476.1 | CCUGUCACGGGAGCCCUGU | A-120477.1 | ACAGGGCUCCCGUGACAGG | 211-229 |
| AD-59608.1 | A-120492.1 | AUUUACUUCAAGGGCCUGU | A-120493.1 | ACAGGCCCUUGAAGUAAAU | 870-888 |
| AD-59609.1 | A-120508.1 | UGCUACCACUUUCUAUCAG | A-120509.1 | CUGAUAGAAAGUGGUAGCA | 389-407 |
| AD-59610.1 | A-120524.1 | GGAACUGUCCAAGGCCAAU | A-120525.1 | AUUGGCCUUGGACAGUUCC | 362-380 |
| AD-59611.1 | A-120446.1 | ACAAAUCCUCCAAGUUAGU | A-120447.1 | ACUAACUUGGAGGAUUUGU | 619-637 |
| AD-59612.1 | A-120462.1 | AUUUACCGCUCCCCGGAGA | A-120463.1 | UCUCCGGGGAGCGGUAAAU | 279-297 |
| AD-59613.1 | A-120478.1 | ACCCCUGAGUAUCUCCACG | A-120479.1 | CGUGGAGAUACUCAGGGGU | 452-470 |
| AD-59614.1 | A-120494.1 | CACUAUCUCCACUUGCCCA | A-120495.1 | UGGGCAAGUGGAGAUAGUG | 79-97 |
| AD-59615.1 | A-120510.1 | AAAUACAAACUACUUCCAU | A-120511.1 | AUGGAAGUAGUUUGUAUUU | 1572-1590 |
| AD-59616.1 | A-120526.1 | CUGGUUAACACCAUUUACU | A-120527.1 | AGUAAAUGGUGUUAACCAG | 858-876 |
| AD-59617.1 | A-120448.1 | UCAUCUUGCCCAAGCCUGA | A-120449.1 | UCAGGCUUGGGCAAGAUGA | 1063-1081 |
| AD-59618.1 | A-120464.1 | CCUCAGAUCACACUAUCUC | A-120465.1 | GAGAUAGUGUGAUCUGAGG | 69-87 |
| AD-59619.1 | A-120480.1 | CUGUCCUCUGGAACCUCUG | A-120481.1 | CAGAGGUUCCAGAGGACAG | 30-Dec |
| AD-59620.1 | A-120496.1 | CCCUGUGGAAGAUUAGCGG | A-120497.1 | CCGCUAAUCUUCCACAGGG | 99-117 |
| AD-59621.1 | A-120512.1 | AUCUCCACGGCUUUUGCUA | A-120513.1 | UAGCAAAAGCCGUGGAGAU | 462-480 |
| AD-59622.1 | A-120528.1 | GUGGCUGGAUGAAUUGGAG | A-120529.1 | CUCCAAUUCAUCCAGCCAC | 1133-1151 |
| AD-59623.1 | A-120450.1 | CAAGUUAGUAUCAGCCAAU | A-120451.1 | AUUGGCUGAUACUAACUUG | 629-647 |
| AD-59624.1 | A-120466.1 | GUGAUGACAUCACCAUGGU | A-120467.1 | ACCAUGGUGAUGUCAUCAC | 1042-1060 |
| AD-59625.1 | A-120482.1 | UUCCAAGAAUGACAAUGAU | A-120483.1 | AUCAUUGUCAUUCUUGGAA | 419-437 |
| AD-59626.1 | A-120498.1 | UGAUGGAGGUAUUUAAGUU | A-120499.1 | AACUUAAAUACCUCCAUCA | 520-538 |
| AD-59627.1 | A-120514.1 | GUAUUCCAAUGUGAUAGGA | A-120515.1 | UCCUAUCACAUUGGAAUAC | 122-140 |
| AD-59628.1 | A-120530.1 | CAGCCAAGCCGCGGGACAU | A-120531.1 | AUGUCCCGCGGCUUGGCUG | 241-259 |
| AD-59629.1 | A-120452.1 | CAUGCCCCGCUUCCGCAUU | A-120453.1 | AAUGCGGAAGCGGGGCAUG | 1172-1190 |
| AD-59630.1 | A-120468.1 | AUGUGAUAGGAACUGUAAC | A-120469.1 | GUUACAGUUCCUAUCACAU | 130-148 |
| AD-59631.1 | A-120484.1 | ACAAAUCCCUUACCUUCAA | A-120485.1 | UUGAAGGUAAGGGAUUUGU | 661-679 |
| AD-59632.1 | A-120500.1 | AGGUUUAUCUUUUGUCCUU | A-120501.1 | AAGGACAAAAGAUAAACCU | 163-181 |
| AD-59633.1 | A-120516.1 | AGAUCCCGGAGGCCACCAA | A-120517.1 | UUGGUGGCCUCCGGGAUCU | 331-349 |
| AD-59634.1 | A-120532.1 | ACAUUUUCCUGUCACCCCU | A-120533.1 | AGGGGUGACAGGAAAAUGU | 439-457 |
| AD-59635.1 | A-120548.1 | GGCCUUUCCUGGUUUUUAU | A-120549.1 | AUAAAAACCAGGAAAGGCC | 1432-1450 |
| AD-59636.1 | A-120564.1 | UUGUGUUAAGUAAAAUGUU | A-120565.1 | AACAUUUUACUUAACACAA | 1502-1520 |
| AD-59637.1 | A-120534.1 | CAAGGAAAAUGCAGAGCAA | A-120535.1 | UUGCUCUGCAUUUUCCUUG | 740-758 |
| AD-59638.1 | A-120550.1 | CUGAGAAAACAUCUGAUCA | A-120551.1 | UGAUCAGAUGUUUUCUCAG | 550-568 |
| AD-59639.1 | A-120566.1 | UUACUUCAAGGGCCUGUGG | A-120567.1 | CCACAGGCCCUUGAAGUAA | 872-890 |
| AD-59640.1 | A-120536.1 | ACCCCAACAGGGUGACUUU | A-120537.1 | AAAGUCACCCUGUUGGGGU | 1402-1420 |
| AD-59641.1 | A-120552.1 | CCAGGUAUUGUUGCAGAAG | A-120553.1 | CUUCUGCAACAAUACCUGG | 1269-1287 |
| AD-59642.1 | A-120568.1 | GCCUGUGGAAGUCAAAGUU | A-120569.1 | AACUUUGACUUCCACAGGC | 883-901 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59643 | .1A-120538 | .1UGGAACCUCUGCGAGAUUU | A-120539 | .1AAAUCUCGCAGAGGUUCCA | 20-38 |
| AD-59644 | .1A-120554 | .1AGCCCUGAGAACACAAGGA | A-120555 | .1UCCUUGUGUUCUCAGGGCU | 903-921 |
| AD-59645 | .1A-120570 | .1CUCUAUGUCUCAGAUGCAU | A-120571 | .1AUGCAUCUGAGACAUAGAG | 1299-1317 |
| AD-59646 | .1A-120540 | .1AAGACCGAAGGCCGAAUCA | A-120541 | .1UGAUUCGGCCUUCGGUCUU | 792-810 |
| AD-59647 | .1A-120556 | .1UAAAAUGUUCUUAUUCUUU | A-120557 | .1AAAGAAUAAGAACAUUUUA | 1512-1530 |
| AD-59648 | .1A-120572 | .1UCUGGAAAAAGGAAGGUUU | A-120573 | .1AAACCUUCCUUUUUCCAGA | 150-168 |
| AD-59649 | .1A-120542 | .1UUCAAGGCCAACAGGCCUU | A-120543 | .1AAGGCCUGUUGGCCUUGAA | 1419-1437 |
| AD-59650 | .1A-120558 | .1GAAGUCAAAGUUCAGCCCU | A-120559 | .1AGGGCUGAACUUUGACUUC | 890-908 |
| AD-59651 | .1A-120574 | .1CCAUCAAUGAGCUCACUGU | A-120575 | .1ACAGUGAGCUCAUUGAUGG | 832-850 |
| AD-59652 | .1A-120544 | .1CUCUGAACACUAUUAUCUU | A-120545 | .1AAGAUAAUAGUGUUCAGAG | 1462-1480 |
| AD-59653 | .1A-120560 | .1UGCUGGUUAACACCAUUUA | A-120561 | .1UAAAUGGUGUUAACCAGCA | 856-874 |
| AD-59654 | .1A-120546 | .1AGAGGAAAGAACCAGUUUU | A-120547 | .1AAAACUGGUUCUUUCCUCU | 39-57 |
| AD-59655 | .1A-120562 | .1UGCCCAGCCCUGUGGAAGA | A-120563 | .1UCUUCCACAGGGCUGGGCA | 92-110 |

TABLE 21

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59267 | .1A-120250 | .1GGAGAAGAAGGCAACUGAGdTdT | A-120251 | .1CUCAGUUGCCUUCUUCUCCdTdT |
| AD-59268 | .1A-120266 | .1UGACCAAGCUGGGUGCCUGdTdT | A-120267 | .1CAGGCACCCAGCUUGGUCAdTdT |
| AD-59269 | .1A-120282 | .1GGUUAACACCAUUUACUUCdTdT | A-120283 | .1GAAGUAAAUGGUGUUAACCdTdT |
| AD-59270 | .1A-120298 | .1GCUGGUUAACACCAUUUACdTdT | A-120299 | .1GUAAAUGGUGUUAACCAGCdTdT |
| AD-59271 | .1A-120314 | .1UAAUGACACCCUCCAGCAAdTdT | A-120315 | .1UUGCUGGAGGGUGUCAUUAdTdT |
| AD-59272 | .1A-120330 | .1CGUGUUCAGCAUCUAUGAUdTdT | A-120331 | .1AUCAUAGAUGCUGAACACGdTdT |
| AD-59273 | .1A-120252 | .1UUGAGGACGGCUUCAGUUUdTdT | A-120253 | .1AAACUGAAGCCGUCCUCAAdTdT |
| AD-59274 | .1A-120268 | .1CGGCGUGUCUGGGAACUGUdTdT | A-120269 | .1ACAGUUCCCAGACACGCCGdTdT |
| AD-59275 | .1A-120284 | .1UUAACACCAUUUACUUCAAdTdT | A-120285 | .1UUGAAGUAAAUGGUGUUAAdTdT |
| AD-59276 | .1A-120300 | .1CCCUGAAAAGUCCAAACUCdTdT | A-120301 | .1GAGUUUGGACUUUUCAGGGdTdT |
| AD-59277 | .1A-120316 | .1CGAGAUGACCUCUAUGUCUdTdT | A-120317 | .1AGACAUAGAGGUCAUCUCGdTdT |
| AD-59278 | .1A-120332 | .1UCUACAAGGCUGAUGGAGAdTdT | A-120333 | .1UCUCCAUCAGCCUUGUAGAdTdT |
| AD-59279 | .1A-120254 | .1AGCUCACUGUUCUGGUGCUdTdT | A-120255 | .1AGCACCAGAACAGUGAGCUdTdT |
| AD-59280 | .1A-120270 | .1AGGAGCAGCUGCAAGACAUdTdT | A-120271 | .1AUGUCUUGCAGCUGCUCCUdTdT |
| AD-59281 | .1A-120286 | .1GCCACCAACCGGCGUGUCUdTdT | A-120287 | .1AGACACGCCGGUUGGUGGCdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59282.1 | A-120302.1 | CAGAACAGAAGAUCCCGGAdTdT | A-120303.1 | UCCGGGAUCUUCUGUUCUGdTdT |
| AD-59283.1 | A-120318.1 | CCUUGUCGAUCUGUUCAGCdTdT | A-120319.1 | GCUGAACAGAUCGACAAGGdTdT |
| AD-59284.1 | A-120334.1 | AGGCAAGUUCCGUUAUCGGdTdT | A-120335.1 | CCGAUAACGGAACUUGCCUdTdT |
| AD-59285.1 | A-120256.1 | UUUUGUCCUUGCUGCUCAUdTdT | A-120257.1 | AUGAGCAGCAAGGACAAAAdTdT |
| AD-59286.1 | A-120272.1 | AGACCUACCAGGACAUCAGdTdT | A-120273.1 | CUGAUGUCCUGGUAGGUCUdTdT |
| AD-59287.1 | A-120288.1 | AACUGAACUGCCGACUCUAdTdT | A-120289.1 | UAGAGUCGGCAGUUCAGUUdTdT |
| AD-59288.1 | A-120304.1 | CAUUUACUUCAAGGGCCUGdTdT | A-120305.1 | CAGGCCCUUGAAGUAAAUGdTdT |
| AD-59289.1 | A-120320.1 | CCCUGGACUUCAAGGAAAAdTdT | A-120321.1 | UUUUCCUUGAAGUCCAGGGdTdT |
| AD-59290.1 | A-120336.1 | AGCUGCAAGUACCGCUGUUdTdT | A-120337.1 | AACAGCGGUACUUGCAGCUdTdT |
| AD-59291.1 | A-120258.1 | ACACAAGGAAGGAACUGUUdTdT | A-120259.1 | AACAGUUCCUUCCUUGUGUdTdT |
| AD-59292.1 | A-120274.1 | GCAACUGAGGAUGAGGGCUdTdT | A-120275.1 | AGCCCUCAUCCUCAGUUGCdTdT |
| AD-59293.1 | A-120290.1 | GUAGCCAACCCUUGUGUUAdTdT | A-120291.1 | UAACACAAGGGUUGGCUACdTdT |
| AD-59294.1 | A-120306.1 | GUUUGUGAACAGAAGUAAAdTdT | A-120307.1 | UUUACUUCUGUUCACAAACdTdT |
| AD-59295.1 | A-120322.1 | GGGUGACUUUCAAGGCCAAdTdT | A-120323.1 | UUGGCCUUGAAAGUCACCCdTdT |
| AD-59296.1 | A-120338.1 | UUAUCGGCGCGUGGCUGAAdTdT | A-120339.1 | UUCAGCCACGCGCCGAUAAdTdT |
| AD-59297.1 | A-120260.1 | CCACUUCUUCUUUGCCAAAdTdT | A-120261.1 | UUUGGCAAAGAAGAAGUGGdTdT |
| AD-59298.1 | A-120276.1 | AACACCAUUUACUUCAAGGdTdT | A-120277.1 | CCUUGAAGUAAAUGGUGUUdTdT |
| AD-59299.1 | A-120292.1 | GAUGGAGAGUCGUGUUCAGdTdT | A-120293.1 | CUGAACACGACUCUCCAUCdTdT |
| AD-59300.1 | A-120308.1 | CACCAUUUACUUCAAGGGCdTdT | A-120309.1 | GCCCUUGAAGUAAAUGGUGdTdT |
| AD-59301.1 | A-120324.1 | UUUACUUCAAGGGCCUGUGdTdT | A-120325.1 | CACAGGCCCUUGAAGUAAAdTdT |
| AD-59302.1 | A-120340.1 | UAAGAGAAGUUCCUCUGAAdTdT | A-120341.1 | UUCAGAGGAACUUCUCUUAdTdT |
| AD-59303.1 | A-120262.1 | GCGGGACAUUCCCAUGAAUdTdT | A-120263.1 | AUUCAUGGGAAUGUCCCGCdTdT |
| AD-59304.1 | A-120278.1 | UGCCCCACCCUGUCCUCUGdTdT | A-120279.1 | CAGAGGACAGGGUGGGGCAdTdT |
| AD-59305.1 | A-120294.1 | UGGUUAACACCAUUUACUUdTdT | A-120295.1 | AAGUAAAUGGUGUUAACCAdTdT |
| AD-59306.1 | A-120310.1 | CGGAUUGCCUCAGAUCACAdTdT | A-120311.1 | UGUGAUCUGAGGCAAUCCGdTdT |
| AD-59307.1 | A-120326.1 | CCAGGACAUCAGUGAGUUGdTdT | A-120327.1 | CAACUCACUGAUGUCCUGGdTdT |
| AD-59308.1 | A-120342.1 | CCAGUUUUCAGGCGGAUUGdTdT | A-120343.1 | CAAUCCGCCUGAAAACUGGdTdT |
| AD-59309.1 | A-120264.1 | CACCAUAUCUGAGAAAACAdTdT | A-120265.1 | UGUUUUCUCAGAUAUGGUGdTdT |
| AD-59310.1 | A-120280.1 | AAGUAAAAAUAAAUACAAAdTdT | A-120281.1 | UUUGUAUUUAUUUUUACUUdTdT |
| AD-59311.1 | A-120296.1 | GCACCCAGGUGCUUGAGUUdTdT | A-120297.1 | AACUCAAGCACCUGGGUGCdTdT |
| AD-59312.1 | A-120312.1 | UAACACCAUUUACUUCAAGdTdT | A-120313.1 | CUUGAAGUAAAUGGUGUUAdTdT |
| AD-59313.1 | A-120328.1 | CCUUCAAAGGUGAUGACAUdTdT | A-120329.1 | AUGUCAUCACCUUUGAAGGdTdT |
| AD-59314.1 | A-120344.1 | CAAGGCCAAUUCCCGCUUUdTdT | A-120345.1 | AAAGCGGGAAUUGGCCUUGdTdT |
| AD-59315.1 | A-120360.1 | UCAGUUUGAAGGAGCAGCUdTdT | A-120361.1 | AGCUGCUCCUUCAAACUGAdTdT |
| AD-59316.1 | A-120376.1 | GGGACUGCGUGACCUGUCAdTdT | A-120377.1 | UGACAGGUCACGCAGUCCCdTdT |
| AD-59317.1 | A-120392.1 | UCAGCCAAUCGCCUUUUUGdTdT | A-120393.1 | CAAAAAGGCGAUUGGCUGAdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59318.1 | A-120408.1 | CCUCGGAAGCCAUCAAUGAdTdT | A-120409.1 | UCAUUGAUGGCUUCCGAGGdTdT |
| AD-59319.1 | A-120424.1 | GACAAUGAUAACAUUUUCCdTdT | A-120425.1 | GGAAAAUGUUAUCAUUGUCdTdT |
| AD-59320.1 | A-120346.1 | CUUAUUCUUUGCACCUCUUdTdT | A-120347.1 | AAGAGGUGCAAAGAAUAAGdTdT |
| AD-59321.1 | A-120362.1 | AUUGCUGGCCGUUCGCUAAdTdT | A-120363.1 | UUAGCGAACGGCCAGCAAUdTdT |
| AD-59322.1 | A-120378.1 | AAAUGAAGAAGGCAGUGAAdTdT | A-120379.1 | UUCACUGCCUUCUUCAUUUdTdT |
| AD-59323.1 | A-120394.1 | UGAGUUGGUAUAUGGAGCCdTdT | A-120395.1 | GGCUCCAUAUACCAACUCAdTdT |
| AD-59324.1 | A-120410.1 | UCCAGCAACUGAUGGAGGUdTdT | A-120411.1 | ACCUCCAUCAGUUGCUGGAdTdT |
| AD-59325.1 | A-120426.1 | AACUGUAACCUCUGGAAAAdTdT | A-120427.1 | UUUUCCAGAGGUUACAGUUdTdT |
| AD-59326.1 | A-120348.1 | UCAACAAAUGGGUGUCCAAdTdT | A-120349.1 | UUGGACACCCAUUUGUUGAdTdT |
| AD-59327.1 | A-120364.1 | GAUUAGCGGCCAUGUAUUCdTdT | A-120365.1 | GAAUACAUGGCCGCUAAUCdTdT |
| AD-59328.1 | A-120380.1 | GUGCUUGAGUUGCCCUUCAdTdT | A-120381.1 | UGAAGGGCAACUCAAGCACdTdT |
| AD-59329.1 | A-120396.1 | UGCAGAAGGCCGAGAUGACdTdT | A-120397.1 | GUCAUCUCGGCCUUCUGCAdTdT |
| AD-59330.1 | A-120412.1 | CUAUUUUUGGUUUGUGAACdTdT | A-120413.1 | GUUCACAAACCAAAAAUAGdTdT |
| AD-59331.1 | A-120428.1 | CAGUGAAGCAGCUGCAAGUdTdT | A-120429.1 | ACUUGCAGCUGCUUCACUGdTdT |
| AD-59332.1 | A-120350.1 | GUGUCCAAUAAGACCGAAGdTdT | A-120351.1 | CUUCGGUCUUAUUGGACACdTdT |
| AD-59333.1 | A-120366.1 | AUGAAUUGGAGGAGAUGAUdTdT | A-120367.1 | AUCAUCUCCUCCAAUUCAUdTdT |
| AD-59334.1 | A-120382.1 | AUCUAUGAUGUACCAGGAAdTdT | A-120383.1 | UUCCUGGUACAUCAUAGAUdTdT |
| AD-59335.1 | A-120398.1 | CCAUAAGGCAUUUCUUGAGdTdT | A-120399.1 | CUCAAGAAAUGCCUUAUGGdTdT |
| AD-59336.1 | A-120414.1 | AUGCAUUCCAUAAGGCAUUdTdT | A-120415.1 | AAUGCCUUAUGGAAUGCAUdTdT |
| AD-59337.1 | A-120430.1 | UGGUGCUGGUUAACACCAUdTdT | A-120431.1 | AUGGUGUUAACCAGCACCAdTdT |
| AD-59338.1 | A-120352.1 | AUCUGUUCAGCCCUGAAAAdTdT | A-120353.1 | UUUUCAGGGCUGAACAGAUdTdT |
| AD-59339.1 | A-120368.1 | AGAUGAUGCUGGUGGUCCAdTdT | A-120369.1 | UGGACCACCAGCAUCAUCUdTdT |
| AD-59340.1 | A-120384.1 | AUAUGGAGCCAAGCUCCAGdTdT | A-120385.1 | CUGGAGCUUGGCUCCAUAUdTdT |
| AD-59341.1 | A-120400.1 | CCGAAUCACCGAUGUCAUUdTdT | A-120401.1 | AAUGACAUCGGUGAUUCGGdTdT |
| AD-59342.1 | A-120416.1 | GCAGAGCAAUCCAGAGCGGdTdT | A-120417.1 | CCGCUCUGGAUUGCUCUGCdTdT |
| AD-59343.1 | A-120432.1 | ACACCAUUUACUUCAAGGGdTdT | A-120433.1 | CCCUUGAAGUAAAUGGUGUdTdT |
| AD-59344.1 | A-120354.1 | GUACCAGGAAGGCAAGUUCdTdT | A-120355.1 | GAACUUGCCUUCCUGGUACdTdT |
| AD-59345.1 | A-120370.1 | UGCCCAAGCCUGAGAAGAGdTdT | A-120371.1 | CUCUUCUCAGGCUUGGGCAdTdT |
| AD-59346.1 | A-120386.1 | UUCUUUGCCAAACUGAACUdTdT | A-120387.1 | AGUUCAGUUUGGCAAAGAAdTdT |
| AD-59347.1 | A-120402.1 | UGGCCAAGGUAGAGAAGGAdTdT | A-120403.1 | UCCUUCUCUACCUUGGCCAdTdT |
| AD-59348.1 | A-120418.1 | UGCUGCAAGAGUGGCUGGAdTdT | A-120419.1 | UCCAGCCACUCUUGCAGCAdTdT |
| AD-59349.1 | A-120434.1 | CCAUGUGCAUUUACCGCUCdTdT | A-120435.1 | GAGCGGUAAAUGCACAUGGdTdT |
| AD-59350.1 | A-120356.1 | AGACAUGGGCCUUGUCGAUdTdT | A-120357.1 | AUCGACAAGGCCCAUGUCUdTdT |
| AD-59351.1 | A-120372.1 | UUUUGGAGACAAAUCCCUUdTdT | A-120373.1 | AAGGGAUUUGUCUCCAAAAdTdT |
| AD-59352.1 | A-120388.1 | GGAUGAGGGCUCAGAACAGdTdT | A-120389.1 | CUGUUCUGAGCCCUCAUCCdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59353.1 | A-120404.1 | CGGCUUUUGCUAUGACCAAdTdT | A-120405.1 | UUGGUCAUAGCAAAAGCCGdTdT |
| AD-59354.1 | A-120420.1 | AGCUCCAGCCCCUGGACUUdTdT | A-120421.1 | AAGUCCAGGGGCUGGAGCUdTdT |
| AD-59355.1 | A-120436.1 | CUGAUCAGAUCCACUUCUUdTdT | A-120437.1 | AAGAAGUGGAUCUGAUCAGdTdT |
| AD-59356.1 | A-120358.1 | UGCUGGUGGUCCACAUGCCdTdT | A-120359.1 | GGCAUGUGGACCACCAGCAdTdT |
| AD-59357.1 | A-120374.1 | GCGAGAUUUAGAGGAAAGAdTdT | A-120375.1 | UCUUUCCUCUAAAUCUCGCdTdT |
| AD-59358.1 | A-120390.1 | CUGCUCAUUGGCUUCUGGGdTdT | A-120391.1 | CCCAGAAGCCAAUGAGCAGdTdT |
| AD-59359.1 | A-120406.1 | CCUUCAAUGAGACCUACCAdTdT | A-120407.1 | UGGUAGGUCUCAUUGAAGGdTdT |
| AD-59360.1 | A-120422.1 | ACCAUUUACUUCAAGGGCCdTdT | A-120423.1 | GGCCCUUGAAGUAAAUGGUdTdT |
| AD-59587.1 | A-120438.1 | GCACCUCUUCCUAUUUUUGdTdT | A-120439.1 | CAAAAAUAGGAAGAGGUGCdTdT |
| AD-59588.1 | A-120454.1 | GUGGCUGAAGGCACCCAGGdTdT | A-120455.1 | CCUGGGUGCCUUCAGCCACdTdT |
| AD-59589.1 | A-120470.1 | UCCGCAUUGAGGACGGCUUdTdT | A-120471.1 | AAGCCGUCCUCAAUGCGGAdTdT |
| AD-59590.1 | A-120486.1 | UGGACAUCUGCACAGCCAAdTdT | A-120487.1 | UUGGCUGUGCAGAUGUCCAdTdT |
| AD-59591.1 | A-120502.1 | GUCCAAACUCCCAGGUAUUdTdT | A-120503.1 | AAUACCUGGGAGUUUGGACdTdT |
| AD-59592.1 | A-120518.1 | AGAAGGAACUCACCCCAGAdTdT | A-120519.1 | UCUGGGGUGAGUUCCUUCUdTdT |
| AD-59593.1 | A-120440.1 | UCUUGAGGUAAAUGAAGAAdTdT | A-120441.1 | UUCUUCAUUUACCUCAAGAdTdT |
| AD-59594.1 | A-120456.1 | AGCCCUGUGGACAUCUGCAdTdT | A-120457.1 | UGCAGAUGUCCACAGGGCUdTdT |
| AD-59595.1 | A-120472.1 | CAGAGCGGCCAUCAACAAAdTdT | A-120473.1 | UUUGUUGAUGGCCGCUCUGdTdT |
| AD-59596.1 | A-120488.1 | AUUUAAGUUUGACACCAUAdTdT | A-120489.1 | UAUGGUGUCAAACUUAAAUdTdT |
| AD-59597.1 | A-120504.1 | UGAGAAGAGCCUGGCCAAGdTdT | A-120505.1 | CUUGGCCAGGCUCUUCUCAdTdT |
| AD-59598.1 | A-120520.1 | UCACCAUGGUCCUCAUCUUdTdT | A-120521.1 | AAGAUGAGGACCAUGGUGAdTdT |
| AD-59599.1 | A-120442.1 | GGAAGGAACUGUUCUACAAdTdT | A-120443.1 | UUGUAGAACAGUUCCUUCCdTdT |
| AD-59600.1 | A-120458.1 | CUGGUUUUUAUAAGAGAAGdTdT | A-120459.1 | CUUCUCUUAUAAAAACCAGdTdT |
| AD-59601.1 | A-120474.1 | CUGGGUGCCUGUAAUGACAdTdT | A-120475.1 | UGUCAUUACAGGCACCCAGdTdT |
| AD-59602.1 | A-120490.1 | GUACCGCUGUUGUGAUUGCdTdT | A-120491.1 | GCAAUCACAACAGCGGUACdTdT |
| AD-59603.1 | A-120506.1 | UCUAUCAGCACCUGGCAGAdTdT | A-120507.1 | UCUGCCAGGUGCUGAUAGAdTdT |
| AD-59604.1 | A-120522.1 | CUGGCAGAUUCCAAGAAUGdTdT | A-120523.1 | CAUUCUUGGAAUCUGCCAGdTdT |
| AD-59605.1 | A-120444.1 | CGAUGUCAUUCCCUCGGAAdTdT | A-120445.1 | UUCCGAGGGAAUGACAUCGdTdT |
| AD-59606.1 | A-120460.1 | GCUUCUGGGACUGCGUGACdTdT | A-120461.1 | GUCACGCAGUCCCAGAAGCdTdT |
| AD-59607.1 | A-120476.1 | CCUGUCACGGGAGCCCUGUdTdT | A-120477.1 | ACAGGGCUCCCGUGACAGGdTdT |
| AD-59608.1 | A-120492.1 | AUUUACUUCAAGGGCCUGUdTdT | A-120493.1 | ACAGGCCCUUGAAGUAAAUdTdT |
| AD-59609.1 | A-120508.1 | UGCUACCACUUUCUAUCAGdTdT | A-120509.1 | CUGAUAGAAAGUGGUAGCAdTdT |
| AD-59610.1 | A-120524.1 | GGAACUGUCCAAGGCCAAUdTdT | A-120525.1 | AUUGGCCUUGGACAGUUCCdTdT |
| AD-59611.1 | A-120446.1 | ACAAAUCCUCCAAGUUAGUdTdT | A-120447.1 | ACUAACUUGGAGGAUUUGUdTdT |
| AD-59612.1 | A-120462.1 | AUUUACCGCUCCCCGGAGAdTdT | A-120463.1 | UCUCCGGGGAGCGGUAAAUdTdT |
| AD-59613.1 | A-120478.1 | ACCCCUGAGUAUCUCCACGdTdT | A-120479.1 | CGUGGAGAUACUCAGGGGUdTdT |
| AD-59614.1 | A-120494.1 | CACUAUCUCCACUUGCCCAdTdT | A-120495.1 | UGGGCAAGUGGAGAUAGUGdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59615.1 | A-120510.1 | AAAUACAAACUACUUCCAUdTdT | A-120511.1 | AUGGAAGUAGUUUGUAUUUdTdT |
| AD-59616.1 | A-120526.1 | CUGGUUAACACCAUUUACUdTdT | A-120527.1 | AGUAAAUGGUGUUAACCAGdTdT |
| AD-59617.1 | A-120448.1 | UCAUCUUGCCCAAGCCUGAdTdT | A-120449.1 | UCAGGCUUGGGCAAGAUGAdTdT |
| AD-59618.1 | A-120464.1 | CCUCAGAUCACACUAUCUCdTdT | A-120465.1 | GAGAUAGUGUGAUCUGAGGdTdT |
| AD-59619.1 | A-120480.1 | CUGUCCUCUGGAACCUCUGdTdT | A-120481.1 | CAGAGGUUCCAGAGGACAGdTdT |
| AD-59620.1 | A-120496.1 | CCCUGUGGAAGAUUAGCGGdTdT | A-120497.1 | CCGCUAAUCUUCCACAGGGdTdT |
| AD-59621.1 | A-120512.1 | AUCUCCACGGCUUUUGCUAdTdT | A-120513.1 | UAGCAAAAGCCGUGGAGAUdTdT |
| AD-59622.1 | A-120528.1 | GUGGCUGGAUGAAUUGGAGdTdT | A-120529.1 | CUCCAAUUCAUCCAGCCACdTdT |
| AD-59623.1 | A-120450.1 | CAAGUUAGUAUCAGCCAAUdTdT | A-120451.1 | AUUGGCUGAUACUAACUUGdTdT |
| AD-59624.1 | A-120466.1 | GUGAUGACAUCACCAUGGUdTdT | A-120467.1 | ACCAUGGUGAUGUCAUCACdTdT |
| AD-59625.1 | A-120482.1 | UUCCAAGAAUGACAAUGAUdTdT | A-120483.1 | AUCAUUGUCAUUCUUGGAAdTdT |
| AD-59626.1 | A-120498.1 | UGAUGGAGGUAUUUAAGUUdTdT | A-120499.1 | AACUUAAAUACCUCCAUCAdTdT |
| AD-59627.1 | A-120514.1 | GUAUUCCAAUGUGAUAGGAdTdT | A-120515.1 | UCCUAUCACAUUGGAAUACdTdT |
| AD-59628.1 | A-120530.1 | CAGCCAAGCCGCGGGACAUdTdT | A-120531.1 | AUGUCCCGCGGCUUGGCUGdTdT |
| AD-59629.1 | A-120452.1 | CAUGCCCCGCUUCCGCAUUdTdT | A-120453.1 | AAUGCGGAAGCGGGGCAUGdTdT |
| AD-59630.1 | A-120468.1 | AUGUGAUAGGAACUGUAACdTdT | A-120469.1 | GUUACAGUUCCUAUCACAUdTdT |
| AD-59631.1 | A-120484.1 | ACAAAUCCCUUACCUUCAAdTdT | A-120485.1 | UUGAAGGUAAGGGAUUUGUdTdT |
| AD-59632.1 | A-120500.1 | AGGUUUAUCUUUUGUCCUUdTdT | A-120501.1 | AAGGACAAAAGAUAAACCUdTdT |
| AD-59633.1 | A-120516.1 | AGAUCCCGGAGGCCACCAAdTdT | A-120517.1 | UUGGUGGCCUCCGGGAUCUdTdT |
| AD-59634.1 | A-120532.1 | ACAUUUUCCUGUCACCCCUdTdT | A-120533.1 | AGGGGUGACAGGAAAAUGUdTdT |
| AD-59635.1 | A-120548.1 | GGCCUUUCCUGGUUUUUAUdTdT | A-120549.1 | AUAAAAACCAGGAAAGGCCdTdT |
| AD-59636.1 | A-120564.1 | UUGUGUUAAGUAAAAUGUUdTdT | A-120565.1 | AACAUUUUACUUAACACAAdTdT |
| AD-59637.1 | A-120534.1 | CAAGGAAAAUGCAGAGCAAdTdT | A-120535.1 | UUGCUCUGCAUUUUCCUUGdTdT |
| AD-59638.1 | A-120550.1 | CUGAGAAAACAUCUGAUCAdTdT | A-120551.1 | UGAUCAGAUGUUUUCUCAGdTdT |
| AD-59639.1 | A-120566.1 | UUACUUCAAGGGCCUGUGGdTdT | A-120567.1 | CCACAGGCCCUUGAAGUAAdTdT |
| AD-59640.1 | A-120536.1 | ACCCCAACAGGGUGACUUUdTdT | A-120537.1 | AAAGUCACCCUGUUGGGGUdTdT |
| AD-59641.1 | A-120552.1 | CCAGGUAUUGUUGCAGAAGdTdT | A-120553.1 | CUUCUGCAACAAUACCUGGdTdT |
| AD-59642.1 | A-120568.1 | GCCUGUGGAAGUCAAAGUUdTdT | A-120569.1 | AACUUUGACUUCCACAGGCdTdT |
| AD-59643.1 | A-120538.1 | UGGAACCUCUGCGAGAUUUdTdT | A-120539.1 | AAAUCUCGCAGAGGUUCCAdTdT |
| AD-59644.1 | A-120554.1 | AGCCCUGAGAACACAAGGAdTdT | A-120555.1 | UCCUUGUGUUCUCAGGGCUdTdT |
| AD-59645.1 | A-120570.1 | CUCUAUGUCUCAGAUGCAUdTdT | A-120571.1 | AUGCAUCUGAGACAUAGAGdTdT |
| AD-59646.1 | A-120540.1 | AAGACCGAAGGCCGAAUCAdTdT | A-120541.1 | UGAUUCGGCCUUCGGUCUUdTdT |
| AD-59647.1 | A-120556.1 | UAAAAUGUUCUUAUUCUUUdTdT | A-120557.1 | AAAGAAUAAGAACAUUUUAdTdT |
| AD-59648.1 | A-120572.1 | UCUGGAAAAAGGAAGGUUUdTdT | A-120573.1 | AAACCUUCCUUUUUCCAGAdTdT |
| AD-59649.1 | A-120542.1 | UUCAAGGCCAACAGGCCUUdTdT | A-120543.1 | AAGGCCUGUUGGCCUUGAAdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59650 | A-120558.1 | GAAGUCAAAGUUCAGCCCUdTdT | A-120559.1 | AGGGCUGAACUUUGACUUCdTdT |
| AD-59651 | A-120574.1 | CCAUCAAUGAGCUCACUGUdTdT | A-120575.1 | ACAGUGAGCUCAUUGAUGGdTdT |
| AD-59652 | A-120544.1 | CUCUGAACACUAUUAUCUUdTdT | A-120545.1 | AAGAUAAUAGUGUUCAGAGdTdT |
| AD-59653 | A-120560.1 | UGCUGGUUAACACCAUUUAdTdT | A-120561.1 | UAAAUGGUGUUAACCAGCAdTdT |
| AD-59654 | A-120546.1 | AGAGGAAAGAACCAGUUUUdTdT | A-120547.1 | AAAACUGGUUCUUUCCUCUdTdT |
| AD-59655 | A-120562.1 | UGCCCAGCCCUGUGGAAGAdTdT | A-120563.1 | UCUUCCACAGGGCUGGGCAdTdT |

Cell Culture and Transfections

HepG2 cells (ATCC, Manassas, Va.) were grown to near confluence at 37° C. in an atmosphere of 5% CO2 in Eagle's Minimum Essential Medium (ATCC) supplemented with 10% FBS, streptomycin, and glutamine (ATCC) before being released from the plate by trypsinization. Transfection was carried out by adding 14.8 μl of Opti-MEM plus 0.2 μl of Lipofectamine RNAiMax per well (Invitrogen, Carlsbad Calif. cat #13778-150) to 5 μl of each of the 164 siRNA duplexes to an individual well in a 96-well plate. The mixture was then incubated at room temperature for 15 minutes. 80 μl of complete growth media without antibiotic containing ~$2.5\times10^4$ HepG2 cells were then added to the siRNA mixture. Cells were incubated for 24 hours prior to RNA purification. Experiments were performed at 20 nM and included naïve cells and cells transfected with AD-1955, a luciferase targeting siRNA as negative controls.

Total RNA Isolation Using DYNABEADS mRNA Isolation Kit (Invitrogen, Part #: 610-12)

Cells were harvested and lysed in 150 μl of Lysis/Binding Buffer then mixed for 5 minute at 700 rpm on a platform shaker (the mixing speed was the same throughout the process). Ten microliters of magnetic beads and 80 μl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 μl Wash Buffer A and mixed for 1 minute. Beads were capture again and supernatant removed. Beads were then washed with 150 μl Wash Buffer B, captured and supernatant was removed. Beads were next washed with 150 μl Elution Buffer, captured and supernatant removed. Beads were allowed to dry for 2 minutes. After drying, 50 μl of Elution Buffer was added and mixed for 5 minutes at 70° C. Beads were captured on magnet for 5 minutes. Forty μl of supernatant, containing the isolated RNA was removed and added to another 96 well plate.

cDNA Synthesis using ABI High Capacity cDNA Reverse Transcription Kit (Applied Biosystems, Foster City, Calif., Cat #4368813)

A master mix of 2 μl 10× Buffer, 0.8 μl 25× dNTPs, 2 μl Random primers, 1 μl Reverse Transcriptase, 1 μl RNase inhibitor and 3.2 μl of H2O per reaction were added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR

Two μl of cDNA were added to a master mix containing 0.50 human GAPDH TaqMan Probe (Applied Biosystems Cat #4326317E), 0.50 human SERPINC1 TaqMan probe (Applied Biosystems cat #Hs00892758_ml) and 50 Lightcycler 480 probe master mix (Roche Cat #04887301001) per well in a 384-well plate (Roche cat #04887301001). Real time PCR was done in an LC480 Real Time PCR machine (Roche).

To calculate relative fold change, real time data were analyzed using the ΔΔCt method and normalized to assays performed with cells transfected with 20 nM AD-1955.

Table 22 shows the results of a single dose screen in HepG2 of the indicated iRNAs.

TABLE 22[2]

20 nM single dose screen of the indicated iRNAs

| Duplex ID | 20 nM Average | Standard Deviation |
|---|---|---|
| AD1955 | 100.4 | 9.1 |
| AD-59267.1 | 9.3 | 2.7 |
| AD-59268.1 | 72.2 | 20.3 |
| AD-59269.1 | 6.9 | 0.4 |
| AD-59270.1 | 18.3 | 5.2 |
| AD-59271.1 | 27.9 | 7.6 |
| AD-59272.1 | 13.0 | 1.1 |
| AD-59273.1 | 79.4 | 10.9 |
| AD-59274.1 | 5.9 | 1.1 |
| AD-59275.1 | 16.1 | 5.5 |
| AD-59276.1 | 6.1 | 2.2 |
| AD-59277.1 | 4.4 | 0.9 |
| AD-59278.1 | 9.3 | 0.4 |
| AD-59279.1 | 12.7 | 4.7 |
| AD-59280.1 | 4.5 | 1.7 |
| AD-59281.1 | 15.7 | 5.6 |
| AD-59282.1 | 25.9 | 6.9 |
| AD-59283.1 | 27.0 | 18.9 |
| AD-59284.1 | 8.6 | 3.7 |
| AD-59285.1 | 11.2 | 3.7 |
| AD-59286.1 | 15.2 | 5.0 |
| AD-59287.1 | 6.9 | 1.9 |
| AD-59288.1 | 74.5 | 16.5 |
| AD-59289.1 | 3.3 | 1.3 |
| AD-59290.1 | 13.8 | 2.5 |
| AD-59291.1 | 9.4 | 2.8 |
| AD-59292.1 | 9.5 | 3.5 |

TABLE 22[2]-continued

| 20 nM single dose screen of the indicated iRNAs | | |
|---|---|---|
| Duplex ID | 20 nM Average | Standard Deviation |
| AD-59293.1 | 2.5 | 1.1 |
| AD-59294.1 | 4.8 | 1.8 |
| AD-59295.1 | 11.8 | 7.2 |
| AD-59296.1 | 32.4 | 4.9 |
| AD-59297.1 | 78.5 | 105.0 |
| AD-59298.1 | 76.3 | 10.7 |
| AD-59299.1 | 4.4 | 0.8 |
| AD-59300.1 | 32.2 | 10.8 |
| AD-59301.1 | 48.5 | 15.2 |
| AD-59302.1 | 7.2 | 3.0 |
| AD-59303.1 | 17.0 | 2.3 |
| AD-59304.1 | 87.1 | 16.4 |
| AD-59305.1 | 4.4 | 0.9 |
| AD-59306.1 | 35.7 | 10.6 |
| AD-59307.1 | 6.3 | 0.4 |
| AD-59308.1 | 65.1 | 9.1 |
| AD-59309.1 | 7.5 | 2.0 |
| AD-59310.1 | 27.1 | 9.5 |
| AD-59311.1 | 8.1 | 1.4 |
| AD-59312.1 | 84.5 | 8.5 |
| AD-59313.1 | 17.8 | 0.2 |
| AD-59314.1 | 21.1 | 0.4 |
| AD-59315.1 | 85.5 | 29.8 |
| AD-59316.1 | 13.0 | 1.6 |
| AD-59317.1 | 64.0 | 10.7 |
| AD-59318.1 | 7.9 | 2.2 |
| AD-59319.1 | 31.8 | 4.7 |
| AD-59320.1 | 5.7 | 2.1 |
| AD-59321.1 | 3.4 | 0.0 |
| AD-59322.1 | 9.6 | 1.3 |
| AD-59323.1 | 100.1 | 4.8 |
| AD-59324.1 | 40.2 | 2.9 |
| AD-59325.1 | 5.8 | 0.7 |
| AD-59326.1 | 20.4 | 10.9 |
| AD-59327.1 | 5.0 | 2.0 |
| AD-59328.1 | 8.0 | 2.8 |
| AD-59329.1 | 54.1 | 5.9 |
| AD-59330.1 | 21.6 | 12.3 |
| AD-59331.1 | 4.3 | 2.4 |
| AD-59332.1 | 12.9 | 3.8 |
| AD-59333.1 | 26.1 | 1.0 |
| AD-59334.1 | 41.9 | 4.7 |
| AD-59335.1 | 12.5 | 1.7 |
| AD-59336.1 | 13.5 | 1.7 |
| AD-59337.1 | 78.6 | 3.6 |
| AD-59338.1 | 17.9 | 12.3 |
| AD-59339.1 | 5.8 | 4.1 |
| AD-59340.1 | 92.3 | 10.0 |
| AD-59341.1 | 8.0 | 1.8 |
| AD-59342.1 | 11.1 | 1.9 |
| AD-59343.1 | 43.6 | 4.2 |
| AD-59344.1 | 6.0 | 2.3 |
| AD-59345.1 | 23.6 | 3.6 |
| AD-59346.1 | 41.0 | 3.2 |
| AD-59347.1 | 12.2 | 1.0 |
| AD-59348.1 | 30.0 | 5.1 |
| AD-59349.1 | 14.4 | 0.9 |
| AD-59350.1 | 9.1 | 1.0 |
| AD-59351.1 | 10.7 | 1.6 |
| AD-59352.1 | 1.9 | 0.4 |
| AD-59353.1 | 4.6 | 0.8 |
| AD-59354.1 | 30.1 | 0.1 |
| AD-59355.1 | 12.2 | 2.2 |
| AD-59356.1 | 63.6 | 11.5 |
| AD-59357.1 | 112.1 | 20.6 |
| AD-59358.1 | 23.2 | 3.0 |
| AD-59359.1 | 7.5 | 0.8 |
| AD-59360.1 | 19.2 | 0.5 |
| AD-59587.1 | 8.4 | 2.7 |
| AD-59588.1 | 24.8 | 5.7 |
| AD-59589.1 | 4.4 | 1.7 |
| AD-59590.1 | 13.6 | 1.3 |
| AD-59591.1 | 3.1 | 0.5 |
| AD-59592.1 | 12.1 | 2.7 |
| AD-59593.1 | 7.6 | 3.5 |

TABLE 22[2]-continued

| 20 nM single dose screen of the indicated iRNAs | | |
|---|---|---|
| Duplex ID | 20 nM Average | Standard Deviation |
| AD-59594.1 | 7.5 | 1.6 |
| AD-59595.1 | 20.1 | 2.9 |
| AD-59596.1 | 7.3 | 1.3 |
| AD-59597.1 | 61.3 | 6.8 |
| AD-59598.1 | 24.4 | 1.6 |
| AD-59599.1 | 4.3 | 0.4 |
| AD-59600.1 | 30.1 | 2.8 |
| AD-59601.1 | 11.4 | 0.8 |
| AD-59602.1 | 6.0 | 0.0 |
| AD-59603.1 | 19.4 | 2.2 |
| AD-59604.1 | 5.8 | 0.6 |
| AD-59605.1 | 6.5 | 0.3 |
| AD-59606.1 | 9.9 | 0.6 |
| AD-59607.1 | 28.0 | 2.8 |
| AD-59608.1 | 66.1 | 8.0 |
| AD-59609.1 | 84.2 | 9.0 |
| AD-59610.1 | 8.0 | 1.7 |
| AD-59611.1 | 6.6 | 1.5 |
| AD-59612.1 | 31.5 | 2.7 |
| AD-59613.1 | 27.6 | 1.7 |
| AD-59614.1 | 20.3 | 0.5 |
| AD-59615.1 | 12.8 | 1.4 |
| AD-59616.1 | 6.8 | 0.3 |
| AD-59617.1 | 13.1 | 0.9 |
| AD-59618.1 | 5.4 | 0.2 |
| AD-59619.1 | 59.1 | 5.4 |
| AD-59620.1 | 6.3 | 1.7 |
| AD-59621.1 | 18.4 | 1.8 |
| AD-59622.1 | 9.6 | 1.2 |
| AD-59623.1 | 8.7 | 2.1 |
| AD-59624.1 | 13.6 | 0.7 |
| AD-59625.1 | 12.0 | 1.5 |
| AD-59626.1 | 14.6 | 1.8 |
| AD-59627.1 | 7.7 | 6.7 |
| AD-59628.1 | 7.6 | 0.3 |
| AD-59629.1 | 55.7 | 8.2 |
| AD-59630.1 | 20.2 | 5.9 |
| AD-59631.1 | 12.3 | 0.1 |
| AD-59632.1 | 3.1 | 0.3 |
| AD-59633.1 | 20.4 | 2.1 |
| AD-59634.1 | 3.7 | 0.0 |
| AD-59635.1 | 16.1 | 1.3 |
| AD-59636.1 | 13.0 | 1.0 |
| AD-59637.1 | 14.4 | 4.8 |
| AD-59638.1 | 7.7 | 1.0 |
| AD-59639.1 | 70.4 | 5.3 |
| AD-59640.1 | 2.5 | 0.1 |
| AD-59641.1 | 18.1 | 2.1 |
| AD-59642.1 | 5.9 | 1.0 |
| AD-59643.1 | 70.7 | 17.8 |
| AD-59644.1 | 17.9 | 4.7 |
| AD-59645.1 | 2.5 | 0.1 |
| AD-59646.1 | 19.9 | 0.1 |
| AD-59647.1 | 74.8 | 12.0 |
| AD-59648.1 | 6.8 | 0.0 |
| AD-59649.1 | 95.2 | 6.2 |
| AD-59650.1 | 71.1 | 1.0 |
| AD-59651.1 | 5.0 | 0.8 |
| AD-59652.1 | 5.5 | 1.2 |
| AD-59653.1 | 15.3 | 1.0 |
| AD-59654.1 | 67.4 | 0.9 |
| AD-59655.1 | 10.8 | 1.0 |
| Naïve | 94.9 | 14.2 |

[2]Modified.

SEQUENCE LISTING

<160> NUMBER OF SEQ ID NOS: 1630

<210> SEQ ID NO 1
<211> LENGTH: 1599
<212> TYPE: DNA
<213> ORGANISM: Homo sapiens

<400> SEQUENCE: 1 tctgccccac cctgtcctct ggaacctctg cgagatttag aggaaagaac cagttttcag 60 gcggattgcc tcagatcaca ctatctccac ttgcccagcc ctgtggaaga ttagcggcca 120 tgtattccaa tgtgatagga actgtaacct ctggaaaaag gaaggtttat cttttgtcct 180 tgctgctcat tggcttctgg gactgcgtga cctgtcacgg gagccctgtg gacatctgca 240 cagccaagcc gcgggacatt cccatgaatc ccatgtgcat ttaccgctcc ccggagaaga 300 aggcaactga ggatgagggc tcagaacaga agatcccgga ggccaccaac cggcgtgtct 360 gggaactgtc caaggccaat tcccgctttg ctaccacttt ctatcagcac ctggcagatt 420 ccaagaatga caatgataac attttcctgt cacccctgag tatctccacg gcttttgcta 480 tgaccaagct gggtgcctgt aatgacaccc tccagcaact gatggaggta tttaagtttg 540 acaccatatc tgagaaaaca tctgatcaga tccacttctt ctttgccaaa ctgaactgcc 600 gactctatcg aaaagccaac aaatcctcca agttagtatc agccaatcgc ctttttggag 660 acaaatccct taccttcaat gagacctacc aggacatcag tgagttggta tatggagcca 720 agctccagcc cctggacttc aaggaaaatg cagagcaatc cagagcggcc atcaacaaat 780 gggtgtccaa taagaccgaa ggccgaatca ccgatgtcat tccctcggaa gccatcaatg 840 agctcactgt tctggtgctg gttaacacca tttacttcaa gggcctgtgg aagtcaaagt 900 tcagccctga gaacacaagg aaggaactgt tctacaaggc tgatggagag tcgtgttcag 960 catctatgat gtaccaggaa ggcaagttcc gttatcggcg cgtggctgaa ggcacccagg 1020 tgcttgagtt gcccttcaaa ggtgatgaca tcaccatggt cctcatcttg cccaagcctg 1080 agaagagcct ggccaaggta gagaaggaac tcaccccaga ggtgctgcaa gagtggctgg 1140 atgaattgga ggagatgatg ctggtggtcc acatgccccg cttccgcatt gaggacggct 1200 tcagtttgaa ggagcagctg caagacatgg gccttgtcga tctgttcagc cctgaaaagt 1260 ccaaactccc aggtattgtt gcagaaggcc gagatgacct ctatgtctca gatgcattcc 1320 ataaggcatt tcttgaggta aatgaagaag gcagtgaagc agctgcaagt accgctgttg 1380 tgattgctgg ccgttcgcta aaccccaaca gggtgacttt caaggccaac aggcctttcc 1440 tggtttttat aagagaagtt cctctgaaca ctattatctt catgggcaga gtagccaacc 1500 cttgtgttaa gtaaaatgtt cttattcttt gcacctcttc ctatttttgg tttgtgaaca 1560 gaagtaaaaa taaatacaaa ctacttccat ctcacatta 1599

<210> SEQ ID NO 2
<211> LENGTH: 1545
<212> TYPE: DNA
<213> ORGANISM: Macaca mulatta

<400> SEQUENCE: 2 ggcacgagga ccatctccac ttgcccagcc ctgtggaaga ttagcgacca tgtattccaa 60 tgtgatagga accgtagcct ctggaaaaag gaaggtttat cttctgtcct tgctgctcat 120 tggcctctgg gactgtatga cctgtcacgg gagccctgtg gacatctgca cagccaagcc 180 gcgggacatt cccatgaatc ccatgtgcat ttaccgctcc ccggagaaga aggcaactga 240

```
ggatgagggc tcagaacaga agatccccga ggccaccaac cggcgcgtct gggaactgtc    300
caaggccaat tcccgctttg ctaccacttt ctatcagcac ctggcagatt ccaagaacga    360
caaggataac attttcctgt cacccctgag tgtctccacg gcttttgcta tgaccaagct    420
gggtgcctgt aatgacaccc tcaagcaact gatggaggta tttaagtttg acaccatatc    480
tgagaaaaca tctgatcaga tccacttctt ctttgccaaa ctgaactgcc gactctatcg    540
aaaagccaac aaatcctcca agttagtatc agccaatcgc ctttttggag acaaatccct    600
taccttcaat gagacctacc aggacatcag tgagttggta tacggagcca agctccagcc    660
cctggacttc aaggaaaatg cagagcaatc cagagcggcc atcaacaaat gggtgtccaa    720
taagaccgaa ggccgaatca ccgatgtcat tcccccggaa gccatcaacg agctcactgt    780
tctggtgctg gttaacacca tttacttcaa gggcctgtgg aagtcaaagt ttagccctga    840
gaacacaagg atggaaccgt tctacaaggc tgatggagag tcgtgttcag cgtctatgat    900
gtaccaggaa ggcaagttct gttatcggcg cgtggctgaa ggcacccagg tgcttgagtt    960
gcccttcaag ggtgatgaca tcaccatggt gctcatcctg cccaagcctg agaagagcct   1020
gaccaaggtg gagcaggaac tcaccccaga ggtgctgcag gagtggctgg atgagttgga   1080
ggagatgatg ctggtggttc acatgccccg cttccgcatt gaggacggct tcagtttgaa   1140
ggagcagctg caagacatgg gccttgtcga tctgttcagc cctgaaaagt ccaaactccc   1200
aggtattgtt gcagaaggcc gggatgacct ctatgtctcc gatgcattcc ataaggcatt   1260
tcttgaggta aatgaagaag gcagtgaagc agctgcaagt accgccattg ggattgctgg   1320
ccgttcgcta aaccccaaca gggtgacctt caaggccaac aggcctttcc tggtttttat   1380
aagagaagtt cctctgaaca ctattatctt catgggcaga gtagccaacc cttgtgtgag   1440
ctaaactgtt cttattcttt gtacctcttc ctattttggt ttgtgaatag aagtaaaaat   1500
aaatacaact actcccatct tacattaaaa aaaaaaaaaa aaaaa                   1545
```

<210> SEQ ID NO 3
<211> LENGTH: 2171
<212> TYPE: DNA
<213> ORGANISM: Mus musculus

<400> SEQUENCE: 3

```
ataggtaatt ttagaaatag atctgatttg tatctgagac attttagtga agtggtgaga     60
tataagacat aatcagaaga catatctacc tgaagacttt aaggggagag ctccctcccc    120
cacctggcct ctggacctct cagatttagg ggaaagaacc agttttcgga gtgatcgtct    180
cagtcagcac catctctgta ggagcatcgg ccatgtattc ccctggggca ggaagtgggg    240
ctgctggtga gaggaagctt tgtctcctct ctctgctcct catcggtgcc ttgggctgtg    300
ctatctgtca cggaaaccct gtggacgaca tctgcatagc gaagccccga gacatccccg    360
tgaatccctt gtgcatttac cgctcccctg ggaagaaggc caccgaggag gatggctcag    420
agcagaaggt tccagaagcc accaaccggc gggtctggga actgtccaag gccaattcgc    480
gatttgccac taacttctac cagcacctgg cagactccaa gaatgacaac gacaacattt    540
tcctgtcacc cttgagcatc tccactgctt ttgctatgac caagctgggt gcctgtaacg    600
acactctcaa gcagctgatg gaggttttta aatttgatac catctccgag aagacatccg    660
accagatcca cttcttcttt gccaaactga actgccgact ctatcgaaaa gccaacaagt    720
cctctgactt ggtatcagcc aaccgccttt ttggagacaa atccctcacc ttcaacgaga    780
```

```
gctatcaaga tgttagtgag gttgtctatg gagccaagct ccagcccctg gacttcaagg    840
agaatccgga gcaatccaga gtgaccatca acaactgggt agctaataag actgaaggcc    900
gcatcaaaga tgtcatccca cagggcgcca ttaacgagct cactgccctg gttctggtta    960
acaccattta cttcaagggc ctgtggaagt caaagttcag ccctgagaac acaaggaagg   1020
aaccgttcta taaggtcgat gggcagtcat gcccagtgcc tatgatgtac caggaaggca   1080
aattcaaata ccggcgcgtg gcagagggca cccaggtgct agagctgccc ttcaaggggg   1140
atgacatcac catggtgctc atcctgccca agcctgagaa gagcctggcc aaggtggagc   1200
aggagctcac cccagagctg ctgcaggagt ggctggatga gctgtcagag actatgcttg   1260
tggtccacat gccccgcttc cgcaccgagg atggcttcag tctgaaggag cagctgcaag   1320
acatgggcct cattgatctc ttcagccctg aaaagtccca actcccaggg atcgttgctg   1380
gaggcaggga cgacctctat gtctccgacg cattccacaa agcatttctt gaggtaaatg   1440
aggaaggcag tgaagcagca gcgagtactt ctgtcgtgat tactggccgg tcactgaacc   1500
ccaatagggt gaccttcaag gccaacaggc ccttcctggt tcttataagg gaagttgcac   1560
tgaacactat tatattcatg gggagagtgg ctaatccttg tgtgaactaa aatattctta   1620
atctttgcac cttttcctac tttggtgttt gtgaatagaa gtaaaaataa atacgactgc   1680
cacctcacga gaatggactt ttccacttga agacgagaga ctggagtaca gatgctacac   1740
cacttttggg caagtgaagg gggagcagcc agccacggtg gcacaaacct atatcctggt   1800
gcttttgaag gtagaagcag ggcggtcagg agttaaggcc agttgaggct gggctgcaga   1860
gtgaaagacc atgtctcaag atggtctttc tcctccccaa agtagaaaag aaaaccataa   1920
aaacaagagg taaatatatt actatttcat cttagaggat agcaggcatc ttgaaagggt   1980
agagggacct taaattctca ttattgcccc catactacaa actaaaaaac aaacccgaat   2040
caatctccca taaagacaga gattcaaata agagtattaa acgttttatt tctcaaacca   2100
ctcacatgca taatgttctt atacacagtg tcaaaataaa gagaaatgca tttttataca   2160
aaaaaaaaaa a                                                        2171
```

<210> SEQ ID NO 4
<211> LENGTH: 1561
<212> TYPE: DNA
<213> ORGANISM: Rattus norvegicus

<400> SEQUENCE: 4

```
cggagggatt gctcagcact gtctccacgg cttctctgca gaagcgtcca ccatgtattc     60
cccgggaata ggaagtgcgg ttgctggaga gaggaagctt tgtctcctct ctctgctact    120
cattggtgcc ttgggctgtg ctgtctgtca tggaaaccct gtggacgaca tctgcatagc    180
gaagccccga gacatccccg tgaaccccat gtgcatttac cgctcccctg cgaagaaggc    240
cacggaggag gatgtcctag agcagaaggt tccggaagcc accaaccggc gggtctggga    300
actgtccaag gccaattctc gatttgccac taacttctat cagcacctgg cagactccaa    360
gaacgacaac gacaacattt tcctgtcacc cttgagcatc tccacggcgt ttgctatgac    420
caagctgggt gcttgtaata acaccctcaa gcagctgatg gaggttttta aatttgatac    480
catctccgag aagacatccg accagatcca cttcttcttt gccaaactga actgccgact    540
ctatcgaaaa gccaacaagt cctctaactt ggtgtcagcc aaccgccttt ttggagacaa    600
atcccttacc ttcaatgaga gctatcaaga cgttagtgag attgtctatg gagccaagct    660
tcagcccctg gacttcaagg agaatccgga gcaatccaga gtgaccatca acaactgggt    720
```

```
agctaataag actgaaggcc gcatcaaaga cgtcatcccc caaggagcca ttgatgagct    780
cactgccctg gtgctggtta acaccattta cttcaagggc ctgtggaagt caaagttcag    840
ccctgagaac acaaggaagg aaccattcca caaagttgat gggcagtcat gcctggtgcc    900
catgatgtac caggaaggca aattcaaata caggcgtgtg ggagagggta cccaggtgct    960
agagatgccc ttcaaggggg acgacatcac catggtgctc atcctgccca agcctgagaa   1020
gagcctggct aaggtggagc aggaactcac cccggagctg ctgcaggagt ggctggatga   1080
gctgtcggag gtcatgcttg tggtccacgt gccccgcttc cgcatcgagg acagcttcag   1140
tctgaaggag cagctgcaag acatgggcct tgttgatctc ttcagccctg agaagtccca   1200
actcccaggg atcattgctg aaggcaggga cgacctcttt gtctccgatg cattccacaa   1260
agcgtttctt gaggtaaatg aggaaggcag tgaagcagca gcgagtactt ctgtcgtgat   1320
tactggccgg tcactgaacc ccagtagggt gaccttcaag gccaacaggc ccttcctggt   1380
tcttataagg gaagtcgcac tgaacactat tatattcatg gggagagtgt ctaatccttg   1440
tgtgaactaa aatattctta atctttgcac cttttcctat ctcggtgttt gttaatggaa   1500
gtaaaaataa atatgactgc cacctcaaaa aaaaaaaaaa aaaaaaaaaa aaaaaaaaaa   1560
a                                                                   1561
```

<210> SEQ ID NO 5
<211> LENGTH: 1599
<212> TYPE: DNA
<213> ORGANISM: Homo sapiens

<400> SEQUENCE: 5

```
taatgtgaga tggaagtagt ttgtatttat ttttacttct gttcacaaac caaaaatagg     60
aagaggtgca aagaataaga acattttact taacacaagg gttggctact ctgcccatga    120
agataatagt gttcagagga acttctctta taaaaaccag gaaaggcctg ttggccttga    180
aagtcaccct gttggggttt agcgaacggc cagcaatcac aacagcggta cttgcagctg    240
cttcactgcc ttcttcattt acctcaagaa atgccttatg gaatgcatct gagacataga    300
ggtcatctcg gccttctgca acaatacctg ggagtttgga cttttcaggg ctgaacagat    360
cgacaaggcc catgtcttgc agctgctcct tcaaactgaa gccgtcctca atgcggaagc    420
ggggcatgtg gaccaccagc atcatctcct ccaattcatc cagccactct tgcagcacct    480
ctggggtgag ttccttctct accttggcca ggctcttctc aggcttgggc aagatgagga    540
ccatggtgat gtcatcacct ttgaagggca actcaagcac ctgggtgcct tcagccacgc    600
gccgataacg gaacttgcct tcctggtaca tcatagatgc tgaacacgac tctccatcag    660
ccttgtagaa cagttccttc cttgtgttct cagggctgaa ctttgacttc cacaggccct    720
tgaagtaaat ggtgttaacc agcaccagaa cagtgagctc attgatggct tccgagggaa    780
tgacatcggt gattcggcct tcggtcttat tggacaccca tttgttgatg gccgctctgg    840
attgctctgc attttccttg aagtccaggg gctggagctt ggctccatat accaactcac    900
tgatgtcctg gtaggtctca ttgaaggtaa gggatttgtc tccaaaaagg cgattggctg    960
atactaactt ggaggatttg ttggcttttc gatagagtcg gcagttcagt ttggcaaaga   1020
agaagtggat ctgatcagat gttttctcag atatggtgtc aaacttaaat acctccatca   1080
gttgctggag ggtgtcatta caggcaccca gcttggtcat agcaaaagcc gtggagatac   1140
tcaggggtga caggaaaatg ttatcattgt cattcttgga atctgccagg tgctgataga   1200
```

```
aagtggtagc aaagcgggaa ttggccttgg acagttccca gacacgccgg ttggtggcct   1260

ccgggatctt ctgttctgag ccctcatcct cagttgcctt cttctccggg gagcggtaaa   1320

tgcacatggg attcatggga atgtcccgcg gcttggctgt gcagatgtcc acagggctcc   1380

cgtgacaggt cacgcagtcc cagaagccaa tgagcagcaa ggacaaaaga taaaccttcc   1440

tttttccaga ggttacagtt cctatcacat tggaatacat ggccgctaat cttccacagg   1500

gctgggcaag tggagatagt gtgatctgag gcaatccgcc tgaaaactgg ttctttcctc   1560

taaatctcgc agaggttcca gaggacaggg tggggcaga                          1599
```

<210> SEQ ID NO 6
<211> LENGTH: 1545
<212> TYPE: DNA
<213> ORGANISM: Macaca mulatta

<400> SEQUENCE: 6

```
tttttttttt tttttttta atgtaagatg ggagtagttg tatttatttt tacttctatt     60

cacaaaccaa aataggaaga ggtacaaaga ataagaacag tttagctcac acaagggttg    120

gctactctgc ccatgaagat aatagtgttc agaggaactt ctcttataaa aaccaggaaa    180

ggcctgttgg ccttgaaggt caccctgttg gggtttagcg aacggccagc aatcccaatg    240

gcggtacttg cagctgcttc actgccttct tcatttacct caagaaatgc cttatggaat    300

gcatcggaga catagaggtc atcccggcct tctgcaacaa tacctgggag tttggacttt    360

tcagggctga acagatcgac aaggcccatg tcttgcagct gctccttcaa actgaagccg    420

tcctcaatgc ggaagcgggg catgtgaacc accagcatca tctcctccaa ctcatccagc    480

cactcctgca gcacctctgg ggtgagttcc tgctccacct tggtcaggct cttctcaggc    540

ttgggcagga tgagcaccat ggtgatgtca tcacccttga agggcaactc aagcacctgg    600

gtgccttcag ccacgcgccg ataacagaac ttgccttcct ggtacatcat agacgctgaa    660

cacgactctc catcagcctt gtagaacggt tccatccttg tgttctcagg gctaaacttt    720

gacttccaca ggcccttgaa gtaaatggtg ttaaccagca ccagaacagt gagctcgttg    780

atggcttccg ggggaatgac atcggtgatt cggccttcgg tcttattgga cacccatttg    840

ttgatggccg ctctggattg ctctgcattt tccttgaagt ccaggggctg gagcttggct    900

ccgtatacca actcactgat gtcctggtag gtctcattga aggtaaggga tttgtctcca    960

aaaaggcgat tggctgatac taacttggag gatttgttgg cttttcgata gagtcggcag   1020

ttcagtttgg caaagaagaa gtggatctga tcagatgttt tctcagatat ggtgtcaaac   1080

ttaaatacct ccatcagttg cttgagggtg tcattacagg cacccagctt ggtcatagca   1140

aaagccgtgg agacactcag gggtgacagg aaaatgttat ccttgtcgtt cttggaatct   1200

gccaggtgct gatagaaagt ggtagcaaag cgggaattgg ccttggacag ttcccagacg   1260

cgccggttgg tggcctcggg gatcttctgt tctgagccct catcctcagt tgccttcttc   1320

tccggggagc ggtaaatgca catgggattc atgggaatgt cccgcggctt ggctgtgcag   1380

atgtccacag ggctcccgtg acaggtcata cagtcccaga ggccaatgag cagcaaggac   1440

agaagataaa ccttcctttt tccagaggct acggttccta tcacattgga atacatggtc   1500

gctaatcttc cacagggctg ggcaagtgga gatggtcctc gtgcc                   1545
```

<210> SEQ ID NO 7
<211> LENGTH: 2171
<212> TYPE: DNA
<213> ORGANISM: Mus musculus

<400> SEQUENCE: 7

```
tttttttttt ttgtataaaa atgcatttct ctttattttg acactgtgta taagaacatt     60
atgcatgtga gtggtttgag aaataaaacg tttaatactc ttatttgaat ctctgtcttt    120
atgggagatt gattcgggtt tgtttttag tttgtagtat gggggcaata atgagaattt    180
aaggtccctc tacccttca agatgcctgc tatcctctaa gatgaaatag taatatattt    240
acctcttgtt tttatggttt tcttttctac tttggggagg agaaagacca tcttgagaca    300
tggtctttca ctctgcagcc cagcctcaac tggccttaac tcctgaccgc cctgcttcta    360
ccttcaaaag caccaggata taggtttgtg ccaccgtggc tggctgctcc cccttcactt    420
gcccaaaagt ggtgtagcat ctgtactcca gtctctcgtc ttcaagtgga aaagtccatt    480
ctcgtgaggt ggcagtcgta tttattttta cttctattca caaacaccaa agtaggaaaa    540
ggtgcaaaga ttaagaatat tttagttcac acaaggatta gccactctcc ccatgaatat    600
aatagtgttc agtgcaactt cccttataag aaccaggaag ggcctgttgg ccttgaaggt    660
caccctattg gggttcagtg accggccagt aatcacgaca gaagtactcg ctgctgcttc    720
actgccttcc tcatttacct caagaaatgc tttgtggaat gcgtcggaga catagaggtc    780
gtccctgcct ccagcaacga tccctgggag ttgggacttt tcagggctga agagatcaat    840
gaggcccatg tcttgcagct gctccttcag actgaagcca tcctcggtgc ggaagcgggg    900
catgtggacc acaagcatag tctctgacag ctcatccagc cactcctgca gcagctctgg    960
ggtgagctcc tgctccacct tggccaggct cttctcaggc ttgggcagga tgagcaccat   1020
ggtgatgtca tccccccttga agggcagctc tagcacctgg gtgccctctg ccacgcgccg   1080
gtatttgaat ttgccttcct ggtacatcat aggcactggg catgactgcc catcgacctt   1140
atagaacggt tccttccttg tgttctcagg gctgaacttt gacttccaca ggcccttgaa   1200
gtaaatggtg ttaaccagaa ccagggcagt gagctcgtta atggcgccct gtgggatgac   1260
atctttgatg cggccttcag tcttattagc tacccagttg ttgatggtca ctctggattg   1320
ctccggattc tccttgaagt ccaggggctg gagcttggct ccatagacaa cctcactaac   1380
atcttgatag ctctcgttga aggtgaggga tttgtctcca aaaaggcggt tggctgatac   1440
caagtcagag gacttgttgg cttttcgata gagtcggcag ttcagtttgg caaagaagaa   1500
gtggatctgg tcggatgtct tctcggagat ggtatcaaat ttaaaaacct ccatcagctg   1560
cttgagagtg tcgttacagg cacccagctt ggtcatagca aaagcagtgg agatgctcaa   1620
gggtgacagg aaaatgttgt cgttgtcatt cttggagtct gccaggtgct ggtagaagtt   1680
agtggcaaat cgcgaattgg ccttggacag ttcccagacc cgccggttgg tggcttctgg   1740
aaccttctgc tctgagccat cctcctcggt ggccttcttc ccaggggagc ggtaaatgca   1800
caagggattc acggggatgt ctcggggctt cgctatgcag atgtcgtcca cagggtttcc   1860
gtgacagata gcacagccca aggcaccgat gaggagcaga gagaggagac aaagcttcct   1920
ctcaccagca gccccacttc ctgccccagg ggaatacatg gccgatgctc ctacagagat   1980
ggtgctgact gagacgatca ctccgaaaac tggttctttc ccctaaatct gagaggtcca   2040
gaggccaggt gggggaggga gctctcccct taaagtcttc aggtagatat gtcttctgat   2100
tatgtcttat atctcaccac ttcactaaaa tgtctcagat acaaatcaga tctatttcta   2160
aaattaccta t                                                        2171
```

<210> SEQ ID NO 8

<211> LENGTH: 1561
<212> TYPE: DNA
<213> ORGANISM: Rattus norvegicus

<400> SEQUENCE: 8

```
tttttttttt tttttttttt tttttttttt tttttgaggt ggcagtcata tttattttta     60

cttccattaa caaacaccga gataggaaaa ggtgcaaaga ttaagaatat tttagttcac    120

acaaggatta gacactctcc ccatgaatat aatagtgttc agtgcgactt cccttataag    180

aaccaggaag ggcctgttgg ccttgaaggt caccctactg gggttcagtg accggccagt    240

aatcacgaca gaagtactcg ctgctgcttc actgccttcc tcatttacct caagaaacgc    300

tttgtggaat gcatcggaga caaagaggtc gtccctgcct tcagcaatga tccctgggag    360

ttgggacttc tcagggctga agagatcaac aaggcccatg tcttgcagct gctccttcag    420

actgaagctg tcctcgatgc ggaagcgggg cacgtggacc acaagcatga cctccgacag    480

ctcatccagc cactcctgca gcagctccgg ggtgagttcc tgctccacct tagccaggct    540

cttctcaggc ttgggcagga tgagcaccat ggtgatgtcg tccccttga agggcatctc    600

tagcacctgg gtaccctctc ccacacgcct gtatttgaat ttgccttcct ggtacatcat    660

gggcaccagg catgactgcc catcaacttt gtggaatggt tccttccttg tgttctcagg    720

gctgaacttt gacttccaca ggcccttgaa gtaaatggtg ttaaccagca ccagggcagt    780

gagctcatca atggctcctt gggggatgac gtctttgatg cggccttcag tcttattagc    840

tacccagttg ttgatggtca ctctggattg ctccggattc tccttgaagt ccaggggctg    900

aagcttggct ccatagacaa tctcactaac gtcttgatag ctctcattga aggtaaggga    960

tttgtctcca aaaaggcggt tggctgacac caagttagag gacttgttgg cttttcgata   1020

gagtcggcag ttcagtttgg caaagaagaa gtggatctgg tcggatgtct tctcggagat   1080

ggtatcaaat ttaaaaacct ccatcagctg cttgagggtg ttattacaag cacccagctt   1140

ggtcatagca aacgccgtgg agatgctcaa gggtgacagg aaaatgttgt cgttgtcgtt   1200

cttggagtct gccaggtgct gatagaagtt agtggcaaat cgagaattgg ccttggacag   1260

ttcccagacc cgccggttgg tggcttccgg aaccttctgc tctaggacat cctcctccgt   1320

ggccttcttc gcaggggagc ggtaaatgca catggggttc acggggatgt ctcggggctt   1380

cgctatgcag atgtcgtcca cagggtttcc atgacagaca gcacagccca aggcaccaat   1440

gagtagcaga gagaggagac aaagcttcct ctctccagca accgcacttc ctattcccgg   1500

ggaatacatg gtggacgctt ctgcagagaa gccgtggaga cagtgctgag caatccctcc   1560

g                                                                   1561
```

<210> SEQ ID NO 9
<211> LENGTH: 16
<212> TYPE: PRT
<213> ORGANISM: Unknown
<220> FEATURE:
<223> OTHER INFORMATION: Description of Unknown: Exemplary
hydrophobic membrane translocation peptide

<400> SEQUENCE: 9

```
Ala Ala Val Ala Leu Leu Pro Ala Val Leu Leu Ala Leu Leu Ala Pro
1               5                   10                  15
```

<210> SEQ ID NO 10
<211> LENGTH: 11
<212> TYPE: PRT
<213> ORGANISM: Unknown

<220> FEATURE:
<223> OTHER INFORMATION: Description of Unknown: RFGF
analogue peptide

<400> SEQUENCE: 10

Ala Ala Leu Leu Pro Val Leu Leu Ala Ala Pro
1 5 10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Arg Pro Pro Gln
1 5 10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1 5 10 15

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 13 cuuacgcuga guacuucgat t 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 14 ucgaaguacu cagcguaagt t 21

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15 cccuguggac aucugcaca 19

<210> SEQ ID NO 16
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 16 cuaccacuuu cuaucagca 19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 17 cuaucgaaaa gccaacaaa 19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18 ggacuucaag gaaaaugca 19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19 guuaacacca uuuacuuca 19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20 ccugguuuuu auaagagaa 19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21 gacauuccca ugaauccca 19

<210> SEQ ID NO 22
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 22 caccuggcag auuccaaga 19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23 cgaaaagcca acaaauccu 19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24 gaaaaugcag agcaaucca 19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25 ggccugugga agucaaagu 19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 26 gaaguuccuc ugaacacua 19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27 ccaugaaucc caugugcau 19

<210> SEQ ID NO 28
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 28 caacugaugg agguauuua 19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 29 ccaaguuagu aucagccaa 19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 30 cggccaucaa caaaugggu 19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 31 gaggacggcu ucaguuuga 19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32 ccucugaaca cuauuaucu 19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33 caugaauccc augugcauu 19

<210> SEQ ID NO 34
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 34 gauggaggua uuuaaguuu 19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35 guaucagcca aucgccuuu 19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36 gggguguccaa uaagaccga 19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37 cagcccugaa aaguccaaa 19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38 cccaugugca uuuaccgcu 19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 39 guauuuaagu uugacacca 19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40 gacaaauccc uuaccuuca 19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 41 cuguucuggu gcugguuaa 19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 42 ccaaacuccc agguauugu 19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 43 cccgcuuugc uaccacuuu 19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44 cuuaccuuca augagaccu 19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 45 cuggugcugg uuaacacca 19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46 caaacuccca gguauuguu 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47 gcuuugcuac cacuuucua 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48 ccuaccagga caucaguga 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49 ggugcugguu aacaccauu 19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50 gccguucgcu aaaccccaa 19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51 ggacaucagu gaguuggua 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52 gugcugguua acaccauuu 19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53 gccuuuccug guuuuuaua 19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54 cuuuugcuau gaccaagcu 19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 55 uguaccagga aggcaaguu 19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 56 acuauuaucu ucaugggca 19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 57 ucaugggcag aguagccaa 19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 58 ccauuuacuu caagggccu 19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 59 uacuucaagg gccugugga 19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 60 acuucaaggg ccuguggaa 19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 61 cgacucuauc gaaaagcca 19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 62 aacugccgac ucuaucgaa 19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 63 acugccgacu cuaucgaaa 19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64 gacucuaucg aaaagccaa 19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 65 ucuucuuugc caaacugaa 19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 66 ugccaaacug aacugccga 19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 67 ccaaacugaa cugccgacu 19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 68 acugaacugc cgacucuau 19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 69 gaacugccga cucuaucga 19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 70 cugccgacuc uaucgaaaa 19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 71 cugguuaaca ccauuuacu 19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 72 ugugcagaug uccacaggg 19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 73 ugcugauaga aaguggguag 19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 74 uuuguuggcu uuucgauag 19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 75 ugcauuuucc uugaagucc 19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 76 ugaaguaaau gguguuaac 19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 77 uucucuuaua aaaaccagg 19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 78 ugggauucau gggaauguc 19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 79 ucuuggaauc ugccaggug 19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 80 aggauuuguu ggcuuuucg 19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 81 uggauugcuc ugcauuuuc 19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82 acuuugacuu ccacaggcc 19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83 uaguguucag aggaacuuc 19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84 augcacaugg gauucaugg 19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85 uaaauaccuc caucaguug 19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 86 uuggcugaua cuaacuugg 19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 87 acccauuugu ugauggccg 19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 88 ucaaacugaa gccguccuc 19

<210> SEQ ID NO 89

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 89 agauaauagu guucagagg 19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 90 aaugcacaug ggauucaug 19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 91 aaacuuaaau accuccauc 19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 92 aaaggcgauu ggcugauac 19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 93 ucggucuuau uggacaccc 19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94 uuuggacuuu ucagggcug 19

<210> SEQ ID NO 95
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 95 agcgguaaau gcacauggg 19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 96 uggugucaaa cuuaaauac 19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 97 ugaagguaag ggauuuguc 19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 98 uuaaccagca ccagaacag 19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 99 acaauaccug ggaguuugg 19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 100 aaagugguag caaagcggg 19

<210> SEQ ID NO 101
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 101 aggucucauu gaagguaag 19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 102 ugguguuaac cagcaccag 19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 103 aacaauaccu gggaguuug 19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104 uagaaagugg uagcaaagc 19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105 ucacugaugu ccugguagg 19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106 aaugguguua accagcacc 19

<210> SEQ ID NO 107
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 107 uuggguuua gcgaacggc 19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 108 uaccaacuca cugaugucc 19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 109 aaauggugu aaccagcac 19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 110 uauaaaaacc aggaaaggc 19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 111 agcuugguca uagcaaaag 19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 112 aacuugccuu ccugguaca 19

<210> SEQ ID NO 113
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 113 ugcccaugaa gauaauagu 19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114 uuggcuacuc ugcccauga 19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115 aggcccuuga aguaaaugg 19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116 uccacaggcc cuugaagua 19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117 uuccacaggc ccuugaagu 19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118 uggcuuuucg auagagucg 19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 119 uucgauagag ucggcaguu 19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120 uuucgauaga gucggcagu 19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121 uuggcuuuuc gauagaguc 19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 122 uucaguuugg caaagaaga 19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123 ucggcaguuc aguuuggca 19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 124 agucggcagu ucaguuugg 19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125 auagagucgg caguucagu 19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 126 ucgauagagu cggcaguuc 19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 127 uuuucgauag agucggcag 19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 128 aguaaauggu guuaaccag 19

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 129 cccuguggac aucugcacat t 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 130 cuaccacuuu cuaucagcat t 21

<210> SEQ ID NO 131
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 131 cuaucgaaaa gccaacaaat t 21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 132 ggacuucaag gaaaaugcat t 21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 133 guuaacacca uuuacuucat t 21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 134 ccugguuuuu auaagagaat t 21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 135 gacauuccca ugaaucccat t 21

<210> SEQ ID NO 136

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 136 caccuggcag auuccaagat t 21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 137 cgaaaagcca acaaauccut t 21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 138 gaaaaugcag agcaauccat t 21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 139 ggccugugga agucaaagut t 21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 140 gaaguuccuc ugaacacuat t 21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 141 ccaugaaucc caugugcaut t 21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 142 caacugaugg agguauuuat t 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 143 ccaaguuagu aucagccaat t 21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 144 cggccaucaa caaaugggut t 21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 145 gaggacggcu ucaguuugat t 21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 146 ccucugaaca cuauuaucut t 21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 147 caugaauccc augugcauut t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 148 gauggaggua uuuaaguuut t 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 149 guaucagcca aucgccuuut t 21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 150 gggguccaa uaagaccgat t 21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 151 cagcccugaa aaguccaaat t 21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 152 cccaugugca uuuaccgcut t 21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 153 guauuuaagu uugacaccat t 21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 154 gacaaauccc uuaccuucat t 21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 155 cuguucuggu gcugguuaat t 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 156 ccaaacuccc agguauugut t 21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 157 cccgcuuugc uaccacuuut t 21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 158 cuuaccuuca augagaccut t 21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 159 cuggugcugg uuaacaccat t 21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 160 caaacuccca gguauuguut t 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 161 gcuuugcuac cacuuucuat t 21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 162 ccuaccagga caucagugat t 21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 163 ggugcugguu aacaccauut t 21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 164 gccguucgcu aaaccccaat t 21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 165 ggacaucagu gaguugguat t 21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 166 gugcugguua acaccauuut t 21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 167 gccuuuccug guuuuuauat t 21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 168 cuuuugcuau gaccaagcut t 21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 169 uguaccagga aggcaaguut t 21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 170 acuauuaucu ucaugggcat t 21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 171 ucaugggcag aguagccaat t 21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 172 ccauuuacuu caagggccut t 21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 173 uacuucaagg gccuguggat t 21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 174 acuucaaggg ccuguggaat t 21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 175 cgacucuauc gaaaagccat t 21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 176 aacugccgac ucuaucgaat t 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 177 acugccgacu cuaucgaaat t 21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 178 gacucuaucg aaaagccaat t 21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 179 ucuucuuugc caaacugaat t 21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 180 ugccaaacug aacugccgat t 21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 181 ccaaacugaa cugccgacut t 21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 182 acugaacugc cgacucuaut t 21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 183 gaacugccga cucuaucgat t 21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 184 cugccgacuc uaucgaaaat t 21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 185 cugguuaaca ccauuuacut t 21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 186 ugugcagaug uccacagggt t 21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 187 ugcugauaga aaguggguagt t 21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 188 uuuguuggcu uuucgauagt t 21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 189 ugcauuuucc uugaagucct t 21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 190 ugaaguaaau gguguuaact t 21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 191 uucucuuaua aaaaccaggt t 21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 192 ugggauucau gggaauguct t 21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 193 ucuuggaauc ugccaggugt t 21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 194 aggauuuguu ggcuuuucgt t 21

<210> SEQ ID NO 195
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 195 uggauugcuc ugcauuuuct t 21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 196 acuuugacuu ccacaggcct t 21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 197 uaguguucag aggaacuuct t 21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 198 augcacaugg gauucauggt t 21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 199 uaaauaccuc caucaguugt t 21

<210> SEQ ID NO 200
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 200 uuggcugaua cuaacuuggt t 21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 201 acccauuugu ugauggccgt t 21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 202 ucaaacugaa gccguccuct t 21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 203 agauaauagu guucagaggt t 21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 204 aaugcacaug ggauucaugt t 21

<210> SEQ ID NO 205
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 205 aaacuuaaau accuccauct t 21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 206 aaaggcgauu ggcugauact t 21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 207 ucggucuuau uggacaccct t 21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 208 uuuggacuuu ucagggcugt t 21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 209 agcgguaaau gcacaugggt t 21

<210> SEQ ID NO 210
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 210 uggugucaaa cuuaaauact t 21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 211 ugaagguaag ggauuuguct t 21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 212 uuaaccagca ccagaacagt t 21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 213 acaauaccug ggaguuuggt t 21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 214 aaagugguag caaagcgggt t 21

<210> SEQ ID NO 215

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 215 aggucucauu gaagguaagt t 21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 216 ugguguuaac cagcaccagt t 21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 217 aacaauaccu gggaguuugt t 21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 218 uagaaagugg uagcaaagct t 21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 219 ucacugaugu ccugguaggt t 21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 220 aaugguguua accagcacct t 21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 221 uuggguuua gcgaacggct t 21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 222 uaccaacuca cugauguccct t 21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 223 aaaugguguu aaccagcact t 21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 224 uauaaaaacc aggaaaggct t 21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 225 agcuugguca uagcaaaagt t 21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 226 aacuugccuu ccugguacat t 21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 227 ugcccaugaa gauaauagut t 21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 228 uuggcuacuc ugcccaugat t 21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 229 aggcccuuga aguaaauggt t 21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 230 uccacaggcc cuugaaguat t 21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 231 uuccacaggc ccuugaagut t 21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 232 uggcuuuucg auagagucgt t 21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 233 uucgauagag ucggcaguut t 21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 234 uuucgauaga gucggcagut t 21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 235 uuggcuuuuc gauagaguct t 21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 236 uucaguuugg caaagaagat t 21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 237 ucggcaguuc aguuuggcat t 21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 238 agucggcagu ucaguuuggt t 21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 239 auagagucgg caguucagut t 21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 240 ucgauagagu cggcaguuct t 21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 241 uuuucgauag agucggcagt t 21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 242 aguaaauggu guuaaccagt t 21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 243 cuaucgaaaa gccaacaaat t 21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 244 cuaucgaaaa gccaacaaat t 21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 245 cuaucgaaaa gccaacaaat t 21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 246 cuaucgaaaa gccaacaaat t 21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 247 cuaucgaaaa gccaacaaat t 21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 248 cuaucgaaaa gccaacaaat t 21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 249 cuaucgaaaa gccaacaaat t 21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 250 cuaucgaaaa gccaacaaat t 21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 251 cuaucgaaaa gccaacaaat t 21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 252 cuaucgaaaa gccaacaaat t 21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 253 cuaucgaaaa gccaacaaat t 21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 254 cuaucgaaaa gccaacaaat t 21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 255 cuaucgaaaa gccaacaaat t 21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 256 ccaugaaucc caugugcaut t 21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 257 ccaugaaucc caugugcaut t 21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 258 ccaugaaucc caugugcaut t 21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 259 ccaugaaucc caugugcaut t 21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 260 ccaugaaucc caugugcaut t 21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 261 ccaugaaucc caugugcaut t 21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 262 ccaugaaucc caugugcaut t 21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 263 ccaugaaucc caugugcaut t 21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 264 ccaugaaucc caugugcaut t 21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 265 ccaugaaucc caugugcaut t 21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 266 ccaugaaucc caugugcaut t 21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 267 ccaugaaucc caugugcaut t 21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 268 ccaugaaucc caugugcaut t 21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 269 cugccgacuc uaucgaaaat t 21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 270 cugccgacuc uaucgaaaat t 21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 271 cugccgacuc uaucgaaaat t 21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 272 cugccgacuc uaucgaaaat t 21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 273 cugccgacuc uaucgaaaat t 21

<210> SEQ ID NO 274
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 274 cugccgacuc uaucgaaaat t 21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 275 cugccgacuc uaucgaaaat t 21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 276 cugccgacuc uaucgaaaat t 21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 277 cugccgacuc uaucgaaaat t 21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 278 cugccgacuc uaucgaaaat t 21

<210> SEQ ID NO 279
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 279 cugccgacuc uaucgaaaat t 21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 280 cugccgacuc uaucgaaaat t 21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 281 cugccgacuc uaucgaaaat t 21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 282 ucuucuuugc caaacugaat t 21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 283 ucuucuuugc caaacugaat t 21

<210> SEQ ID NO 284
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 284 ucuucuuugc caaacugaat t 21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 285 ucuucuuugc caaacugaat t 21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 286 ucuucuuugc caaacugaat t 21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 287 ucuucuuugc caaacugaat t 21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 288 ucuucuuugc caaacugaat t 21

<210> SEQ ID NO 289
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 289 ucuucuuugc caaacugaat t 21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 290 ucuucuuugc caaacugaat t 21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 291 ucuucuuugc caaacugaat t 21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 292 ucuucuuugc caaacugaat t 21

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 293 ucuucuuugc caaacugaat t 21

<210> SEQ ID NO 294

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 294 gguuaacacc auuuacuuca a 21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 295 uaguaucagc caaucgccuu u 21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 296 cgcuuugcua ccacuuucua u 21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 297 cuuugcuacc acuuucuauc a 21

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 298 aucgaaaagc caacaaaucc u 21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 299 ucccaugaau cccaugugca u 21

<210> SEQ ID NO 300
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 300 uaaggcauuu cuugagguaa a 21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301 gcaacugaug gagguauuua a 21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302 uuuaaguuug acaccauauc u 21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303 ccaugaaucc caugugcauu u 21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304 ugcugguuaa caccauuuac u 21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305 ucuaucgaaa agccaacaaa u 21

<210> SEQ ID NO 306
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 306 uucccgcuuu gcuaccacuu u 21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 307 gauggaggua uuuaaguuug a 21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308 agacaaaucc cuuaccuuca a 21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309 ugcuaccacu uucuaucagc a 21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 310 uguauuccaa ugugauagga a 21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 311 aacugccgac ucuaucgaaa a 21

<210> SEQ ID NO 312
<211> LENGTH: 21
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 312 gccgacucua ucgaaaagcc a 21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 313 uauuuaaguu ugacaccaua u 21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 314 ugggccuugu cgaucuguuc a 21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 315 caaaucccuu accuucaaug a 21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 316 uccaaacucc cagguauugu u 21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 317 gaacugccga cucuaucgaa a 21

<210> SEQ ID NO 318
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 318 ucaacaaaug gguguccaau a 21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 319 cacuguucug gugcugguua a 21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 320 ggacggcuuc aguuugaagg a 21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 321 cuggacuuca aggaaaaugc a 21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 322 agguauuuaa guuugacacc a 21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323 uuacuucaag ggccugugga a 21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 324 uuuuuggaga caaaucccuu a 21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325 gauugcuggc cguucgcuaa a 21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326 ccgacucuau cgaaaagcca a 21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327 caccauuuac uucaagggcc u 21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328 caagcugggu gccuguaaug a 21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329 acacuauuau cuucaugggc a 21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330 aggaaaaugc agagcaaucc a 21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 331 ucuggugcug guuaacacca u 21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 332 agcccugugg acaucugcac a 21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 333 cuucuucuuu gccaaacuga a 21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 334 ucuccacggc uuuugcuaug a 21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 335 gcaccuggca gauuccaaga a 21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 336 cuucaugggc agaguagcca a 21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 337 cuccaaguua guaucagcca a 21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 338 gguuaacacc auuuacuuca a 21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 339 gguuaacacc auuuacuuca a 21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 340 gguuaacacc auuuacuuca a 21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341 gguuaacacc auuuacuuca a 21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 342 gguuaacacc auuuacuuca a 21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 343 gguuaacacc auuuacuuca a 21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 344 gguuaacacc auuuacuuca a 21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 345 gguuaacacc auuuacuuca a 21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 346 gguuaacacc auuuacuuca a 21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 347 gguuaacacc auuuacuuca a 21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 348 gguuaacacc auuuacuuca a 21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 349 gguuaacacc auuuacuuca a 21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 350 gguuaacacc auuuacuuca a 21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 351 gguuaacacc auuuacuuca a 21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 352 gguuaacacc auuuacuuca a 21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 353 gguuaacacc auuuacuuca a 21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 354 gguuaacacc auuuacuuca a 21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 355 gguuaacacc auuuacuuca a 21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 356 gguuaacacc auuuacuuca a 21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 357 gguuaacacc auuuacuuca a 21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 358 gguuaacacc auuuacuuca a 21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 359 gguuaacacc auuuacuuca a 21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 360 gguuaacacc auuuacuuca a 21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 361 gguuaacacc auuuacuuca a 21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 362 gguuaacacc auuuacuuca a 21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363 gguuaacacc auuuacuuca a 21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364 gguuaacacc auuuacuuca a 21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365 gguuaacacc auuuacuuca a 21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366 gguuaacacc auuuacuuca a 21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367 gguuaacacc auuuacuuca a 21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368 gguuaacacc auuuacuuca a 21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369 gguuaacacc auuuacuuca a 21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370 gguuaacacc auuuacuuca a 21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371 gguuaacacc auuuacuuca a 21

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372 gguuaacacc auuuacuuca a 21

<210> SEQ ID NO 373

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 373 gguuaacacc auuuacuuca a 21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 374 gguuaacacc auuuacuuca a 21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 375 gguuaacacc auuuacuuca a 21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 376 gguuaacacc auuuacuuca a 21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 377 gguuaacacc auuuacuuca a 21

<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 378 gguuaacacc auuuacuuca a 21

<210> SEQ ID NO 379
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 379 gguuaacacc auuuacuuca a 21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380 gguuaacacc auuuacuuca a 21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381 gguuaacacc auuuacuuca a 21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382 gguuaacacc auuuacuuca a 21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383 gguuaacacc auuuacuuca a 21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384 gguuaacacc auuuacuuca a 21

<210> SEQ ID NO 385
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 385 gguuaacacc auuuacuuca a 21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386 gguuaacacc auuuacuuca a 21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387 gguuaacacc auuuacuuca a 21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388 gguuaacacc auuuacuuca a 21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389 gguuaacacc auuuacuuca a 21

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390 gguuaacacc auuuacuuca a 21

<210> SEQ ID NO 391
<211> LENGTH: 21
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 391 gguuaacacc auuuacuuca a 21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392 gguuaacacc auuuacuuca a 21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393 gguuaacacc auuuacuuca a 21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394 gguuaacacc auuuacuuca a 21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395 gguuaacacc auuuacuuca a 21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 396 gguuaacacc auuuacuuca a 21

<210> SEQ ID NO 397
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 397 gguuaacacc auuuacuuca a 21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 398 gguuaacacc auuuacuuca a 21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 399 gguuaacacc auuuacuuca a 21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 400 gguuaacacc auuuacuuca a 21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 401 gguuaacacc auuuacuuca a 21

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 402 gguuaacacc auuuacuuca a 21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 403 gguuaacacc auuuacuuca a 21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404 gguuaacacc auuuacuuca a 21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405 gguuaacacc auuuacuuca a 21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406 gguuaacacc auuuacuuca a 21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407 gguuaacacc auuuacuuca a 21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408 gguuaacacc auuuacuuca a 21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409 gguuaacacc auuuacuuca a 21

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410 gguuaacacc auuuacuuca a 21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411 gguuaacacc auuuacuuca a 21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412 gguuaacacc auuuacuuca a 21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 413 gguuaacacc auuuacuuca a 21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 414 gguuaacacc auuuacuuca a 21

<210> SEQ ID NO 415
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 415 gguuaacacc auuuacuuca a 21

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416 gguuaacacc auuuacuuca a 21

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417 gguuaacacc auuuacuuca a 21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418 gguuaacacc auuuacuuca a 21

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419 gguuaacacc auuuacuuca a 21

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 420 gguuaacacc auuuacuuca a 21

<210> SEQ ID NO 421
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421 gguuaacacc auuuacuuca a 21

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 422 gguuaacacc auuuacuuca a 21

<210> SEQ ID NO 423
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 423 gguuaacacc auuuacuuca a 21

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 424 gguuaacacc auuuacuuca a 21

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 425 gguuaacacc auuuacuuca a 21

<210> SEQ ID NO 426
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426 gguuaacacc auuuacuuca a 21

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427 gguuaacacc auuuacuuca a 21

<210> SEQ ID NO 428
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428 gguuaacacc auuuacuuca a 21

<210> SEQ ID NO 429
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 429 gguuaacacc auuuacuuca a 21

<210> SEQ ID NO 430
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430 gguuaacacc auuuacuuca a 21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431 gguuaacacc auuuacuuca a 21

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 432 gguuaacacc auuuacuuca a 21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 433 gguuaacacc auuuacuuca a 21

<210> SEQ ID NO 434
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 434 gguuaacacc auuuacuuca a 21

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435 gguuaacacc auuuacuuca a 21

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436 gguuaacacc auuuacuuca a 21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 437 gguuaacacc auuuacuuca a 21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438 gguuaacacc auuuacuuca a 21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439 gguuaacacc auuuacuuca a 21

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440 gguuaacacc auuuacuuca a 21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441 gguuaacacc auuuacuuca a 21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442 gguuaacacc auuuacuuca a 21

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443 gguuaacacc auuuacuuca a 21

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 444 gguuaacacc auuuacuuca a 21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 445 gguuaacacc auuuacuuca a 21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 446 gguuaacacc auuuacuuca a 21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 447 gguuaacacc auuuacuuca a 21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 448 gguuaacacc auuuacuuca a 21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 449 gguuaacacc auuuacuuca a 21

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 450 gguuaacacc auuuacuuca a 21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 451 gguuaacacc auuuacuuca a 21

<210> SEQ ID NO 452

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 452 gguuaacacc auuuacuuca a 21

<210> SEQ ID NO 453
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 453 gguuaacacc auuuacuuca a 21

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 454 gguuaacacc auuuacuuca a 21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 455 gguuaacacc auuuacuuca a 21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 456 gguuaacacc auuuacuuca a 21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 457 gguuaacacc auuuacuuca a 21

<210> SEQ ID NO 458
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 458 gguuaacacc auuuacuuca a 21

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 459 gguuaacacc auuuacuuca a 21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 460 gguuaacacc auuuacuuca a 21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 461 gguuaacacc auuuacuuca a 21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 462 gguuaacacc auuuacuuca a 21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 463 gguuaacacc auuuacuuca a 21

<210> SEQ ID NO 464
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 464 gguuaacacc auuuacuuca a 21

<210> SEQ ID NO 465
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465 gguuaacacc auuuacuuca a 21

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466 gguuaacacc auuuacuuca a 21

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467 gguuaacacc auuuacuuca a 21

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468 gguuaacacc auuuacuuca a 21

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469 gguuaacacc auuuacuuca a 21

<210> SEQ ID NO 470
<211> LENGTH: 21
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 470 gguuaacacc auuuacuuca a 21

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 471 gguuaacacc auuuacuuca a 21

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 472 gguuaacacc auuuacuuca a 21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 473 gguuaacacc auuuacuuca a 21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 474 gguuaacacc auuuacuuca a 21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 475 gguuaacauc auuuacuuca a 21

<210> SEQ ID NO 476
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 476 gguuaacaac auuuacuuca a 21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477 gguuaacacu auuuacuuca a 21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478 gguuaacaca auuuacuuca a 21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479 gguuaacacc auuuacuuca a 21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 480 gguuaacacc auuuacuuca a 21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 481 gguuaacacc auuuacuuca a 21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 482 gguuaacacc auuuacuuca a 21

<210> SEQ ID NO 483
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 483 uuaacaccau uuacuucaa 19

<210> SEQ ID NO 484
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 484 uuaacaccau uuacuucaa 19

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 485 uuaacaccau uuacuucaa 19

<210> SEQ ID NO 486
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 486 uuaacaccau uuacuucaa 19

<210> SEQ ID NO 487
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487 aacaccauuu acuucaa 17

<210> SEQ ID NO 488
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 488 aacaccauuu acuucaa 17

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 489 gguuaacacc auuuacuuca a 21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 490 gguuaacacc auuuacuuca a 21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 491 gguuaacacc auuuacuuca a 21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 492 gguuaacacc auuuacuuca a 21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 493 gguuaacacc auuuacuuca a 21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 494 gguuaacacc auuuacuuca a 21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 495 gguuaacacc auuuacuuca a 21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 496 gguuaacacc auuuacuuca a 21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 497 gguuaacacc auuuacuuca a 21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 498 gguuaacacc auuuacuuca a 21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 499 gguuaacacc auuuacuuca a 21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 500 gguuaacacc auuuacuuca a 21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 501 gguuaacacc auuuacuuca a 21

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 502 gguuaacacc auuuacuuca a 21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 503 gguuaacacc auuuacuuca a 21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 504 gguuaacacc auuuacutca a 21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 505 gguuaacacc auuuacutca a 21

<210> SEQ ID NO 506
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 506 ggutaacacc auuuacutca a 21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 507 ggutaacacc auuuacutca a 21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 508 ggutaacacc auutacutca a 21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 509 ggutaacacc atutacutca a 21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 510 ggutaacacc atutacutca a 21

<210> SEQ ID NO 511
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 511 uuuguuggcu uuucgauagt t 21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 512 uuuguuggcu uuucgauagt t 21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 513 uuuguuggcu uuucgauagt t 21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 514 uuuguuggcu uuucgauagt t 21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 515 uuuguuggcu uuucgauagt t 21

<210> SEQ ID NO 516
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 516 uuuguuggcu uuucgauagt t 21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 517 uuuguuggcu uuucgauagt t 21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 518 uuuguuggcu uuucgauagt t 21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 519 uuuguuggcu uuucgauagt t 21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 520 uuuguuggcu uuucgauagt t 21

<210> SEQ ID NO 521

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 521 uuuguuggcu uuucgauagt t 21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 522 uuuguuggcu uuucgauagt t 21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 523 uuuguuggcu uuucgauagt t 21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 524 augcacaugg gauucauggt t 21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 525 augcacaugg gauucauggt t 21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 526 augcacaugg gauucauggt t 21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 527 augcacaugg gauucauggt t 21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 528 augcacaugg gauucauggt t 21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 529 augcacaugg gauucauggt t 21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 530 augcacaugg gauucauggt t 21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 531 augcacaugg gauucauggt t 21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 532 augcacaugg gauucauggt t 21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 533 augcacaugg gauucauggt t 21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 534 augcacaugg gauucauggt t 21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 535 augcacaugg gauucauggt t 21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 536 augcacaugg gauucauggt t 21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 537 uuuucgauag agucggcagt t 21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 538 uuuucgauag agucggcagt t 21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 539 uuuucgauag agucggcagt t 21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 540 uuuucgauag agucggcagt t 21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 541 uuuucgauag agucggcagt t 21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 542 uuuucgauag agucggcagt t 21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 543 uuuucgauag agucggcagt t 21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 544 uuuucgauag agucggcagt t 21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 545 uuuucgauag agucggcagt t 21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 546 uuuucgauag agucggcagt t 21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 547 uuuucgauag agucggcagt t 21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 548 uuuucgauag agucggcagt t 21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 549 uuuucgauag agucggcagt t 21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 550 uucaguuugg caaagaagat t 21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 551 uucaguuugg caaagaagat t 21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 552 uucaguuugg caaagaagat t 21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 553 uucaguuugg caaagaagat t 21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 554 uucaguuugg caaagaagat t 21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 555 uucaguuugg caaagaagat t 21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 556 uucaguuugg caaagaagat t 21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 557 uucaguuugg caaagaagat t 21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 558 uucaguuugg caaagaagat t 21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 559 uucaguuugg caaagaagat t 21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 560 uucaguuugg caaagaagat t 21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 561 uucaguuugg caaagaagat t 21

<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562 uugaaguaaa ugguguuaac cag 23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563 aaaggcgauu ggcugauacu aac 23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564 auagaaagug guagcaaagc ggg 23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565 ugauagaaag ugguagcaaa gcg 23

<210> SEQ ID NO 566
<211> LENGTH: 23
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 566 aggauuuguu ggcuuuucga uag 23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 567 augcacaugg gauucauggg aau 23

<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 568 uuuaccucaa gaaaugccuu aug 23

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 569 uuaaauaccu ccaucaguug cug 23

<210> SEQ ID NO 570
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 570 agauauggug ucaaacuuaa aua 23

<210> SEQ ID NO 571
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 571 aaaugcacau gggauucaug gga 23

<210> SEQ ID NO 572
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 572 aguaaauggu guuaaccagc acc 23

<210> SEQ ID NO 573
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 573 auuuguuggc uuuucgauag agu 23

<210> SEQ ID NO 574
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 574 aaagugguag caaagcggga auu 23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 575 ucaaacuuaa auaccuccau cag 23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 576 uugaagguaa gggauuuguc ucc 23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 577 ugcugauaga aagugguagc aaa 23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 578 uuccuaucac auuggaauac aug 23

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 579 uuuucgauag agucggcagu uca 23

<210> SEQ ID NO 580
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 580 uggcuuuucg auagagucgg cag 23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 581 auaugguguc aaacuuaaau acc 23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 582 ugaacagauc gacaaggccc aug 23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 583 ucauugaagg uaagggauuu guc 23

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 584 aacaauaccu gggaguuugg acu 23

<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 585 uuucgauaga gucggcaguu cag 23

<210> SEQ ID NO 586
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 586 uauuggacac ccauuuguug aug 23

<210> SEQ ID NO 587
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 587 uuaaccagca ccagaacagu gag 23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 588 uccuucaaac ugaagccguc cuc 23

<210> SEQ ID NO 589
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 589 ugcauuuucc uugaagucca ggg 23

<210> SEQ ID NO 590
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 590 uggugucaaa cuuaaauacc ucc 23

<210> SEQ ID NO 591
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 591 uuccacaggc ccuugaagua aau 23

<210> SEQ ID NO 592
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 592 uaagggauuu gucuccaaaa agg 23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 593 uuuagcgaac ggccagcaau cac 23

<210> SEQ ID NO 594
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 594 uuggcuuuuc gauagagucg gca 23

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 595 aggcccuuga aguaaauggu guu 23

<210> SEQ ID NO 596
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 596 ucauuacagg cacccagcuu ggu 23

<210> SEQ ID NO 597
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 597 ugcccaugaa gauaauagug uuc 23

<210> SEQ ID NO 598
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 598 uggauugcuc ugcauuuucc uug 23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 599 augguguuaa ccagcaccag aac 23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 600 ugugcagaug uccacagggc ucc 23

<210> SEQ ID NO 601
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 601 uucaguuugg caaagaagaa gug 23

<210> SEQ ID NO 602
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 602 ucauagcaaa agccguggag aua 23

<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 603 uucuuggaau cugccaggug cug 23

<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 604 uuggcuacuc ugcccaugaa gau 23

<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 605 uuggcugaua cuaacuugga gga 23

<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 606 uugaaguaaa ugguguuaac cag 23

<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 607 uugaaguaaa ugguguuaac cag 23

<210> SEQ ID NO 608
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 608 uugaaguaaa ugguguuaac cag 23

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 609 uugaaguaaa ugguguuaac cag 23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 610 uugaaguaaa ugguguuaac cag 23

<210> SEQ ID NO 611
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 611 uugaaguaaa ugguguuaac cag 23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 612 uugaaguaaa ugguguuaac cag 23

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 613 uugaaguaaa ugguguuaac cag 23

<210> SEQ ID NO 614
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 614 uugaaguaaa ugguguuaac cag 23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 615 uugaaguaaa ugguguuaac cag 23

<210> SEQ ID NO 616
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 616 uugaaguaaa ugguguuaac cag 23

<210> SEQ ID NO 617
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 617 uugaaguaaa ugguguuaac cag 23

<210> SEQ ID NO 618
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 618 uugaaguaaa ugguguuaac cag 23

<210> SEQ ID NO 619
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 619 uugaaguaaa ugguguuaac cag 23

<210> SEQ ID NO 620
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 620 uugaaguaaa ugguguuaac cag 23

<210> SEQ ID NO 621
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 621 uugaaguaaa ugguguuaac cag 23

<210> SEQ ID NO 622
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 622 uugaaguaaa ugguguuaac cag 23

<210> SEQ ID NO 623
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 623 uugaaguaaa ugguguuaac cag 23

<210> SEQ ID NO 624
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 624 uugaaguaaa ugguguuaac cag 23

<210> SEQ ID NO 625
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 625 uugaaguaaa ugguguuaac cag 23

<210> SEQ ID NO 626
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 626 uugaaguaaa ugguguuaac cag 23

<210> SEQ ID NO 627

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 627 uugaaguaaa ugguguuaac cag 23

<210> SEQ ID NO 628
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 628 uugaaguaaa ugguguuaac cag 23

<210> SEQ ID NO 629
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 629 uugaaguaaa ugguguuaac cag 23

<210> SEQ ID NO 630
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 630 uugaaguaaa ugguguuaac cag 23

<210> SEQ ID NO 631
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 631 uugaaguaaa ugguguuaac cag 23

<210> SEQ ID NO 632
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 632 uugaaguaaa ugguguuaac cag 23

<210> SEQ ID NO 633
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 633 uugaaguaaa ugguguuaac cag 23

<210> SEQ ID NO 634
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 634 uugaaguaaa ugguguuaac cag 23

<210> SEQ ID NO 635
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 635 uugaaguaaa ugguguuaac cag 23

<210> SEQ ID NO 636
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 636 uugaaguaaa ugguguuaac cag 23

<210> SEQ ID NO 637
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 637 uugaaguaaa ugguguuaac cag 23

<210> SEQ ID NO 638
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 638 uugaaguaaa ugguguuaac cag 23

<210> SEQ ID NO 639
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 639 uugaaguaaa ugguguuaac cag 23

<210> SEQ ID NO 640
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 640 uugaaguaaa ugguguuaac cag 23

<210> SEQ ID NO 641
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 641 uugaaguaaa ugguguuaac cag 23

<210> SEQ ID NO 642
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 642 uugaaguaaa ugguguuaac cag 23

<210> SEQ ID NO 643
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 643 uugaaguaaa ugguguuaac cag 23

<210> SEQ ID NO 644
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 644 uugaaguaaa ugguguuaac cag 23

<210> SEQ ID NO 645
<211> LENGTH: 23
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 645 uugaaguaaa ugguguuaac cag 23

<210> SEQ ID NO 646
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646 uugaaguaaa ugguguuaac cag 23

<210> SEQ ID NO 647
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 647 uugaaguaaa ugguguuaac cag 23

<210> SEQ ID NO 648
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 648 uugaaguaaa ugguguuaac cag 23

<210> SEQ ID NO 649
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 649 uugaaguaaa ugguguuaac cag 23

<210> SEQ ID NO 650
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 650 uugaaguaaa ugguguuaac cag 23

<210> SEQ ID NO 651
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 651 uugaaguaaa ugguguuaac cag 23

<210> SEQ ID NO 652
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 652 uugaaguaaa ugguguuaac cag 23

<210> SEQ ID NO 653
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 653 uugaaguaaa ugguguuaac cag 23

<210> SEQ ID NO 654
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 654 uugaaguaaa ugguguuaac cag 23

<210> SEQ ID NO 655
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 655 uugaaguaaa ugguguuaac cag 23

<210> SEQ ID NO 656
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 656 uugaaguaaa ugguguuaac cag 23

<210> SEQ ID NO 657
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 657 uugaaguaaa ugguguuaac cag 23

<210> SEQ ID NO 658
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 658 uugaaguaaa ugguguuaac cag 23

<210> SEQ ID NO 659
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 659 uugaaguaaa ugguguuaac cag 23

<210> SEQ ID NO 660
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 660 uugaaguaaa ugguguuaac cag 23

<210> SEQ ID NO 661
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 661 uugaaguaaa ugguguuaac cag 23

<210> SEQ ID NO 662
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 662 uugaaguaaa ugguguuaac cag 23

<210> SEQ ID NO 663
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 663 uugaaguaaa ugguguuaac cag 23

<210> SEQ ID NO 664
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 664 uugaaguaaa ugguguuaac cag 23

<210> SEQ ID NO 665
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 665 uugaaguaaa ugguguuaac cag 23

<210> SEQ ID NO 666
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 666 uugaaguaaa ugguguuaac cag 23

<210> SEQ ID NO 667
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 667 uugaaguaaa ugguguuaac cag 23

<210> SEQ ID NO 668
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 668 uugaaguaaa ugguguuaac cag 23

<210> SEQ ID NO 669
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 669 uugaaguaaa ugguguuaac cag 23

<210> SEQ ID NO 670
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 670 uugaaguaaa ugguguuaac cag 23

<210> SEQ ID NO 671
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 671 uugaaguaaa ugguguuaac cag 23

<210> SEQ ID NO 672
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 672 uugaaguaaa ugguguuaac cag 23

<210> SEQ ID NO 673
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 673 uugaaguaaa ugguguuaac cag 23

<210> SEQ ID NO 674
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 674 uugaaguaaa ugguguuaac cag 23

<210> SEQ ID NO 675
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 675 uugaaguaaa ugguguuaac cag 23

<210> SEQ ID NO 676
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 676 uugaaguaaa ugguguuaac cag 23

<210> SEQ ID NO 677
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 677 uugaaguaaa ugguguuaac cag 23

<210> SEQ ID NO 678
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 678 uugaaguaaa ugguguuaac cag 23

<210> SEQ ID NO 679
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 679 uugaaguaaa ugguguuaac cag 23

<210> SEQ ID NO 680
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 680 uugaaguaaa ugguguuaac cag 23

<210> SEQ ID NO 681
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 681 uugaaguaaa ugguguuaac cag 23

<210> SEQ ID NO 682
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682 uugaaguaaa ugguguuaac cag 23

<210> SEQ ID NO 683
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 683 uugaaguaaa ugguguuaac cag 23

<210> SEQ ID NO 684
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 684 uugaaguaaa ugguguuaac cag 23

<210> SEQ ID NO 685
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 685 uugaaguaaa ugguguuaac cag 23

<210> SEQ ID NO 686
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 686 uugaaguaaa ugguguuaac cag 23

<210> SEQ ID NO 687
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 687 uugaaguaaa ugguguuaac cag 23

<210> SEQ ID NO 688
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 688 uugaaguaaa ugguguuaac cag 23

<210> SEQ ID NO 689
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 689 uugaaguaaa ugguguuaac cag 23

<210> SEQ ID NO 690
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 690 uugaaguaaa ugguguuaac cag 23

<210> SEQ ID NO 691
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 691 uugaaguaaa ugguguuaac cag 23

<210> SEQ ID NO 692
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 692 uugaaguaaa ugguguuaac cag 23

<210> SEQ ID NO 693
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 693 uugaaguaaa ugguguuaac cag 23

<210> SEQ ID NO 694
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 694 uugaaguaaa ugguguuaac cag 23

<210> SEQ ID NO 695
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 695 uugaaguaaa ugguguuaac cag 23

<210> SEQ ID NO 696
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 696 uugaaguaaa ugguguuaac cag 23

<210> SEQ ID NO 697
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 697 uugaaguaaa ugguguuaac cag 23

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 698 uugaaguaaa ugguguuaac cag 23

<210> SEQ ID NO 699
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 699 uugaaguaaa ugguguuaac cag 23

<210> SEQ ID NO 700
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 700 uugaaguaaa ugguguuaac cag 23

<210> SEQ ID NO 701
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 701 uugaaguaaa ugguguuaac cag 23

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 702 uugaaguaaa ugguguuaac cag 23

<210> SEQ ID NO 703
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 703 uugaaguaaa ugguguuaac cag 23

<210> SEQ ID NO 704
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 704 uugaaguaaa ugguguuaac cag 23

<210> SEQ ID NO 705
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 705 uugaaguaaa ugguguuaac cag 23

<210> SEQ ID NO 706

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 706 uugaaguaaa ugguguuaac cag 23

<210> SEQ ID NO 707
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 707 uugaaguaaa ugguguuaac cag 23

<210> SEQ ID NO 708
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 708 uugaaguaaa ugguguuaac cag 23

<210> SEQ ID NO 709
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 709 uugaaguaaa ugguguuaac cag 23

<210> SEQ ID NO 710
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710 uugaaguaaa ugguguuaac cag 23

<210> SEQ ID NO 711
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 711 uugaaguaaa ugguguuaac cag 23

<210> SEQ ID NO 712
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712 uugaaguaaa ugguguuaac cag 23

<210> SEQ ID NO 713
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 713 uugaaguaaa ugguguuaac cag 23

<210> SEQ ID NO 714
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714 uugaaguaaa ugguguuaac cag 23

<210> SEQ ID NO 715
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 715 uugaaguaaa ugguguuaac cag 23

<210> SEQ ID NO 716
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716 uugaaguaaa ugguguuaac cag 23

<210> SEQ ID NO 717
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717 uugaaguaaa ugguguuaac cag 23

<210> SEQ ID NO 718
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 718 uugaaguaaa ugguguuaac cag 23

<210> SEQ ID NO 719
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719 uugaaguaaa ugguguuaac cag 23

<210> SEQ ID NO 720
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720 uugaaguaaa ugguguuaac cag 23

<210> SEQ ID NO 721
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721 uugaaguaaa ugguguuaac cag 23

<210> SEQ ID NO 722
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 722 uugaaguaaa ugguguuaac cag 23

<210> SEQ ID NO 723
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 723 uugaaguaaa ugguguuaac cag 23

<210> SEQ ID NO 724
<211> LENGTH: 23
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 724 uugaaguaaa ugguguuaac cag 23

<210> SEQ ID NO 725
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 725 uugaaguaaa ugguguuaac cag 23

<210> SEQ ID NO 726
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 726 uugaaguaaa ugguguuaac cag 23

<210> SEQ ID NO 727
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 727 uugaaguaaa ugguguuaac cag 23

<210> SEQ ID NO 728
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 728 uugaaguaaa ugguguuaac cag 23

<210> SEQ ID NO 729
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 729 uugaaguaaa ugguguuaac cag 23

<210> SEQ ID NO 730
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 730 uugaaguaaa ugguguuaac cag 23

<210> SEQ ID NO 731
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 731 uugaaguaaa ugguguuaac cag 23

<210> SEQ ID NO 732
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 732 uugaaguaaa ugguguuaac cag 23

<210> SEQ ID NO 733
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 733 uugaaguaaa ugguguuaac cag 23

<210> SEQ ID NO 734
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 734 uugaaguaaa ugguguuaac cag 23

<210> SEQ ID NO 735
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 735 uugaaguaaa ugguguuaac cag 23

<210> SEQ ID NO 736
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736 uugaaguaaa ugguguuaac cag 23

<210> SEQ ID NO 737
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 737 uugaaguaaa ugguguuaac cag 23

<210> SEQ ID NO 738
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 738 uugaaguaaa ugguguuaac cag 23

<210> SEQ ID NO 739
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 739 uugaaguaaa ugguguuaac cag 23

<210> SEQ ID NO 740
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 740 uugaaguaaa ugguguuaac cag 23

<210> SEQ ID NO 741
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 741 uugaaguaaa ugguguuaac cag 23

<210> SEQ ID NO 742
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 742 uugaaguaaa ugguguuaac cag 23

<210> SEQ ID NO 743
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 743 uugaaguaaa ugguguuaac cag 23

<210> SEQ ID NO 744
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 744 uugaaguaaa ugguguuaac cag 23

<210> SEQ ID NO 745
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 745 uugaaguaaa ugguguuaac cag 23

<210> SEQ ID NO 746
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 746 uugaaguaaa ugguguuaac cag 23

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 747 uugaaguaaa ugguguuaac c 21

<210> SEQ ID NO 748
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 748 uugaaguaaa ugguguuaac c 21

<210> SEQ ID NO 749
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 749 uugaaguaaa ugguguuaac c 21

<210> SEQ ID NO 750
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 750 uugaaguaaa ugguguuaac c 21

<210> SEQ ID NO 751
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 751 uugaaguaaa ugguguuaac c 21

<210> SEQ ID NO 752
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 752 uugaaguaaa ugguguuaa 19

<210> SEQ ID NO 753
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 753 uugaaguaaa ugguguuaa 19

<210> SEQ ID NO 754
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 754 uugaaguaaa ugguguuaa 19

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 755 uugaaguaaa ugguguuaa 19

<210> SEQ ID NO 756
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 756 uugaaguaaa ugguguuaa 19

<210> SEQ ID NO 757
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757 uugaaguaaa ugguguuaac cag 23

<210> SEQ ID NO 758
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758 uugaaguaaa ugguguuaac cag 23

<210> SEQ ID NO 759
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759 uugaaguaaa ugguguuaac cag 23

<210> SEQ ID NO 760
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760 uugaaguaaa ugguguuaac cag 23

<210> SEQ ID NO 761
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761 uugaaguaaa ugguguuaac cag 23

<210> SEQ ID NO 762
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 762 uugaaguaaa uggtguuaac cag 23

<210> SEQ ID NO 763
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 763 uugaaguaaa ugguguuaac cag 23

<210> SEQ ID NO 764
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 764 uugaaguaaa uggugtuaac cag 23

<210> SEQ ID NO 765
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 765 uugaaguaaa uggugutaac cag 23

<210> SEQ ID NO 766
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 766 uugaaguaaa ugguguuaac cag 23

<210> SEQ ID NO 767
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 767 uugaaguaaa ugguguuaac cag 23

<210> SEQ ID NO 768
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 768 uugaaguaaa ugguguuaac cag 23

<210> SEQ ID NO 769
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 769 uugaaguaaa ugguguuaac cag 23

<210> SEQ ID NO 770
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 770 uugaaguaaa ugguguuaac cag 23

<210> SEQ ID NO 771
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 771 uugaaguaaa tgguguuaa 19

<210> SEQ ID NO 772
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 772 uugaaguaaa ugguguuaac cag 23

<210> SEQ ID NO 773
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 773 uugaaguaaa ugguguuaac cag 23

<210> SEQ ID NO 774
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 774 uugaaguaaa ugguguuaac cag 23

<210> SEQ ID NO 775
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 775 uugaaguaaa ugguguuaac cag 23

<210> SEQ ID NO 776
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 776 uugaaguaaa ugguguuaac cag 23

<210> SEQ ID NO 777
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 777 uugaaguaaa ugguguuaac cag 23

<210> SEQ ID NO 778

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 778 uugaaguaaa ugguguuaac cag 23

<210> SEQ ID NO 779
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 779 gguuaacacc auuuacuuca a 21

<210> SEQ ID NO 780
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 780 gguuaacacc auuuacuuca a 21

<210> SEQ ID NO 781
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 781 gguuaacacc auuuacuuca a 21

<210> SEQ ID NO 782
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 782 gguuaacacc auuuacuuca a 21

<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 783 gguuaacacc auuuacuuca a 21

<210> SEQ ID NO 784
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 784 gguuaacacc auuuacuuca a 21

<210> SEQ ID NO 785
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 785 gguuaacacc auuuacuuca a 21

<210> SEQ ID NO 786
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 786 gguuaacacc auuuacuuca a 21

<210> SEQ ID NO 787
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 787 gguuaacacc auuuacuuca a 21

<210> SEQ ID NO 788
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 788 gguuaacacc auuuacuuca a 21

<210> SEQ ID NO 789
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 789 gguuaacacc auuuacuuca a 21

<210> SEQ ID NO 790
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 790 gguuaacacc auuuacuuca a 21

<210> SEQ ID NO 791
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 791 gguuaacacc auuuacuuca a 21

<210> SEQ ID NO 792
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 792 gguuaacacc auuuacuuca a 21

<210> SEQ ID NO 793
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 793 gguuaacacc auuuacuuca a 21

<210> SEQ ID NO 794
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 794 gguuaacacc auuuacuuca a 21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 795 ggutaacacc auuuacutca a 21

<210> SEQ ID NO 796

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 796 ggutaacacc auutacutca a 21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 797 ggutaacacc auuuacutca a 21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 798 ggutaacacc auutacutca a 21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 799 ggutaacacc auuuacutca a 21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 800 gguuaacacc auuuacutca a 21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 801 ggutaacacc auuuacutca a 21

<210> SEQ ID NO 802
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 802 gguuaacacc auuuacuuca a 21

<210> SEQ ID NO 803
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 803 gguuaacacc auuuacuuca a 21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 804 gguuaacacc auuuacutca a 21

<210> SEQ ID NO 805
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 805 gguuaacacc auuuacuuca a 21

<210> SEQ ID NO 806
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 806 gguuaacacc auuuacuuca a 21

<210> SEQ ID NO 807
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 807 gguuaacacc auuuacuuca a 21

<210> SEQ ID NO 808
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 808 gguuaacacc auuuacuuca a 21

<210> SEQ ID NO 809
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 809 uugaaguaaa ugguguuaac cag 23

<210> SEQ ID NO 810
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 810 uugaaguaaa ugguguuaac cag 23

<210> SEQ ID NO 811
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 811 uugaaguaaa ugguguuaac cag 23

<210> SEQ ID NO 812
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 812 uugaaguaaa ugguguuaac cag 23

<210> SEQ ID NO 813
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 813 uugaaguaaa ugguguuaac cag 23

<210> SEQ ID NO 814
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 814 uugaaguaaa ugguguuaac cag 23

<210> SEQ ID NO 815
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 815 uugaaguaaa ugguguuaac cag 23

<210> SEQ ID NO 816
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 816 uugaaguaaa ugguguuaac cag 23

<210> SEQ ID NO 817
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 817 uugaaguaaa ugguguuaac cag 23

<210> SEQ ID NO 818
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 818 uugaaguaaa ugguguuaac cag 23

<210> SEQ ID NO 819
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 819 uugaaguaaa ugguguuaac cag 23

<210> SEQ ID NO 820
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 820 uugaaguaaa ugguguuaac cag 23

<210> SEQ ID NO 821
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 821 uugaaguaaa ugguguuaac cag 23

<210> SEQ ID NO 822
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 822 uugaaguaaa ugguguuaac cag 23

<210> SEQ ID NO 823
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 823 uugaaguaaa ugguguuaac c 21

<210> SEQ ID NO 824
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 824 uugaaguaaa ugguguuaac cag 23

<210> SEQ ID NO 825
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 825 uugaaguaaa ugguguuaac cag 23

<210> SEQ ID NO 826
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 826 uugaaguaaa ugguguuaac cag 23

<210> SEQ ID NO 827
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 827 uugaaguaaa ugguguuaac cag 23

<210> SEQ ID NO 828
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 828 uugaaguaaa ugguguuaac cag 23

<210> SEQ ID NO 829
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829 uugaaguaaa ugguguuaac cag 23

<210> SEQ ID NO 830
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830 uugaaguaaa ugguguuaac cag 23

<210> SEQ ID NO 831
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831 uugaaguaaa ugguguuaac cag 23

<210> SEQ ID NO 832
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 832 uugaaguaaa ugguguuaac cag 23

<210> SEQ ID NO 833
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 833 uugaaguaaa ugguguuaac cag 23

<210> SEQ ID NO 834
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 834 uugaaguaaa ugguguuaac cag 23

<210> SEQ ID NO 835
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 835 uugaaguaaa ugguguuaac cag 23

<210> SEQ ID NO 836
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 836 uugaaguaaa ugguguuaac cag 23

<210> SEQ ID NO 837
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 837 uugaaguaaa ugguguuaac cag 23

<210> SEQ ID NO 838
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 838 uugaaguaaa ugguguuaac cag 23

<210> SEQ ID NO 839
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 839 gguuaacacc auuuacuuca a 21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 840 gguuaacacc auuuacutca a 21

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 841 ggutaacacc auutacutca a 21

<210> SEQ ID NO 842
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 842 gguuaacacc auuuacuuca a 21

<210> SEQ ID NO 843
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 843 gguuaacacc auuuacuuca a 21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 844 ggutaacacc auuuacutca a 21

<210> SEQ ID NO 845
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 845 gguuaacacc auuuacuuca a 21

<210> SEQ ID NO 846
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 846 gguuaacacc auuuacuuca a 21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 847 ggutaacacc auutacutca a 21

<210> SEQ ID NO 848
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 848 gguuaacacc auuuacuuca a 21

<210> SEQ ID NO 849
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 849 gguuaacacc auuuacuuca a 21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 850 ggutaacacc auuuacutca a 21

<210> SEQ ID NO 851
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 851 gguuaacacc auuuacuuca a 21

<210> SEQ ID NO 852
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 852 gguuaacacc auuuacuuca a 21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 853 gguuaacacc auuuacutca a 21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 854 ggutaacacc auuuacutca a 21

<210> SEQ ID NO 855
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 855 gguuaacacc auuuacuuca a 21

<210> SEQ ID NO 856
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 856 gguuaacacc auuuacuuca a 21

<210> SEQ ID NO 857
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 857 gguuaacacc auuuacuuca a 21

<210> SEQ ID NO 858
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 858 gguuaacacc auuuacuuca a 21

<210> SEQ ID NO 859
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 859 gguuaacacc auuuacuuca a 21

<210> SEQ ID NO 860
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 860 gguuaacacc auuuacuuca a 21

<210> SEQ ID NO 861
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 861 gguuaacacc auuuacuuca a 21

<210> SEQ ID NO 862
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 862 gguuaacacc auuuacuuca a 21

<210> SEQ ID NO 863
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 863 gguuaacacc auuuacuuca a 21

<210> SEQ ID NO 864
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 864 gguuaacacc auuuacuuca a 21

<210> SEQ ID NO 865
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 865 gguuaacacc auuuacuuca a 21

<210> SEQ ID NO 866
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 866 gguuaacacc auuuacuuca a 21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 867 ggutaacacc auuuacutca a 21

<210> SEQ ID NO 868
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 868 gguuaacacc auuuacuuca a 21

<210> SEQ ID NO 869
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 869 uugaaguaaa ugguguuaac cag 23

<210> SEQ ID NO 870
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 870 uugaaguaaa ugguguuaac cag 23

<210> SEQ ID NO 871
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 871 uugaaguaaa ugguguuaac cag 23

<210> SEQ ID NO 872
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 872 uugaaguaaa ugguguuaac cag 23

<210> SEQ ID NO 873
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 873 uugaaguaaa ugguguuaac cag 23

<210> SEQ ID NO 874
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 874 uugaaguaaa ugguguuaac cag 23

<210> SEQ ID NO 875
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 875 uugaaguaaa ugguguuaac cag 23

<210> SEQ ID NO 876
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 876 uugaaguaaa ugguguuaac cag 23

<210> SEQ ID NO 877
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 877 uugaaguaaa ugguguuaac cag 23

<210> SEQ ID NO 878
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 878 uugaaguaaa ugguguuaac cag 23

<210> SEQ ID NO 879
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 879 uugaaguaaa ugguguuaac cag 23

<210> SEQ ID NO 880
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 880 uugaaguaaa ugguguuaac cag 23

<210> SEQ ID NO 881
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 881 uugaaguaaa ugguguuaac cag 23

<210> SEQ ID NO 882
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 882 uugaaguaaa ugguguuaac cag 23

<210> SEQ ID NO 883
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 883 uugaaguaaa ugguguuaac cag 23

<210> SEQ ID NO 884
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 884 uugaaguaaa ugguguuaac cag 23

<210> SEQ ID NO 885
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 885 uugaaguaaa ugguguuaac cag 23

<210> SEQ ID NO 886
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 886 uugaaguaaa ugguguuaac cag 23

<210> SEQ ID NO 887
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 887 uugaaguaaa ugguguuaac cag 23

<210> SEQ ID NO 888
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 888 uugaaguaaa ugguguuaac cag 23

<210> SEQ ID NO 889
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 889 uugaaguaaa ugguguuaac cag 23

<210> SEQ ID NO 890
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 890 uugaaguaaa ugguguuaac cag 23

<210> SEQ ID NO 891
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 891 uugaaguaaa ugguguuaac cag 23

<210> SEQ ID NO 892
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 892 uugaaguaaa ugguguuaac cag 23

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 893 uugaaguaaa ugguguuaac cag 23

<210> SEQ ID NO 894
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 894 uugaaguaaa ugguguuaac cag 23

<210> SEQ ID NO 895
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 895 uugaaguaaa ugguguuaac cag 23

<210> SEQ ID NO 896
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 896 uugaaguaaa ugguguuaac c 21

<210> SEQ ID NO 897
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 897 uugaaguaaa ugguguuaac cag 23

<210> SEQ ID NO 898
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 898 uugaaguaaa ugguguuaac cag 23

<210> SEQ ID NO 899
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 899 gguuaacacc auuuacuuca a 21

<210> SEQ ID NO 900
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 900 gguuaacacc auuuacuuca a 21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 901 ggutaacacc auutacutca a 21

<210> SEQ ID NO 902
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 902 gguuaacacc auuuacuuca a 21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 903 gguuaacacc auuuacutca a 21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 904 ggutaacacc auuuacutca a 21

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 905 ggutaacacc auutacutca a 21

<210> SEQ ID NO 906
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906 gguuaacacc auuuacuuca a 21

<210> SEQ ID NO 907
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 907 ggutaacacc auuuacutca a 21

<210> SEQ ID NO 908
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 908 gguuaacacc auuuacuuca a 21

<210> SEQ ID NO 909
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 909 gguuaacacc auuuacuuca a 21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 910 ggutaacacc auuuacutca a 21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 911 gguuaacacc auuuacutca a 21

<210> SEQ ID NO 912
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 912 guuaacacca uuuacuucaa 20

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 913 gguuaacacc auutacuuca a 21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 914 ggutaacacc auutacutca a 21

<210> SEQ ID NO 915
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 915 aacugccgac ucuaucgaaa a 21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 916 gguuaacacc autuactuca a 21

<210> SEQ ID NO 917
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 917 guuaacacca uuuacuucaa 20

<210> SEQ ID NO 918
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 918 gguuaacacc auuuacuuca a 21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 919 ggutaacacc auuuacutca a 21

<210> SEQ ID NO 920
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 920 uugaaguaaa ugguguuaac cag 23

<210> SEQ ID NO 921
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 921 uugaaguaaa ugguguuaac cag 23

<210> SEQ ID NO 922
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 922 uugaaguaaa ugguguuaac cag 23

<210> SEQ ID NO 923
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 923 uugaaguaaa ugguguuaac cag 23

<210> SEQ ID NO 924
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 924 uugaaguaaa ugguguuaac cag 23

<210> SEQ ID NO 925
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 925 uugaaguaaa ugguguuaac cag 23

<210> SEQ ID NO 926
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 926 uugaaguaaa ugguguuaac cag 23

<210> SEQ ID NO 927
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 927 uugaaguaaa ugguguuaac cag 23

<210> SEQ ID NO 928
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 928 uugaaguaaa ugguguuaac cag 23

<210> SEQ ID NO 929
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 929 uugaaguaaa ugguguuaac cag 23

<210> SEQ ID NO 930
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 930 uugaaguaaa ugguguuaac cag 23

<210> SEQ ID NO 931
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 931 uugaaguaaa ugguguuaac cag 23

<210> SEQ ID NO 932
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 932 uugaaguaaa ugguguuaac cag 23

<210> SEQ ID NO 933
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 933 uugaaguaaa ugguguuaac ca 22

<210> SEQ ID NO 934
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 934 utgaagtaaa uggtguuaac cag 23

<210> SEQ ID NO 935
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 935 uugaaguaaa ugguguuaac cag 23

<210> SEQ ID NO 936
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 936 uuuucgauag agucggcagu uca 23

<210> SEQ ID NO 937
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 937 utgaagtaaa uggtguuaac cag 23

<210> SEQ ID NO 938
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 938 uugaaguaaa ugguguuaac ca 22

<210> SEQ ID NO 939
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 939 uugaaguaaa ugguguuaac cag 23

<210> SEQ ID NO 940
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 940 uugaaguaaa ugguguuaac cag 23

<210> SEQ ID NO 941
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 941 gguuaacacc auuuacuuca a 21

<210> SEQ ID NO 942
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 942 gguuaacacc auuuacuuca a 21

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 943 gguuaacacc auuuacuuca a 21

<210> SEQ ID NO 944
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 944 gguuaacacc auuuacuuca a 21

<210> SEQ ID NO 945
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 945 gguuaacacc auuuacuuca a 21

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 946 gguuaacacc auuuacuuca a 21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 947 ggutaacacc auutacutca a 21

<210> SEQ ID NO 948
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948 gguuaacacc auuuacuuca a 21

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 949 gguuaacacc auuuacuuca a 21

<210> SEQ ID NO 950
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 950 gguuaacacc auuuacuuca a 21

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 951 gguuaacacc auuuacuuca a 21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 952 gguuaacacc auuuacuuca a 21

<210> SEQ ID NO 953
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953 gguuaacacc auuuacuuca a 21

<210> SEQ ID NO 954
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 954 ggutaacacc auutacutca a 21

<210> SEQ ID NO 955
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 955 gguuaacacc auuuacuuca a 21

<210> SEQ ID NO 956
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 956 gguuaacacc auuuacuuca a 21

<210> SEQ ID NO 957
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 957 gguuaacacc auuuacuuca a 21

<210> SEQ ID NO 958
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 958 gguuaacacc auuuacuuca a 21

<210> SEQ ID NO 959
<211> LENGTH: 21
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 959 gguuaacacc auuuacuuca a 21

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 960 uugaaguaaa ugguguuaac cag 23

<210> SEQ ID NO 961
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 961 uugaaguaaa ugguguuaac cag 23

<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 962 uugaaguaaa ugguguuaac cag 23

<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 963 uugaaguaaa ugguguuaac cag 23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 964 uugaaguaaa ugguguuaac cag 23

<210> SEQ ID NO 965
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 965 uugaaguaaa ugguguuaac cag 23

<210> SEQ ID NO 966
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 966 uugaaguaaa ugguguuaac cag 23

<210> SEQ ID NO 967
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 967 uugaaguaaa ugguguuaac cag 23

<210> SEQ ID NO 968
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 968 uugaaguaaa ugguguuaac cag 23

<210> SEQ ID NO 969
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 969 uugaaguaaa ugguguuaac cag 23

<210> SEQ ID NO 970
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 970 uugaaguaaa ugguguuaac cag 23

<210> SEQ ID NO 971
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971 uugaaguaaa ugguguuaac cag 23

<210> SEQ ID NO 972
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 972 uugaaguaaa ugguguuaac cag 23

<210> SEQ ID NO 973
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 973 uugaaguaaa ugguguuaac cag 23

<210> SEQ ID NO 974
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 974 uugaaguaaa ugguguuaac cag 23

<210> SEQ ID NO 975
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 975 uugaaguaaa ugguguuaac cag 23

<210> SEQ ID NO 976
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 976 uugaaguaaa ugguguuaac cag 23

<210> SEQ ID NO 977
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 977 uugaaguaaa ugguguuaac cag 23

<210> SEQ ID NO 978
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 978 uugaaguaaa ugguguuaac cag 23

<210> SEQ ID NO 979
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 979 ggagaagaag gcaacugag 19

<210> SEQ ID NO 980
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 980 ugaccaagcu gggugccug 19

<210> SEQ ID NO 981
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 981 gguuaacacc auuuacuuc 19

<210> SEQ ID NO 982
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 982 gcugguuaac accauuuac 19

<210> SEQ ID NO 983
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 983 uaaugacacc cuccagcaa 19

<210> SEQ ID NO 984
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 984 cguguucagc aucuaugau 19

<210> SEQ ID NO 985
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 985 uugaggacgg cuucaguuu 19

<210> SEQ ID NO 986
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 986 cggcgugucu gggaacugu 19

<210> SEQ ID NO 987
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 987 uuaacaccau uuacuucaa 19

<210> SEQ ID NO 988
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 988 cccugaaaag uccaaacuc 19

<210> SEQ ID NO 989
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 989 cgagaugacc ucuaugucu 19

<210> SEQ ID NO 990
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 990 ucuacaaggc ugauggaga 19

<210> SEQ ID NO 991
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 991 agcucacugu ucuggugcu 19

<210> SEQ ID NO 992
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 992 aggagcagcu gcaagacau 19

<210> SEQ ID NO 993
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 993 gccaccaacc ggcgugucu 19

<210> SEQ ID NO 994
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 994 cagaacagaa gaucccgga 19

<210> SEQ ID NO 995
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 995 ccuugucgau cuguucagc 19

<210> SEQ ID NO 996
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 996 aggcaaguuc cguuaucgg 19

<210> SEQ ID NO 997
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 997 uuuuguccuu gcugcucau 19

<210> SEQ ID NO 998
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998 agaccuacca ggacaucag 19

<210> SEQ ID NO 999
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999 aacugaacug ccgacucua 19

<210> SEQ ID NO 1000
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000 cauuuacuuc aagggccug 19

<210> SEQ ID NO 1001
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001 cccuggacuu caaggaaaa 19

<210> SEQ ID NO 1002
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002 agcugcaagu accgcuguu 19

<210> SEQ ID NO 1003
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003 acacaaggaa ggaacuguu 19

<210> SEQ ID NO 1004
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1004 gcaacugagg augagggcu 19

<210> SEQ ID NO 1005
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005 guagccaacc cuuguguua 19

<210> SEQ ID NO 1006
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006 guuugugaac agaaguaaa 19

<210> SEQ ID NO 1007
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1007 gggugacuuu caaggccaa 19

<210> SEQ ID NO 1008
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008 uuaucggcgc guggcugaa 19

<210> SEQ ID NO 1009
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009 ccacuucuuc uuugccaaa 19

<210> SEQ ID NO 1010
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1010 aacaccauuu acuucaagg 19

<210> SEQ ID NO 1011
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1011 gauggagagu cguguucag 19

<210> SEQ ID NO 1012
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1012 caccauuuac uucaagggc 19

<210> SEQ ID NO 1013
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1013 uuuacuucaa gggccugug 19

<210> SEQ ID NO 1014
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1014 uaagagaagu uccucugaa 19

<210> SEQ ID NO 1015
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1015 gcgggacauu cccaugaau 19

<210> SEQ ID NO 1016
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1016 ugccccaccc uguccucug 19

<210> SEQ ID NO 1017
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1017 ugguuaacac cauuuacuu 19

<210> SEQ ID NO 1018
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1018 cggauugccu cagaucaca 19

<210> SEQ ID NO 1019
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1019 ccaggacauc agugaguug 19

<210> SEQ ID NO 1020

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1020 ccaguuuuca ggcggauug 19

<210> SEQ ID NO 1021
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1021 caccauaucu gagaaaaca 19

<210> SEQ ID NO 1022
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022 aaguaaaaau aaauacaaa 19

<210> SEQ ID NO 1023
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1023 gcacccaggu gcuugaguu 19

<210> SEQ ID NO 1024
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1024 uaacaccauu uacuucaag 19

<210> SEQ ID NO 1025
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1025 ccuucaaagg ugaugacau 19

<210> SEQ ID NO 1026
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1026 caaggccaau ucccgcuuu 19

<210> SEQ ID NO 1027
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1027 ucaguuugaa ggagcagcu 19

<210> SEQ ID NO 1028
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1028 gggacugcgu gaccuguca 19

<210> SEQ ID NO 1029
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1029 ucagccaauc gccuuuuug 19

<210> SEQ ID NO 1030
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1030 ccucggaagc caucaauga 19

<210> SEQ ID NO 1031
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1031 gacaaugaua acauuuucc 19

<210> SEQ ID NO 1032
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1032 cuuauucuuu gcaccucuu 19

<210> SEQ ID NO 1033
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1033 auugcuggcc guucgcuaa 19

<210> SEQ ID NO 1034
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1034 aaaugaagaa ggcagugaa 19

<210> SEQ ID NO 1035
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1035 ugaguuggua uauggagcc 19

<210> SEQ ID NO 1036
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1036 uccagcaacu gauggaggu 19

<210> SEQ ID NO 1037
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1037 aacuguaacc ucuggaaaa 19

<210> SEQ ID NO 1038
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 1038 ucaacaaaug gguguccaa 19

<210> SEQ ID NO 1039
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1039 gauuagcggc cauguauuc 19

<210> SEQ ID NO 1040
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1040 gugcuugagu ugcccuuca 19

<210> SEQ ID NO 1041
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1041 ugcagaaggc cgagaugac 19

<210> SEQ ID NO 1042
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1042 cuauuuuugg uuugugaac 19

<210> SEQ ID NO 1043
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1043 cagugaagca gcugcaagu 19

<210> SEQ ID NO 1044
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1044 guguccaaua agaccgaag 19

<210> SEQ ID NO 1045
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1045 augaauugga ggagaugau 19

<210> SEQ ID NO 1046
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1046 aucuaugaug uaccaggaa 19

<210> SEQ ID NO 1047
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1047 ccauaaggca uuucuugag 19

<210> SEQ ID NO 1048
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1048 augcauucca uaaggcauu 19

<210> SEQ ID NO 1049
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1049 uggugcuggu uaacaccau 19

<210> SEQ ID NO 1050
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1050 aucuguucag cccugaaaa 19

<210> SEQ ID NO 1051
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1051 agaugaugcu gguggucca 19

<210> SEQ ID NO 1052
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1052 auauggagcc aagcuccag 19

<210> SEQ ID NO 1053
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1053 ccgaaucacc gaugucauu 19

<210> SEQ ID NO 1054
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054 gcagagcaau ccagagcgg 19

<210> SEQ ID NO 1055
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1055 acaccauuua cuucaaggg 19

<210> SEQ ID NO 1056
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056 guaccaggaa ggcaaguuc 19

<210> SEQ ID NO 1057
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1057 ugcccaagcc ugagaagag 19

<210> SEQ ID NO 1058
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1058 uucuuugcca aacugaacu 19

<210> SEQ ID NO 1059
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1059 uggccaaggu agagaagga 19

<210> SEQ ID NO 1060
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1060 ugcugcaaga guggcugga 19

<210> SEQ ID NO 1061
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1061 ccaugugcau uuaccgcuc 19

<210> SEQ ID NO 1062
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1062 agacaugggc cuugucgau 19

<210> SEQ ID NO 1063
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1063 uuuuggagac aaaucccuu 19

<210> SEQ ID NO 1064
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1064 ggaugagggc ucagaacag 19

<210> SEQ ID NO 1065
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1065 cggcuuuugc uaugaccaa 19

<210> SEQ ID NO 1066
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1066 agcuccagcc ccuggacuu 19

<210> SEQ ID NO 1067
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1067 cugaucagau ccacuucuu 19

<210> SEQ ID NO 1068
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1068 ugcugguggu ccacaugcc 19

<210> SEQ ID NO 1069
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1069 gcgagauuua gaggaaaga 19

<210> SEQ ID NO 1070
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1070 cugcucauug gcuucuggg 19

<210> SEQ ID NO 1071
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1071 ccuucaauga gaccuacca 19

<210> SEQ ID NO 1072
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1072 accauuuacu ucaagggcc 19

<210> SEQ ID NO 1073
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1073 gcaccucuuc cuauuuuug 19

<210> SEQ ID NO 1074
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1074 guggcugaag gcacccagg 19

<210> SEQ ID NO 1075
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1075 uccgcauuga ggacggcuu 19

<210> SEQ ID NO 1076
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1076 uggacaucug cacagccaa 19

<210> SEQ ID NO 1077
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077 guccaaacuc ccagguauu 19

<210> SEQ ID NO 1078
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078 agaaggaacu caccccaga 19

<210> SEQ ID NO 1079
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079 ucuugaggua aaugaagaa 19

<210> SEQ ID NO 1080
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080 agcccugugg acaucugca 19

<210> SEQ ID NO 1081
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081 cagagcggcc aucaacaaa 19

<210> SEQ ID NO 1082
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082 auuuaaguuu gacaccaua 19

<210> SEQ ID NO 1083
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1083 ugagaagagc cuggccaag 19

<210> SEQ ID NO 1084
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084 ucaccauggu ccucaucuu 19

<210> SEQ ID NO 1085
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085 ggaaggaacu guucuacaa 19

<210> SEQ ID NO 1086
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086 cugguuuuua uaagagaag 19

<210> SEQ ID NO 1087
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087 cugggugccu guaaugaca 19

<210> SEQ ID NO 1088
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088 guaccgcugu ugugauugc 19

<210> SEQ ID NO 1089
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089 ucuaucagca ccuggcaga 19

<210> SEQ ID NO 1090
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1090 cuggcagauu ccaagaaug 19

<210> SEQ ID NO 1091
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1091 cgaugucauu cccucggaa 19

<210> SEQ ID NO 1092
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1092 gcuucuggga cugcgugac 19

<210> SEQ ID NO 1093
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1093 ccugucacgg gagcccugu 19

<210> SEQ ID NO 1094
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1094 auuuacuuca agggccugu 19

<210> SEQ ID NO 1095
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1095 ugcuaccacu uucuaucag 19

<210> SEQ ID NO 1096
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096 ggaacugucc aaggccaau 19

<210> SEQ ID NO 1097
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097 acaaauccuc caaguuagu 19

<210> SEQ ID NO 1098
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098 auuuaccgcu ccccggaga 19

<210> SEQ ID NO 1099

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1099 accccugagu aucuccacg 19

<210> SEQ ID NO 1100
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1100 cacuaucucc acuugccca 19

<210> SEQ ID NO 1101
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1101 aaauacaaac uacuuccau 19

<210> SEQ ID NO 1102
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1102 cugguuaaca ccauuuacu 19

<210> SEQ ID NO 1103
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1103 ucaucuugcc caagccuga 19

<210> SEQ ID NO 1104
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1104 ccucagauca cacuaucuc 19

<210> SEQ ID NO 1105
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105 cuguccucug gaaccucug 19

<210> SEQ ID NO 1106
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106 cccuguggaa gauuagcgg 19

<210> SEQ ID NO 1107
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107 aucuccacgg cuuuugcua 19

<210> SEQ ID NO 1108
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1108 guggcuggau gaauuggag 19

<210> SEQ ID NO 1109
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1109 caaguuagua ucagccaau 19

<210> SEQ ID NO 1110
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1110 gugaugacau caccauggu 19

<210> SEQ ID NO 1111
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1111 uuccaagaau gacaaugau 19

<210> SEQ ID NO 1112
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1112 ugauggaggu auuuaaguu 19

<210> SEQ ID NO 1113
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1113 guauuccaau gugauagga 19

<210> SEQ ID NO 1114
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1114 cagccaagcc gcgggacau 19

<210> SEQ ID NO 1115
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1115 caugccccgc uuccgcauu 19

<210> SEQ ID NO 1116
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1116 augugauagg aacuguaac 19

<210> SEQ ID NO 1117
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 1117 acaaaucccu uaccuucaa 19

<210> SEQ ID NO 1118
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1118 agguuuaucu uuuguccuu 19

<210> SEQ ID NO 1119
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1119 agaucccgga ggccaccaa 19

<210> SEQ ID NO 1120
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1120 acauuuuccu gucaccccu 19

<210> SEQ ID NO 1121
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1121 ggccuuuccu gguuuuuau 19

<210> SEQ ID NO 1122
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1122 uuguguuaag uaaaauguu 19

<210> SEQ ID NO 1123
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1123 caaggaaaau gcagagcaa 19

<210> SEQ ID NO 1124
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1124 cugagaaaac aucugauca 19

<210> SEQ ID NO 1125
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1125 uuacuucaag ggccugugg 19

<210> SEQ ID NO 1126
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1126 accccaacag ggugacuuu 19

<210> SEQ ID NO 1127
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1127 ccagguauug uugcagaag 19

<210> SEQ ID NO 1128
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1128 gccuguggaa gucaaaguu 19

<210> SEQ ID NO 1129
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1129 uggaaccucu gcgagauuu 19

<210> SEQ ID NO 1130
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130 agcccugaga acacaagga 19

<210> SEQ ID NO 1131
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1131 cucuaugucu cagaugcau 19

<210> SEQ ID NO 1132
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1132 aagaccgaag gccgaauca 19

<210> SEQ ID NO 1133
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1133 uaaaauguuc uuauucuuu 19

<210> SEQ ID NO 1134
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1134 ucuggaaaaa ggaagguuu 19

<210> SEQ ID NO 1135
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1135 uucaaggcca acaggccuu 19

<210> SEQ ID NO 1136
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1136 gaagucaaag uucagcccu 19

<210> SEQ ID NO 1137
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1137 ccaucaauga gcucacugu 19

<210> SEQ ID NO 1138
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138 cucugaacac uauuaucuu 19

<210> SEQ ID NO 1139
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139 ugcugguuaa caccauuua 19

<210> SEQ ID NO 1140
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140 agaggaaaga accaguuuu 19

<210> SEQ ID NO 1141
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141 ugcccagccc uguggaaga 19

<210> SEQ ID NO 1142
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1142 cucaguugcc uucuucucc 19

<210> SEQ ID NO 1143
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1143 caggcaccca gcuugguca 19

<210> SEQ ID NO 1144
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1144 gaaguaaaug guguuaacc 19

<210> SEQ ID NO 1145
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1145 guaaauggug uuaaccagc 19

<210> SEQ ID NO 1146
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1146 uugcuggagg gugucauua 19

<210> SEQ ID NO 1147
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1147 aucauagaug cugaacacg 19

<210> SEQ ID NO 1148
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1148 aaacugaagc cguccucaa 19

<210> SEQ ID NO 1149
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1149 acaguuccca gacacgccg 19

<210> SEQ ID NO 1150
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1150 uugaaguaaa ugguguuaa 19

<210> SEQ ID NO 1151
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1151 gaguuuggac uuuucaggg 19

<210> SEQ ID NO 1152
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1152 agacauagag gucaucucg 19

<210> SEQ ID NO 1153
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1153 ucuccaucag ccuuguaga 19

<210> SEQ ID NO 1154
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1154 agcaccagaa cagugagcu 19

<210> SEQ ID NO 1155
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1155 augucuugca gcugcuccu 19

<210> SEQ ID NO 1156
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1156 agacacgccg guuggugge 19

<210> SEQ ID NO 1157
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1157 uccgggaucu ucuguucug 19

<210> SEQ ID NO 1158
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1158 gcugaacaga ucgacaagg 19

<210> SEQ ID NO 1159
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1159 ccgauaacgg aacuugccu 19

<210> SEQ ID NO 1160
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1160 augagcagca aggacaaaa 19

<210> SEQ ID NO 1161
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1161 cugauguccu gguaggucu 19

<210> SEQ ID NO 1162
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1162 uagagucggc aguucaguu 19

<210> SEQ ID NO 1163
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1163 caggcccuug aaguaaaug 19

<210> SEQ ID NO 1164
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1164 uuuuccuuga aguccaggg 19

<210> SEQ ID NO 1165
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1165 aacagcggua cuugcagcu 19

<210> SEQ ID NO 1166
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1166 aacaguuccu uccuugugu 19

<210> SEQ ID NO 1167
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1167 agcccucauc cucaguugc 19

<210> SEQ ID NO 1168
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1168 uaacacaagg guuggcuac 19

<210> SEQ ID NO 1169
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1169 uuuacuucug uucacaaac 19

<210> SEQ ID NO 1170
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1170 uuggccuuga aagucaccc 19

<210> SEQ ID NO 1171
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1171 uucagccacg cgccgauaa 19

<210> SEQ ID NO 1172
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1172 uuuggcaaag aagaagugg 19

<210> SEQ ID NO 1173
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1173 ccuugaagua aaugguguu 19

<210> SEQ ID NO 1174
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1174 cugaacacga cucuccauc 19

<210> SEQ ID NO 1175
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1175 gcccuugaag uaaauggug 19

<210> SEQ ID NO 1176
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1176 cacaggcccu ugaaguaaa 19

<210> SEQ ID NO 1177
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1177 uucagaggaa cuucucuua 19

<210> SEQ ID NO 1178

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1178 auucauggga augucccgc 19

<210> SEQ ID NO 1179
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1179 cagaggacag gguggggca 19

<210> SEQ ID NO 1180
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1180 aaguaaaugg uguuaacca 19

<210> SEQ ID NO 1181
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1181 ugugaucuga ggcaauccg 19

<210> SEQ ID NO 1182
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1182 caacucacug auguccugg 19

<210> SEQ ID NO 1183
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1183 caauccgccu gaaaacugg 19

<210> SEQ ID NO 1184
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1184 uguuuucuca gauauggug 19

<210> SEQ ID NO 1185
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1185 uuuguauuua uuuuuacuu 19

<210> SEQ ID NO 1186
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1186 aacucaagca ccugggugc 19

<210> SEQ ID NO 1187
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1187 cuugaaguaa augguguua 19

<210> SEQ ID NO 1188
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1188 augucaucac cuuugaagg 19

<210> SEQ ID NO 1189
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1189 aaagcgggaa uuggccuug 19

<210> SEQ ID NO 1190
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1190 agcugcuccu ucaaacuga 19

<210> SEQ ID NO 1191
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1191 ugacagguca cgcaguccc 19

<210> SEQ ID NO 1192
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1192 caaaaaggcg auuggcuga 19

<210> SEQ ID NO 1193
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1193 ucauugaugg cuuccgagg 19

<210> SEQ ID NO 1194
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1194 ggaaaauguu aucauuguc 19

<210> SEQ ID NO 1195
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1195 aagaggugca aagaauaag 19

<210> SEQ ID NO 1196
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 1196 uuagcgaacg gccagcaau 19

<210> SEQ ID NO 1197
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1197 uucacugccu ucuucauuu 19

<210> SEQ ID NO 1198
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1198 ggcuccauau accaacuca 19

<210> SEQ ID NO 1199
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199 accuccauca guugcugga 19

<210> SEQ ID NO 1200
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200 uuuuccagag guuacaguu 19

<210> SEQ ID NO 1201
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201 uuggacaccc auuuguuga 19

<210> SEQ ID NO 1202
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1202 gaauacaugg ccgcuaauc 19

<210> SEQ ID NO 1203
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1203 ugaagggcaa cucaagcac 19

<210> SEQ ID NO 1204
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1204 gucaucucgg ccuucugca 19

<210> SEQ ID NO 1205
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1205 guucacaaac caaaaauag 19

<210> SEQ ID NO 1206
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1206 acuugcagcu gcuucacug 19

<210> SEQ ID NO 1207
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1207 cuucggucuu auuggacac 19

<210> SEQ ID NO 1208
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1208 aucaucuccu ccaauucau 19

<210> SEQ ID NO 1209
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1209 uuccugguac aucauagau 19

<210> SEQ ID NO 1210
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1210 cucaagaaau gccuuaugg 19

<210> SEQ ID NO 1211
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1211 aaugccuuau ggaaugcau 19

<210> SEQ ID NO 1212
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1212 augguguuaa ccagcacca 19

<210> SEQ ID NO 1213
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1213 uuuucagggc ugaacagau 19

<210> SEQ ID NO 1214
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1214 uggaccacca gcaucaucu 19

<210> SEQ ID NO 1215
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1215 cuggagcuug gcuccauau 19

<210> SEQ ID NO 1216
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1216 aaugacaucg gugauucgg 19

<210> SEQ ID NO 1217
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1217 ccgcucugga uugcucugc 19

<210> SEQ ID NO 1218
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1218 cccuugaagu aaauggugu 19

<210> SEQ ID NO 1219
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1219 gaacuugccu uccugguac 19

<210> SEQ ID NO 1220
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1220 cucuucucag gcuugggca 19

<210> SEQ ID NO 1221
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1221 aguucaguuu ggcaaagaa 19

<210> SEQ ID NO 1222
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1222 uccuucucua ccuuggcca 19

<210> SEQ ID NO 1223
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1223 uccagccacu cuugcagca 19

<210> SEQ ID NO 1224
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1224 gagcgguaaa ugcacaugg 19

<210> SEQ ID NO 1225
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1225 aucgacaagg cccaugucu 19

<210> SEQ ID NO 1226
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1226 aagggauuug ucuccaaaa 19

<210> SEQ ID NO 1227
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1227 cuguucugag cccucaucc 19

<210> SEQ ID NO 1228
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1228 uuggucauag caaaagccg 19

<210> SEQ ID NO 1229
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1229 aaguccaggg gcuggagcu 19

<210> SEQ ID NO 1230
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1230 aagaagugga ucugaucag 19

<210> SEQ ID NO 1231
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1231 ggcaugugga ccaccagca 19

<210> SEQ ID NO 1232
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1232 ucuuuccucu aaaucucgc 19

<210> SEQ ID NO 1233
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1233 cccagaagcc aaugagcag 19

<210> SEQ ID NO 1234
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1234 ugguaggucu cauugaagg 19

<210> SEQ ID NO 1235
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1235 ggcccuugaa guaaauggu 19

<210> SEQ ID NO 1236
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1236 caaaaauagg aagaggugc 19

<210> SEQ ID NO 1237
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1237 ccugggugcc uucagccac 19

<210> SEQ ID NO 1238
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1238 aagccguccu caaugcgga 19

<210> SEQ ID NO 1239
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1239 uuggcugugc agaugucca 19

<210> SEQ ID NO 1240
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1240 aauaccuggg aguuuggac 19

<210> SEQ ID NO 1241
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1241 ucugggguga guuccuucu 19

<210> SEQ ID NO 1242
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1242 uucuucauuu accucaaga 19

<210> SEQ ID NO 1243
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1243 ugcagauguc cacagggcu 19

<210> SEQ ID NO 1244
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1244 uuuguugaug gccgcucug 19

<210> SEQ ID NO 1245
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1245 uaugguguca aacuuaaau 19

<210> SEQ ID NO 1246
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1246 cuuggccagg cucuucuca 19

<210> SEQ ID NO 1247
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1247 aagaugagga ccaugguga 19

<210> SEQ ID NO 1248
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1248 uuguagaaca guuccuucc 19

<210> SEQ ID NO 1249
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1249 cuucucuuau aaaaaccag 19

<210> SEQ ID NO 1250
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1250 ugucauuaca ggcacccag 19

<210> SEQ ID NO 1251
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1251 gcaaucacaa cagcgguac 19

<210> SEQ ID NO 1252
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1252 ucugccaggu gcugauaga 19

<210> SEQ ID NO 1253
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1253 cauucuugga aucugccag 19

<210> SEQ ID NO 1254
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1254 uuccgaggga augacaucg 19

<210> SEQ ID NO 1255
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1255 gucacgcagu cccagaagc 19

<210> SEQ ID NO 1256
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1256 acagggcucc cgugacagg 19

<210> SEQ ID NO 1257

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1257 acaggcccuu gaaguaaau 19

<210> SEQ ID NO 1258
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1258 cugauagaaa gugguagca 19

<210> SEQ ID NO 1259
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1259 auuggccuug gacaguucc 19

<210> SEQ ID NO 1260
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1260 acuaacuugg aggauuugu 19

<210> SEQ ID NO 1261
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1261 ucuccgggga gcgguaaau 19

<210> SEQ ID NO 1262
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1262 cguggagaua cucaggggu 19

<210> SEQ ID NO 1263
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1263 ugggcaagug gagauagug 19

<210> SEQ ID NO 1264
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1264 auggaaguag uuuguauuu 19

<210> SEQ ID NO 1265
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1265 aguaaauggu guuaaccag 19

<210> SEQ ID NO 1266
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1266 ucaggcuugg gcaagauga 19

<210> SEQ ID NO 1267
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1267 gagauagugu gaucugagg 19

<210> SEQ ID NO 1268
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1268 cagagguucc agaggacag 19

<210> SEQ ID NO 1269
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1269 ccgcuaaucu uccacaggg 19

<210> SEQ ID NO 1270
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1270 uagcaaaagc cguggagau 19

<210> SEQ ID NO 1271
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1271 cuccaauuca uccagccac 19

<210> SEQ ID NO 1272
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1272 auuggcugau acuaacuug 19

<210> SEQ ID NO 1273
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1273 accaugguga ugucaucac 19

<210> SEQ ID NO 1274
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1274 aucauuguca uucuuggaa 19

<210> SEQ ID NO 1275
<211> LENGTH: 19
<212> TYPE: RNA
<213> ORGANISM: Artificial Sequence <220> FEATURE:
<223> OTHER INFORMATION: Description of Artificial Sequence: Synthetic
oligonucleotide

<400> SEQUENCE: 1275 aacuuaaaua ccuccauca 19

<210> SEQ ID NO 1276
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1276 uccuaucaca uuggaauac 19

<210> SEQ ID NO 1277
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1277 augucccgcg gcuuggcug 19

<210> SEQ ID NO 1278
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1278 aaugcggaag cggggcaug 19

<210> SEQ ID NO 1279
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1279 guuacaguuc cuaucacau 19

<210> SEQ ID NO 1280
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1280 uugaagguaa gggauuugu 19

<210> SEQ ID NO 1281
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1281 aaggacaaaa gauaaaccu 19

<210> SEQ ID NO 1282
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1282 uuggguggccu ccgggaucu 19

<210> SEQ ID NO 1283
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1283 aggggugaca ggaaaaugu 19

<210> SEQ ID NO 1284
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1284 auaaaaacca ggaaaggcc 19

<210> SEQ ID NO 1285
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1285 aacauuuuac uuaacacaa 19

<210> SEQ ID NO 1286
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1286 uugcucugca uuuuccuug 19

<210> SEQ ID NO 1287
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1287 ugaucagaug uuuucucag 19

<210> SEQ ID NO 1288
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1288 ccacaggccc uugaaguaa 19

<210> SEQ ID NO 1289
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1289 aaagucaccc uguuggggu 19

<210> SEQ ID NO 1290
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1290 cuucugcaac aauaccugg 19

<210> SEQ ID NO 1291
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1291 aacuuugacu uccacaggc 19

<210> SEQ ID NO 1292
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1292 aaaucucgca gagguucca 19

<210> SEQ ID NO 1293
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1293 uccuuguguu cucagggcu 19

<210> SEQ ID NO 1294
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1294 augcaucuga gacauagag 19

<210> SEQ ID NO 1295
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1295 ugauucggcc uucggucuu 19

<210> SEQ ID NO 1296
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1296 aaagaauaag aacauuuua 19

<210> SEQ ID NO 1297
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1297 aaaccuuccu uuuuccaga 19

<210> SEQ ID NO 1298
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1298 aaggccuguu ggccuugaa 19

<210> SEQ ID NO 1299
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1299 agggcugaac uuugacuuc 19

<210> SEQ ID NO 1300
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1300 acagugagcu cauugaugg 19

<210> SEQ ID NO 1301
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1301 aagauaauag uguucagag 19

<210> SEQ ID NO 1302
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1302 uaaauggugu uaaccagca 19

<210> SEQ ID NO 1303
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1303 aaaacugguu cuuuccucu 19

<210> SEQ ID NO 1304
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1304 ucuuccacag ggcugggca 19

<210> SEQ ID NO 1305
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1305 ggagaagaag gcaacugagt t 21

<210> SEQ ID NO 1306
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1306 ugaccaagcu gggugccugt t 21

<210> SEQ ID NO 1307
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1307 gguuaacacc auuuacuuct t 21

<210> SEQ ID NO 1308
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1308 gcugguuaac accauuuact t 21

<210> SEQ ID NO 1309
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1309 uaaugacacc cuccagcaat t 21

<210> SEQ ID NO 1310
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 1310 cguguucagc aucuaugaut t 21

<210> SEQ ID NO 1311
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1311 uugaggacgg cuucaguuut t 21

<210> SEQ ID NO 1312
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1312 cggcgugucu gggaacugut t 21

<210> SEQ ID NO 1313
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1313 uuaacaccau uuacuucaat t 21

<210> SEQ ID NO 1314
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1314 cccugaaaag uccaaacuct t 21

<210> SEQ ID NO 1315
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1315 cgagaugacc ucuaugucut t 21

<210> SEQ ID NO 1316
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1316 ucuacaaggc ugauggagat t 21

<210> SEQ ID NO 1317
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1317 agcucacugu ucuggugcut t 21

<210> SEQ ID NO 1318
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1318 aggagcagcu gcaagacaut t 21

<210> SEQ ID NO 1319
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1319 gccaccaacc ggcgugucut t 21

<210> SEQ ID NO 1320
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1320 cagaacagaa gaucccggat t 21

<210> SEQ ID NO 1321
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1321 ccuugucgau cuguucagct t 21

<210> SEQ ID NO 1322
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1322 aggcaaguuc cguuaucggt t 21

<210> SEQ ID NO 1323
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1323 uuuuguccuu gcugcucaut t 21

<210> SEQ ID NO 1324
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1324 agaccuacca ggacaucagt t 21

<210> SEQ ID NO 1325
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1325 aacugaacug ccgacucuat t 21

<210> SEQ ID NO 1326
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1326 cauuuacuuc aagggccugt t 21

<210> SEQ ID NO 1327
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1327 cccuggacuu caaggaaaat t 21

<210> SEQ ID NO 1328
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1328 agcugcaagu accgcuguut t 21

<210> SEQ ID NO 1329
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1329 acacaaggaa ggaacuguut t 21

<210> SEQ ID NO 1330
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1330 gcaacugagg augagggcut t 21

<210> SEQ ID NO 1331
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1331 guagccaacc cuuguguuat t 21

<210> SEQ ID NO 1332
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1332 guuugugaac agaaguaaat t 21

<210> SEQ ID NO 1333
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1333 gggugacuuu caaggccaat t 21

<210> SEQ ID NO 1334
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1334 uuaucggcgc guggcugaat t 21

<210> SEQ ID NO 1335
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1335 ccacuucuuc uuugccaaat t 21

<210> SEQ ID NO 1336
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1336 aacaccauuu acuucaaggt t 21

<210> SEQ ID NO 1337
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1337 gauggagagu cguguucagt t 21

<210> SEQ ID NO 1338
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1338 caccauuuac uucaagggct t 21

<210> SEQ ID NO 1339
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1339 uuuacuucaa gggccugugt t 21

<210> SEQ ID NO 1340
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1340 uaagagaagu uccucugaat t 21

<210> SEQ ID NO 1341
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1341 gcgggacauu cccaugaaut t 21

<210> SEQ ID NO 1342
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1342 ugccccaccc uguccucugt t 21

<210> SEQ ID NO 1343
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1343 ugguuaacac cauuuacuut t 21

<210> SEQ ID NO 1344
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1344 cggauugccu cagaucacat t 21

<210> SEQ ID NO 1345

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1345 ccaggacauc agugaguugt t 21

<210> SEQ ID NO 1346
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1346 ccaguuuuca ggcggauugt t 21

<210> SEQ ID NO 1347
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1347 caccauaucu gagaaaacat t 21

<210> SEQ ID NO 1348
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1348 aaguaaaaau aaauacaaat t 21

<210> SEQ ID NO 1349
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1349 gcacccaggu gcuugaguut t 21

<210> SEQ ID NO 1350
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1350 uaacaccauu uacuucaagt t 21

<210> SEQ ID NO 1351
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1351 ccuucaaagg ugaugacaut t 21

<210> SEQ ID NO 1352
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1352 caaggccaau ucccgcuuut t 21

<210> SEQ ID NO 1353
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1353 ucaguuugaa ggagcagcut t 21

<210> SEQ ID NO 1354
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1354 gggacugcgu gaccugucat t 21

<210> SEQ ID NO 1355
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1355 ucagccaauc gccuuuuugt t 21

<210> SEQ ID NO 1356
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1356 ccucggaagc caucaaugat t 21

<210> SEQ ID NO 1357
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1357 gacaaugaua acauuuucct t 21

<210> SEQ ID NO 1358
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1358 cuuauucuuu gcaccucuut t 21

<210> SEQ ID NO 1359
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1359 auugcuggcc guucgcuaat t 21

<210> SEQ ID NO 1360
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1360 aaaugaagaa ggcagugaat t 21

<210> SEQ ID NO 1361
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1361 ugaguuggua uauggagcct t 21

<210> SEQ ID NO 1362
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1362 uccagcaacu gauggaggut t 21

<210> SEQ ID NO 1363
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1363 aacuguaacc ucuggaaaat t 21

<210> SEQ ID NO 1364
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1364 ucaacaaaug gguguccaat t 21

<210> SEQ ID NO 1365
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1365 gauuagcggc cauguauuct t 21

<210> SEQ ID NO 1366
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1366 gugcuugagu ugcccuucat t 21

<210> SEQ ID NO 1367
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1367 ugcagaaggc cgagaugact t 21

<210> SEQ ID NO 1368
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1368 cuauuuuugg uuugugaact t 21

<210> SEQ ID NO 1369
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1369 cagugaagca gcugcaagut t 21

<210> SEQ ID NO 1370
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1370 guguccaaua agaccgaagt t 21

<210> SEQ ID NO 1371
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1371 augaauugga ggagaugaut t 21

<210> SEQ ID NO 1372
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1372 aucuaugaug uaccaggaat t 21

<210> SEQ ID NO 1373
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1373 ccauaaggca uuucuugagt t 21

<210> SEQ ID NO 1374
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1374 augcauucca uaaggcauut t 21

<210> SEQ ID NO 1375
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1375 uggugcuggu uaacaccaut t 21

<210> SEQ ID NO 1376
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1376 aucuguucag cccugaaaat t 21

<210> SEQ ID NO 1377
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1377 agaugaugcu gguguccat t 21

<210> SEQ ID NO 1378
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1378 auauggagcc aagcuccagt t 21

<210> SEQ ID NO 1379
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1379 ccgaaucacc gaugucauut t 21

<210> SEQ ID NO 1380
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1380 gcagagcaau ccagagcggt t 21

<210> SEQ ID NO 1381
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1381 acaccauuua cuucaagggt t 21

<210> SEQ ID NO 1382
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1382 guaccaggaa ggcaaguuct t 21

<210> SEQ ID NO 1383
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1383 ugcccaagcc ugagaagagt t 21

<210> SEQ ID NO 1384
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1384 uucuuugcca aacugaacut t 21

<210> SEQ ID NO 1385
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1385 uggccaaggu agagaaggat t 21

<210> SEQ ID NO 1386
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1386 ugcugcaaga guggcuggat t 21

<210> SEQ ID NO 1387
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1387 ccaugugcau uuaccgcuct t 21

<210> SEQ ID NO 1388
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1388 agacaugggc cuugucgaut t 21

<210> SEQ ID NO 1389
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 1389 uuuuggagac aaaucccuut t 21

<210> SEQ ID NO 1390
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1390 ggaugagggc ucagaacagt t 21

<210> SEQ ID NO 1391
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1391 cggcuuuugc uaugaccaat t 21

<210> SEQ ID NO 1392
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1392 agcuccagcc ccuggacuut t 21

<210> SEQ ID NO 1393
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1393 cugaucagau ccacuucuut t 21

<210> SEQ ID NO 1394
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1394 ugcugguggu ccacaugcct t 21

<210> SEQ ID NO 1395
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1395 gcgagauuua gaggaaagat t 21

<210> SEQ ID NO 1396
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1396 cugcucauug gcuucugggt t 21

<210> SEQ ID NO 1397
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1397 ccuucaauga gaccuaccat t 21

<210> SEQ ID NO 1398
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1398 accauuuacu ucaagggcct t 21

<210> SEQ ID NO 1399
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1399 gcaccucuuc cuauuuuugt t 21

<210> SEQ ID NO 1400
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1400 guggcugaag gcacccaggt t 21

<210> SEQ ID NO 1401
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1401 uccgcauuga ggacggcuut t 21

<210> SEQ ID NO 1402
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1402 uggacaucug cacagccaat t 21

<210> SEQ ID NO 1403
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1403 guccaaacuc ccagguauut t 21

<210> SEQ ID NO 1404
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1404 agaaggaacu caccccagat t 21

<210> SEQ ID NO 1405
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1405 ucuugaggua aaugaagaat t 21

<210> SEQ ID NO 1406
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1406 agcccugugg acaucugcat t 21

<210> SEQ ID NO 1407
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1407 cagagcggcc aucaacaaat t 21

<210> SEQ ID NO 1408
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1408 auuuaaguuu gacaccauat t 21

<210> SEQ ID NO 1409
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1409 ugagaagagc cuggccaagt t 21

<210> SEQ ID NO 1410
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1410 ucaccauggu ccucaucuut t 21

<210> SEQ ID NO 1411
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1411 ggaaggaacu guucuacaat t 21

<210> SEQ ID NO 1412
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1412 cugguuuuua uaagagaagt t 21

<210> SEQ ID NO 1413
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1413 cugggugccu guaaugacat t 21

<210> SEQ ID NO 1414
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1414 guaccgcugu ugugauugct t 21

<210> SEQ ID NO 1415
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1415 ucuaucagca ccuggcagat t 21

<210> SEQ ID NO 1416
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1416 cuggcagauu ccaagaaugt t 21

<210> SEQ ID NO 1417
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1417 cgaugucauu cccucggaat t 21

<210> SEQ ID NO 1418
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1418 gcuucuggga cugcgugact t 21

<210> SEQ ID NO 1419
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1419 ccugucacgg gagcccugut t 21

<210> SEQ ID NO 1420
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1420 auuuacuuca agggccugut t 21

<210> SEQ ID NO 1421
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1421 ugcuaccacu uucuaucagt t 21

<210> SEQ ID NO 1422
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1422 ggaacugucc aaggccaaut t 21

<210> SEQ ID NO 1423
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1423 acaaauccuc caaguuagut t 21

<210> SEQ ID NO 1424

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1424 auuuaccgcu ccccggagat t 21

<210> SEQ ID NO 1425
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1425 accccugagu aucuccacgt t 21

<210> SEQ ID NO 1426
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1426 cacuaucucc acuugcccat t 21

<210> SEQ ID NO 1427
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1427 aaauacaaac uacuuccaut t 21

<210> SEQ ID NO 1428
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1428 cugguuaaca ccauuuacut t 21

<210> SEQ ID NO 1429
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1429 ucaucuugcc caagccugat t 21

<210> SEQ ID NO 1430
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1430 ccucagauca cacuaucuct t 21

<210> SEQ ID NO 1431
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1431 cuguccucug gaaccucugt t 21

<210> SEQ ID NO 1432
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1432 cccuguggaa gauuagcggt t 21

<210> SEQ ID NO 1433
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1433 aucuccacgg cuuuugcuat t 21

<210> SEQ ID NO 1434
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1434 guggcuggau gaauuggagt t 21

<210> SEQ ID NO 1435
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1435 caaguuagua ucagccaaut t 21

<210> SEQ ID NO 1436
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1436 gugaugacau caccauggut t 21

<210> SEQ ID NO 1437
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1437 uuccaagaau gacaaugaut t 21

<210> SEQ ID NO 1438
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1438 ugauggaggu auuuaaguut t 21

<210> SEQ ID NO 1439
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1439 guauuccaau gugauaggat t 21

<210> SEQ ID NO 1440
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1440 cagccaagcc gcgggacaut t 21

<210> SEQ ID NO 1441
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1441 caugccccgc uuccgcauut t 21

<210> SEQ ID NO 1442
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1442 augugauagg aacuguaact t 21

<210> SEQ ID NO 1443
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1443 acaaaucccu uaccuucaat t 21

<210> SEQ ID NO 1444
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1444 agguuuaucu uuuguccuut t 21

<210> SEQ ID NO 1445
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1445 agaucccgga ggccaccaat t 21

<210> SEQ ID NO 1446
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1446 acauuuuccu gucaccccut t 21

<210> SEQ ID NO 1447
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1447 ggccuuuccu gguuuuuaut t 21

<210> SEQ ID NO 1448
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1448 uuguguuaag uaaaauguut t 21

<210> SEQ ID NO 1449
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1449 caaggaaaau gcagagcaat t 21

<210> SEQ ID NO 1450
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1450 cugagaaaac aucugaucat t 21

<210> SEQ ID NO 1451
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1451 uuacuucaag ggccuguggt t 21

<210> SEQ ID NO 1452
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1452 accccaacag ggugacuuut t 21

<210> SEQ ID NO 1453
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1453 ccagguauug uugcagaagt t 21

<210> SEQ ID NO 1454
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1454 gccuguggaa gucaaaguut t 21

<210> SEQ ID NO 1455
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1455 uggaaccucu gcgagauuut t 21

<210> SEQ ID NO 1456
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1456 agcccugaga acacaaggat t 21

<210> SEQ ID NO 1457
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1457 cucuaugucu cagaugcaut t 21

<210> SEQ ID NO 1458
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1458 aagaccgaag gccgaaucat t 21

<210> SEQ ID NO 1459
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1459 uaaaauguuc uuauucuuut t 21

<210> SEQ ID NO 1460
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1460 ucuggaaaaa ggaagguuut t 21

<210> SEQ ID NO 1461
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1461 uucaaggcca acaggccuut t 21

<210> SEQ ID NO 1462
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1462 gaagucaaag uucagcccut t 21

<210> SEQ ID NO 1463
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1463 ccaucaauga gcucacugut t 21

<210> SEQ ID NO 1464
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1464 cucugaacac uauuaucuut t 21

<210> SEQ ID NO 1465
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1465 ugcugguuaa caccauuuat t 21

<210> SEQ ID NO 1466
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1466 agaggaaaga accaguuuut t 21

<210> SEQ ID NO 1467
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1467 ugcccagccc uguggaagat t 21

<210> SEQ ID NO 1468
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 1468 cucaguugcc uucuucucct t 21

<210> SEQ ID NO 1469
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1469 caggcaccca gcuuggucat t 21

<210> SEQ ID NO 1470
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1470 gaaguaaaug guguuaacct t 21

<210> SEQ ID NO 1471
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1471 guaaauggug uuaaccagct t 21

<210> SEQ ID NO 1472
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1472 uugcuggagg gugucauuat t 21

<210> SEQ ID NO 1473
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1473 aucauagaug cugaacacgt t 21

<210> SEQ ID NO 1474
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1474 aaacugaagc cguccucaat t 21

<210> SEQ ID NO 1475
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1475 acaguuccca gacacgccgt t 21

<210> SEQ ID NO 1476
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1476 uugaaguaaa ugguguuaat t 21

<210> SEQ ID NO 1477
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1477 gaguuuggac uuuucagggt t 21

<210> SEQ ID NO 1478
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1478 agacauagag gucaucucgt t 21

<210> SEQ ID NO 1479
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1479 ucuccaucag ccuuguagat t 21

<210> SEQ ID NO 1480
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1480 agcaccagaa cagugagcut t 21

<210> SEQ ID NO 1481
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1481 augucuugca gcugcuccut t 21

<210> SEQ ID NO 1482
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1482 agacacgccg guugguggct t 21

<210> SEQ ID NO 1483
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1483 uccgggaucu ucuguucugt t 21

<210> SEQ ID NO 1484
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1484 gcugaacaga ucgacaaggt t 21

<210> SEQ ID NO 1485
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1485 ccgauaacgg aacuugccut t 21

<210> SEQ ID NO 1486
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1486 augagcagca aggacaaaat t 21

<210> SEQ ID NO 1487
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1487 cugauguccu gguaggucut t 21

<210> SEQ ID NO 1488
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1488 uagagucggc aguucaguut t 21

<210> SEQ ID NO 1489
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1489 caggcccuug aaguaaaugt t 21

<210> SEQ ID NO 1490
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1490 uuuuccuuga aguccagggt t 21

<210> SEQ ID NO 1491
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1491 aacagcggua cuugcagcut t 21

<210> SEQ ID NO 1492
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1492 aacaguuccu uccuugugut t 21

<210> SEQ ID NO 1493
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1493 agcccucauc cucaguugct t 21

<210> SEQ ID NO 1494
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1494 uaacacaagg guuggcuact t 21

<210> SEQ ID NO 1495
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1495 uuuacuucug uucacaaact t 21

<210> SEQ ID NO 1496
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1496 uuggccuuga aagucaccct t 21

<210> SEQ ID NO 1497
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1497 uucagccacg cgccgauaat t 21

<210> SEQ ID NO 1498
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1498 uuuggcaaag aagaaguggt t 21

<210> SEQ ID NO 1499
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1499 ccuugaagua aaugguguut t 21

<210> SEQ ID NO 1500
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1500 cugaacacga cucuccauct t 21

<210> SEQ ID NO 1501
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1501 gcccuugaag uaaauggugt t 21

<210> SEQ ID NO 1502
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1502 cacaggcccu ugaaguaaat t 21

<210> SEQ ID NO 1503

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1503 uucagaggaa cuucucuuat t 21

<210> SEQ ID NO 1504
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1504 auucauggga augucccgct t 21

<210> SEQ ID NO 1505
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1505 cagaggacag gguggggcat t 21

<210> SEQ ID NO 1506
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1506 aaguaaaugg uguuaaccat t 21

<210> SEQ ID NO 1507
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1507 ugugaucuga ggcaauccgt t 21

<210> SEQ ID NO 1508
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1508 caacucacug auguccuggt t 21

<210> SEQ ID NO 1509
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1509 caauccgccu gaaaacuggt t 21

<210> SEQ ID NO 1510
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1510 uguuuucuca gauauggugt t 21

<210> SEQ ID NO 1511
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1511 uuuguauuua uuuuuacuut t 21

<210> SEQ ID NO 1512
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1512 aacucaagca ccugggugct t 21

<210> SEQ ID NO 1513
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1513 cuugaaguaa augguguuat t 21

<210> SEQ ID NO 1514
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1514 augucaucac cuuugaaggt t 21

<210> SEQ ID NO 1515
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1515 aaagcgggaa uuggccuugt t 21

<210> SEQ ID NO 1516
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1516 agcugcuccu ucaaacugat t 21

<210> SEQ ID NO 1517
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1517 ugacagguca cgcaguccct t 21

<210> SEQ ID NO 1518
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1518 caaaaaggcg auuggcugat t 21

<210> SEQ ID NO 1519
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1519 ucauugaugg cuuccgaggt t 21

<210> SEQ ID NO 1520
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1520 ggaaaauguu aucauuguct t 21

<210> SEQ ID NO 1521
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1521 aagaggugca aagaauaagt t 21

<210> SEQ ID NO 1522
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1522 uuagcgaacg gccagcaaut t 21

<210> SEQ ID NO 1523
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1523 uucacugccu ucuucauuut t 21

<210> SEQ ID NO 1524
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1524 ggcuccauau accaacucat t 21

<210> SEQ ID NO 1525
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1525 accuccauca guugcuggat t 21

<210> SEQ ID NO 1526
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1526 uuuuccagag guuacaguut t 21

<210> SEQ ID NO 1527
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1527 uuggacaccc auuuguugat t 21

<210> SEQ ID NO 1528
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1528 gaauacaugg ccgcuaauct t 21

<210> SEQ ID NO 1529
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1529 ugaagggcaa cucaagcact t 21

<210> SEQ ID NO 1530
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1530 gucaucucgg ccuucugcat t 21

<210> SEQ ID NO 1531
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1531 guucacaaac caaaaauagt t 21

<210> SEQ ID NO 1532
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1532 acuugcagcu gcuucacugt t 21

<210> SEQ ID NO 1533
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1533 cuucggucuu auuggacact t 21

<210> SEQ ID NO 1534
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1534 aucaucuccu ccaauucaut t 21

<210> SEQ ID NO 1535
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1535 uuccugguac aucauagaut t 21

<210> SEQ ID NO 1536
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1536 cucaagaaau gccuuauggt t 21

<210> SEQ ID NO 1537
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1537 aaugccuuau ggaaugcaut t 21

<210> SEQ ID NO 1538
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1538 augguguuaa ccagcaccat t 21

<210> SEQ ID NO 1539
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1539 uuuucagggc ugaacagaut t 21

<210> SEQ ID NO 1540
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1540 uggaccacca gcaucaucut t 21

<210> SEQ ID NO 1541
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1541 cuggagcuug gcuccauaut t 21

<210> SEQ ID NO 1542
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1542 aaugacaucg gugauucggt t 21

<210> SEQ ID NO 1543
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1543 ccgcucugga uugcucugct t 21

<210> SEQ ID NO 1544
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1544 cccuugaagu aaauggugut t 21

<210> SEQ ID NO 1545
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1545 gaacuugccu uccugguact t 21

<210> SEQ ID NO 1546
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1546 cucuucucag gcuugggcat t 21

<210> SEQ ID NO 1547
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 1547 aguucaguuu ggcaaagaat t 21

<210> SEQ ID NO 1548
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1548 uccuucucua ccuuggccat t 21

<210> SEQ ID NO 1549
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1549 uccagccacu cuugcagcat t 21

<210> SEQ ID NO 1550
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1550 gagcgguaaa ugcacauggt t 21

<210> SEQ ID NO 1551
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1551 aucgacaagg cccaugucut t 21

<210> SEQ ID NO 1552
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1552 aagggauuug ucuccaaaat t 21

<210> SEQ ID NO 1553
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1553 cuguucugag cccucaucct t 21

<210> SEQ ID NO 1554
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1554 uuggucauag caaaagccgt t 21

<210> SEQ ID NO 1555
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1555 aaguccaggg gcuggagcut t 21

<210> SEQ ID NO 1556
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1556 aagaagugga ucugaucagt t 21

<210> SEQ ID NO 1557
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1557 ggcaugugga ccaccagcat t 21

<210> SEQ ID NO 1558
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1558 ucuuuccucu aaaucucgct t 21

<210> SEQ ID NO 1559
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1559 cccagaagcc aaugagcagt t 21

<210> SEQ ID NO 1560
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1560 ugguaggucu cauugaaggt t 21

<210> SEQ ID NO 1561
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1561 ggcccuugaa guaaauggut t 21

<210> SEQ ID NO 1562
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1562 caaaaauagg aagaggugct t 21

<210> SEQ ID NO 1563
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1563 ccugggugcc uucagccact t 21

<210> SEQ ID NO 1564
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1564 aagccguccu caaugcggat t 21

<210> SEQ ID NO 1565
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1565 uuggcugugc agauguccat t 21

<210> SEQ ID NO 1566
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1566 aauaccuggg aguuuggact t 21

<210> SEQ ID NO 1567
<211> LENGTH: 21
<212> TYPE: DNA
<213> ORGANISM: Artificial Sequence <220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1567 ucuggggguga guuccuucut t 21

<210> SEQ ID NO 1568
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1568 uucuucauuu accucaagat t 21

<210> SEQ ID NO 1569
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1569 ugcagauguc cacagggcut t 21

<210> SEQ ID NO 1570
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1570 uuuguugaug gccgcucugt t 21

<210> SEQ ID NO 1571
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1571 uaugguguca aacuuaaaut t 21

<210> SEQ ID NO 1572
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1572 cuuggccagg cucuucucat t 21

<210> SEQ ID NO 1573
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1573 aagaugagga ccauggugat t 21

<210> SEQ ID NO 1574
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1574 uuguagaaca guuccuucct t 21

<210> SEQ ID NO 1575
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1575 cuucucuuau aaaaaccagt t 21

<210> SEQ ID NO 1576
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1576 ugucauuaca ggcacccagt t 21

<210> SEQ ID NO 1577
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1577 gcaaucacaa cagcgguact t 21

<210> SEQ ID NO 1578
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1578 ucugccaggu gcugauagat t 21

<210> SEQ ID NO 1579
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1579 cauucuugga aucugccagt t 21

<210> SEQ ID NO 1580
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1580 uuccgaggga augacaucgt t 21

<210> SEQ ID NO 1581
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1581 gucacgcagu cccagaagct t 21

<210> SEQ ID NO 1582

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1582 acagggcucc cgugacaggt t 21

<210> SEQ ID NO 1583
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1583 acaggcccuu gaaguaaaut t 21

<210> SEQ ID NO 1584
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1584 cugauagaaa gugguagcat t 21

<210> SEQ ID NO 1585
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1585 auuggccuug gacaguucct t 21

<210> SEQ ID NO 1586
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1586 acuaacuugg aggauuugut t 21

<210> SEQ ID NO 1587
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1587 ucuccgggga gcgguaaaut t 21

<210> SEQ ID NO 1588
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1588 cguggagaua cucaggggut t 21

<210> SEQ ID NO 1589
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1589 ugggcaagug gagauagugt t 21

<210> SEQ ID NO 1590
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1590 auggaaguag uuuguauuut t 21

<210> SEQ ID NO 1591
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1591 aguaaauggu guuaaccagt t 21

<210> SEQ ID NO 1592
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1592 ucaggcuugg gcaagaugat t 21

<210> SEQ ID NO 1593
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1593 gagauagugu gaucugaggt t 21

<210> SEQ ID NO 1594
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1594 cagagguucc agaggacagt t 21

<210> SEQ ID NO 1595
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1595 ccgcuaaucu uccacagggt t 21

<210> SEQ ID NO 1596
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1596 uagcaaaagc cguggagaut t 21

<210> SEQ ID NO 1597
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1597 cuccaauuca uccagccact t 21

<210> SEQ ID NO 1598
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1598 auuggcugau acuaacuugt t 21

<210> SEQ ID NO 1599
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1599 accaugguga ugucaucact t 21

<210> SEQ ID NO 1600
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1600 aucauuguca uucuuggaat t 21

<210> SEQ ID NO 1601
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1601 aacuuaaaua ccuccaucat t 21

<210> SEQ ID NO 1602
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1602 uccuaucaca uuggaauact t 21

<210> SEQ ID NO 1603
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1603 augucccgcg gcuuggcugt t 21

<210> SEQ ID NO 1604
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1604 aaugcggaag cggggcaugt t 21

<210> SEQ ID NO 1605
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1605 guuacaguuc cuaucacaut t 21

<210> SEQ ID NO 1606
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1606 uugaagguaa gggauuugut t 21

<210> SEQ ID NO 1607
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1607 aaggacaaaa gauaaaccut t 21

<210> SEQ ID NO 1608
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1608 uugguggccu ccgggaucut t 21

<210> SEQ ID NO 1609
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1609 aggggugaca ggaaaaugut t 21

<210> SEQ ID NO 1610
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1610 auaaaaacca ggaaaggcct t 21

<210> SEQ ID NO 1611
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1611 aacauuuuac uuaacacaat t 21

<210> SEQ ID NO 1612
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1612 uugcucugca uuuuccuugt t 21

<210> SEQ ID NO 1613
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1613 ugaucagaug uuuucucagt t 21

<210> SEQ ID NO 1614
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1614 ccacaggccc uugaaguaat t 21

<210> SEQ ID NO 1615
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1615 aaagucaccc uguuggggut t 21

<210> SEQ ID NO 1616
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1616 cuucugcaac aauaccuggt t 21

<210> SEQ ID NO 1617
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1617 aacuuugacu uccacaggct t 21

<210> SEQ ID NO 1618
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1618 aaaucucgca gagguuccat t 21

<210> SEQ ID NO 1619
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1619 uccuuguguu cucagggcut t 21

<210> SEQ ID NO 1620
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1620 augcaucuga gacauagagt t 21

<210> SEQ ID NO 1621
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1621 ugauucggcc uucggucuut t 21

<210> SEQ ID NO 1622
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1622 aaagaauaag aacauuuuat t 21

<210> SEQ ID NO 1623
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1623 aaaccuuccu uuuuccagat t 21

<210> SEQ ID NO 1624
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1624 aaggccuguu ggccuugaat t 21

<210> SEQ ID NO 1625
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1625 agggcugaac uuugacuuct t 21

<210> SEQ ID NO 1626
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
Synthetic oligonucleotide

<400> SEQUENCE: 1626 acagugagcu cauugauggt t 21

<210> SEQ ID NO 1627
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1627 aagauaauag uguucagagt t 21

<210> SEQ ID NO 1628
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1628 uaaauggugu uaaccagcat t 21

<210> SEQ ID NO 1629
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1629 aaaacugguu cuuuccucut t 21

<210> SEQ ID NO 1630
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1630 ucuuccacag ggcugggcat t 21

We claim:

1. A double-stranded ribonucleic acid [(dsRNA)] for inhibiting expression of Serpinc1, wherein said [dsRNA] *double-stranded ribonucleic acid* comprises a sense strand and an antisense strand, wherein the sense strand comprises the nucleotide sequence of 5'-GfsgsUfuAfaCfaCfCfAfuUfuAfcUfuCfaAf-3' (SEQ ID NO:941) and the antisense strand comprises the nucleotide sequence of 5'-usUfsgAfaGfuAfaAfuggUfgUfuAfaCfcsasg-3' (SEQ ID NO:960), wherein a, g, c, and u are 2'-O-methyl[(2'-OMe)] A, [U] *G*, C, [or G] *and U, respectively*; Af, [Cf] *Gf*, [Gf or] *Cf, and* Uf are 2'-fluoro A, G, C [or]*, and* U*, respectively*; and s is a phosphorothioate linkage.

2. The [dsRNA] *double-stranded ribonucleic acid* of claim 1, further comprising a ligand.

3. The [dsRNA] *double-stranded ribonucleic acid* of claim 2, wherein the ligand is conjugated to the [3' end] *3'-end* of the sense strand of the [dsRNA] *double-stranded ribonucleic acid.*

4. The [dsRNA] *double-stranded ribonucleic acid* of claim 2, wherein the ligand is an N-acetylgalactosamine [(GalNAc)] derivative.

5. The [dsRNA] *double-stranded ribonucleic acid* of claim 4, wherein the ligand is

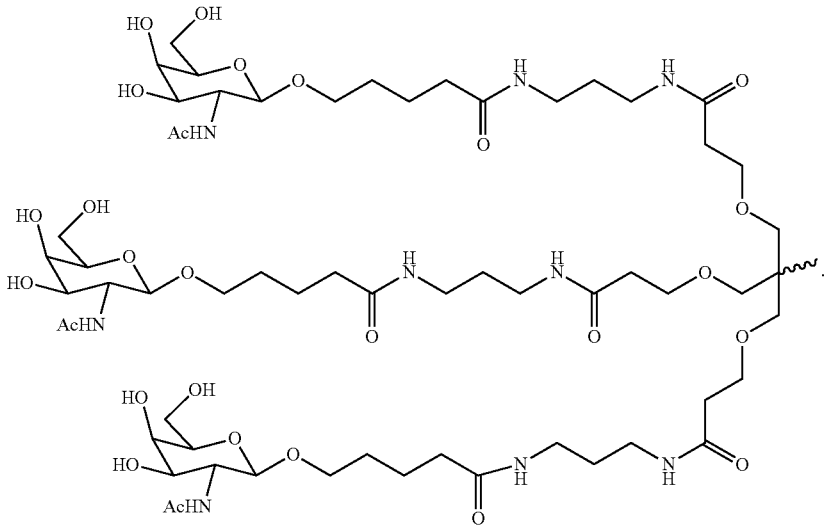

6. The [dsRNA] *double-stranded ribonucleic acid* of claim [4] *3*, wherein the [dsRNA] *double-stranded ribonucleic acid* is conjugated to the ligand as shown in the following schematic and[,] wherein X is O or S.

7. The [dsRNA] *double-stranded ribonucleic acid* of claim 6, wherein the X is O.

8. A cell containing the [dsRNA] *double-stranded ribonucleic acid* of claim 1.

9. A pharmaceutical composition for inhibiting expression of a Serpinc1 gene comprising the [dsRNA] *double-stranded ribonucleic acid* of claim 1.

10. A method of inhibiting Serpinc1 expression in a cell, the method comprising:

(a) contacting the cell with the [dsRNA] *double-stranded ribonucleic acid* of claim 1; and (b) maintaining the cell produced in step (a) for a time sufficient to obtain degradation of the mRNA transcript of a Serpinc1 gene, thereby inhibiting expression of the Serpinc1 gene in the cell.

11. The method of claim 10, wherein said cell is within a subject.

12. The method of claim 11, wherein the subject is a human.

13. The method of claim 12, wherein the human subject suffers from a bleeding disorder.

14. The method of claim 13, wherein the bleeding disorder is a hemophilia.

15. The method of any one of claims 10-14, wherein the Serpinc1 expression is inhibited by at least about 30%.

16. A method of treating a subject having a disorder that would benefit from reduction in Serpinc1 expression, comprising administering to the subject a [therapeutically] *prophylactically* effective amount of the [dsRNA] *double-stranded ribonucleic acid* of claim 1, thereby treating said subject.

17. A method of preventing at least one symptom in a subject having a disorder that would benefit from reduction in Serpinc1 expression, comprising administering to the subject a [therapeutically] *prophylactically* effective amount of the [dsRNA] *double-stranded ribonucleic acid* of claim 1, thereby preventing at least one symptom in the subject having [a] *the* disorder that would benefit from reduction in Serpinc1 expression.

18. The method of claim 16, wherein the disorder is a bleeding disorder.

19. The method of claim 18, wherein the bleeding disorder is a hemophilia.

20. The method of claim 16, wherein the administration of the [dsRNA] *double-stranded ribonucleic acid* to the subject causes an increase in blood clotting and/or a decrease in Serpinc1 protein accumulation.

21. The method of claim 16, wherein the [dsRNA] *double-stranded ribonucleic acid* is conjugated to a ligand.

22. The method of claim 21, wherein the ligand is conjugated to the 3'-end of the sense strand of the [dsRNA] *double-stranded ribonucleic acid*.

23. The method of claim 22, wherein the ligand is an N-acetylgalactosamine [(GalNAc)] derivative.

[24. The method of claim 17, wherein the dsRNA is administered at a dose of about 0.01 mg/kg to about 50 mg/kg.]

[25. The method of claim 24, wherein the dsRNA is administered at a dose of about 10 mg/kg to about 30 mg/kg.]

[26. The method of claim 24, wherein the dsRNA is administered at a dose selected from the group consisting of 0.3 mg/kg 0.5 mg/kg 1 mg/kg, 1.5 mg/kg, 3 mg/kg, 10 mg/kg, and 30 mg/kg.]

27. The method of claim [25 or 26] *17*, wherein the [dsRNA] *double-stranded ribonucleic acid* is administered to the subject once a week.

28. The method of claim [25 or 26] *17*, wherein the [dsRNA] *double-stranded ribonucleic acid* is administered to the subject twice a month.

29. The method of claim 16, further comprising measuring thrombin levels in said subject.

[30. The method of claim 17, wherein the dsRNA is administered to the subject subcutaneously at a cumulative weekly dose of about 0.5 mg/kg to about 5 mg/kg.]

31. A method of inhibiting the expression of Serpinc1 in a subject, the method comprising administering to said subject a [therapeutically] *prophylactically* effective amount of the [dsRNA] *double-stranded ribonucleic acid* of claim 1, thereby inhibiting the expression of Serpinc1 in said subject.

32. The method of claim 31, wherein the [dsRNA] *double-stranded ribonucleic acid* is conjugated to a ligand.

33. The method of claim 32, wherein the ligand is conjugated to the 3'-end of the sense strand of the [dsRNA] *double-stranded ribonucleic acid*.

34. The method of claim 33, wherein the ligand is an N-acetylgalactosamine [(GalNAc)] derivative.

[35. The method of claim 31, wherein the dsRNA is administered at a dose of about 0.01 mg/kg to about 50 mg/kg.]

[36. The method of claim 35, wherein the dsRNA is administered at a dose of about 10 mg/kg to about 30 mg/kg.]

[37. The method of claim 35, wherein the dsRNA is administered at a dose selected from the group consisting of 1 mg/kg, 3 mg/kg, 10 mg/kg, and 30 mg/kg.]

38. The method of claim [37] *31*, wherein the [dsRNA] *double-stranded ribonucleic acid* is administered to the subject once a week.

39. The method of claim [37] *31*, wherein the [dsRNA] *double-stranded ribonucleic acid* is administered to the subject twice a month.

[40. The method of claim 31, wherein the dsRNA is administered to the subject subcutaneously at a cumulative weekly dose of about 0.5 mg/kg to about 5 mg/kg.]

41. The method of claim 31, further comprising measuring thrombin levels in said subject.

42. The method of claim 21, wherein the ligand is

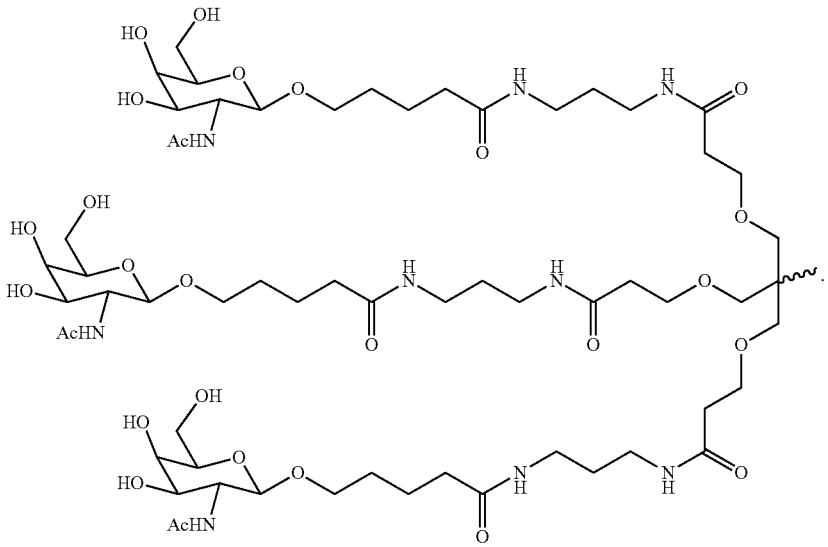

43. The method of claim [21] *22*, wherein the [dsRNA] *double-stranded ribonucleic acid* is conjugated to the ligand as shown in the following schematic

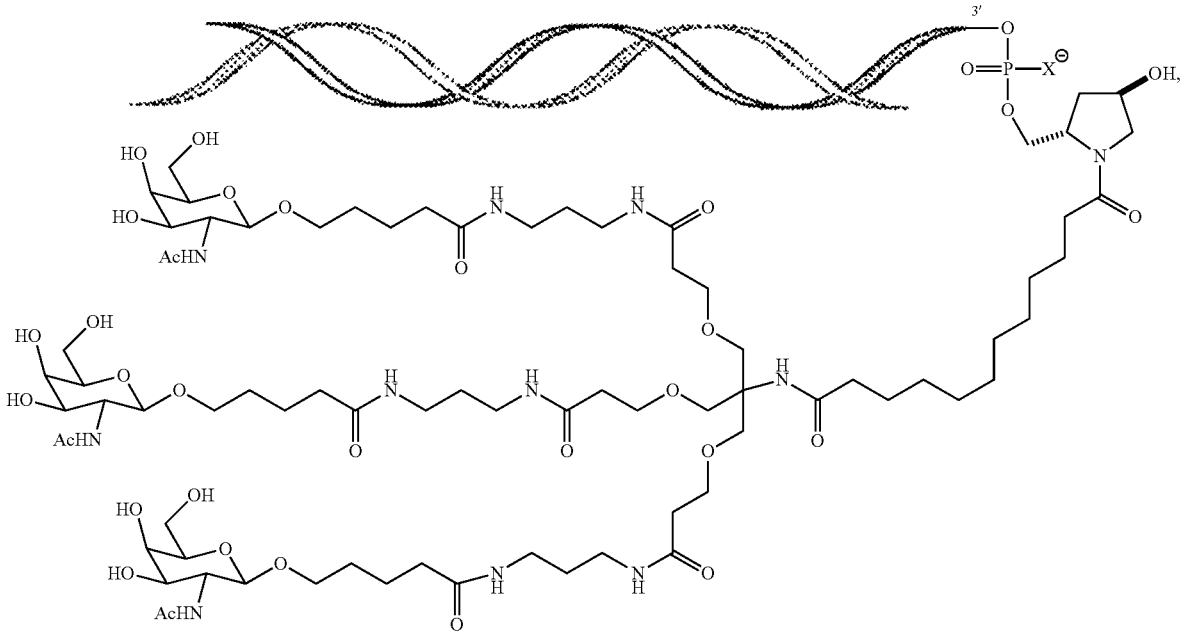

and[,] wherein X is O or S.

44. The [dsRNA] *method* of claim 43, wherein the X is O.

[45. The method of claim 16, wherein the dsRNA is administered at a dose of about 0.01 mg/kg to about 50 mg/kg.]

[46. The method of claim 45, wherein the dsRNA is administered at a dose of about 10 mg/kg to about 30 mg/kg.]

[47. The method of claim 45, wherein the dsRNA is administered at a dose selected from the group consisting of 0.3 mg/kg 0.5 mg/kg 1 mg/kg, 1.5 mg/kg, 3 mg/kg, 10 mg/kg, and 30 mg/kg.]

48. The method of claim [46 or 47] *16*, wherein the [dsRNA] *double-stranded ribonucleic acid* is administered to the subject once a week.

49. The method of claim [46 or 47] *16*, wherein the [dsRNA] *double-stranded ribonucleic acid* is administered to the subject twice a month.

50. The method of claim 17, wherein the disorder is a bleeding disorder.

51. The method of claim 50, wherein the bleeding disorder is a hemophilia.

52. The method of claim 17, wherein the administration of the [dsRNA] *double-stranded ribonucleic acid* to the subject causes an increase in blood clotting and/or a decrease in Serpinc1 protein accumulation.

53. The method of claim 17, wherein the [dsRNA] *double-stranded ribonucleic acid* is conjugated to a ligand.

54. The method of claim 53, wherein the ligand is conjugated to the 3'-end of the sense strand of the [dsRNA] *double-stranded ribonucleic acid*.

55. The method of claim 54, wherein the ligand is an N-acetylgalactosamine [(GalNAc)] derivative.

56. The method of claim 55, wherein the ligand is

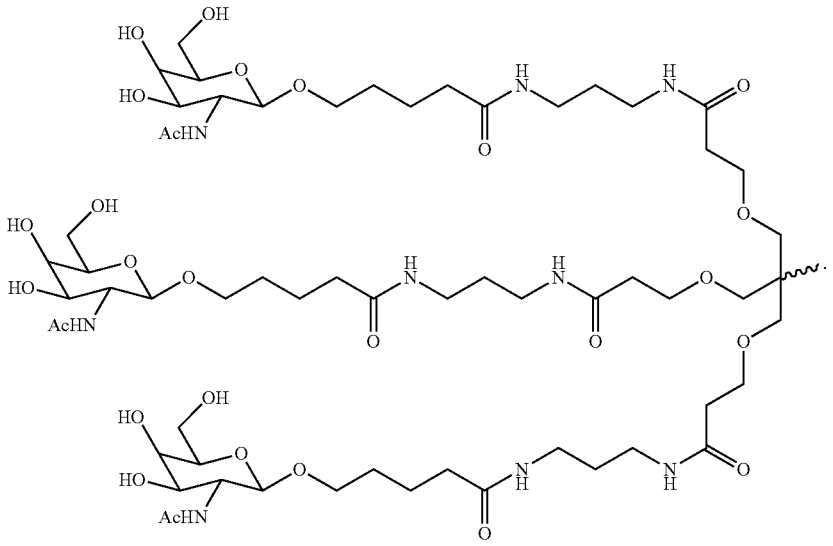

57. The method of claim 55, wherein the [dsRNA] *double-stranded ribonucleic acid* is conjugated to the ligand as shown in the following schematic

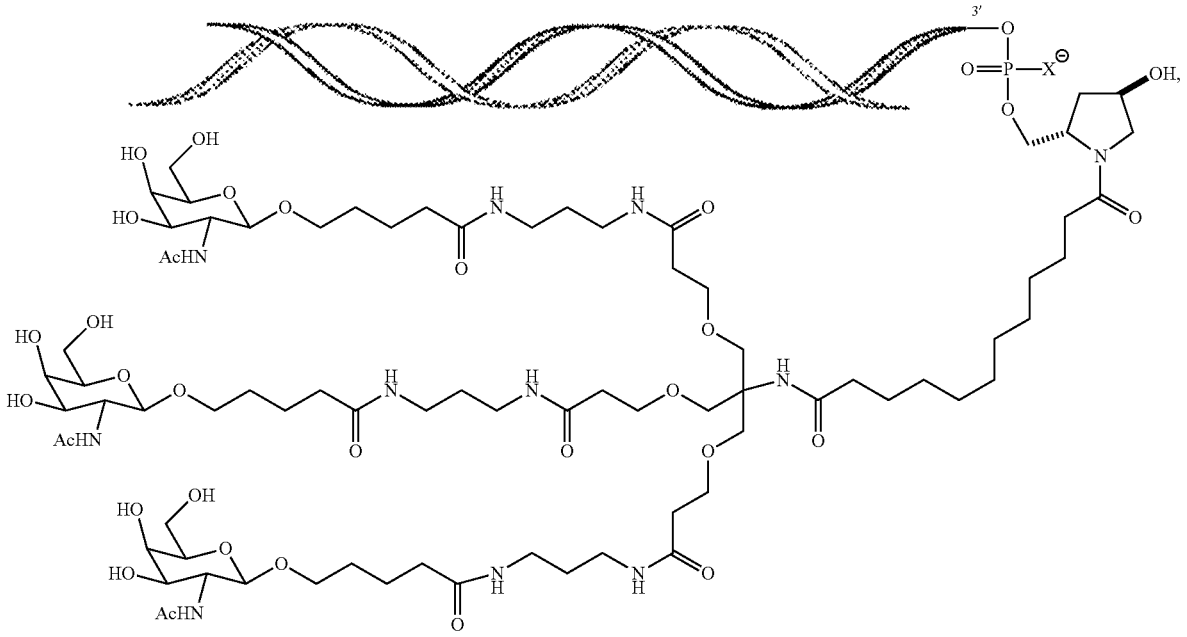

and[.] wherein X is O or S.

58. The method of claim 57, wherein the X is O.

59. The method of claim 17, further comprising measuring thrombin levels in said subject.

60. The method of claim 34, wherein the ligand is

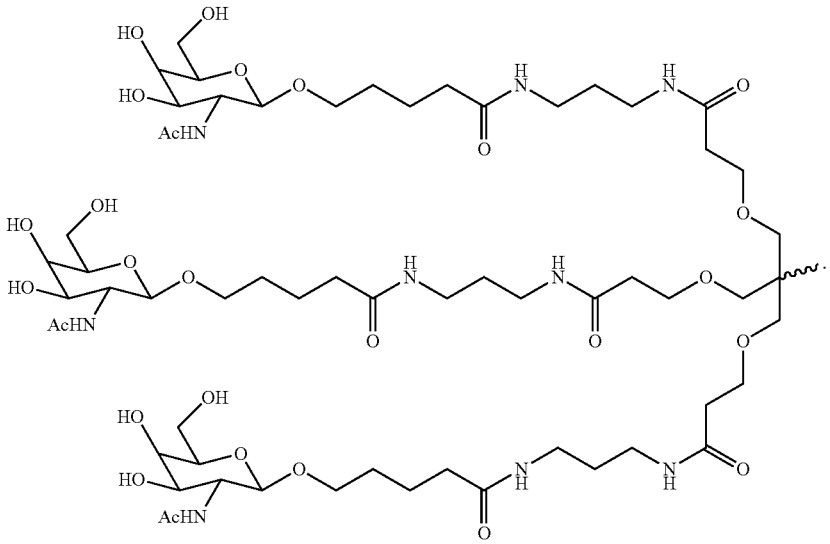

61. The method of claim 34, wherein the [dsRNA] *double-stranded ribonucleic acid* is conjugated to the ligand as shown in the following schematic

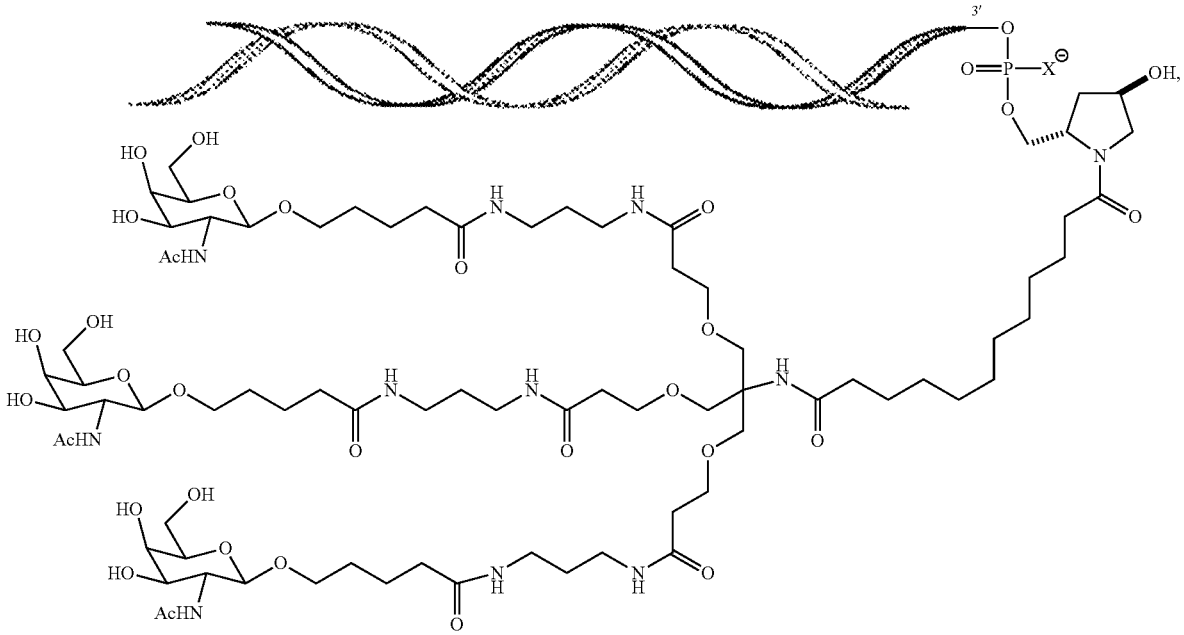

and[,] wherein X is O or S.

62. The method of claim 61, wherein the X is O.

*63. A double-stranded ribonucleic acid comprising a sense strand, an antisense strand, and a ligand, wherein the nucleotide sequence of the sense strand consists of 5'-GfsgsUfuAfaCfaCfCfAfuUfuAfcUfuCfaAf-3'* (*SEQ ID NO:941*) *and the nucleotide sequence of the antisense strand consists of 5'-usUfsgAfaGfuAfaAfuggUfgUfuAfaCfcsasg-3'*

(*SEQ ID NO:960*), *wherein a, g, c, and u are 2'-O-methyl A, G, C, and U, respectively; Af, Gf, Cf, and Uf are 2'-fluoro A, G, C, and U, respectively; and s is a phosphorothioate linkage, wherein the ligand is conjugated to the 3' end of the sense strand as shown in the schematic*

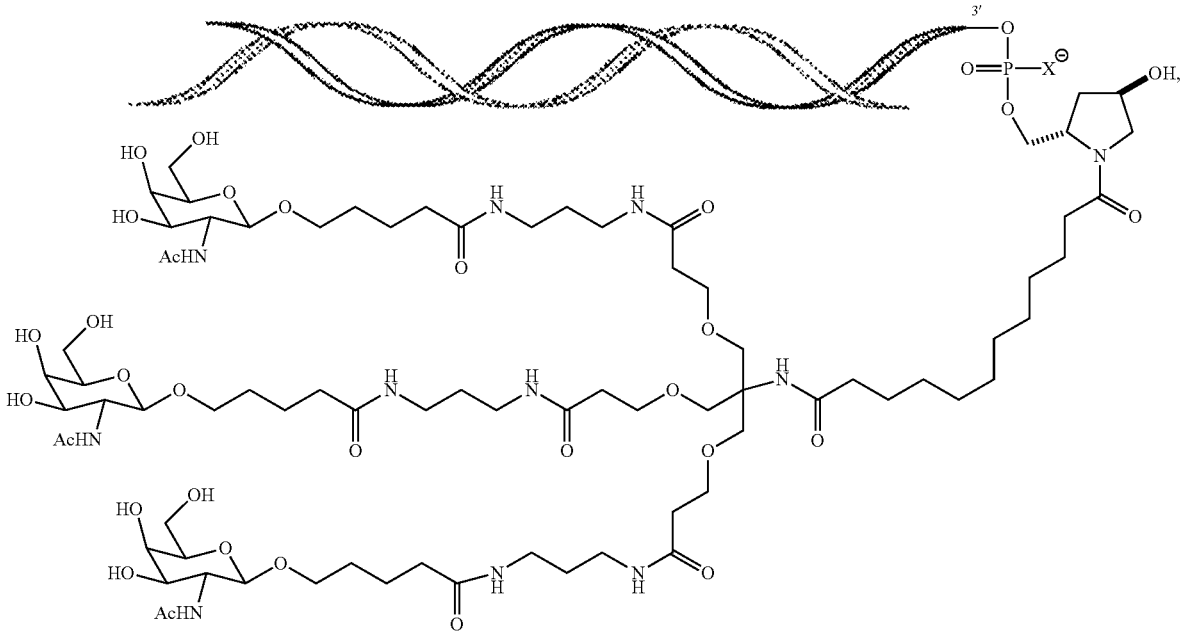

*and wherein X is O.*

*64. A pharmaceutical composition comprising the double-stranded ribonucleic acid of claim 63 and phosphate buffered saline.*

*65. The pharmaceutical composition of claim 9, wherein the pharmaceutical composition comprises phosphate buffered saline.*

*66. A method of treating hemophilia A or hemophilia B prophylactically in a subject in need thereof, comprising administering the double-stranded ribonucleic acid of claim 63 in a prophylactically effective amount to the subject in need thereof.*

*67. The method of claim 66, wherein the subject is a hemophilia A or hemophilia B patient with inhibitors.*

*68. A method of treating hemophilia A or hemophilia B prophylactically in a subject in need thereof, comprising administering the pharmaceutical composition of claim 64 in a prophylactically effective amount to the subject in need thereof.*

*69. The method of claim 68, wherein the subject is a hemophilia A or hemophilia B patient with inhibitors.*

*70. A method of treating hemophilia A or hemophilia B prophylactically in a subject in need thereof, comprising administering the pharmaceutical composition of claim 65 in a prophylactically effective amount to the subject in need thereof.*

*71. The method of any one of claims 44, 58, 62, 66, 68, or 70, wherein the subject is a hemophilia A patient with inhibitors.*

*72. The method of any one of claims 44, 58, 62, 66, 68, and 70, wherein the subject is a hemophilia B patient with inhibitors.*

*73. The method of any one of claims 44, 58, 62, 66, 68, and 70, wherein the subject is a hemophilia A patient without inhibitors.*

*74. The method of any one of claims 44, 58, 62, 66, 68, and 70, wherein the subject is a hemophilia B patient without inhibitors.*

* * * * *